(12) United States Patent
Choudhary et al.

(10) Patent No.: US 12,391,685 B2
(45) Date of Patent: Aug. 19, 2025

(54) INHIBITORS OF RNA-GUIDED NUCLEASE TARGET BINDING AND USES THEREOF

(71) Applicants: THE BROAD INSTITUTE, INC., Cambridge, MA (US); THE BRIGHAM AND WOMEN'S HOSPITAL, INC., Boston, MA (US)

(72) Inventors: Amit Choudhary, Boston, MA (US); Basudeb Maji, Cambridge, MA (US); Soumyashree Ashok Gangopadhyay, Boston, MA (US); Miseon Lee, Cambridge, MA (US); Mengchao Shi, Boston, MA (US)

(73) Assignees: The Broad Institute, Inc., Cambridge, MA (US); The Brigham and Women's Hospital, Inc., Boston, MA (US)

( * ) Notice: Subject to any disclaimer, the term of this patent is extended or adjusted under 35 U.S.C. 154(b) by 1041 days.

(21) Appl. No.: 17/269,900

(22) PCT Filed: Aug. 20, 2019

(86) PCT No.: PCT/US2019/047364
§ 371 (c)(1),
(2) Date: Feb. 19, 2021

(87) PCT Pub. No.: WO2020/068304
PCT Pub. Date: Apr. 2, 2020

(65) Prior Publication Data
US 2021/0177832 A1 Jun. 17, 2021

Related U.S. Application Data

(60) Provisional application No. 62/831,143, filed on Apr. 8, 2019, provisional application No. 62/784,268, filed on Dec. 21, 2018, provisional application No. 62/774,012, filed on Nov. 30, 2018, provisional application No. 62/765,357, filed on Aug. 20, 2018.

(51) Int. Cl.
| | |
|---|---|
| C07D 471/04 | (2006.01) |
| A61K 31/4745 | (2006.01) |
| A61K 31/7105 | (2006.01) |
| A61K 38/46 | (2006.01) |
| A61K 47/54 | (2017.01) |
| C12N 9/99 | (2006.01) |

(52) U.S. Cl.
CPC ........ *C07D 471/04* (2013.01); *A61K 31/4745* (2013.01); *A61K 31/7105* (2013.01); *A61K 38/465* (2013.01); *A61K 47/54* (2017.08); *A61K 47/545* (2017.08); *C12N 9/99* (2013.01)

(58) Field of Classification Search
CPC .............. C07D 471/04; A61K 31/4745; A61K 31/7105; A61K 38/465
USPC ........................................................ 546/84
See application file for complete search history.

(56) References Cited

U.S. PATENT DOCUMENTS

| | | | |
|---|---|---|---|
| 5,223,409 | A | 6/1993 | Ladner et al. |
| 5,686,281 | A | 11/1997 | Roberts |
| 5,843,728 | A | 12/1998 | Seed et al. |
| 5,851,828 | A | 12/1998 | Seed et al. |
| 5,858,358 | A | 1/1999 | June et al. |
| 5,883,223 | A | 3/1999 | Gray |
| 5,906,936 | A | 5/1999 | Eshhar et al. |
| 5,912,170 | A | 6/1999 | Seed et al. |
| 5,912,172 | A | 6/1999 | Eshhar et al. |
| 6,004,811 | A | 12/1999 | Seed et al. |
| 6,284,240 | B1 | 9/2001 | Seed et al. |
| 6,352,694 | B1 | 3/2002 | June et al. |
| 6,392,013 | B1 | 5/2002 | Seed et al. |
| 6,410,014 | B1 | 6/2002 | Seed et al. |
| 6,489,458 | B2 | 12/2002 | Hackett et al. |
| 6,534,055 | B1 | 3/2003 | June et al. |
| 6,753,162 | B1 | 6/2004 | Seed et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,144,575 | B2 | 12/2006 | June et al. |
| 7,148,203 | B2 | 12/2006 | Hackett et al. |
| 7,160,682 | B2 | 1/2007 | Hackett et al. |
| 7,175,843 | B2 | 2/2007 | June et al. |
| 7,232,566 | B2 | 6/2007 | June et al. |
| 7,572,631 | B2 | 8/2009 | Berenson et al. |
| 7,741,465 | B1 | 6/2010 | Eshhar et al. |

(Continued)

FOREIGN PATENT DOCUMENTS

| | | |
|---|---|---|
| CN | 104004782 A | 8/2014 |
| WO | 92/15322 A1 | 9/1992 |

(Continued)

OTHER PUBLICATIONS

Gerard et al. ACS Combinatorial Science (2012), 14(11), 621-630.*

(Continued)

*Primary Examiner* — Kahsay Habte
(74) *Attorney, Agent, or Firm* — F. Brent Nix, Esq.; Johnson, Marcou, Isaacs & Nix, LLC; Jerrin Kuriakose

(57) ABSTRACT

Compositions and methods for inhibiting the activity of RNA-guided endonucleases, and methods for identifying such compositions are included. Methods of treatment using the inhibitory compounds, formulations and methods are also detailed, as well as control of nucleic acid editing systems and methods using said compounds.

23 Claims, 51 Drawing Sheets

Specification includes a Sequence Listing.

(56) References Cited

U.S. PATENT DOCUMENTS

| | | |
|---|---|---|
| 7,985,739 B2 | 7/2011 | Kay et al. |
| 8,088,379 B2 | 1/2012 | Robbins et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,697,854 B2 | 4/2014 | Schendel et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 2012/0252699 A1 | 10/2012 | Jaffrey et al. |
| 2013/0071414 A1 | 3/2013 | Dotti et al. |
| 2014/0220560 A1 | 8/2014 | Jaffrey et al. |
| 2015/0356239 A1 | 12/2015 | Zhang et al. |

FOREIGN PATENT DOCUMENTS

| | | |
|---|---|---|
| WO | 03/020763 | 5/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2008/064289 A2 | 5/2008 |
| WO | 2010/096488 A1 | 8/2010 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/059173 A2 | 4/2014 |
| WO | 2014/066505 A1 | 5/2014 |
| WO | 2014/083173 A1 | 6/2014 |
| WO | 2014/093622 A2 | 6/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2015/002755 A2 | 1/2015 |
| WO | 2015/105928 A1 | 7/2015 |
| WO | 2015/109752 A1 | 7/2015 |
| WO | 2015/138855 A1 | 9/2015 |
| WO | 2016/011210 A2 | 1/2016 |
| WO | 2017/011804 A1 | 1/2017 |
| WO | 2018085288 A1 | 5/2018 |
| WO | 2019/071048 A1 | 4/2019 |
| WO | 2019/084063 A1 | 5/2019 |
| WO | 2019/126709 A1 | 6/2019 |
| WO | 2019/126716 A1 | 6/2019 |
| WO | 2019/126762 A2 | 6/2019 |
| WO | 2019/126774 A1 | 6/2019 |
| WO | 2020/068304 A2 | 4/2020 |

OTHER PUBLICATIONS

"International Search Report and Written Opinion for PCT/US2019/047364", issued by The European Patent Office (EPO), as International Searching Authority on Aug. 3, 2020.

Gerard, et al., "Application of a Catalytic Asymmetric Povarov Reaction using Chiral Ureas to the Synthesis of a Tetrahydroquinoline Library", ACS Combinatorial Science, vol. 14, No. 11, pp. 621-630, Nov. 12, 2012.

Gerard, et al., "Supporting Information Application of a Catalytic Asymmetric Povarov Reaction using Chiral Ureas to the Synthesis of a Tetrahydroquinoline Library", ACS Combinatorial Science, vol. 14, No. 11, pp. S1-S85, Oct. 22, 2012.

Duvall, et al., "Novel diversity-oriented synthesis-derived respiratory syncytial virus inhibitors identified via a high throughput replicon-based screen", Antiviral Research, Elsevier, vol. 131, pp. 19-25, Apr. 6, 2016.

The Broad Institute, Inc., International Preliminary Report on Patentability received for PCT Application Serial No. PCT/US2019/047364 dated Mar. 4, 2021, 8 pages.

Carell, et al., "A Solution-Phase Screening Procedure for the Isolation of Active Compounds from a Library of Molecules", Angewandte Chemie International Edition England, vol. 33, No. 20, 1994, all enclosed pages cited.

Carell, et al., "A Novel Procedure for the Synthesis of Libraries Containing Small Organic Molecules", Angewandte Chemie International Edition England, vol. 33, No. 20, 1994, 2061-2064.

Cho, et al., "An Unnatural Biopolymer", Science, vol. 261, 1993, 1303-1305.

Comer, et al., "Diversity-Oriented Synthesis-Facilitated Medicinal Chemistry: Toward the Development of Novel Antimalarial Agents", Journal of Medicinal Chemistry, vol. 57, Sep. 11, 2014, 8496-8502.

Comer, et al., "Fragment-Based Domain Shuffling Approach for the Synthesis of Pyran-Based Macrocycles", PNAS, vol. 108, No. 17, Apr. 26, 2011, 6751-6756.

Comer, et al., "Utilizing Diversity-oriented Synthesis in Antimicrobial Drug Discovery", Future Medicinal Chemistry, vol. 6, No. 17, 2014, 1927-1942.

Cull, et al., "Screening for Receptor Ligands Using Large Libraries of Peptides Linked to the C Terminus of the Lac Repressor", The Proceedings of the National Academy of Sciences USA, Mar. 1992, 1865-1869.

Cwirla, et al., "Peptides on Phage: a Vast Library of Peptides for Identifying Ligands", The Proceedings of the National Academy of Sciences USA, vol. 87, Aug. 1990, 6378-6382.

Dandapani, et al., "Grand Challenge Commentary: Accessing New Chemical Space for 'undruggable' Targets", Nature Chemical Biology, vol. 6, Dec. 2010, 861-863.

Dandapani, et al., "Hits, Leads and Drugs Against Malaria Through Diversity-oriented Synthesis", Future Medicinal Chemistry, vol. 4, 2012, 2279-2294.

Davis, et al., "Small Molecule-Triggered Cas9 Protein with Improved Genome-Editing Specificity", Nature Chemical Biology, vol. 11, No. 5, May 2015, 9 pages.

Devlin, et al., "Random Peptide Libraries: a Source of Specific Protein Binding Molecules", Science, vol. 249, No. 4967, 1990, 404-406.

Dewitt, et al., "Diversomers": An Approach to Nonpeptide, Nonoligomeric Chemical Diversity, The Proceedings of the National Academy of Sciences USA, vol. 90, Aug. 1993, 6909-6913.

Erb, et al., "Recursive Deconvolution Of Combinatorial Chemical Libraries", The Proceedings of the National Academy of Sciences USA, vol. 91, Nov. 1994, 11422-11426.

Felici, et al., "Selection of Antibody Ligands From a Large Library of Oligopeptides Expressed on a Multivalent Exposition Vector", Journal of Molecular Biology, vol. 222, 1991, 301-310.

Fodor, et al., "Multiplexed Biochemical Assays With Biological Chips", Nature, vol. 364, Aug. 5, 1993, 555-556.

Gallop, et al., "Applications of Combinatorial Technologies to Drug Discovery. 1. Background and Peptide Combinatorial Libraries", Journal of Medicinal Chemistry, vol. 37, No. 9, Apr. 29, 1994, 1233-1251.

Gonzalez, et al., "An Icrispr Platform for Rapid, Multiplexable and Inducible Genome Editing in Human Pluripotent Stem Cells", Cell Stem Cell, vol. 15, No. 2, Aug. 7, 2014, 215-226.

Houghten, et al., "The Use of Synthetic Peptide Combinatorial Libraries for the Identification of Bioactive Peptides", BioTechniques, vol. 13, No. 3, 1992, 10 pages.

Kato, et al., "Diversity-oriented systhesis yields novel multistage antimalarial inhibitors", Nature, vol. 538, No. 7625, XP055645378, ISSN: 0028-0836, DOI 10.1038/nature19804, Sep. 7, 2016, 344-349.

(56) References Cited

OTHER PUBLICATIONS

Lam, et al., "A New Type of Synthetic Peptide Library for Identifying Ligand-binding Activity", Nature, vol. 354, Nov. 7, 1991, 82-84.

Lowe, et al., "Synthesis and Profiling of a Diverse Collection of Azetidine-Based Scaffolds for the Development of CNS-Focused Lead-Like Libraries", The Journal of Organic Chemistry, vol. 77, No. 17, Sep. 7, 2012, 58 pages.

Maji, et al., "Multidimensional Chemical Control of CRISPR-Cas9", Nature Chemical Biology, vol. 13, No. 1, Jan. 2017, 11 pages.

Marcaurelle, et al., "An Aldol-Based Build/Couple/Pair Strategy for the Synthesis of Medium- and Large-Sized Rings: Discovery of Macrocyclic Histone Deacetylase Inhibitors", Journal of the American Chemical Society, vol. 132, No. 47, Dec. 1, 2010, 35 pages.

Marcaurelle, et al., "Application of Natural Product-inspired Diversity-oriented Synthesis to Drug Discovery", Progress in Drug Research, vol. 66, 2008, 189-216.

Nunez, et al., "Chemical and Biophysical Modulation of Cas9 for Tunable Genome Engineering", ACS Chemical Biology, vol. 11, Issue 3, Feb. 9, 2016, 8 pages.

Schreiber, et al., "Target-Oriented and Diversity-Oriented Organic Synthesis in Drug Discovery", Science, vol. 287, Mar. 17, 2000, 1964-1969.

Schreiber, et al., "Towards Patient-Based Cancer Therapeutics", Nature Biotechnology, vol. 28, No. 9, Sep. 2010, 904-906.

Scott, et al., "Searching for Peptide Ligands With an Epitope Library", Science, vol. 249, No. 4967, Jul. 27, 1990, 386-390.

Senis, et al., "CRISPR/Cas9-Mediated Genome Engineering: An Adeno-Associated Viral (AAV) Vector Toolbox", Biotechnology Journal, vol. 9, No. 11, Nov. 2014, 32 pages.

Shin, et al., "Disabling Cas9 by an Anti-CRISPR DNA Mimic", Science Advances, vol. 3, No. e1701620, Jul. 12, 2017, 1-9.

Tan, et al., "Indium-Mediated Asymmetric Allylation of Acylhydrazones using a Chiral Urea Catalyst", Angewandte Chemie International Edition, vol. 46, No. 8, Jan. 9, 2007, 1315-1317.

Wawer, et al., "Toward Performance-diverse Small-molecule Libraries for Cell-based Phenotypic Screening Using Multiplexed High-dimensional Profiling", PNAS, vol. 111, No. 30, Jul. 29, 2014, 10911-10916.

Wright, et al., "Rational Design of a Split-Cas9 Enzyme Complex", Proceedings of the National Academy of Sciences of the United States of America, vol. 112, No. 10, Mar. 10, 2015, 2984-2989.

Xu, et al., "Chiral Sulfinamidourea and Strong Brønsted Acid-cocatalyzed Enantioselective Povarov Reaction to Access Tetrahydroquinolines", Nature Protocols, vol. 9, No. 8, Aug. 2014, 17 pages.

Zetsche, et al., "A Split-Cas9 Architecture for Inducible Genome Editing and Transcription Modulation", Nature Biotechnology, vol. 33, No. 2, Feb. 2015, 139-142.

Zuckermann, et al., "Discovery of Nanomolar Ligands for 7-Transmembrane G-Protein-Coupled Receptors from a Civerse N-(Substituted)Glycine Peptoid Library", Journal of Medicinal Chemistry, vol. 37, 1994, 2678-2685.

\* cited by examiner

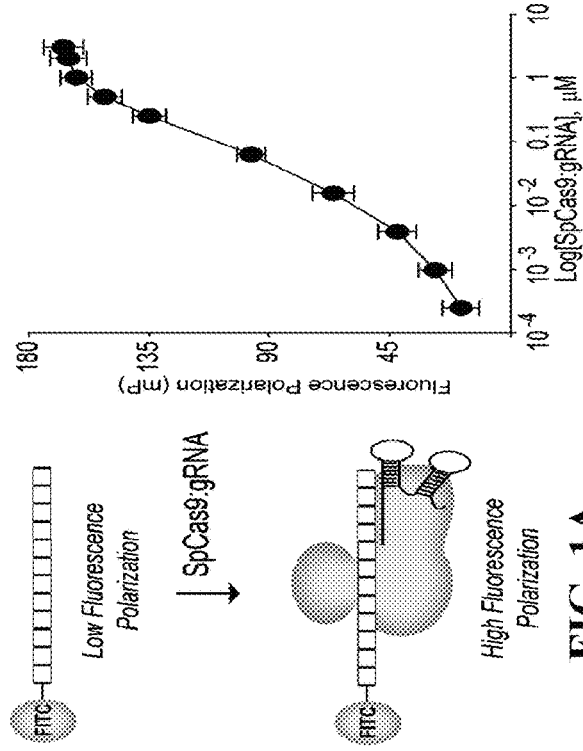

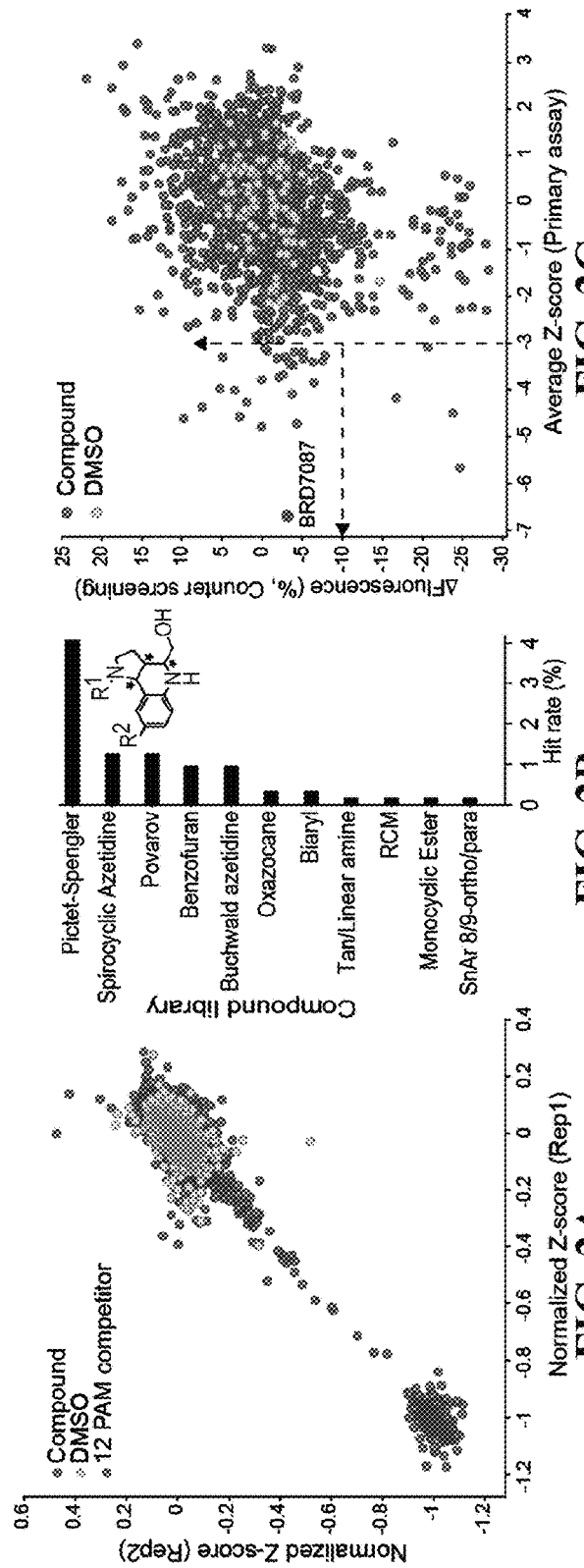
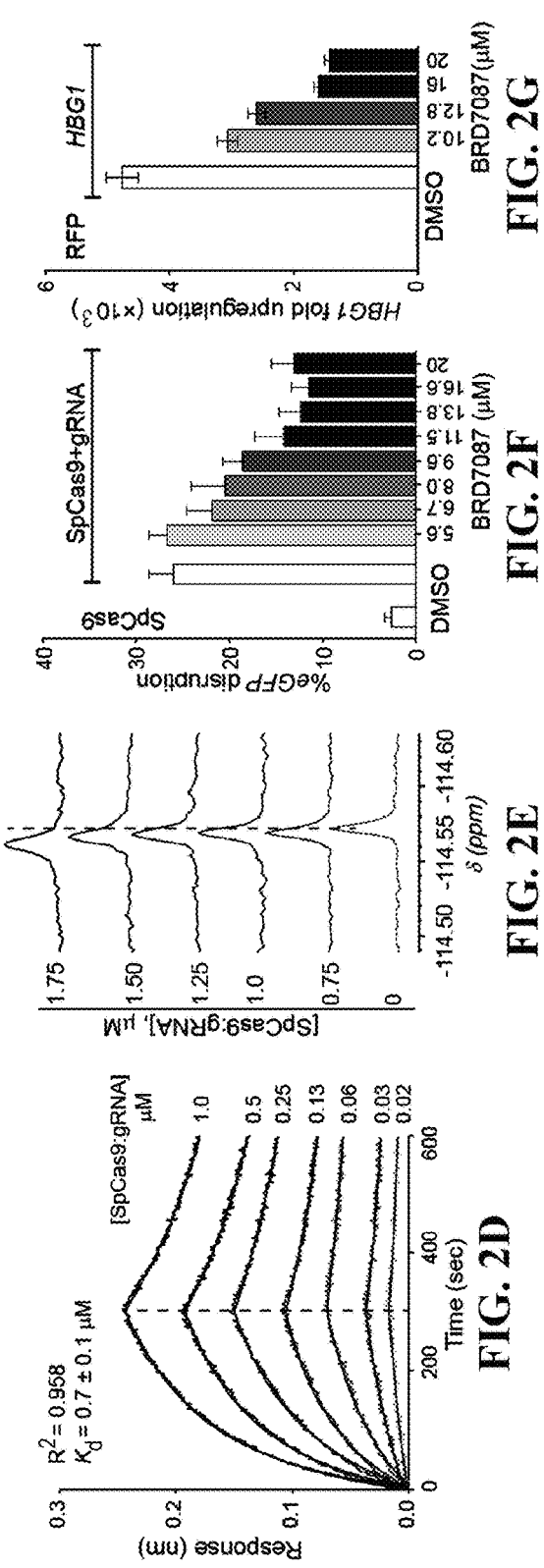

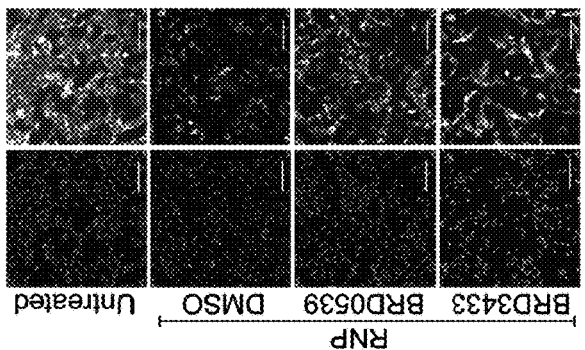
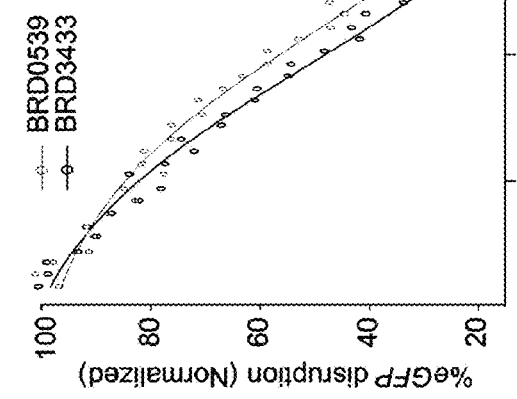
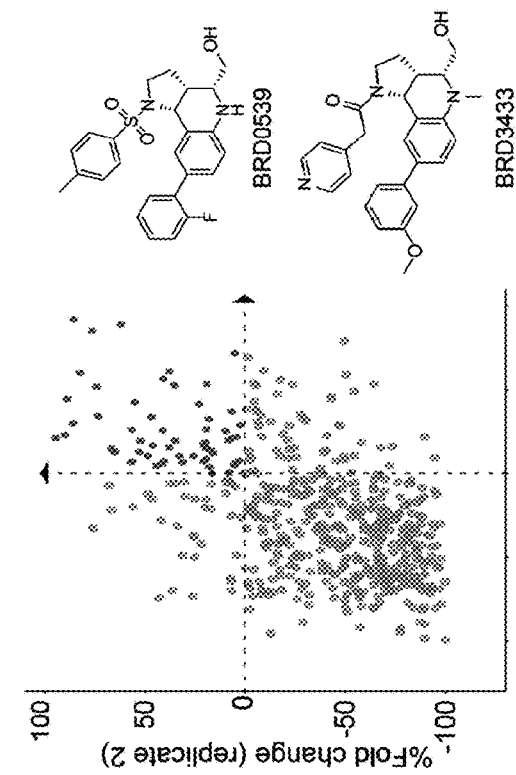
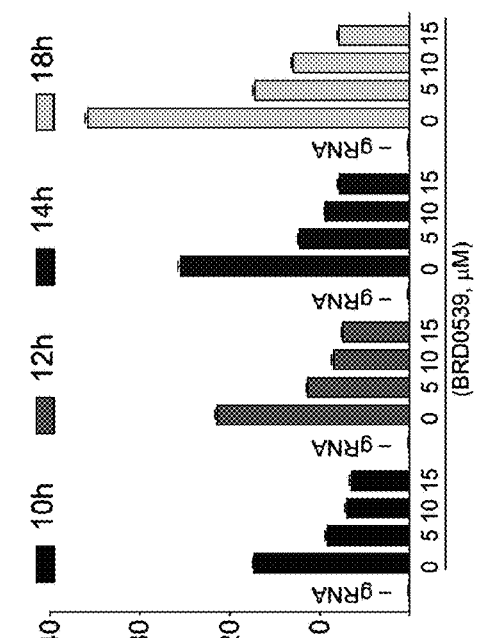
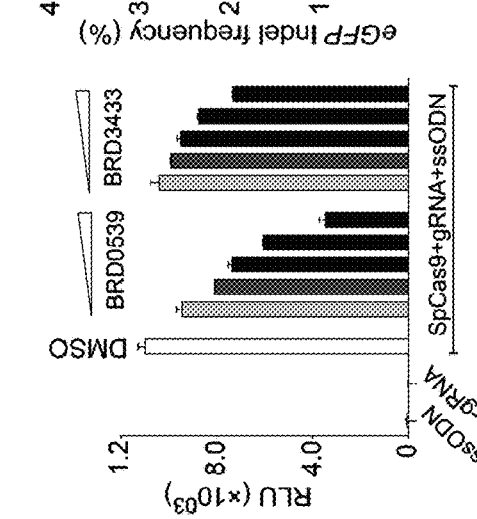
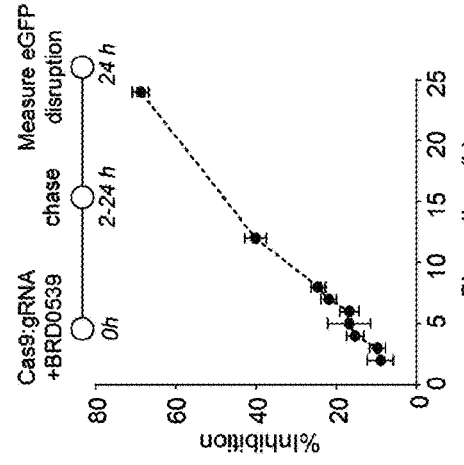

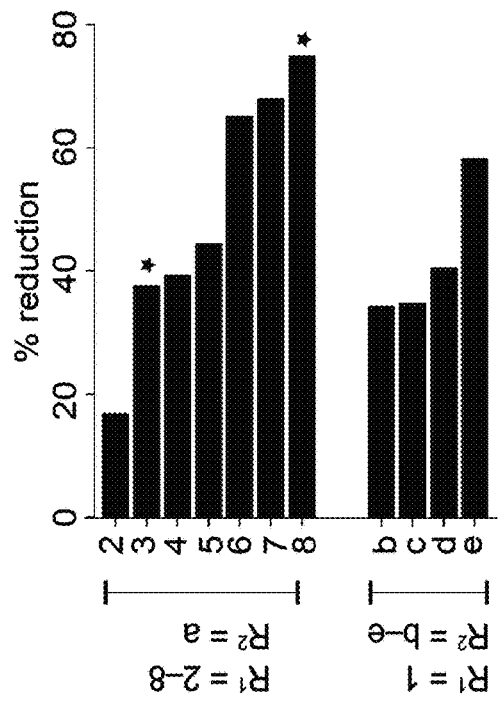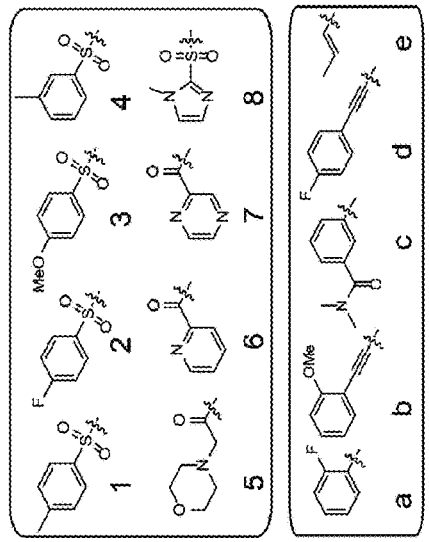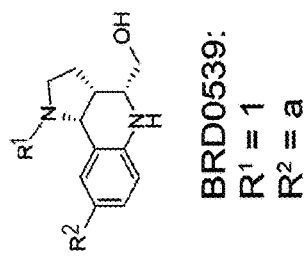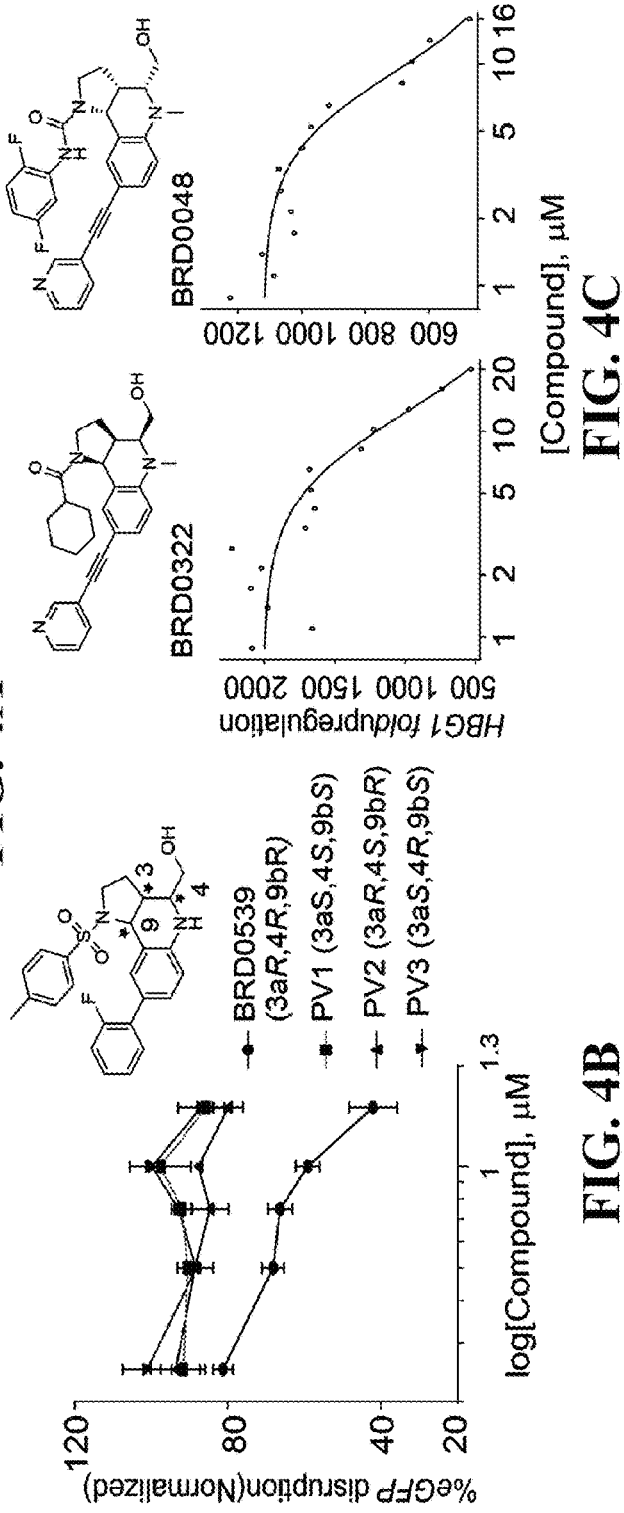
FIG. 4A
FIG. 4B
FIG. 4C

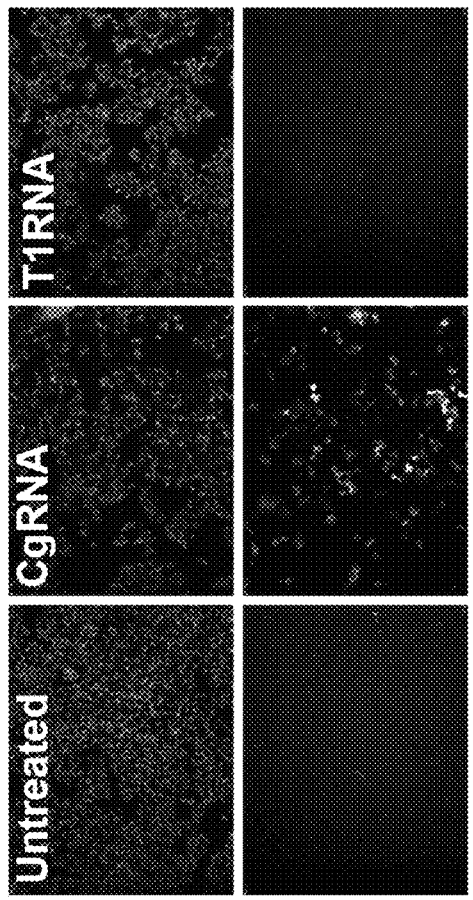
FIG. 5C
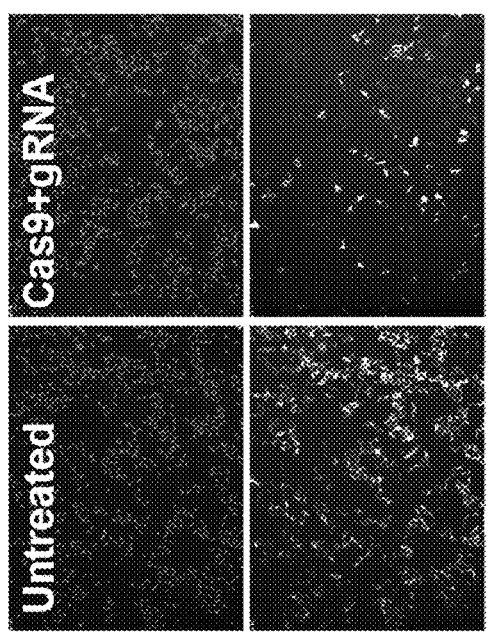
FIG. 5B
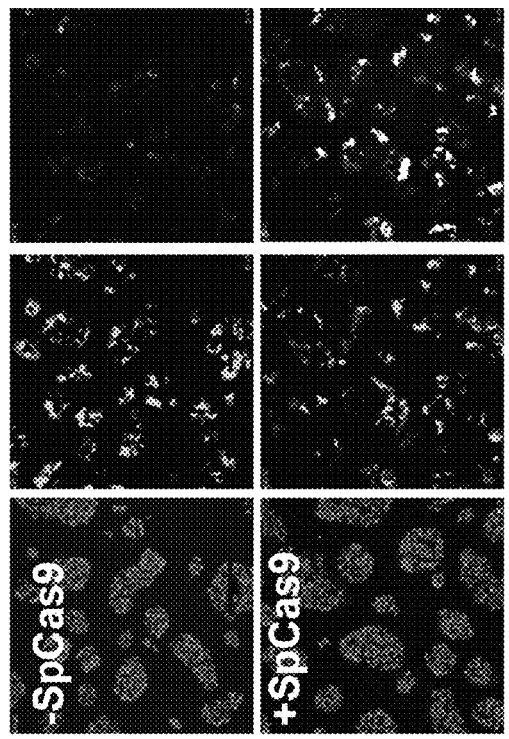
FIG. 5D
| Assay | Z-score | |
|---|---|---|
| | 96-well | 384-well |
| eGFP-disruption | 0.48 | 0.49 |
| mKate2-disruption | 0.37 | 0.36 |
| NHEJ-assay | 0.32 | 0.46 |
FIG. 5E

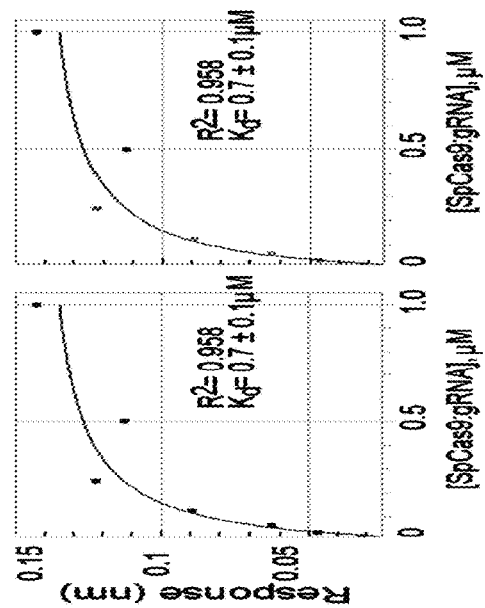
FIG. 6A
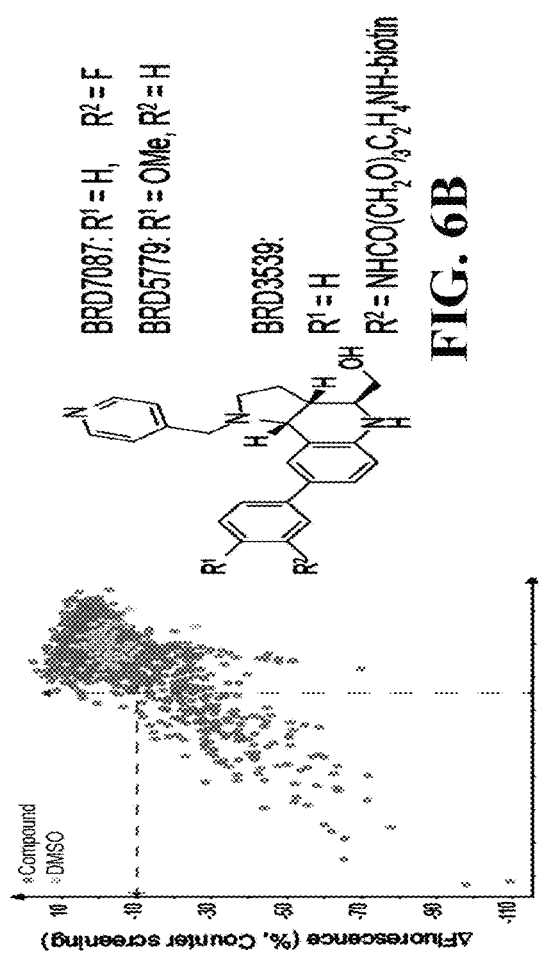
FIG. 6B
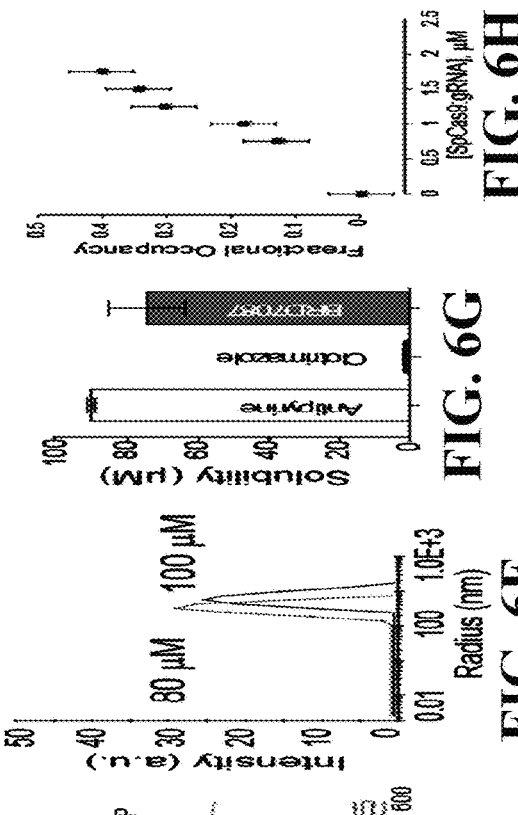
FIG. 6C
FIG. 6D
FIG. 6E
FIG. 6F
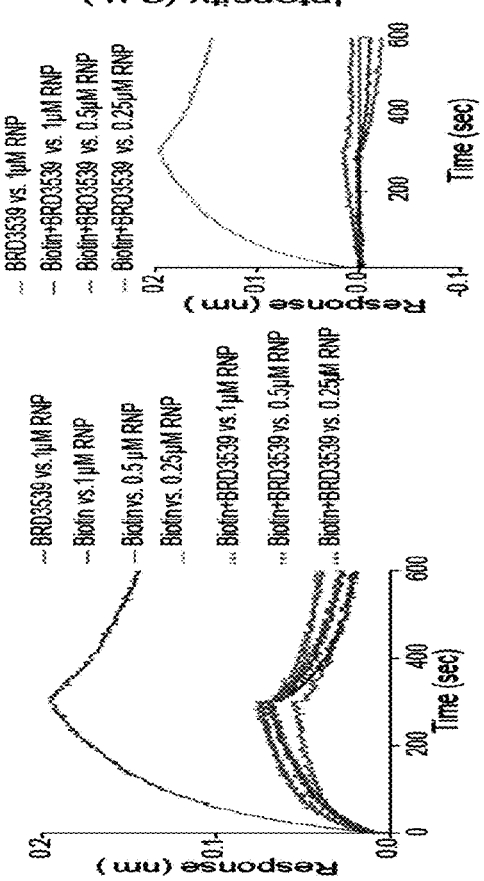
FIG. 6G
FIG. 6H

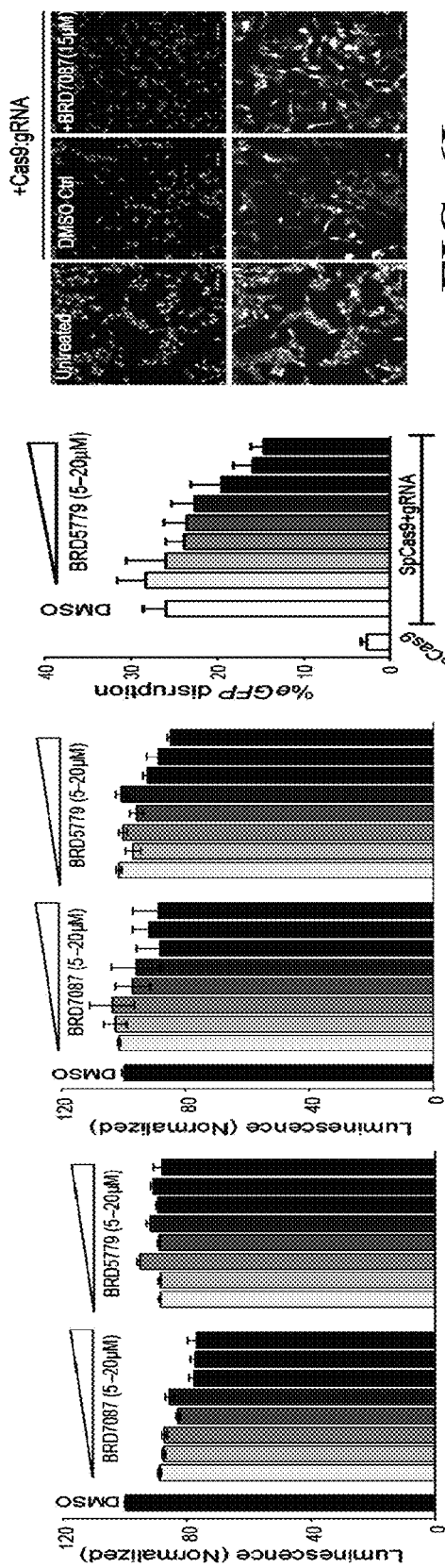
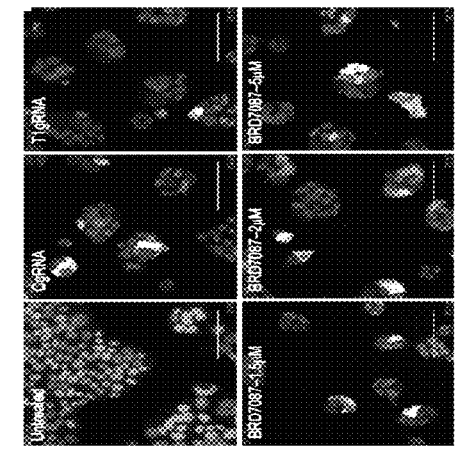
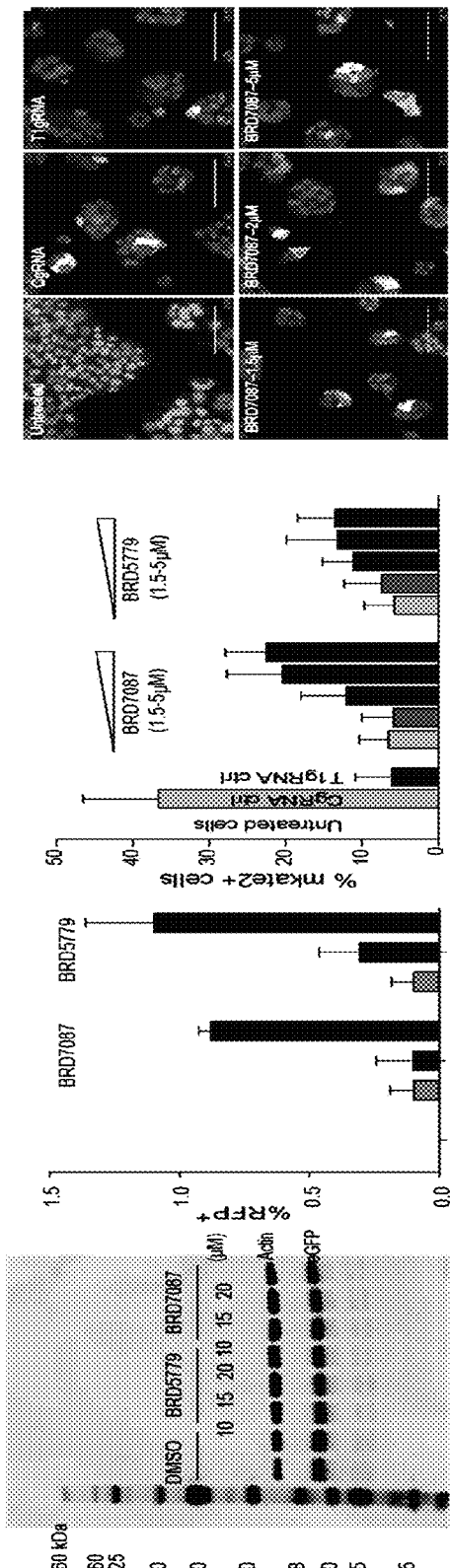
FIG. 6I  FIG. 6J  FIG. 6K  FIG. 6L
FIG. 6M  FIG. 6N  FIG. 6O  FIG. 6P

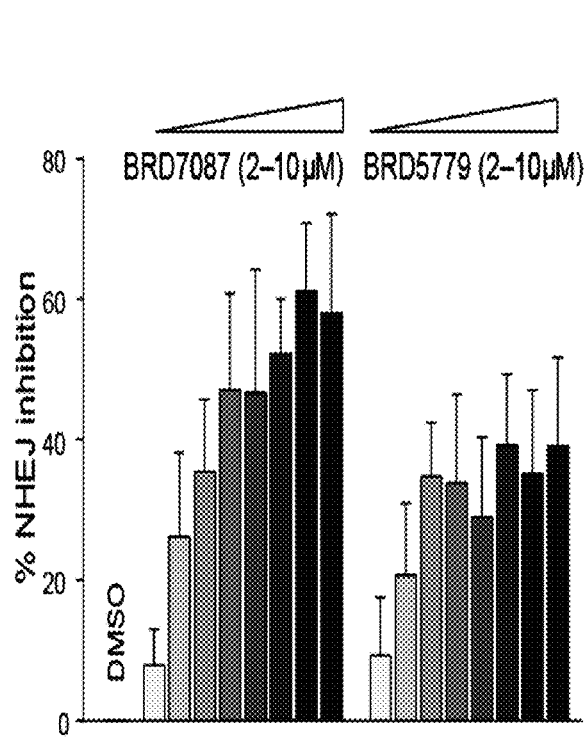
FIG. 6Q
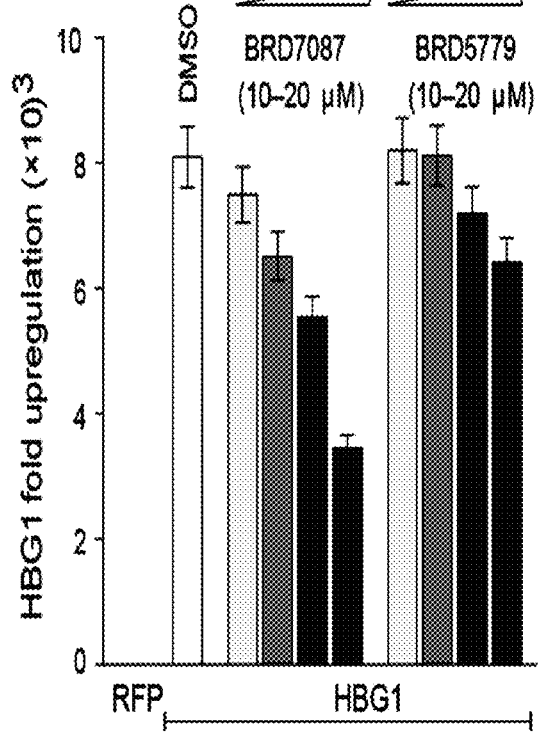
FIG. 6R
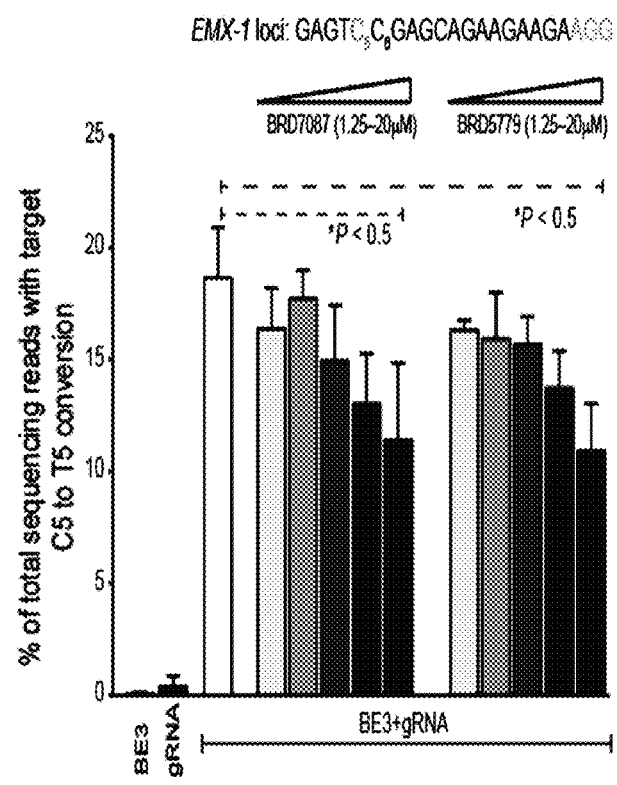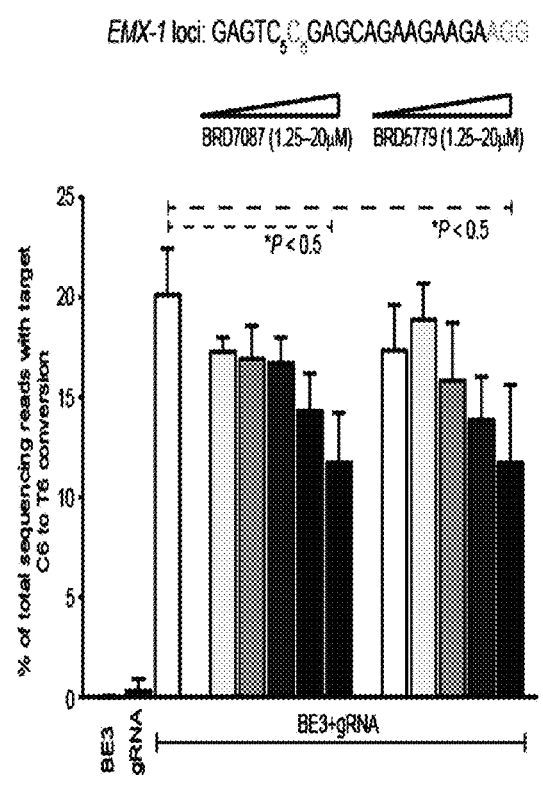
FIG. 6S

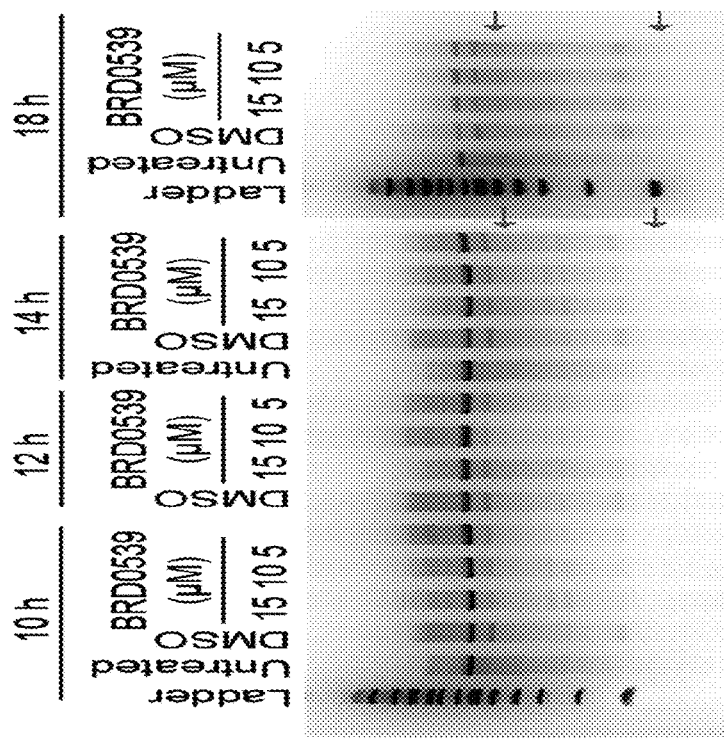
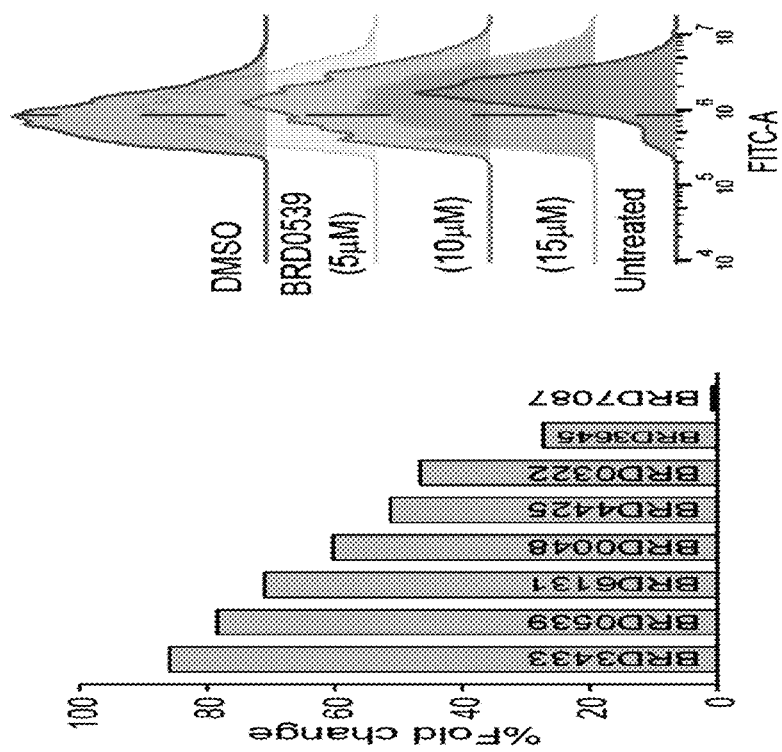
FIG. 7A  FIG. 7B  FIG. 7C

FIG. 10D
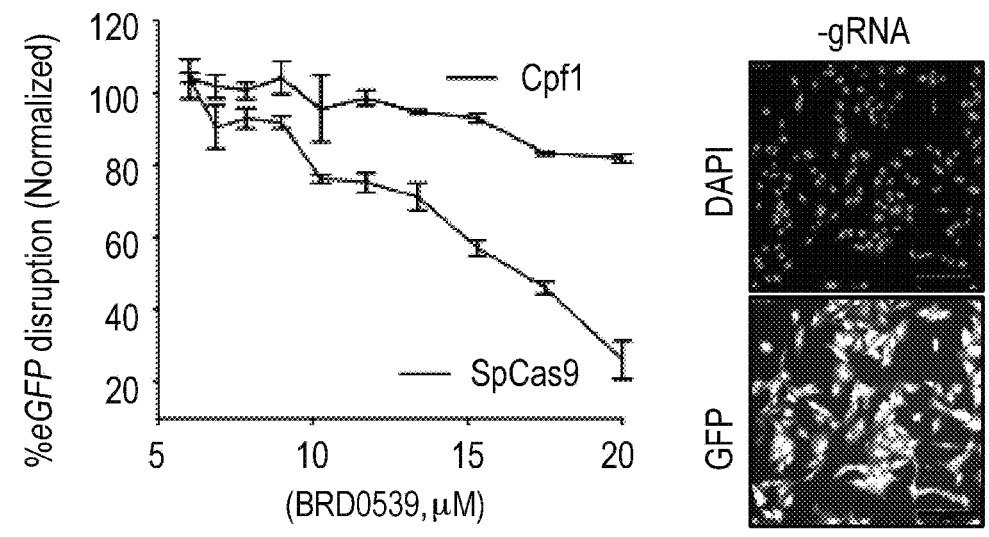
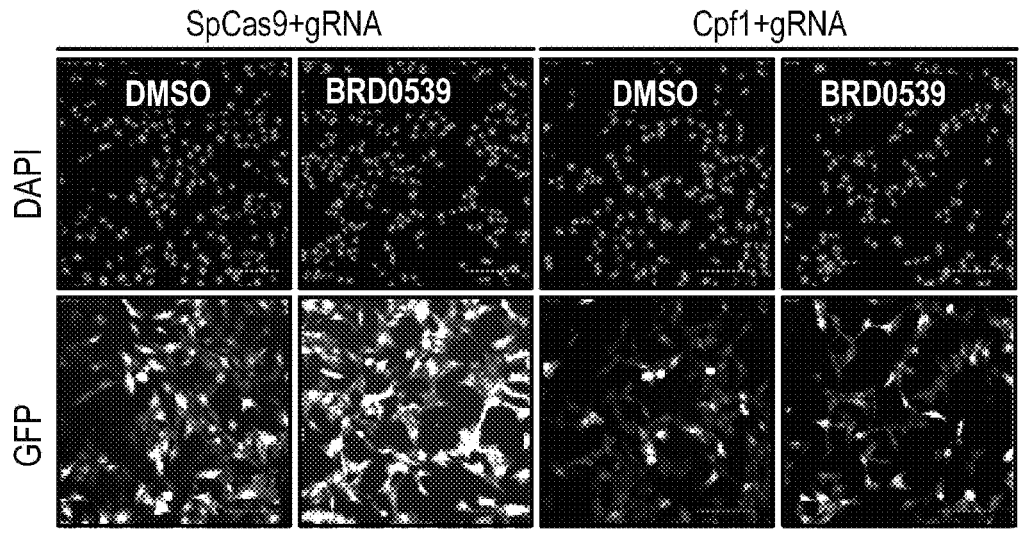
FIG. 10E

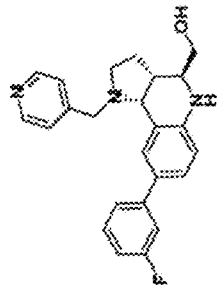
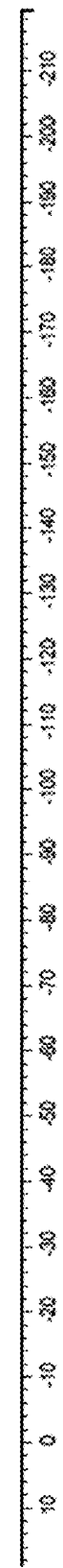
FIG. 13

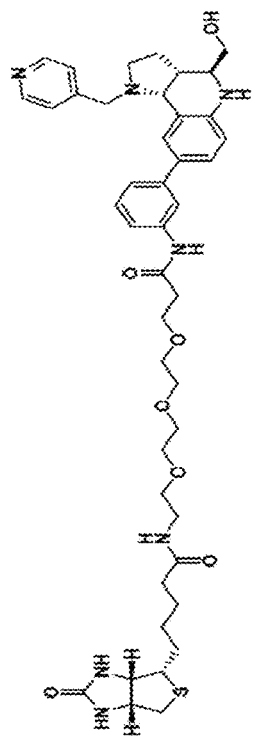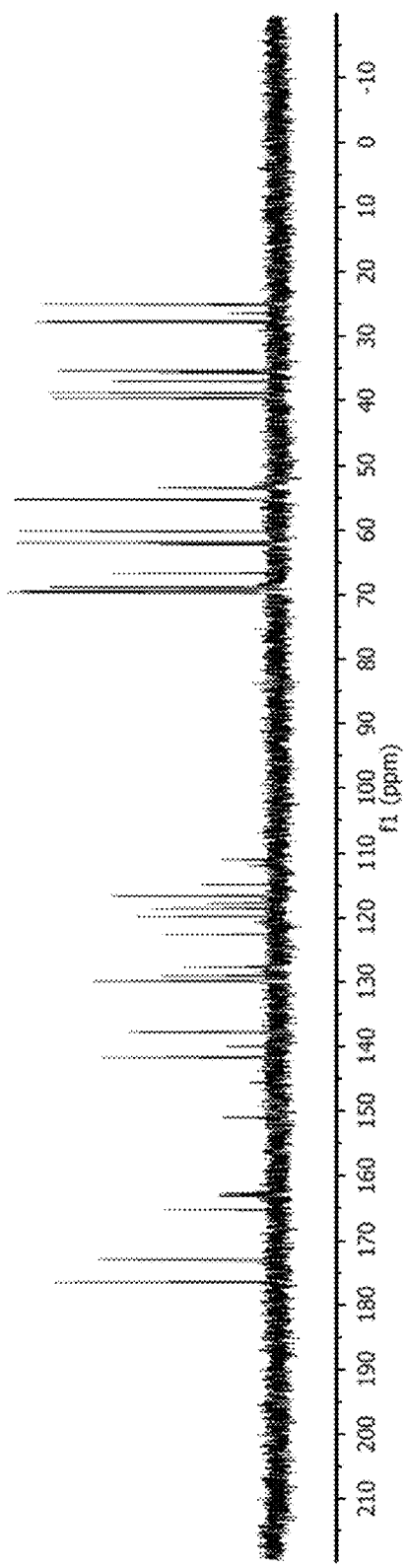
FIG. 17

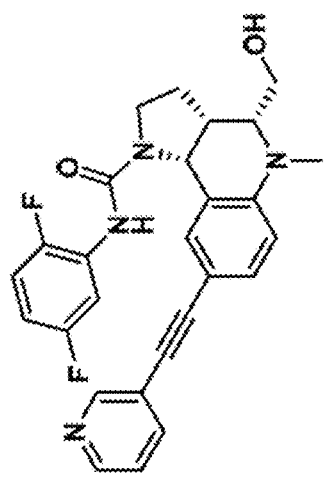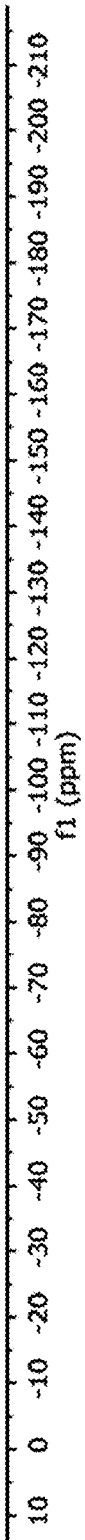
FIG. 31

```
                              SEQUENCE LISTING

<160> NUMBER OF SEQ ID NOS: 43

<210> SEQ ID NO 1
    <211> LENGTH: 106
    <212> TYPE: RNA
    <213> ORGANISM: Artificial Sequence
    <220> FEATURE:
    <223> OTHER INFORMATION: Synthetic Oligonucleotide

<400> SEQUENCE: 1
gggagacgca acugaaugaa auggugaagg acgggccag guguggcugc uucggcagug       60
cagcuuguug aguagagugu gagcuccgcg uaacuagucg cgucac                    106

<210> SEQ ID NO 2
    <211> LENGTH: 100
    <212> TYPE: RNA
    <213> ORGANISM: Artificial Sequence
    <220> FEATURE:
    <223> OTHER INFORMATION: Synthetic Oligonucleotide

<400> SEQUENCE: 2
gcuauaggac gcgaccgaaa guuuuagagc uagaaauagc aaguuaaaau aaggcuaguc       60
cguuaucaac uugaaaaagu ggcaccgagu cggugcuuuu                           100

<210> SEQ ID NO 3
    <211> LENGTH: 58
    <212> TYPE: DNA
    <213> ORGANISM: Artificial Sequence
    <220> FEATURE:
    <223> OTHER INFORMATION: Synthetic Oligonucleotide
    <220> FEATURE:
    <221> NAME/KEY: misc_feature
    <222> LOCATION: (58)..(58)
    <223> OTHER INFORMATION: 3' 36-FAM modification

<400> SEQUENCE: 3
agctgcataa cgcgaaaaaa tatatttatc tgcttgatct tcaaatgttg tattgttt        58

<210> SEQ ID NO 4
    <211> LENGTH: 58
    <212> TYPE: DNA
    <213> ORGANISM: Artificial Sequence
    <220> FEATURE:
    <223> OTHER INFORMATION: Synthetic Oligonucleotide

<400> SEQUENCE: 4
aaacaataca acatttgaag atcaagcaga taaatatatt ttttcgcgtt atgcagct        58

<210> SEQ ID NO 5
    <211> LENGTH: 58
    <212> TYPE: DNA
    <213> ORGANISM: Artificial Sequence
    <220> FEATURE:
    <223> OTHER INFORMATION: Synthetic Oligonucleotide
    <220> FEATURE:
    <221> NAME/KEY: misc_feature
    <222> LOCATION: (58)..(58)
    <223> OTHER INFORMATION: 3' 36-FAM modification
```

-continued

<400> SEQUENCE: 5
agctgcataa cgcgaaaaaa tatatttatc tggttgatct ccaaatgttg tattgttt        58

<210> SEQ ID NO 6
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 6
aaacaataca acatttggag atcaaccaga taaatatatt ttttcgcgtt atgcagct        58

<210> SEQ ID NO 7
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (58)..(58)
<223> OTHER INFORMATION: 3' 36-FAM modification

<400> SEQUENCE: 7
agctgcataa cgcgggaaaa tccatttatc tgcttgatct tcggatgttc cattgttt        58

<210> SEQ ID NO 8
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 8
aaacaatgga acatccgaag atcaagcaga taaatggatt ttcccgcgtt atgcagct        58

<210> SEQ ID NO 9
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (58)..(58)
<223> OTHER INFORMATION: 3' 36-FAM modification

<400> SEQUENCE: 9
ggctgcacca cgcgggaaaa tccatttagg tgcttcctct tcggatgttc cattgttt        58

<210> SEQ ID NO 10
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 10
aaacaatgga acatccgaag aggaagcacc taaatggatt ttcccgcgtg gtgcagcc        58

<210> SEQ ID NO 11
<211> LENGTH: 58
<212> TYPE: DNA
<213> ORGANISM: Artificial Sequence
<220> FEATURE:

<223> OTHER INFORMATION: Synthetic Oligonucleotide
<220> FEATURE:
<221> NAME/KEY: misc_feature
<222> LOCATION: (58)..(58)
<223> OTHER INFORMATION: 3' 36-FAM modification

<400> SEQUENCE: 11
ggctggacca cgcgggaaaa tccacctagg tggttcctct tcggatgttc catccttt    58

<210> SEQ ID NO 12
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 12
aaaggatgga acatccgaag aggaaccacc taggtggatt ttcccgcgtg gtccagcc    58

<210> SEQ ID NO 13
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 13
agctgcataa cgcgaaaaaa tatatttatc tgcttgatct tcaaatgttg tattgttt    58

<210> SEQ ID NO 14
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 14
aaacaataca acatttgaag atcaagcaga taaatatatt ttttcgcgtt atgcagct    58

<210> SEQ ID NO 15
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 15
agctgcataa cgcgaaaaaa tatatttatc tggttgatct ccaaatgttg tattgttt    58

<210> SEQ ID NO 16
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 16
aaacaataca acatttggag atcaaccaga taaatatatt ttttcgcgtt atgcagct    58

<210> SEQ ID NO 17
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 17

```
agctgcataa cgcgggaaaa tccatttatc tgcttgatct tcggatgttc cattgttt      58
```

<210> SEQ ID NO 18
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 18

```
aaacaatgga acatccgaag atcaagcaga taaatggatt ttcccgcgtt atgcagct      58
```

<210> SEQ ID NO 19
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 19

```
ggctgcacca cgcgggaaaa tccatttagg tgcttcctct tcggatgttc cattgttt      58
```

<210> SEQ ID NO 20
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 20

```
aaacaatgga acatccgaag aggaagcacc taaatggatt ttcccgcgtg gtgcagcc      58
```

<210> SEQ ID NO 21
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 21

```
ggctggacca cgcgggaaaa tccacctagg tggttcctct tcggatgttc catccttt      58
```

<210> SEQ ID NO 22
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 22

```
aaaggatgga acatccgaag aggaaccacc taggtggatt ttcccgcgtg gtccagcc      58
```

<210> SEQ ID NO 23
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 23

```
caatacaaca tttgaagatc aagcagataa atatattttt tcgcgttatg cagct         55
```

<210> SEQ ID NO 24
<211> LENGTH: 55
<212> TYPE: DNA

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' biotin modification

<400> SEQUENCE: 24
agctgcataa cgcgaaaaaa tatatttatc tggttgatct ccaaatgttg tattg      55

<210> SEQ ID NO 25
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 25
caatacaaca tttggagatc aaccagataa atatatttt tcgcgttatg cagct       55

<210> SEQ ID NO 26
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' biotin modification

<400> SEQUENCE: 26
agctgcataa cgcgggaaaa tccatttatc tgcttgatct tcggatgttc cattg      55

<210> SEQ ID NO 27
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 27
caatggaaca tccgaagatc aagcagataa atggattttc ccgcgttatg cagct      55

<210> SEQ ID NO 28
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' biotin modification

<400> SEQUENCE: 28
aaacaatgga acatccgaag aggaagcacc taaatggatt ttcccgcgtg gtgcagcc   58

<210> SEQ ID NO 29
<211> LENGTH: 58
<212> TYPE: DNA
<213> ORGANISM: Artificial Sequence
<220> FEATURE:
<223> OTHER INFORMATION: Synthetic Oligonucleotide

<400> SEQUENCE: 29
ggctgcacca cgcgggaaaa tccatttagg tgcttcctct tcggatgttc cattgttt   58
```

```
<210> SEQ ID NO 30
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 30
gaggagctgt tcaccggg                                                      18

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31
gcatggacga gctgtacaag                                                    20

<210> SEQ ID NO 32
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (34)..(37)
<223> OTHER INFORMATION: n is a, c, g, or t

<400> SEQUENCE: 32
acactctttc cctacacgac gctcttccga tctnnnnacg taaacggcca caagttc          57

<210> SEQ ID NO 33
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 33
tggagttcag acgtgtgctc ttccgatctg tcgtccttga agaagatggt g                51

<210> SEQ ID NO 34
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 34
taatacgact cactataggg agtccgagca gaagaagaag ttttagagct agaaatagca       60

<210> SEQ ID NO 35
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 35
aaaaaaagca ccgactcggt gccac                                              25

<210> SEQ ID NO 36
```

```
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 36
aaaagcaccg actcggtgcc acttttcaa gttgataacg gactagcctt attttaactt      60
gctatttcta gctctaaaac                                                  80

<210> SEQ ID NO 37
<211> LENGTH: 54
<212> TYPE: DNA
<213> ORGANISM: Artificial Sequence
<220> FEATURE:
<223> OTHER INFORMATION: Synthetic Oligonucleotide

<400> SEQUENCE: 37
taatacgact cactatagct ataggacgcg accgaaagtt ttagagctag aaat            54

<210> SEQ ID NO 38
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 38
caccgggcaa ggctggccaa cccat                                            25

<210> SEQ ID NO 39
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 39
aaacatgggt tggccagcct tgcc                                             24

<210> SEQ ID NO 40
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 40
caccggtcca ggggtcttac tcct                                             24

<210> SEQ ID NO 41
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 41
aaacaggagt aagacccctg gacc                                             24

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 42
gaggagctgt tcaccggg                                         18

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
cttgtacagc tcgtccatgc                                       20
```

INHIBITORS OF RNA-GUIDED NUCLEASE TARGET BINDING AND USES THEREOF

CROSS-REFERENCE TO RELATED APPLICATIONS

This application is a U.S. National Stage of International Application No. PCT/US2019/047364, filed Aug. 20, 2019, which claims the benefit of U.S. Provisional Application No. 62/765,357, filed Aug. 20, 2018, U.S. Provisional Application No. 62/774,012, filed Nov. 30, 2018, U.S. Provisional Application No. 62/784,268, filed Dec. 21, 2018, and U.S. Provisional Application No. 62/831,143, filed Apr. 8, 2019. The entire contents of the above-identified applications are hereby fully incorporated herein by reference.

STATEMENT REGARDING FEDERALLY SPONSORED RESEARCH

This invention was made with government support under Grant No. AI126239 awarded by the National Institutes of Health, N66001-17-2-4055 awarded by the Defense Advanced Research Projects Agency, and Grant No. W911NF1610586 awarded by the United States Department of the Army. The government has certain rights in the invention.

REFERENCE TO AN ELECTRONIC SEQUENCE LISTING

The contents of the electronic sequence listing ("BROD-3880WP_ST25.txt"; Size is 10,005 bytes and it was created on Jul. 25, 2019) is herein incorporated by reference in its entirety.

TECHNICAL FIELD

The subject matter disclosed herein is generally directed to compounds modulating the activity of RNA-guided nucleases.

BACKGROUND

The CRISPR (clustered regularly interspaced short palindromic repeat) system is an adaptive immune system used by bacteria and archaea to defend against invading phages or mobile genetic elements. The most studied CRISPR system employs an RNA-guided endonuclease Cas9, which can cleave double-stranded target DNA in multiple cell types.

Cas9 identifies the target sequence by two recognition mechanisms: (i) Watson-Crick base-pairing between the target DNA sequence and guide RNA and (ii) Protospacer Adjacent Motif (PAM) sequence on the target DNA upon target recognition, Cas9 induces double-strand breaks in the target gene, which when repaired by non-homologous end joining (NHEJ) can result in frameshift mutations and gene knockdown. Alternatively, homology-directed repair (HDR) at the double-strand break site can allow insertion of the desired sequence.

Two common variants of Cas9 are SpCas9 and SaCas9, which naturally occur in *Streptococcus pyogenes* and *Staphylococcus aureus*, respectively, and recently another endonuclease called Cpf1 has been reported. The relative ease of targeting Cas9/Cpf1 to specific genomic loci has enabled the development of revolutionary biomedical technologies. For example, catalytically inactive Cas9 (called dCas9), when fused to transcriptional activators, has enabled genome-wide screening of gene targets. Further, by targeting dCas9 to the promoter or exonic sequences, transcriptional repression has been accomplished. In yet another example, a fusion of dCas9 to acetyltransferases has enabled epigenome editing. Imaging of specific genomic loci has been accomplished by fusing dCas9 to GFP.

There are multiple reasons to establish controls on Cas9 activity. First, dosable control of the therapeutic activity is important for effective therapeutic strategies. Second, it is desirable for gene delivery systems that have constitutively active Cas9 to be terminated rapidly following on-target gene-editing. Third, Cas9-based technologies (e.g., transcriptional regulation) would benefit from dosable and temporal control of Cas9 activity.

The rapid ascension of CRISPR-based genome editing technologies has raised serious biosafety and bioterrorism concerns, leading to calls for a moratorium and responsible conduct. In particular, much concern has surrounded CRISPR-based gene drives. In sexual reproduction, the progenies receive two versions of a gene, one from each parent. Gene drives enable replacement of one version of the gene with the other "selfish" version of the gene, thereby converting a heterozygous individual to homozygous individual. In laboratory settings, CRISPR-based gene drives have successfully enabled self-propagation of engineered genes in multiple organisms (e.g., mosquitoes) and complete annihilation of wild-type genes. For example, mosquitoes engineered using gene drives have been generated that can wipe out the entire species by ensuring that every female progeny is infertile. Gene drives can be used to propagate a particular trait in the entire ecosystem, which may find use in the elimination of diseases (e.g., malaria, dengue fever) or invasive species, and reversing pesticide resistance in plants. On the other hand, there also exists the potential for malevolent use of gene drives in entomological and agricultural settings.

Reports of small-molecule controlled Cas9 activity are present in literature and involve fusing Cas9 to small-molecule controlled protein domains. Genetic-fusions of Cas9 to small-molecule controlled degrons (e.g., Wandless' destabilized domains) may allow aforementioned controls, but such fusions to have unacceptably high background activity presumably owing to the large size of Cas9. These systems also do not ensure dosage control-the small molecules act merely as an inducer of Cas9 activity. Further, these "inducer" small molecules cannot control gene drives containing wild-type Cas9/Cpf1. A general approach would be desirable to control all variants of Cas9/Cpf1, including the wild type and engineered versions. The use of "inducible" systems to control gene drives is also questionable given that some "inducer" small molecules are toxic at the organismal level (albeit not at the cellular level, where these systems were developed).

A need exists for compositions and methods for inhibiting one or more activities of RNA-guided nuclease (e.g., Cas9, Cpf1). Such compositions and methods are useful for regulating the activity of RNA guided-nucleases (e.g., in genome editing).

SUMMARY

In some aspects, provide herein include compounds having the structure of Formula (I):

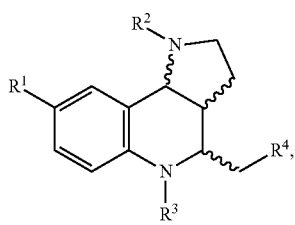

wherein R¹ is independently selected from alkynyl or aryl;

R² is independently selected from -L₁-X or -L₁-R;

R³ is independently selected from hydrogen, —X, —R, -L₂-X, or -L₂-R;

R⁴ is —(CH2)—OH; where

L₁ is independently selected from —CO— or —S(O)₂—;

L₂ is independently selected from —(CH₂)$_n$—, —(CH₂)$_n$—C(O)O—, —(CH₂)$_n$—C(O)—NH—, —C(O)—NH—(CH₂)$_n$—, —(CH₂)$_n$—NH—C(O)—, —(CH₂)$_n$—NH—SO₂—, —NH—SO₂—(CH₂)$_n$—, —(CH₂)$_n$—SO₂—NH—, —(CH₂)$_n$—SO₂—, —(CH₂)$_n$—SO₂—NH—C(O)—, —(CH₂)$_n$—R$^{L2}$—, —R$^{L2}$—C(O)—O—, —R$^{L2}$—NH—C(O)—(CH₂)$_n$—, —R$^{L2}$—NH—S(O)₂—(CH₂)$_n$—, —S—, —S(O)—, or —S(O)₂—, wherein n is independently at each occurrence 0, 1, 2, 3, 4, 5, or 6;

X is independently selected from hydrogen, CN, OH, CF₃, COOH, OR, OR, NR₂, or halogen;

R$^{L2}$ is independently selected from C₁-C₁₂ linear and/or branched and/or cyclic and/or aromatic bivalent radicals; optionally substituted with one or more groups X and/or with 1-6 heteroatoms selected from O, S, N, P, F, Cl, Br, I, or a combination thereof, and R is independently selected from C₁₋₁₂ hydrocarbons, optionally substituted with one or more groups X and/or with 1-10 heteroatoms selected from O, S, N, P, F, Cl, Br, I, or a combination thereof.

In some embodiments, the L₁ is —S(O)₂—. In some embodiments, the R in R² is benzyl.

In some embodiments, the compound has the structure:

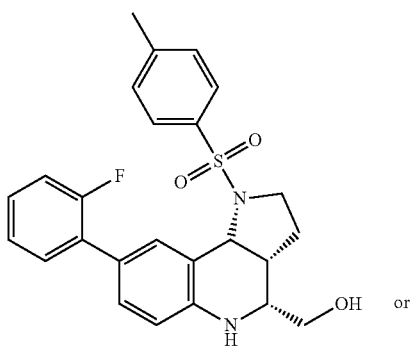 or

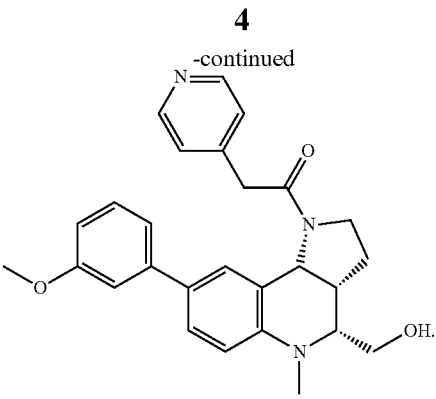

In some embodiments, compound has the structure:

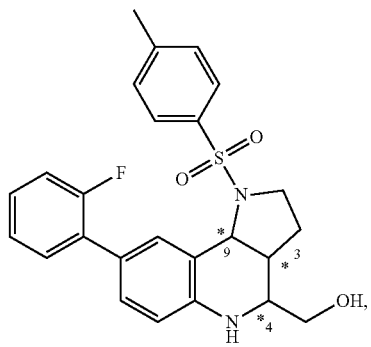 [SMILES: Cc1ccc(S(=O)(=O)N2CCC3C(CO)Nc4ccc(-c5ccccc5F)cc4C32)cc1]

wherein the structure has a stereochemistry of (3aR, 4R, 9bR).

In some embodiments, the compound has the structure:

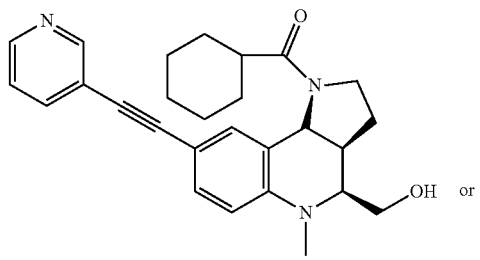 or

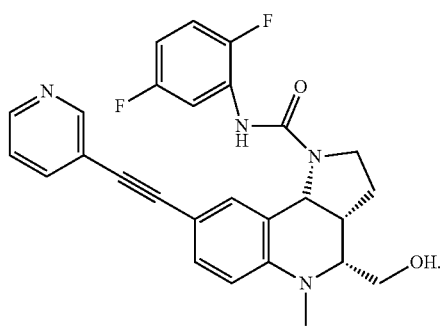

In certain aspects, provide herein include compounds having the structure of Formula (IA), (IB), (IC), or (ID):

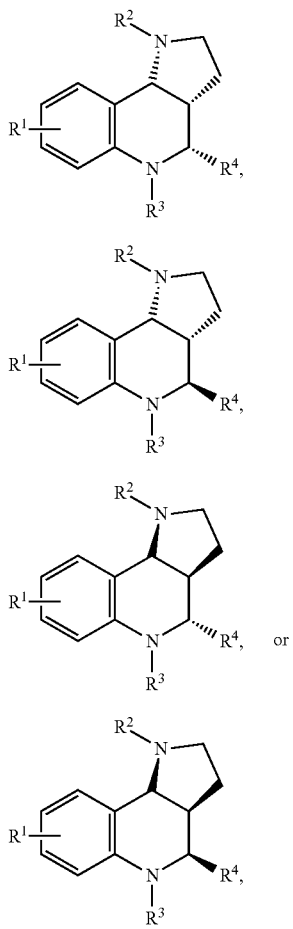

wherein $R^1$ is independently selected from alkynyl or aryl;
$R^2$ is independently selected from -$L_1$-X or -$L_1$-R;
$R^3$ is independently selected from hydrogen, —X, —R, -$L_2$-X, or -$L_2$-R;
$R^4$ is —(CH$_2$)—OH; where
$L_1$ is independently selected from —CO— or —S(O)$_2$—;
$L_2$ is independently selected from —(CH$_2$)$_n$—, —(CH$_2$)$_n$—C(O)O—, —(CH$_2$)$_n$—C(O)—NH—, —C(O)—NH—(CH$_2$)$_n$—, —(CH$_2$)$_n$—NH—C(O)—, —(CH$_2$)$_n$—NH—SO$_2$—, —NH—SO$_2$—(CH$_2$)$_n$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$^n$—R$^{L2}$—, —R$^{L2}$—C(O)—O—, —R$^{L2}$—NH—C(O)—(CH$_2$)$_n$—, —R$^{L2}$—NH—S(O)$_2$—(CH$_2$)$_n$—, —S—, —S(O)—, or —S(O)$_2$—, wherein n is independently at each occurrence 0, 1, 2, 3, 4, 5, or 6;
X is independently selected from hydrogen, CN, OH, CF$_3$, COOH, OR, OR, NR$_2$, or halogen;
$R^{L2}$ is independently selected at each occurrence from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I, or a combination thereof; and
R is independently selected from $C_{1-12}$ hydrocarbons, optionally substituted with one or more groups X and/or with 1-10 heteroatoms selected from O, S, N, P, F, Cl, Br, I, or a combination thereof.

In some embodiments, the $L_1$ is —S(O)$_2$—. In some embodiments, the R in $R^2$ is benzyl.

In certain aspects, provided herein include methods of inhibiting an activity of an RNA-guided endonuclease, the method comprising contacting the RNA-guided endonuclease with the compound disclosed herein. In some embodiments, the compound inhibits the activity of an RNA-guided endonuclease reversibly. In some embodiments, the method is performed in vitro. In some embodiments, wherein the method is performed in vivo. In some embodiments, the method is performed in a cell. In some embodiments, the cell is a germline cell. In some embodiments, the cell is a prokaryotic cell. In some embodiments, the prokaryotic cell is a bacterium. In some embodiments, the cell is a eukaryotic cell. In some embodiments, the eukaryotic cell is a human cell, a mammalian cell, an insect cell, a plant cell, or a yeast cell. In some embodiments, the cell is in an organism. In some embodiments, the organism is a human, mammal, vertebrate, invertebrate, insect, or plant. In some embodiments, the RNA-guided endonuclease is Cas9. In some embodiments, the RNA-guided endonuclease is *Streptococcus pyogenes* Cas9 or a variant thereof.

In certain aspects, provide herein include methods of treating a subject, comprising: administering an RNA-guided endonuclease-RNA complex or a reagent causing expression of the RNA-guided endonuclease-RNA complex to the subject; and administering an effective amount of a compound disclosed herein.

In certain aspects, provide herein include pharmaceutical formulations comprising the compound disclosed herein and a pharmaceutically acceptable carrier.

In certain aspects, provide herein include kits comprising the compound disclosed herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 1A-1I-Development of a screening workflow for identification of SpCas9 inhibitors. (FIG. 1A) Schematic representation of the fluorescence polarization (FP) assay for monitoring SpCas9:gRNA and DNA binding. (FIG. 1B) Dose-dependent increase in the FP signal upon binding of 12PAM-DNA to the SpCas9:gRNA complex. Error bars represent ±s.d. across technical replicates (n=3). (FIG. 1C) Competition experiment demonstrating PAM-specific DNA-SpCas9:gRNA binding. 0-12 PAM refers to unlabeled competitor DNA containing the indicated number of PAM sequences. Unlabeled competitor DNA was used in two different ratios viz. 10× (250 nM) and 50× (1250 nM). Error bars represent ±s.d. across technical replicates (n=3). (FIG. 1D) Differential scanning fluorimetry assay showing an increase in the thermal stability of SpCas9:gRNA complex upon binding to DNA containing an increasing number of PAM sequences. Error bars represent ±s.d. across technical replicates (n=3). (FIG. 1E) Representative bio-layer interferometry (BLI) sensogram showing the interaction of SpCas9:gRNA with dsDNA containing a variable number of PAM sequences. Streptavidin sensors were loaded with 300 nM biotin-dsDNA with a variable number of PAM sequences and the interaction was followed by incubating with 200 nM SpCas9:gRNA complex. Data are for one of the two replicates. (FIG. 1F) Schematic representation of the eGFP-disruption assay. Quantification of eGFP-disruption by SpCas9 at 48 h post-nucleofection. U2OS.eGFP.PEST cells were nucleofected with SpCas9 and gRNA plasmids followed by incubation for 48 h before imaging. Error bars represent ±s.d. across technical replicates (n=4). (FIG. 1G) Quantification of mKate2-disruption assay in HEK293T cells. Cells were transfected with a plasmid encoding the mKate 2 reporter, SpCas9 and either a non-targeting guide (CgRNA plasmid) or a targeting guide (T1gRNA plasmid). Cells transfected with the CgRNA plasmid showed a high number of mKate2 positive cells while cells transfected with the T1gRNA plasmid showed a significant reduction in the number mKate2 positive cells 48 h after transfection. Error bars represent ±s.d. across technical replicates (n=4). (FIG. 1H) Quantification of NHEJ assay in HEK293T cells. SpCas9 induced NHEJ was quantified by measuring mCherry and GFP expression in HEK293T cells after 48 h. Cells were transfected with the reporter construct encoding mCherry-Stop codon (TAG)-GFP, SpCas9, and gRNA or the reporter construct alone. GFP fluorescence observed in the cells transfected with only the reporter indicates the basal level of NHEJ. The GFP fluorescence increases significantly in cells transfected with the reporter, SpCas9, and gRNA indicating an increase in NHEJ following dsDNA break by SpCas9. Error bars represent ±s.d. across technical replicates (n=4). (FIG. 1I) Z' factor values for cell-based secondary assays (eGFP-disruption, mKate2-disruption, and NHEJ) in two different plate formats. Assays were performed in 16 technical replicates for 48 h.

FIGS. 2A-2G-High-throughput screening and identification of inhibitor scaffold. (FIG. 2A) Screening results of FP-based assay against 9,549 DOS compounds. Dots in yellow, blue, and green represent DMSO controls, small molecules, and unlabeled 12PAM competitor, respectively. (FIG. 2B) Hit-rate distribution across the DOS informer set in the FP-based primary assay. (FIG. 2C) Screening and counterscreening results against the Povarov library. Dots in yellow and blue represent DMSO controls and small molecules, respectively. BRD7087 is indicated in red. (FIG. 2D) Bio-layer interferometry (BLI) measuring small-molecule binding with the SpCas9:gRNA complex. Streptavidin sensors were loaded with 1 µM BRD3539, and the interaction was followed by varying the SpCas9:gRNA complex from 0.15-1 µM. Global fitting of the response curves against ribonucleoprotein concentration provides the dissociation constant (FIG. 6C). (FIG. 2E) Binding interaction of BRD7087 and SpCas9:gRNA ribonucleoprotein complex probed with $^{19}$F NMR spectrometry. Line broadening in the $^{19}$F peak signal indicates the association of BRD7087 with SpCas9. (FIG. 2F) Dose-dependent inhibition of SpCas9 by BRD7087 in U2OS.eGFP.PEST cells. Compound was tested from 5-20 µM. U2OS.eGFP.PEST cells were nucleofected with SpCas9- and gRNA-expressing plasmids, and incubated with the compound at the indicated concentration for 24 h before imaging. Error bars represent ±s.d. across technical replicates (n=4). **$P\leq0.0001$ for small molecule at 20 µM and DMSO. (unpaired t test, two-tailed). (FIG. 2G) Dose-dependent inhibition of dSpCas9-based transcriptional activation of HBG1 in HEK293FT cells. Cells were transfected with dSpCas9, MS2.p65.HSF1.GFP plasmids along with either RFP or HBG1 and incubated in the presence of the small molecule at the indicated concentrations before processing for RT-qPCR. The experiments were performed in three biological replicates, and each biological replicate was processed in six technical replicates. The data represent mean±s.e.m. for technical replicates. **$P<0.0001$ for the small-molecule at 20 µM and DMSO. (unpaired t-test, two-tailed).

FIGS. 3A-3J-Identification and validation of small-molecule inhibitors of SpCas9. (FIG. 3A) Scatter plot of activity of BRD7087 analogs in the eGFP-disruption assay. U2OS.eGFP.PEST cells were nucleofected with SpCas9 and gRNA expressing plasmids, and incubated with 15 µM compounds for 24 h before imaging. The top right quadrant represents the compounds with higher activity than that of BRD7087 in both replicates. (FIG. 3B) Chemical structures of BRD0539 and BRD3433. (FIG. 3C) Dose-dependent inhibition of SpCas9 by BRD0539 and BRD3433 in U2OS.eGFP.PEST cells with $EC_{50}$ of 11.5 µM and 9.3 µM, respectively. Inhibitors were tested from 2.8-17.3 µM. U2OS.eGFP.PEST cells were nucleofected with either SpCas9 or preformed SpCas9:gRNA ribonucleoprotein complex and incubated with the compounds at the indicated concentrations for 24 h before imaging. Error bars represent ±s.d. across technical replicates (n=3). ****$P<0.0001$ for both small-molecules at 15 µM and DMSO (unpaired t-test, two-tailed). (FIG. 3D) Representative images of the eGFP-disruption assay. U2OS.eGFP.PEST cells were nucleofected with either SpCas9 alone (untreated) or preformed SpCas9:gRNA ribonucleoprotein complex and treated with vehicle or inhibitors BRD0539 and BRD3433 at 15 µM for 24 h. Left and right panels represent DAPI and GFP channels, respectively. (FIG. 3E) Dose-dependent inhibition of SpCas9 by BRD0539 and BRD3433 in the HiBiT assay. Inhibitors were tested from 6-20 µM. U2OS.eGFP.PEST cells were nucleofected with SpCas9- and gRNA-expressing plasmids along with ssODN containing the HiBiT tag. The cells were incubated with compounds at the indicated concentrations for 24 h before cell lysis and luminescence measurement. Error bars represent ±s.d. across technical replicates (n=2). (FIG. 3F) Next-generation sequencing analysis of eGFP indicating dose and time-dependent inhibition of SpCas9 by BRD0539 in U2OS.eGFP.PEST cells. Cells were nucleofected with either SpCas9 or preformed SpCas9:gRNA ribonucleoprotein complex targeting the eGFP gene and incubated with BRD0539 at the indicated concentrations for 10, 12, 14, and 18 h before harvesting genomic DNA. Error bars represent ±s.d. across technical replicates (n=2) of two biological replicates. (FIG. 3G) Reversal of BRD0539-mediated inhibition of SpCas9 in U2OS.eGFP.PEST cells in the eGFP-disruption assay. Cells were nucleofected with either SpCas9 or preformed SpCas9: gRNA ribonucleoprotein complex targeting the eGFP gene and incubated with either DMSO or 15 µM BRD0539 followed by a pulse-chase over 2-24 h before imaging. Error bars represent ±s.d. across technical replicates (n=2) of two biological replicates. (FIG. 3H) Differential scanning fluorimetry showing the formation of a more stable SpCas9 complex (shaded region) upon binding with increasing concentration (0.25, 0.5, 1, and 2 µM) of 8PAM DNA. Error bars represent ±s.d. across technical replicates (n=2). (FIG. 3I) Differential scanning fluorimetry depicting the destabilization of SpCas9:8PAM DNA (1 µM: 2 µM) complexes (shaded region) upon incubation with an increasing concentration (5, 10, 15, and 20 µM) of BRD0539. Error bars represent ±s.d. across technical replicates (n=2). (FIG. 3J) Cellular thermal shift assay (CETSA) for SpCas9 in WM793 melanoma cells in the absence or presence of BRD0539. WM793 cells stably expressing SpCas9 were incubated with 15 µM BRD0539 for 24 h before performing CETSA and analyzed by western blot. The top panel is the immunoblot representation of the thermal stability of SpCas9 in WM793 cells treated with either vehicle or BRD0539. The bottom panel is the quantified thermal stability plot for SpCas9. Error bars represent ±s.d. across biological replicates (n=3).

FIGS. 4A-4F-Structure-activity analysis and inhibition of dCas9-based transcriptional upregulation. (FIG. 4A) A Structure-activity relationship studies of BRD0539 in the eGFP-disruption assay in U2OS.eGFP.PEST cells. The set of functional groups on top represents variation at the 1-N-cap position ($R^1$) whereas those in the bottom set represent the functional group variation at the 8-position ($R^2$). Bar plot depicts the reduction in activity of different structural analogs with respect to that of BRD0539. Asterisk-labeled compounds have a methyl group at the 4-N position, while others have a proton. The data is an average of two biological replicates. (FIG. 4B) Chemical structures of BRD0539 stereoisomers and their dose-dependent inhibition of SpCas9 in U2OS.eGFP.PEST cells. Inhibitors were tested from 2.5-15 μM. Cells were nucleofected with either SpCas9 or preformed SpCas9:gRNA ribonucleoprotein complex and incubated with the compounds at the indicated concentration for 24 h before imaging. Error bars represent ±s.d. across technical replicates (n=3). (FIG. 4C) Chemical structure of BRD0322 and BRD0048 and their dose-dependent inhibition of dCas9-based transcriptional upregulation of HBG1 gene in HEK293FT cells. Cells were transfected with dSpCas9, MS2.p65.HSF1.GFP plasmids along with either RFP or HBG1 and incubated in the presence of small molecules at the indicated concentrations before processing for RT-qPCR. The experiments were performed in three biological replicates, and each biological replicates were processed in six technical replicates. The data represent mean±s.e.m. for technical replicates. ****P<0.0001 for both small-molecules at 15 μM and DMSO. (unpaired t-test, two-tailed). (FIG. 4D) Dose-dependent inhibition of SpCas9 by BRD0539, BRD3497, and BRD9419 in U2OS.eGFP.PEST cells. The inhibitors were tested from 2.8-17.3 μM. U2OS.eGFP.PEST cells were nucleofected with either SpCas9 or preformed SpCas9:gRNA ribonucleoprotein complex and were incubated with the compounds at the indicated concentrations for 24 h before imaging. Error bars represent #s.d. across technical replicates (n=3). (FIG. 4E) Representative images of the eGFP-disruption assay. U2OS.eGFP.PEST cells were nucleofected with either SpCas9 alone (untreated) or preformed SpCas9:gRNA ribonucleoprotein complex and were treated with either vehicle alone or the indicated compounds at 15 μM for 24 h. The top and bottom panels represent DAPI and GFP channels, respectively. (FIG. 4F) Dose-dependent inhibition of SpCas9 by BRD0539, BRD3497, and BRD9419 in the HiBiT assay. Inhibitors were tested from 4.8-15 μM. U2OS.eGFP.PEST cells were nucleofected with SpCas9- and gRNA-expressing plasmids along with ssODN containing the HiBiT tag. The cells were incubated with compounds at the indicated concentrations for 24 h before cell lysis and luminescence measurements. Error bars represent #s.d. across technical replicates (n=2).

FIGS. 5A-5E-Chemical structure of DOS library and representative images of eGFP-disruption assay, mKate2-disruption assay, and NHEJ assay. (FIG. 5A) Structural diversity of the DOS library. (FIG. 5B) Representative images of the eGFP-disruption assay. U2OS.eGFP.PEST cells were nucleofected with either SpCas9 alone or SpCas9- and eGFP-targeting gRNA plasmids. Left panel shows cells nucleofected with SpCas9 alone (untreated). Right panel shows cells nucleofected with SpCas9- and eGFP-targeting gRNA expressing plasmids and treated with vehicle for 48 h. Scale bar=200 μm. (FIG. 5C) Representative images of the mKate2-disruption assay. Representative images of untreated HEK293T cells and cells transfected with T1gRNA or CgRNA. The nuclei are counter-stained with DAPI and the expression level of mKate2 was measured using the red channel. Left, middle, and right panels represent untreated cells, cells transfected with CgRNA plasmid, and T1gRNA plasmids, respectively. Scale bar=200 μm. (FIG. 5D) Representative images of NHEJ inhibition by BRD7087. HEK293T cells transfected with a plasmid encoding SpCas9 and gRNA and another plasmid encoding the reporter mCherry-Stop Codon (TAG)-GFP. The nuclei are counter-stained with DAPI and the red and green channels represent the expression levels of mCherry and GFP respectively. Scale bar=200 μm. (FIG. 5E) Z-score values for cell-based secondary assays (eGFP-disruption, mKate2-disruption, and NHEJ) in two different plate formats. Assays were performed in 16 technical replicates for 24 h.

FIGS. 6A-6S—Biochemical and cellular characterization of Povarov scaffold. (FIG. 6A) Scatter plot for primary screening assay of the Pictet-Spengler library. Dots in yellow, blue, and green represent DMSO controls, small molecules, and unlabeled 12PAM DNA competitor, respectively. (FIG. 6B) Chemical structures of BRD7087, BRD5799, and BRD3539. (FIG. 6C) Bio-layer interferometry binding plots for BRD3539 and SpCas9:gRNA complex. BLI experiment was performed using 1 μM BRD3539 on streptavidin sensors, followed by association with different concentration of SpCas9:gRNA complex and subsequent dissociation. Response data were plotted along Y-axis and concentration of SpCas9:gRNA complex was plotted along X-axis. A global 2:1 (small molecule:protein) model was used to plot the steady state and determine the binding constant. Two binding plots correspond to two biological replicates. (FIG. 6D) Binding competition between BRD3539 and biotin in BLI. BLI sensogram showing the interaction of streptavidin sensors loaded either with BRD3539 or biotin and SpCas9:gRNA RNP complex. 1 μM BRD3539 or 10 μM biotin in 20 mM Tris buffer (pH 7.4, 100 mM KCl, 5 mM $MgCl_2$, 1 mM DTT, 0.01% Tween) was loaded onto the streptavidin sensors. In the competition assay, streptavidin sensors were pre-loaded with 10 μM of biotin followed by loading of 1 μM BRD3539. SpCas9: gRNA complex concentration was varied from 0.25-1 μM. Competitive BLI experiment with BRD3539 in the presence of 10-fold excess biotin. (FIG. 6E) Background-subtracted BLI responses of BRD3539 with SpCas9:gRNA RNP complex in the presence of 10-fold excess biotin as the competitor in 20 mM Tris buffer (pH 7.4, 100 mM KCl, 5 mM MgCl$_2$, 1 mM DTT, 0.01% Tween). SpCas9:gRNA complex concentration was varied from 0.25-1 μM. (FIG. 6F) Aggregation behavior of BRD7087. Aggregate formation for BRD7087 was determined using dynamic light scattering, between 40-100 μM in PBS. BRD7087 forms aggregates beyond 80 μM. Aggregate size distribution plots are an average of 10 individual reads. BRD7087 did not show any detectable aggregation up to ~60 μM. (FIG. 6G) Determination of BRD7087 solubility in PBS. The solubility of BRD7087 compound in PBS was determined by mass spectroscopy after 24 h incubation at room temperature. Antipyrine and clotrimazole are positive controls. (FIG. 6H) NMR binding of BRD7087 to SpCas9:gRNA complex. $^{19}$F NMR titration plot for BRD7087 with SpCas9:gRNA complex in 20 mM Tris buffer (pH 7.4, 100 mM KCl, 5 mM MgCl$_2$, 1 mM DTT). 50 μM BRD7087 was titrated against increasing concentrations of SpCas9:gRNA (0.75-1.75 μM) complex. (FIG. 6I) Cell viability of U2OS.eGFP.PEST cells in the presence of small molecules. Cell viability was determined by measurement of ATP content of U2OS.eGFP.PEST cells upon incubation with BRD7087 or BRD5779 (5-20 μM) for 24 h. Error bars represent ±s.d. across technical replicates (n=3). (FIG. 6J) Cell viability of HEK293T cells in the presence of small molecules. Cell viability was determined by measurement of ATP content of HEK293T cells upon incubation with BRD7087 or BRD5779 (5-20 μM) for 24 h. Error bars represent ±s.d. across technical replicates (n=3). (FIG. 6K) Dose-dependent inhibition of SpCas9 by BRD5779 in U2OS.eGFP.PEST cells. Compound was tested in 5-20 μM concentration range with 1.2 fold dilution. U2OS.eGFP.PEST cells were nucleofected with SpCas9- and gRNA-expressing plasmids, and incubated with the indicated concentration of compound for 24 h before imaging. Error bars represent ±s.d. across technical replicates (n=4). ****P<0.0001 for small molecule at 20 μM and DMSO. (unpaired t test, two-tailed). (FIG. 6L) Representative images of the eGFP-disruption assay. U2OS.eGFP.PEST cells were nucleofected with either SpCas9 alone or SpCas9- and eGFP-targeting gRNA plasmids and treated with vehicle or small molecules. Left panel represents cells nucleofected with SpCas9 alone. Middle panel represents cells nucleofected with SpCas9 and eGFP targeting gRNA expressing plasmids and treated with vehicle. Right panel represents cells nucleofected with SpCas9- and eGFP-targeting gRNA and treated with 15 μM BRD7087 for 24 h. Scale bar=100 μm. (FIG. 6M) Effect of inhibitors on eGFP protein expression in U2OS.eGFP.PEST cells. Western blot analysis of eGFP protein expression in U2OS.eGFP.PEST cells was performed in the presence of DMSO and the inhibitors BRD5779 or BRD7087. Cells were incubated with compound BRD5779 or BRD7087 at the indicated concentrations for 24 h before harvesting and processing for Western blotting. No change was observed in eGFP expression levels in presence or absence of compounds. (FIG. 6N) Auto-fluorescence of U2OS.eGFP.PEST cells treated with the inhibitors in the eGFP-disruption assay. Cells were imaged in the RFP channel with the same exposure time as that used for the GFP channel in the eGFP-disruption assay. Small molecule-treated cells showed a maximum of ~1% auto-fluorescent population, indicating no significant contribution of auto-fluorescence. Error bars represent ±s.d. across technical replicates (n=4). (FIG. 6O) Dose-dependent inhibition of SpCas9 by the inhibitors in mKate2-disruption assay. HEK293T cells were transfected with a single plasmid encoding SpCas9, gRNA, and mKate2 (T1gRNA). Cells transfected with a plasmid encoding SpCas9, mKate2 and a non-targeting gRNA (CgRNA) was used as the positive control. Cells transfected with T1gRNA were incubated either in presence of DMSO or inhibitors (1.5-5 μM) for 24 h. Error bars represent ±s.d. across technical replicates (n=3). (FIG. 6P) Representative images of the mKate2-disruption assay. Representative images of untreated HEK293T cells and cells transfected with T1gRNA or CgRNA. The nuclei are counter-stained with DAPI and expression level of mKate2 was measured using the red channel. Top panels represent untreated cells or cells transfected with the indicated plasmid and incubated with DMSO. Bottom panels represent cells transfected with T1gRNA and incubated with compound BRD7087 at the indicated concentrations. Scale bar=100 μm. (FIG. 6Q) Dose-dependent inhibition of SpCas9-mediated NHEJ. HEK293T cells were transfected with a plasmid encoding SpCas9, and gRNA and another plasmid encoding the reporter mCherry-Stop Codon (TAG)-GFP. Transfected cells were incubated with either DMSO or small molecules (2-10 μM) for 24 h. Error bars represent ±s.d. across technical replicates (n=3). (FIG. 6R) Dose-dependent inhibition of dSpCas9-based transcriptional activation of HBG1 gene in HEK293FT cells. Cells were transfected with dSpCas9, MS2.p65.HSF1.GFP plasmids along with either RFP or HBG1 gRNA plasmid and incubated in the presence of the small molecules at the indicated concentration for 48 h before RT-qPCR analysis. Error bars represent ±s.e.m. for technical replicates (n=6). (FIG. 6S) Dose-dependent inhibition of the SpCas9 (A840H)-cytidine deaminase conjugate (BE3) targeting EMX1 gene in HEK293T cells. Small molecules preincubated with BE3:gRNA ribonucleoprotein were delivered to HEK293T cells and incubated in the presence of either DMSO or small molecules at the indicated concentration for 72 h. The cells were then harvested and processed for DNA sequencing to evaluate the extent of $C_5 \rightarrow T5$ or $C_6 \rightarrow T6$ conversion. Error bars represent ±s.d. across biological replicates (n=3).

FIGS. 7A-7Q-Biochemical and cellular characterization of SpCas9 inhibitors. (FIG. 7A) Inhibition of SpCas9 by BRD7087 and its analogs in U2OS.eGFP.PEST cells. Cells were nucleofected with either SpCas9 or preformed SpCas9: gRNA ribonucleoprotein complex, and incubated with 15 μM compound for 24 h before imaging. Error bars represent ±s.d. across technical replicates (n=4). (FIG. 7B) Flow-cytometric analysis of eGFP-disruption assay. Inhibition of SpCas9 by BRD0539 in U2OS.eGFP.PEST cells. Cells were nucleofected with either SpCas9 or preformed SpCas9: gRNA ribonucleoprotein complex, and incubated with the indicated concentration of compound for 24 h before analysis. (FIG. 7C) Surveyor assay analysis of eGFP gene from U2OS.eGFP.PEST cells indicating inhibition of SpCas9-induced indel bands. Cells were nucleofected with either SpCas9 or preformed SpCas9:gRNA ribonucleoprotein complex, and incubated with the compound at the indicated concentration for 10, 12, 14, and 16 h before isolating the genomic DNA and analyzed by surveyor assay. (FIG. 7Q) Differential scanning fluorimetry studies showing inhibition of SpCas9: gRNA binding to 4PAM DNA by BRD0539. SpCas9:gRNA (1 μM) was incubated with 4PAM DNA (2 μM) in the presence of either DMSO or BRD0539 (20 μM). Data are for one of the two replicates.

(FIG. 8A) Structure-activity relationship studies of BRD3433 in the eGFP-disruption assay in U2OS.eGFP.PEST cells. The set of functional groups on top represents variation at the 1-N-cap position ($R^1$) whereas those at the bottom represents the functional group variation at the 8-position ($R^2$). Bar plot depicts the reduction in the activity of different structural analogs with respect to that of BRD3433. Asterisk-labeled compounds contain a methyl group at the 4-N position, while others have a proton. The data are an average of two biological replicates. (FIG. 8B) Inhibition of dSpCas9-based transcriptional upregulation of HBG1 gene in HEK293FT cells by BRD7087. Cells were transfected with dSpCas9, MS2.p65.HSF1.GFP plasmids along with either RFP or HBG1 gRNA plasmid and incubated in the presence of the small molecules at the indicated concentration for 48 h before RT-qPCR analysis. Data represents average of 6 technical replicates. Y-axis represents % fold change in the compound activity with respect to BRD7087. (FIG. 8C) Dose-dependent inhibition of dSpCas9-based transcriptional upregulation of HBG1 gene in HEK293FT cells. Cells were transfected with dSpCas9, MS2.p65.HSF1.GFP plasmids along with either RFP or HBG1 gRNA plasmid and incubated in the presence of the small molecules at the indicated concentration for 48 h before RT-qPCR analysis. The experiments were performed in three biological replicates, and each biological replicate was processed in six technical replicates. The data represent mean±s.e.m. for technical replicates. ****$P \leq 0.0001$ for both small-molecules at 15 μM and DMSO (unpaired t-test, two-tailed). (FIG. 8D) Cellular impermeability of the anti-CRISPR protein AcrIIA4 assessed by lack of SpCas9 inhibition in the eGFP-disruption assay when AcrLLA4 is incubated in the media. Cells were nucleofected either with SpCas9 or SpCas9:gRNA ribonucleoprotein complex followed by incubating with AcrIIA4 in the media. In another instance, cells were nucleofected with SpCas9:gRNA:AcrIIA4 and incubated for 48 h before imaging. Error bars represent #s.d. across technical replicates (n=4). (FIG. 8E) Reversal of AcrIIA4-mediated inhibition of SpCas9 in U2OS.eGFP.PEST cells in the eGFP-disruption assay. U2OS.eGFP.PEST cells were nucleofected with either SpCas9 or preformed SpCas9: gRNA:AcrIIA4 (1:1.2:5) complex targeting the eGFP gene and incubated at 37° C. followed by a pulse-chase over 2-24 h before imaging. Error bars represent ±s.d. across technical replicates (n=2) of two biological replicates. (FIG. 8F) Human plasma stability of compound as determined by UPLC/MS in MRM method. 5 μM compound was incubated with 50% human plasma in PBS for 5 h before processed for analysis. Error bars represent ±s.e.m. for technical replicates (n=3). (FIG. 8G) Representative images of the eGFP-disruption assay. U2OS.eGFP.PEST cells were nucleofected with either SpCas9 alone or preformed SpCas9:gRNA ribonucleoprotein complex and were treated with the vehicle alone or the compounds at 15 μM for 24 h. The top and bottom panels represent the DAPI and GFP channels, respectively. (FIG. 8H) In vitro pulldown assay of SpCas9 by the BRD0539-biotin conjugate from WM793-SpCas9 cell lysate. Streptavidin magnetic beads pre-loaded with either BRD0539-biotin or biotin-azide were incubated with WM793-SpCas9 cell lysate for 12 h before processing the samples for western blotting. BRD0539 (20 µM) was used as a competitor. F and E represent flow-through and eluent, respectively.

FIG. 9A shows a schematic of the molecular mechanism of dCas9-based transcription upregulation. FIG. 9B shows results from screening various compounds.

FIGS. 10A-10E—(FIG. 10A) Fluorescence polarization assay for detecting SpCas9-gRNA binding. A FITC-labeled crRNA:tracrRNA (25 nM) was titrated with an increasing amount of SpCas9 (7.5-250 nM). Error bars represent ±s.d. across technical replicates (n=3). (FIG. 10B) Competition experiment demonstrating sequence specific gRNA-SpCas9 binding. An unlabeled crRNA:tracrRNA (25 nM) was pre-incubated with SpCas9 (25 nM) for 10 min before the addition of FITCcrRNA:tracrRNA (25 nM). Error bars represent ±s.d. across technical replicates (n=3). (FIG. 10C) Fluorescence polarization assay for determining the effect of BRD0539 in the SpCas9-FITCcrRNA:tracrRNA binding. SpCas9 (25 nM) was incubated with the indicated amount of BRD0539 (10-30 µM) for 15 min followed by the addition of FITC-crRNA:tracrRNA (25 nM), which was incubated for 30 min before measuring the FP signal. Error bars represent ±s.d. across technical replicates (n=3). (FIG. 10D) In vitro pulldown assay of SpCas9 by the BRD0539-biotin conjugate from WM793-SpCas9 cell lysate. Streptavidin magnetic beads pre-loaded with either BRD0539-biotin or biotin-azide were incubated with WM793-SpCas9 cell lysate for 12 h before processing the samples for western blotting. BRD0539 (20 µM) was used as a competitor. F and E represent the flow-through and eluent, respectively. (FIG. 10E) Dose-dependent inhibition study of BRD0539 (6-20 µM) against SpCas9 or FnCpf1 in U2OS.eGFP.PEST cells. Cells were nucleofected with SpCas9 or FnCpf1 plasmids and their corresponding gRNA-expressing plasmids and were incubated with the inhibitor at the indicated concentration for 30 h before imaging and analysis. Error bars represent ±s.d. across technical replicates (n=4). Representative images of the eGFP-disruption assay for SpCas9 and FnCpf1 in U2OS.eGFP.PEST cells. Cells were nucleofected with either SpCas9 plasmid alone (-gRNA) or either the SpCas9 or FnCpf1 plasmids with their corresponding gRNA-expressing plasmids containing the eGFP gene target and were incubated with the inhibitor (15 µM) for 30 h before imaging. The top and bottom panels represent the DAPI and GFP channels, respectively.

FIGS. 11-31 show NMR characterization of the compounds.

Figure 3J:
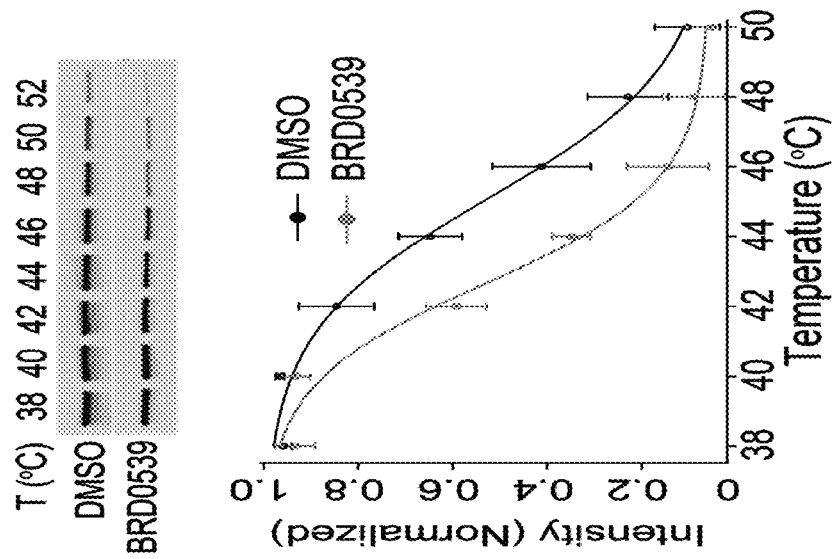

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011)

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. In a broad aspect, the permissible substituents include acyclic and cyclic, branched and unbranched, carbocyclic and heterocyclic, aromatic and nonaromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Non-limiting examples of optional substituents as referred to herein include halogen, alkyl, aralkyl, heteroalkyl, alkenyl, alkynyl, cycloalkyl, hydroxyl, alkoxy, amino, amido, nitro, cyano, carbonyl, carboxyl, silyl, ether, alkylthio, sulfonyl, sulfonamido, ketone, aldehyde, ester, heterocyclyl, aryl, and heteroaryl.

A "substituted" hydrocarbon may have as a substituent one or more hydrocarbon radicals, substituted hydrocarbon radicals, or may comprise one or more heteroatoms.

Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalented bound to a carbon atom in the chain or backbone, as in "oxo").

In some embodiments, any hydrocarbon or substituted hydrocarbon disclosed herein may be substituted with one or more substituents X, where X is independently selected at each occurrence from one or more (e.g., 1-20) heteroatoms or one or more (e.g., 1-10) heteroatom-containing groups, where, for example, X may be selected from —F; —$C_1$; —Br; —I; —OH; —OR*; —$NH_2$; —NHR*; —N(R*)$_2$; —N(R*)$_3$+; —N(R*)—OH; —N(→O)(R*)$_2$; —O—N(R*)$_2$; —N(R*)—O—R*; —N(R*)—N(R*)$_2$; —C=N—R*; —N=C(R*)$_2$; —C=N—N(R*)$_2$; —C(=NR*) (—N(R*)$_2$); —C(H)(=N—OH); —SH; —SR*; —CN; —NC; —C(=O)—R*; —CHO; —$CO_2$H; —$CO_2$—; —$CO_2$R*; —C(=O)—S—R*; —O—(C=O)—H; —O—(C=O)—R*; —S—C(=O)—R*; —(C=O)—$NH_2$; —C(=O)—N(R*)$_2$; —NH—(C=O)—R*; —NH—(C=O)—R*; —N(R*)—C(=O)—R*; —C(=O)—$NHNH_2$; —O—C(=O)—$NHNH_2$; —C(=S)—$NH_2$; —(C=S)—N(R*)$_2$; —N(R*)—CHO; —N(R*)—C(=O)—R*; —C(=NR*)—O—R*; —O—C(=NR*)—R*; —SCN; —NCS; —NSO; —SSR*; —N(R*)—C(=O)—N(R*)$_2$; —N(R*)—C(=S)—N(R*)$_2$; —S(=O)$_2$—R*; —O—S(=O)$_2$—R*; —S(=O)$_2$—OR*; —N(R*)—S(=O)$_2$—R*; —S(=O)$_2$—N(R*)$_2$; —O—$SO_3$; —O—S(=O)$_2$—OR*; —O—S(=O)—OR*; —O—S(=O)—R*; —S(=O)—OR*; —S(=O)—R*; —NO; —$NO_2$; —$NO_3$; —O—NO; —O—$NO_2$; —$N_3$; —$N_2$—R*; —N($C_2H_4$); —Si(R*)$_3$; —$CF_3$; —O—$CF_3$; —O—$CH_3$; —O—$(CH_2)_{1-6}CH_3$; —PR*$_2$; —O—P(=O)(OR*)$_2$; and —P(=O)(OR*)$_2$; where, independently at each occurrence, R* may be H or a $C_{1-10}$ or $C_{1-8}$ or $C_{1-6}$ or $C_{1-4}$ hydrocarbon, including without limitation alkyl, alkenyl, alkynyl, aryl (e.g., phenyl), alkyl-aryl (e.g., benzyl), aryl-alkyl (e.g., toluyl), etc. In other embodiments, X may comprise a $C_1$-$C_8$ or $C_1$-$C_6$ or $C_2$-$C_4$ perfluoroalkyl. In other embodiments, X may a $C_1$-$C_8$ or $C_2$-$C_6$ or $C_3$-$C_8$ heterocycle (e.g., heteroaryl radical). The term "halo" or "halogen" refers to any radical of fluorine, chlorine, bromine or iodine. In some embodiments, X is independently selected at each occurrence from —OH, —SH, —$NH_2$; —N(R*)$_2$; —F, and —$C_1$.

In addition, the phrase "substituted with a [n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl.

As used herein, the term "straight chain Cn-m alkylene," employed alone or in combination with other terms, refers to a non-branched divalent alkyl linking group having n to m carbon atoms. Any atom can be optionally substituted, e.g., by one or more substituents. Examples include methylene (i.e., —CH$_2$—).

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl).

Alkoxy can be, for example, methoxy (—OCH$_3$), ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). Finally, the terms "haloalkoxy" and "halothioalkoxy" refer to —O(haloalkyl) and —S(haloalkyl), respectively. The term "sulfhydryl" refers to —SH. As used herein, the term "hydroxyl," employed alone or in combination with other terms, refers to a group of formula —OH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from 0, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N(C$_1$-C$_6$ alkyl), NC(O) (C$_1$-C$_6$ alkyl), O, and S; and wherein said heterocyclic ring is optionally substituted with from 1-3 independently selected Ra" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclohexenyl, cyclohexadienyl, or norbornenyl.

As used herein, the term "cycloalkylene" refers to a divalent monocyclic cycloalkyl group having the indicated number of ring atoms.

As used herein, the term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The terms "arylcycloalkyl" and "arylheterocyclyl" refer to bicyclic, tricyclic, or other polycyclic ring systems that include an aryl ring fused to a cycloalkyl and heterocyclyl, respectively. Similarly, the terms "heteroarylheterocyclyl," and "heteroarylcycloalkyl" refer to bicyclic, tricyclic, or other polycyclic ring systems that include a heteroaryl ring fused to a heterocyclyl and cycloalkyl, respectively. Any atom can be substituted, e.g., by one or more substituents. For example, arylcycloalkyl can include indanyl; arylheterocyclyl can include 2,3-dihy drobenzofuryl, 1,2,3,4-tetrahy droisoquinolyl, and 2,2-dimethy lchromanyl.

The term "vicinal" refers to the configuration in which any two atoms or groups are, respectively, bonded to two adjacent atoms (i.e., the two atoms are directly bonded to one another). The term "geminal" describes a configuration in which any atoms or two functional groups are bonded to the same atom. As used herein, when any two groups are said to together form a ring, unless otherwise indicated, it is meant that a bond is formed between each of said two groups, with the valences of the atoms appropriately adjusted to accommodate at least a bond (e.g., a hydrogen atom may be removed from each group).

The descriptors "C=O" or "C(O)" or "carbonyl" refers to a carbon atom that is doubly bonded to an oxygen atom "Alkyl carbonyl" has a common formula of R—C(O)— wherein R may be C1-12 alkyl, C2-12 alkenyl, C2-12 alkynyl, C3-12 cycloalkyl, C6-12 aryl, C3-12 heteroaryl, or C3-12 heterocyclyl.

The term "oxo" refers to double bonded oxygen which can be a substituent on carbon or other atoms. When oxo is a substituent on nitrogen or sulfur, it is understood that the resultant groups has the structures N→O$^-$ and S(O) and SO$_2$, respectively.

As used herein, the term "cyano," employed alone or in combination with other terms, refers to a group of formula —CN, wherein the carbon and nitrogen atoms are bound together by a triple bond. The term "azide" refers to a group of formula —N$_3$. The term "nitro" refers to a group of formula —NO$_2$. The term "amine" includes primary (—NH$_2$), secondary (—NHR), tertiary (—NRR'), and quaternary (—N'RR'R") amine having one, two or three independently selected substituents such as straight chain or branched chain alkyl, alkenyl, alkynyl, cycloalkyl, aryl, heteroaryl, heterocycle, and the like.

When any variable (e.g., R$^1$) occurs more than one time in any constituent or formula for a compound, its definition at each occurrence is independent of its definition at every other occurrence. Thus, for example, if a group is shown to be substituted with one or more R$^1$ moieties, then R$^1$ at each occurrence is selected independently from the Markush group recited for R$^1$. Also, combinations of substituents and/or variables are permissible, but only if such combinations result in stable compounds within a designated atom's normal valency.

As used herein, "unsaturated" refers to compounds or structures having at least one degree of unsaturation (e.g., at least one double or triple bond).

The term "pharmaceutically acceptable salt" refers to those salts that are within the scope of proper medicinal assessment, suitable for use in contact with human tissues and organs and those of lower animals, without undue toxicity, irritation, allergic response or similar and are consistent with a reasonable benefit/risk ratio. In some embodiments, pharmaceutically acceptable salts can be formed by the reaction of a disclosed compound with an equimolar or excess amount of acid. Alternatively, hemi-salts can be formed by the reaction of a compound with the desired acid in a 2:1 ratio, compound to acid. The reactants are generally combined in a mutual solvent such as diethyl ether, tetrahydrofuran, methanol, ethanol, iso-propanol, benzene, or the like. The salts normally precipitate out of solution within, e.g., about one hour to about ten days and can be isolated by filtration or other conventional methods.

Inorganic acids commonly employed to form pharmaceutically acceptable salts include hydrochloric acid, hydrobromic acid, hydroiodic acid, sulfuric acid, phosphoric acid, and the like. Organic acids commonly employed to form pharmaceutically acceptable salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, iso-butyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, -hydroxybutyrate, glycolate, tartrate, methanesulfonate, propanesulfonate, naphthalene-1-sulfonate, naphthalene-2-sulfonate, mandalate and the like.

By "agent" is meant any small molecule chemical compound, antibody, nucleic acid molecule, or polypeptide, or fragments thereof.

By "decreases" is meant a negative alteration. Such alterations are by 5%, 10%, 25%, 50%, 75%, 85%, 90% or even by 100% of a reference value. By "increases" is meant a positive alteration. Such alterations are by 5%, 10%, 25%, 50%, 75%, 85%, 90% or even by 100% of a reference value.

By "effective amount" is meant the amount of an agent required to ameliorate the symptoms of a condition, disease or disorder relative to an untreated subject or organism. In particular embodiments, the subject or organism expresses an active RNA guided endonuclease polypeptide. The effective amount of active agent(s) used to practice the present invention varies depending upon the manner of administration, the age, body weight, and general health of the subject.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "identity" is meant the amino acid or nucleic acid sequence identity between a sequence of interest and a reference sequence. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-ioo indicating a closely related sequence.

By "hybridize" is meant pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, AR. (1987) Methods Enzymol. 152:507). For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol --- which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(+)" is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. In some chemical structures, stereocenters may be identified with "wavy" bonds indicating that the stereocenter may be in the R or S configuration, unless otherwise specified. However, stereocenters without a wavy bond (i.e., a "straight" bond) may also be in the (R) or(S) configuration, unless otherwise specified. Compositions comprising compounds may comprise stereocenters which each may independently be in the (R) configuration, the(S) configuration, or racemic mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound.

Optically active compounds can also be obtained by using active starting materials. In some embodiments, these isomers can be in the form of a free acid, a free base, an ester or a salt.

In certain embodiments, a disclosed compound can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4 (1H)-one tautomers.

All chiral, diastereomeric, racemic, and geometric isomeric forms of a structure are intended, unless specific stereochemistry or isomeric form is specifically indicated. All processes used to prepare compounds and intermediates made therein are encompassed by the present disclosure. All tautomers of shown or described compounds are also encompassed by the present disclosure.

The terms "pharmaceutical" or "pharmaceutically acceptable", when used herein as an adjective, mean substantially non-toxic and substantially non-deleterious to the subject.

By "pharmaceutical formulation" it is meant that the carrier, solvent, excipient(s) and/or salt must be compatible with the active ingredient of the formulation (e.g. a disclosed compound). It is understood by those of ordinary skill in this art that the terms "pharmaceutical formulation" and "pharmaceutical composition" are generally interchangeable, and they are so used for the purposes of this application.

By "reference" is meant a standard or control condition. A "reference sequence" is a defined sequence used as a basis for sequence comparison. In one embodiment, the reference sequence is Cas9.

By "small molecule" is meant any chemical compound.

The terms "selecting a subject" or "identifying a subject" are understood as choosing one or more members of a mixed population of individuals based on specific characteristics including, but not limited to, physical symptoms, and/or clinical characteristics as determined by diagnostic methods.

The term "solvate" means a solvent addition form that contains either a stoichiometric or non-stoichiometric amount of solvent. Some compounds have a tendency to trap a fixed molar ratio of solvent molecules in a solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrates.

The term "suitable solvent" refers to any solvent, or mixture of solvents, that may be inert to the ongoing reaction that sufficiently solubilizes the reactants to afford a medium within which to affect the desired reaction.

By "specifically binds" is meant recognizes and binds a polynucleotide or polypeptide of the invention, but which does not substantially recognize and bind other molecules in a sample.

By "subject" is meant an organism, including, but not limited to, a human or non-human mammal, such as a bovine, equine, canine, ovine, or feline; vertebrate; invertebrate, such as an insect; or plant; or any commercially relevant organism.

As used herein, the terms "treat," treating," "treatment," and the like refer to reducing or ameliorating a disorder and/or symptom associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present disclosure provides compositions and methods for inhibiting the activity of RNA-guided nucleases, methods of use therefore (e.g., inhibition or prevention of genome editing by the RNA-guided nuclease), and methods of identifying inhibitors of RNA-guided nucleases. In some examples, the RNA-guided nucleases may be RNA-guided endonucleases. By "RNA-guided endonuclease" is meant a polypeptide having RNA binding activity, DNA binding activity, and/or DNA cleavage activity. RNA-guided endonucleases form a complex with a guide RNA, which contains a sequence that is able to bind a target sequence on double-stranded DNA. In some embodiments, the RNA-guided endonuclease cleaves the double stranded target DNA. Exemplary RNA-guided endonucleases include, without limitation, Cpf1, Cas9, and active fragments, derivatives, and variants thereof. As used herein, a RNA-guided nucleases further include variants and fragments thereof. For example, RNA-guided nucleases also include variants, e.g., mutated or inactive forms of RNA-guide nucleases.

In some embodiments, the compositions and methods herein are based, at least in part, on the discovery of the small molecule inhibitors of RNA-guided endonucleases disclosed herein. Methods involving small molecule inhibitors of RNA guided endonucleases are useful for the modulation of RNA-guided endonuclease activity, including rapid, reversible, dosage, and/or temporal control of RNA-guided endonuclease technologies.

Compounds

Provides herein include small molecule compounds that modulate (e.g., inhibit) RNA-guided endonuclease activity. The compounds may allow for rapid, dosable, and/or temporal control of RNA-guided endonuclease (e.g., Cas9) activity. In some embodiments, the compounds may increase the specificity of RNA-guided endonuclease and may enable external control and manipulation of gene targeting.

In some embodiments, the small molecule compounds herein are compounds having the structure of Formula (I):

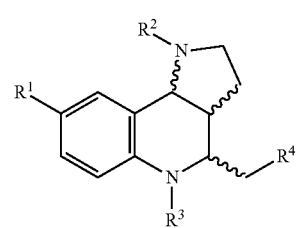

(I)

wherein each wavy bond indicates the presence of a stereocenter, and each stereocenter may be independently at each occurrence in the R or S configuration. In some embodiments, both stereocenters of the five membered fused ring are in the same configuration (i.e., both (R) or both(S)). The groups $R^1$—$R^4$ may be defined as shown below.

In some embodiments, the small molecule compounds may have the structure of Formula IA, IB, IC, or ID:

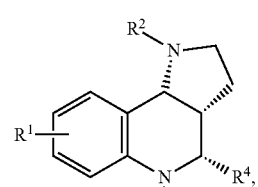

(IA)

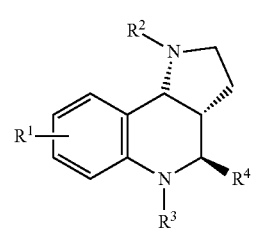

(IB)

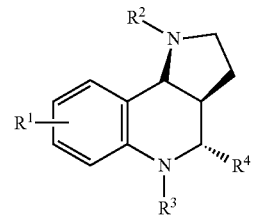

(IC)

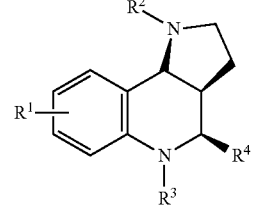

(ID)

wherein $R^1$ is independently selected at each occurrence from alkynyl or aryl; and
$R^2$ is independently selected from -$L_1$-X or -$L_1$-R;
$R^3$ is independently selected from hydrogen, —X, —R, -$L_2$-X, or -$L_2$-R;
$R^4$ is —($CH_2$)—OH; where
$L_1$ is independently selected from —CO— or —S(O)$_2$—;
$L_2$ is independently selected from —($CH_2$)$_n$—, —($CH_2$)$_n$—C(O)O—, —($CH_2$)$_n$—C(O)—NH—, —C(O)—NH—(CH$_2$)$_n$—, —(CH$_2$)$_n$—NH—C(O)—, —(CH$_2$)$_n$—NH—SO$_2$—, —NH—SO$_2$—(CH$_2$)$_n$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^{L2}$—, —R$^{L2}$—C(O)—O—, —R$^{L2}$—NH—C(O)—(CH$_2$)$_n$—, —R$^{L2}$—NH—S(O)$_2$—(CH$_2$)$_n$—, —S—, —S(O)—, —S(O)$_2$—, wherein n is independently at each occurrence 0, 1, 2, 3, 4, 5, or 6;

X is independently selected from hydrogen, CN, OH, CF$_3$, COOH, OR, OR, NR$_2$, or halogen (e.g., —C$_1$, —F, —Br, etc.);

R$^{L2}$ is independently selected at each occurrence from C$_1$-C$_{12}$ linear and/or branched and/or cyclic and/or aromatic bivalent radicals; optionally substituted with one or more groups X and/or with 1-6 heteroatoms selected from O, S, N, P, F, Cl, Br, I, and a combination thereof; and R is independently selected from C$_{1-12}$ hydrocarbons (e.g., alkyl, alkenyl, alkynyl, aryl, alkyl-aryl, aryl-alkyl, and combinations thereof), optionally substituted with one or more groups X and/or with 1-10 heteroatoms selected from O, S, N, P, F, Cl, Br, I, and a combination thereof.

In some embodiments, R$^1$ is alkynyl. In some embodiments, R$^1$ is aryl.

In some embodiments, R in R$^2$ may be benzyl. For example, R in R$^2$ may have the structure:

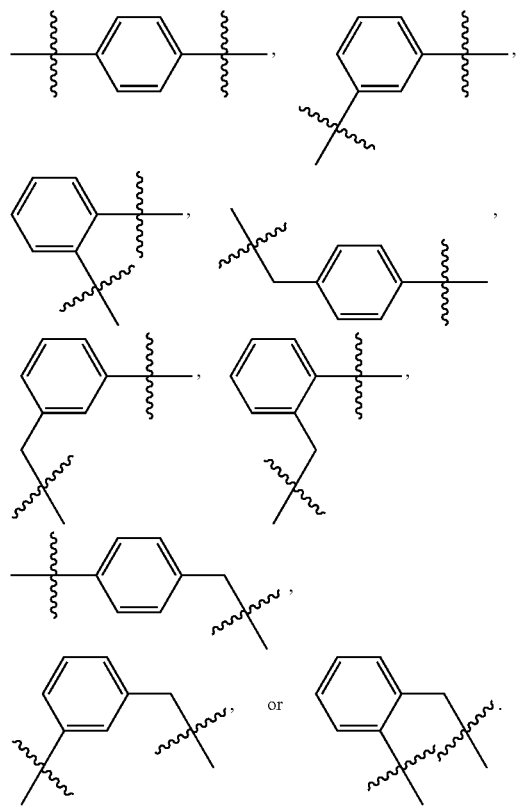

For example, the R in R$^2$ may have the structure of

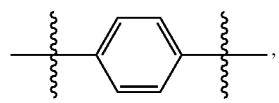

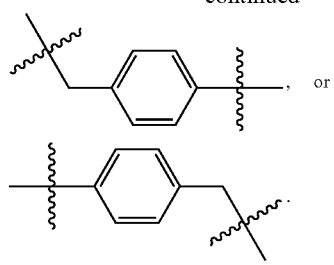

In some embodiments, L$_1$ is —S(O)$_2$—. In some embodiments, L$_1$ is —CO—.

In some embodiments, R$^3$ is selected from Hydrogen, aryl, heteroaryl, —C$_{1-6}$alkyl, —C$_{2-6}$alkenyl, —C$_{2-6}$alkynyl, —(CH$_2$)$_n$COOH, —(CH$_2$)$_n$COOC$_{1-6}$alkyl, —(CH$_2$)$_n$COC$_{1-6}$alkyl, —(CH$_2$)$_n$OH, —(CH$_2$)$_n$CONHR, —(CH$_2$)$_n$NHCOR, —(CH$_2$)$_n$NHCOC$_{1-6}$alkyl, —(CH$_2$)$_n$NHSO$_2$R, —(CH$_2$)$_n$SO$_2$NHR, —(CH$_2$)$_n$SO$_2$R, —(CH$_2$)$_n$SO$_2$NHCOR, —(CH$_2$)$_n$SO$_2$NHCOOR, —(CH$_2$)$_n$SO$_2$NHCONRR, —(CH$_2$)$_n$CONHSO$_2$R, —(CH$_2$)$_n$NHCONRR, —(CH$_2$)$_n$C$_{3-10}$cycloalkyl-COOR, —SC$_{1-6}$alkyl, SOC$_{1-6}$alkyl, SO$_2$C$_{1-6}$alkyl, —C$_{3-10}$cycloheteroalkenyl, —C$_{3-10}$cycloheteroalkyl, substituted or unsubstituted phenyl, —(CH$_2$)$_n$-phenyl, —(CH$_2$)$_n$-aryl and —(CH$_2$)$_n$-heteroaryl, —(CH$_2$)$_n$C$_{3-10}$cycloalkyl, —(CH$_2$)$_n$C$_{3-10}$cycloalkyl-aryl, —(CH$_2$)$_n$C$_{3-10}$cycloalkyl-heteroaryl, —(CH$_2$)C$_{4-10}$cycloalkenyl, —(CH$_2$)$_n$C$_{4-10}$cycloalkenyl-aryl, —(CH$_2$)$_n$C$_{4-10}$cycloalkenyl-heteroaryl, —(CH$_2$)$_n$C$_{2-10}$cycloheteroalkyl, —(CH$_2$)$_n$C$_{2-10}$cycloheteroalkenyl, —C$_{2-6}$alkenyl-alykl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkynyl-(CH$_2$)$_n$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{3-7}$cycloheteroalkyl, —C$_{2-6}$alkynyl-C$_{3-7}$cycloheteroalkenyl, —CONH—(CH$_2$)$_n$phenyl, wherein n equals to 0 to 6 (i.e., 0, 1, 2, 3, 4, 5, or 6), and each CH$_2$ is unsubstituted or substituted with one or two substituents selected from C$_1$-C$_6$alkyl, —OH, —CN, —CF$_3$, halogen, COOH, COC$_1$-C$_6$alkyl, COOC$_1$-C$_6$alkyl, and —NH$_2$, wherein each NH is unsubstituted or substituted with C$_1$-C$_6$alkyl, —OH, halogen, COOH, COC$_1$-C$_6$alkyl, COOC$_1$-C$_6$alkyl.

In some embodiments, the compounds may have structure

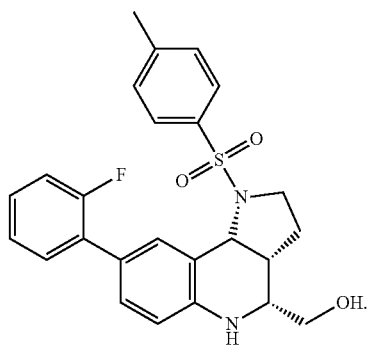

In some cases, when the compounds has the structure

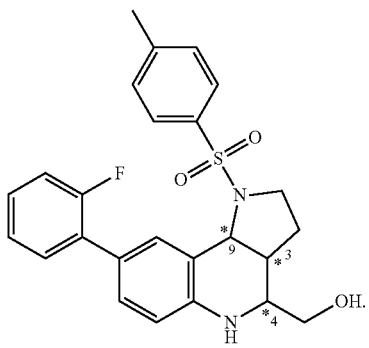 [SMILES: Cc1ccc(S(=O)(=O)N2CCC3C(CO)Nc4ccc(-c5ccccc5F)cc4C32)cc1]

wherein the structure has a stereochemistry of (3aR, 4R, 9bR), (3aS, 3S, 9bS), (3aR, 4S, 9bS), or (3aS, 4R, 9bS). For example, the structure may have a stereochemistry of (3aR, 4R, 9bR).

In some embodiments, the compounds may have structure

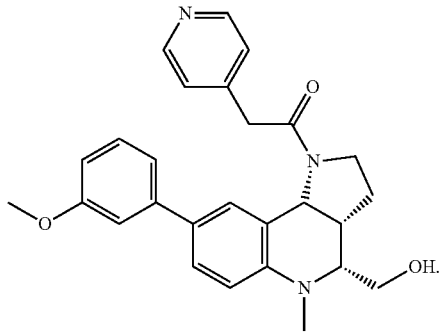

In some embodiments, the compounds may have structure

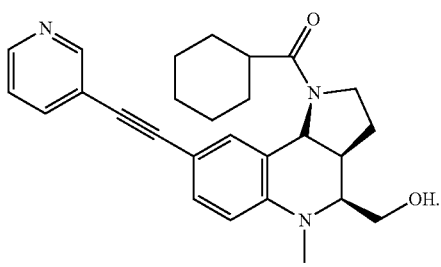

In some embodiments, the compounds may have structure

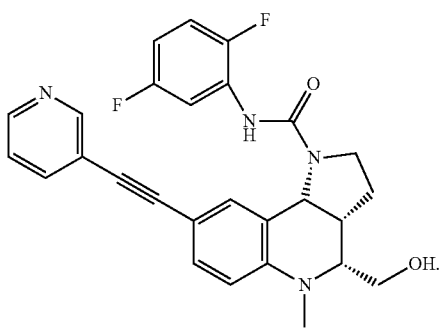

The disclosed compounds may be in free base form unassociated with other ions or molecules. In some cases, the compounds may be pharmaceutically acceptable salts, solvates, or prodrugs thereof. One aspect provides a disclosed compound or a pharmaceutically acceptable salt. One aspect provides a disclosed compound or a pharmaceutically acceptable salt or solvate thereof. One aspect provides a pharmaceutically acceptable salt of a disclosed compound. One aspect provides a solvate of a disclosed compound. One aspect provides a hydrate of a disclosed compound.

One aspect provides a prodrug of a disclosed compound. By "prodrug" is meant any compound that must undergo bioactivation before exhibiting its intended pharmacological effects. Since prodrugs are known to enhance numerous desirable qualities of pharmaceuticals (e.g., solubility, bioavailability, manufacturing, etc.), the disclosed compounds can be delivered in prodrug form. Thus, both prodrugs of the compounds, methods of delivering the same and compositions containing the same are disclosed herein. Prodrugs are intended to include any covalently bonded carriers that release an active parent drug (compound) in vivo when such prodrug is administered to a subject. Prodrugs are prepared, for example, by modifying functional groups present in the compound in such a way that the modifications are cleaved, either in routine manipulation or in vivo, to the parent compound. Prodrugs include compounds wherein a hydroxyl or amino group is bonded to any group that, when the prodrug is administered to a subject, it cleaves to form a free hydroxyl or free amino group, respectively. Examples of prodrugs include, but are not limited to, acetate, formate, and benzoate derivatives of alcohol and amine functional groups in the disclosed compounds. Examples of prodrugs include, but are not limited to, benzamide derivatives of an amine functional group in the active compound and the like. Other examples of prodrugs include compounds that comprise-NO, —NO$_2$, —ONO, or —ONO$_2$ moieties. For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_{1-8}$)alkyl, ($C_{1-12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_{1-2}$) alkylamino ($C_{2-3}$)alkyl (such as 3-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino ($C_{2-3}$)alkyl.

Similarly, if a disclosed compound or a pharmaceutically acceptable form of the compound contains an alcohol functional group, a prodrug can be formed by the replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$) alkoxycarbonyloxymethyl, N—($C_{1-6}$)alkoxy carbonylaminomethyl, succinoyl, ($C_{1-6}$)alkanoyl, a-amino ($C_{1-4}$)alkanoyl, arylacyl, and a-aminoacyl, or a-aminoacyl-a-aminoacyl, where each a-aminoacyl group is independently selected from the naturally occurring L-amino acids, —P(O)(OH)$_2$, —P(O)(O(C$_1$-

₆)alkyl)₂ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where Rand R' are each independently $(C_{1-10})$alkyl, $(C_{3-7})$ cycloalkyl, benzyl, a natural a-aminoacyl or natural «-aminoacyl-natural-«-aminoacyl, —C(OH)C(O)OY1 wherein Y1 is H, $(C_{1-6})$ alkyl or benzyl, C(OY2)Y3 wherein Y2 is $(C_{1-4})$alkyl and Y3 is $(C_{1-6})$alkyl, carboxy $(C_{1-6})$alkyl, amino $(C_{1-4})$alkyl or mono-N- or di-N,N-$(C_{1-6})$alkylaminoalkyl, —C(Y4) Y5 wherein Y4 is H or methyl and Y5 is mono-N- or di-N,-$(C_{1-6})$alkylamino, morpholino, piperidin-1-yl or pyrrolidin-1-yl.

In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

Pharmaceutical Formulations

In another aspect, the present disclosure provides pharmaceutical formulations comprising one or more of the small molecule compounds herein.

The small molecule compounds herein may be in the form of a pharmaceutically acceptable salt. When used in medicine the salts should be pharmaceutically acceptable, but non-pharmaceutically acceptable salts may conveniently be used to prepare pharmaceutically acceptable salts thereof. Examples of pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group. Suitable buffering agents include: acetic acid and a salt (about 1-2% w/v); citric acid and a salt (about 1-3% w/v); boric acid and a salt (about 0.5-2.5% w/v); and phosphoric acid and a salt (about 0.8-2% w/v). Suitable preservatives include benzalkonium chloride (about 0.003-0.03% w/v); chlorobutanol (about 0.3-0.9% w/v); parabens (about 0.01-0.25% w/v) and thimerosal (about 0.004-0.02% w/v).

Also disclosed herein may be pharmaceutical formulations that comprise an effective amount of one or more compounds disclosed herein optionally included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds, and with each other, in a manner such that there is no interaction which would substantially impair the desired pharmaceutical efficiency.

As used herein, "pharmaceutically acceptable carrier" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self-emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as a-, P—, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

For oral administration, one or more compounds herein can be formulated readily by combining the active compound(s) with pharmaceutically acceptable carriers well known in the art. Such carriers enable the compounds to be formulated as tablets, pills, dragees, capsules, liquids, gels, syrups, slurries, suspensions and the like, for oral ingestion by a subject to be treated.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also contemplated are oral dosage forms of one or more disclosed compounds. The compound(s) may be chemically modified so that oral delivery of the derivative is efficacious. Generally, the chemical modification contemplated is the attachment of at least one moiety to the compound itself, where said moiety permits (a) inhibition of proteolysis; and (b) uptake into the blood stream from the stomach or intestine. Also desired is the increase in overall stability of the compound(s) and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Other polymers that could be used are poly-1,3-dioxolane and poly-1,3,6-tioxocane. In some aspects for pharmaceutical usage, as indicated above, are polyethylene glycol moieties.

The location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. In some aspects, the release will avoid the deleterious effects of the stomach environment, either by protection of the compound or by release of the biologically active material beyond the stomach environment, such as in the intestine.

To ensure full gastric resistance a coating impermeable to at least pH 5.0 is important. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The disclosed compounds can be included in the formulation as fine multiparticulates in the form of granules or pellets of particle size about 1 mm. The formulation of the material for capsule administration could also be as a powder, lightly compressed plugs or even as tablets. The compound could be prepared by compression.

Colorants and flavoring agents may all be included. For example, the compound may be formulated (such as by liposome or microsphere encapsulation) and then further contained within an edible product, such as a refrigerated beverage containing colorants and flavoring agents.

One may dilute or increase the volume of compound delivered with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicel. Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the compound to prevent sticking during the formulation process. Lubricants may be used as a layer between the compound and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compound into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the disclosure. The compound is delivered to the lungs of a mammal while inhaling and traverses across the lung epithelial lining to the blood stream using methods well known in the art. Contemplated for use in the practice of methods disclosed herein are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of these methods are the Ultravent nebulizer, manufactured by Mallinckrodt, Inc., St. Louis, Missouri; the Acorn II nebulizer, manufactured by Marquest Medical Products, Englewood, Colorado; the Ventolin metered dose inhaler, manufactured by Glaxo Inc., Research Triangle Park, North Carolina; and the Spinhaler powder inhaler, manufactured by Fisons Corp., Bedford, Massachusetts.

All such devices require the use of formulations suitable for the dispensing of compound. Typically, each formulation is specific to the type of device employed and may involve the use of an appropriate propellant material, in addition to the usual diluents, and/or carriers useful in therapy. Also, the use of liposomes, microcapsules or microspheres, inclusion complexes, or other types of carriers is contemplated. Chemically modified compound may also be prepared in different formulations depending on the type of chemical modification or the type of device employed. Formulations suitable for use with a nebulizer, either jet or ultrasonic, will typically comprise compound dissolved in water at a concentration of about 0.1 to about 25 mg of biologically active compound per mL of solution. The formulation may also include a buffer and a simple sugar (e.g., for stabilization and regulation of osmotic pressure). The nebulizer formulation may also contain a surfactant, to reduce or prevent surface induced aggregation of the compound caused by atomization of the solution in forming the aerosol.

Formulations for use with a metered-dose inhaler device will generally comprise a finely divided powder containing the compound suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound and may also include a bulking agent, such as lactose, sorbitol, sucrose, or mannitol in amounts which facilitate dispersal of the powder from the device, e.g., about 50 to about 90% by weight of the formulation. The compound should most advantageously be prepared in particulate form with an average particle size of less than 10 mm (or microns), such as about 0.5 to about 5 mm, for an effective delivery to the distal lung.

Nasal delivery of a disclosed compound is also contemplated. Nasal delivery allows the passage of a compound to the blood stream directly after administering the therapeutic product to the nose, without the necessity for deposition of the product in the lung.

Formulations for nasal delivery include those with dextran or cyclodextran. For nasal administration, a useful device is a small, hard bottle to which a metered dose sprayer is attached. In one embodiment, the metered dose is delivered by drawing the pharmaceutical composition solution into a chamber of defined volume, which chamber has an aperture dimensioned to aerosolize and aerosol formulation by forming a spray when a liquid in the chamber is compressed. The chamber is compressed to administer the pharmaceutical composition. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. In some aspects, the nasal inhaler will provide a metered amount of the aerosol formulation, for administration of a measured dose of the drug.

The compounds herein, when it is desirable to deliver them systemically, may be formulated for parenteral administration by injection, e.g., by bolus injection or continuous infusion.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro) capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

Methods of Screening

Further disclosed herein include methods for screening, identifying, analyzing, and/or evaluating compounds herein that modulate (e.g., inhibit) RNA-guided nucleases. In some embodiments, such methods may comprise a combination of biochemical and cellular assays.

The methods may be performed for screening, identifying, analyzing, and/or evaluating compounds that modulate (e.g., inhibit) any RNA-guided nucleases, such as RNA-guided nucleases in any CRISPR-Cas system.

Detecting Nuclease Activity

The methods detecting nuclease activity, for example in Cas9, are based in part on displacement of a weakly held distal non-target strand (FIG. 1A) that can be displaced upon addition of excess complementary single stranded DNA. Systems designed for use in the nuclease activity methods comprise fluorescently labeling 5' end of the non-target strand which can be quenched in a cleavage-dependent manner by adding in excess a complementary DNA strand labeled with a 3' quencher. Upon displacement of the unlabeled strand and annealing of the two labeled strands, fluorescence is quenched by a FRET mechanism, providing a proxy measurement for Cas9 activity at the RuvC domain based on the extent of fluorescence loss. This concept can be applied, for example in the Cas12 systems utilizing 3' end of the non-target strand where the Pam is located 5' of the target sequence as with a Cas12a enzyme. Accordingly, this approach can be extrapolated further for Cas proteins based on PAM location and with an understanding of the cleavage activity of the particular Cas protein complexes utilized.

In other aspects, the invention provides a method of detecting nuclease activity of an RNA-guided nuclease, and a method of identifying an inhibitor of an RNA-guided nuclease. The invention can be used to detect nuclease activity or identify inhibitors of nuclease activity of CRISPR systems.

In certain embodiments, the invention provides a method of detecting nuclease activity of an RNA guided endonuclease-guide complex comprising: contacting a) an RNA guided endonuclease-guide complex, b) a double-stranded probe comprising a first oligonucleotide comprising at least one PAM site and a fluorescent reporter at the 5' terminus and a second oligonucleotide complementary to the first oligonucleotide, wherein the second oligonucleotide is designed to hybridize to the guide whereby the first oligonucleotide and the second oligonucleotide are cleaved by the endonuclease, and c) a third oligonucleotide comprising a fluorescence quencher at the 3' terminus and designed to hybridize to and displace the cleaved first oligonucleotide from the cleaved second oligonucleotide, and detecting a decrease in fluorescence polarization relative to a reference, thereby detecting nuclease activity of the RNA guided endonuclease-guide complex. The method is generally applicable for an RNA guided endonuclease system, wherein the PAM is located 3' to the target sequence along the non-target strand (NTS) of the DNA, for instance Cas9.

In certain embodiments, the invention provides a method of detecting nuclease activity of an RNA guided endonuclease-guide complex comprising: contacting a) an RNA guided endonuclease-guide complex, b) a double-stranded probe comprising a first oligonucleotide comprising at least one PAM site and a fluorescent reporter at the 3' terminus and a second oligonucleotide complementary to the first oligonucleotide, wherein the second oligonucleotide is designed to hybridize to the guide whereby the first oligonucleotide and the second oligonucleotide are cleaved by the endonuclease, and c) a third oligonucleotide comprising a fluorescence quencher at the 5' terminus and designed to hybridize to and displace the cleaved first oligonucleotide from the cleaved second oligonucleotide, and detecting a decrease in fluorescence polarization relative to a reference, thereby detecting nuclease activity of the RNA guided endonuclease-guide complex.

The third oligonucleotide may also be referred to herein as a displacer oligonucleotide.

The method is generally applicable for an RNA guided endonuclease system wherein the PAM is located 5' to the target sequence along the non-target strand (NTS) of the DNA, for instance Cas12a (Cpf1).

In an aspect, the methods can further comprise contacting the elements i) an RNA guided nuclease-guide complex, ii) a double-stranded probe comprising a first oligonucleotide comprising at least one PAM site and a fluorescent reporter at the 5' terminus or the 3' terminus and a second oligonucleotide complementary to the first oligonucleotide, wherein the second oligonucleotide is designed to hybridize to the guide whereby the first oligonucleotide and the second oligonucleotide are cleaved by the endonuclease, and iii) a third oligonucleotide comprising a fluorescence quencher, the fluorescent quencher located at the 3' terminus when the fluorescent reporter is at the 5' terminus of the first oligonucleotide, or at the 5' terminus when the fluorescent reporter is at the 3' terminus of the first oligonucleotide, and designed to hybridize to and displace the cleaved first oligonucleotide from the cleaved second oligonucleotide with an agent. The step of detecting the decrease in the reduction of fluorescence polarization relative to the reference can thereby identify the agent as an inhibitor of the nuclease activity of the RNA guided endonuclease-guide complex. The quantitation of the reduction of fluorescence polarization can be indicative of the amount of inhibition by an agent, and therefore, its relative level of effectiveness as an inhibitor. Thus, the use of an agent in the agent in the detection methods can further allow for screening of inhibitors.

Primary Assays

The methods may comprise one or more primary assays. The primary assays may be biochemical assays that assess the binding of the RNA-guided endonuclease with a target DNA. In some embodiments, the primary assay may be a fluorescence Polarization-based Assays.

The Fluorescence Polarization (FP)-based Assay may monitor the change in the fluorescence polarization of the fluorophore-labelled PAM-rich target DNA (e.g., a 12PAM-DNA) upon binding to [Cas9:guideRNA]complex. In this assay, the complexation of [Cas9:guideRNA] to PAM-rich target DNA shows a dose-dependent increase in fluorophore polarization.

Fluorescence polarization is a useful technique to monitor the interaction between two molecules, including for example, Cas9-gRNA (ribonucleoprotein) complex and target DNA (e.g., 12PAM). In this assay, the complexation of CRISPR:guideRNA complex to the double-stranded PAM-containing substrate DNA results in cleavage of the substrate DNA. Upon cleavage, the length of the double-stranded region of the substrate DNA is reduced. The fluorophore-bearing first strand can then be displaced from the complementary strand by a displacer strand bearing a quencher moiety (Disp-Q).

Fluorescence polarization may be used to measure the binding constants and kinetics of reactions that cause a change in the rotational time of the molecules. The technique is based on the change in the tumbling rate or mass after complexation. Smaller fragments may be fluorescently labelled and polarizations may be compared before and after complexation in the presence and absence of compounds. If the fluorophore is bound to a small molecule, the rate at which it tumbles can decrease significantly when it is bound tightly to a large protein. If the fluorophore is attached to the larger protein in a binding pair, the difference in polarization between bound and unbound states will be smaller (because the unbound protein will already be fairly stable and tumble slowly to begin with) and the measurement will be less accurate. The degree of binding is calculated by using the difference in anisotropy of the partially bound, free and fully bound (large excess of protein) states measured by titrating the two binding partners. If the fluorophore is bound to a relatively large molecule like a protein or an RNA, the change in the mobility accompanying folding can be used to study the dynamics of folding. This provides a measure of the dynamics of how the protein achieves its final, stable 3D shape.

The FP-based method was shown to be PAM dependent and can be optimized by adjusting, e.g., the DS-Fluor:CRISPR ratio, the DS-Fluor:Disp-Q ratio, incubation time, and other parameters. The method was also shown to be sensitive to inhibition of SpCas9 by AcrIIA4.

The FP-based method was then performed to screen 50,000 compounds consisting of structurally diverse scaffolds with vast functional variability against SaCas9. DMSO (the solvent) was used as the negative control and ApoSa-Cas9 nuclease was used as a positive control. Interestingly, a portion of the hit compounds were found to have similarity in their molecular scaffold with variation in the stereochemistry and functionality. Compounds were examined for dose dependence on activity and showed dose dependent Cas9 inhibition activity with low $IC_{50}$ values. These finding further confirms and validate the primary assay. The FP-based method is generally useful to screen for CRISPR nuclease inhibitor compounds. In particular, the method has also been used to screen for inhibitors of SaCas9 and FnCas9.

According to the invention, the method can be optimized by adjusting absolute and relative reagent concentrations, probe lengths, probe sequences and base-paring capacity, time course, and other parameters.

The relative concentration of DS-Fluor to CRISPR protein is adjustable and can be, without limitation, 5:1, 2:1, 1:1, 1:2, 1:5, 1:10, 1:20, 1:50, or from 5:1 to 2:1, or from 2:1 to 1:1, or from 1:1 to 1:2, or from 1:2 to 1:5, or from 1:5 to 1:10, or from 1:10 to 1:20, or from 1:20 to 1:50.

The relative concentration of DS-Fluor to Disp-Q quencher is adjustable and can be, without limitation, 5:1, 2:1, 1:1, 1:2, 1:5, 1:10, 1:20, 1:50, or from 5:1 to 2:1, or from 2:1 to 1:1, or from 1:1 to 1:2, or from 1:2 to 1:5, or from 1:5 to 1:10, or from 1:10 to 1:20, or from 1:20 to 1:50.

The reaction time is adjustable and can be, without limitation 5 min, 10 min, 15 min, 20 min, 30 min, 45 min, 60 min, 90 min, 120 min, 150 min, 180 min, 210 min, 240 min, or longer or from 5 to 10 min., from 10 to 15 min., from 15 to 20 min, from 20 to 30 min, from 30 to 45 min, from 45 to 60 min, from 60 to 90 min, from 90 to 120 min, from 120 to 150 min, from 150 to 180 min, from 180 to 210 min, from 210 to 240 min.

In various embodiments such as exemplified herein, the double-stranded probe. In other embodiments, other quenchers, e.g., those shown in the following.

TABLE 1

Quencher labels for fluorescent hybridization probes

| Quencher | Absorption Maximum (nm) |
|---|---|
| DDQ-I | 430 |
| Dabcyl | 475 |
| Eclipse | 530 |
| Iowa Black FQ | 532 |
| BHQ-1 | 534 |
| QSY-7 | 571 |
| BHQ-2 | 580 |
| DDQ-II | 630 |
| Iowa Black RQ | 645 |
| QSY-21 | 660 |
| BHQ-3 | 670 |

DDQ or Deep Dark Quenchers are available from Eurogentec; Eclipse quenchers are available from Epoch Biosciences; Iowa quenchers are available from Integrated DNA Technologies; BHQ or Black Hole quenchers are available from Biosearch Technologies; and QSY quenchers are available from Molecular Probes.

In the above sequences, the PAM is bold, protospacer italicized, and displacer binding site underlined.

The following table provides additional fluorophores useful for the invention.

TABLE 2

Fluorophore labels for fluorescent hybridization probes

| Fluorophore | Alternative Fluorophore | Excitation (nm) | Emission (nm) |
|---|---|---|---|
| FAM | | 495 | 515 |
| TET | CAL Fluor Gold 540 | 525 | 540 |
| HEX | JOE, VIC, CAL Fluor Orange 560 | 535 | 555 |
| Cy3 | NED, Quasar 570, Oyster 556 | 550 | 570 |
| TMR | CAL Fluor Red 590 | 555 | 575 |
| ROX | LC red 610, CAL Fluor Red 610 | 575 | 605 |
| Texas red | LC red 610, CAL Fluor Red 610 | 585 | 605 |
| LC red 640 | CAL Fluor Red 635 | 625 | 640 |
| Cy5 | LC red 670, Quasar 670, Oyster 645 | 650 | 670 |
| LC red 705 | Cy5.5 | 680 | 710 |

CAL and Quasar fluorophores are available from Biosearch Technologies; VIC and NED are available from Applied Biosystems; Cy dyes are available from Amersham Biosciences; Oyster fluorophores are available from Integrated DNA Technologies; and LC (Light Cycler) fluorophores are available from Roche Applied Science.

Secondary Assays

The methods may further comprise one or more secondary assays. The secondary assays may be cell-based assays for testing the effect of candidate compounds on RNA-guided endonuclease activity in cells.

In some embodiments, the secondary assay may be an EGFP disruption assay. In such assay, a quantitative human cell-based reporter assay that enables rapid quantitation of targeted nuclease activities is used to characterize off-target cleavage of Cas9-based RNA guided endonucleases. In this assay, the activities of nucleases targeted to a single integrated EGFP reporter gene can be quantified by assessing loss of fluorescence signal in human U2OS.EGFP cells caused by inactivating frameshift insertion/deletion (indel) mutations introduced by error prone non-homologous end-joining (NHEJ) repair of nuclease-induced double-stranded breaks (DSBs).

In one protocol, U2OS.EGFP cells harboring a single integrated copy of an EGFP-PEST fusion gene are cultured (see e.g., Reyon et al., Nat Biotech 30, 460-465 (2012), which is herein incorporated by reference in its entirety). For transfections, 200,000 cells are Nucleofected with gRNA expression plasmid and pJDS246 together with 30 ng of a Td-tomato-encoding plasmid using the SE Cell Line 4D-Nucleofector™ X Kit (Lonza) according to the manufacturer's protocol. Cells are analyzed 2 days post-transfection using a BD LSRII flow cytometer. Transfections for optimizing gRNA/Cas9 plasmid concentration are performed in triplicate and all other transfections are performed in duplicate. PCR amplification is used for sequence verification of endogenous human genomic sites. PCR reactions are performed using Phusion Hot Start II high-fidelity DNA polymerase (NEB). Loci are amplified using touchdown PCR (98° C., 10 s; 72-62° C., −1° C./cycle, 15 s; 72° C., 30 s] 10 cycles, [98° C., 10 s; 62° C., 15 s; 72° C., 30 s] 25 cycles). Alternatively, PCR for other targets are performed with 35 cycles at a constant annealing temperature of 68° C. or 72° C., and 3% DMSO or 1M betaine, if necessary. PCR products are analyzed on a QIAXCEL capillary electrophoresis system to verify both size and purity. Validated products are treated with ExoSap-IT (Affymetrix) and sequenced by the Sanger method (MGH DNA Sequencing Core) to verify each target site.

In some embodiments, the secondary assay may be a fluorescence-based assay using cells expressing a single plasmid construct containing coding sequence for an RNA-guided endonuclease, a fluorescent peptide or protein, and a guide RNA. An example of such assays is disclosed in Moore R., Spinhirne et al., (2015). CRISPR-based self-cleaving mechanism for controllable gene delivery in human cells. Nucleic Acids Res 43, 1297-1303, which is incorporated by reference herein in its entirety.

In some embodiments, the secondary assay may be a loss-of-signal, non-homologous end joining (NHEJ) assay. An example of such assays is disclosed in Nguyen D P et al., (2016). Ligand-binding domains of nuclear receptors facilitate tight control of split CRISPR activity. Nat Commun 7, 12009, which is incorporated by reference herein in its entirety.

Other assays may be used in the methods discussed herein. In some embodiments, the methods may include a spinach transcription assay, which detects the activity of an RNA-guided endonuclease. In one embodiment, the level of transcription is suppressed by Cas9 nuclease activity in an in vitro assay. In various embodiments, the transcription assay involves expression of a nucleic acid aptamer that binds a molecular fluorophore to generate a fluorescent signal. Such aptamer-fluorophore combinations are known in the art, including for example, the Spinach aptamer having the sequence 5'-GGGAGACGCAACUGAAUGAAAUG-GUGAAGGACGGGUCCAGGUGUGGCUGCUU CGGCAGUGCAGCUUGUUGAGUAGAGUGUGAG-CUCCGCG UAACUAGUCGCGUCAC-3' (SEQ ID NO:1), and the fluorophore 4-(3,5-difluoro-4-hydroxy benzylidene)-1,2-dimethyl-1H-imidazol-5-one (DFHBI) (see, e.g., US20120252699 and US20140220560, each of which is incorporated herein in their entirety). In the Spinach assay, Cas9 can cleave the DNA template and thus inhibit in vitro transcription of the nucleic acid aptamer. In certain embodiments, the guide RNA targeting the Spinach aptamer has the sequence 5'-GCUAUAGGACGCGACCGAAAGUUUUA-GAGCUAGAAAUAGCAAGUUAAAAUAA GGCUA-GUCCGUUAUCAACUUGAAAAAGUGGCACCGA GUCGGUGCUUUU-3' (SEQ ID NO: 2).

In the presence of fluorophore, suppression in transcription results in the reduction of RNA aptamer-fluorophore concentration and hence in the fluorescence signal. In vitro transcription reactions may comprise a purified linear DNA template containing a promoter operatively linked to a nucleic acid sequence encoding an RNA aptamer, ribonucleotide triphosphates, a buffer system (e.g., including DTT and magnesium ions, and an appropriate phage RNA polymerase (e.g., T7 polymerase).

In some embodiments, the methods may include a SURVEYOR nuclease assay. In various embodiments, a SURVEYOR nuclease assay is used to assess genome modification (see e.g., US20150356239, which is herein incorporated by reference in its entirety. In one protocol, 293 FT cells are transfected with plasmid DNA. Cells were incubated at 37° C. for 72 hours post-transfection prior to genomic DNA extraction. Genomic DNA is extracted using the QuickExtract DNA Extraction Solution (Epicentre) following the manufacturer's protocol. Briefly, pelleted cells are resuspended in QuickExtract solution and incubated at 65° C. for 15 minutes and 98° C. for 10 minutes. The genomic region flanking the CRISPR target site for each gene is PCR amplified, and products are purified using QiaQuick Spin Column (Qiagen) following the manufacturer's protocol. 400 ng total of the purified PCR products are mixed with 2 µL 10× Taq DNA Polymerase PCR buffer (Enzytrsaties) and ultrapure water to a final volume of 20 µL, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products are treated with SURVEYOR nuclease and SURVEYOR enhancer S (Transgenomics) following the manufacturer's recommended protocol, and analyzed on 4-20% Novex TBE poly-acrylamide gels (Life Technologies). Gels are stained with SYBR Gold DNA stain (Life Technologies) for 30 minutes and imaged with a Gel Doe gel imaging system (Bio-rad). Quantification is based on relative band intensities.

Small molecule inhibitors of RNA guided endonucleases can also be used to regulate genome editing technologies in other organisms, including invertebrates, plants, and unicellular organisms (e.g., bacteria). Potential uses include regulating gene drives for entomological and agricultural uses. In addition, it is anticipated that Cas9 inhibitors will be valuable probes to understand the role of Cas9 in CRISPR-mediated bacterial immunity (e.g., spacer acquisition) (Nunez et al., Nature. 2015 Mar. 12; 519 (7542):193-8; Heler et al., Nature 2015, 519, 199-202). Along similar lines, Cas9 inhibitors can be deployed for directed evolution of Cas9. It is hypothesized that Cas9 inhibitors will disrupt bacterial immunity against bacteriophages (or toxic DNA) by interfering with the CRISPR-Cas9-based immune surveillance system in bacteria. Akin to the development of antibiotic resistance, bacteria will be forced to evolve Cas9 protein.

Nuclease inhibitors of the invention are useful to inhibit the nuclease activity of a CRISPR protein—guide complex.

The guide need not be naturally occurring and can comprise, e.g., non-naturally occurring nucleotides, analogs, and/or chemical modifications.

Test Compounds and Extracts

Various types of compounds libraries may be used for screening the inhibitors disclosed herein. In general, small molecule compounds are known in the art or are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N. H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. For example, a library of 8,000 novel small molecules is available, which was created using combinatorial methods of Diversity-Oriented Synthesis (DOS) (corner et al, Proc Natl Acad Sci USA 108, 6751 (Apr. 26, 2011); Lowe et al, J Org Chem 77, 7187 (Sep. 7, 2012); Marcaurelle et al, J Am Chem Soc 132, 16962 (Dec. 1, 2010))—to investigate chemical compounds not represented in traditional pharmaceutical libraries (Schreiber, S. L. (2000). Science 287, 1964-1969; Schreiber et al, Nat Biotechnol 28, 904 (September 2010), each of which is herein incorporated by reference in their entirety). Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., Proc. Natl. Acad. Sci. U.S.A. 90:6909, 1993; Erb et al., Proc. Natl. Acad. Sci. USA 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl. 33:2061, 1994; and Gallop et al., J. Med. Chem. 37:1233, 1994. Furthermore, if desired, any library or compound is readily modified using standard chemical, physical, or biochemical methods.

Libraries of compounds may be presented in solution (e.g., Houghten, Biotechniques 13:412-421, 1992), or on beads (Lam, Nature 354:82-84, 1991), chips (Fodor, Nature 364:555-556, 1993), bacteria (Ladner, U.S. Pat. No. 5,223,409), spores (Ladner U.S. Pat. No. 5,223,409), plasmids (Cull et al., Proc Natl Acad Sci USA 89:1865-1869, 1992) or on phage (Scott and Smith, Science 249:386-390, 1990; Devlin, Science 249:404-406, 1990; Cwirla et al. Proc. Natl. Acad. Sci. 87:63786382, 1990; Felici, J. Mol. Biol. 222: 301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is identified as containing a compound of interest, further fractionation of the positive lead extract is necessary to isolate chemical constituents responsible for the observed effect. Thus, the goal of the extraction, fractionation, and purification process is the careful characterization and identification of a chemical entity within the crude extract that achieves a desired biological effect. Methods of fractionation and purification of such heterogenous extracts are known in the art.

Small molecule compounds herein may have a molecular weight below 2,000 Daltons, more preferably between 300 and 1,000 Daltons, and most preferably between 400 and 700 Daltons. It is preferred that these small molecules are organic molecules.

Methods of Use

Small molecule inhibitors of RNA-guided endonucleases (e.g., Cas9) were developed that have the potential to allow rapid, dosable, and/or temporal control of Cas9 activities. In some embodiments, provided herein include methods for inhibiting an RNA-guided endonuclease comprising contacting the RNA-guided endonuclease with one or more compounds described herein. In some examples, methods herein may include a method for treating a subject, comprising administering an RNA-guided endonuclease-RNA complex or a reagent causing expression of the RNA-guided endonuclease-RNA complex to the subject, and administering one or more compounds described herein.

The methods may be performed in vitro. Alternatively or additionally, the methods may be performed in vivo. In some examples, the methods may be performed in a cell. The cell may be a germline cell. The cell may also be any types of cell, e.g., a stem cell such as an embryonic stem cell or a induced pluripotent stem cell. In certain examples, the methods may be performed in a cell in an organism (e.g., human, mammal, vertebrate, invertebrate, insect, plant). In some cases, the cell may be a prokaryotic cell, e.g., a bacterium. In certain cases, the cell may be a eukaryotic cell, e.g., a mammalian (e.g., human) cell, an insect cell, a plant cell, a fungal cell (e.g., a yeast cell).

Reports of small-molecule controlled Cas9 activity are present in literature (Senis et al., BiotechnolJ 2014, 9, 1402-12; Wrightetal., Proc. Natl. Acad. Sci USA. 2015 Mar.

10; 112(10):2984-9; Gonzalez et al., Cell Stem Cell 2014, 15, 215-26; Davis et al., Nat Chem Biol 2015, 11, 316-8). However, none of them ensure dosability—the small molecules act merely as inducers of Cas9 activity. Further, most of these small molecule systems are not reversible upon removal of the small molecule (Zetsche et al., Nat Biotech 2015, 33, 139-142; Davis et al., Nat Chem Biol 2015, 11, 316-8), and therefore, do not allow precise temporal control in transcriptional regulatory technologies.

Small molecule inhibitors of RNA guided endonucleases (e.g., Cas9) have potential therapeutic uses for regulating genome editing technologies involving RNA-guided endonucleases. Dosable control of the therapeutic activity of RNA-guided endonucleases introduced into a subject or cell of a subject is important for effective genome editing therapeutic strategies. Small molecule inhibitors of RNA-guided endonucleases can be administered to a subject undergoing RNA guided endonuclease based gene therapy or any other RNA guided endonuclease based therapy. In certain embodiments, the subject is a human or mammal. Small molecule inhibitors of RNA-guided endonucleases eliminate or reduce undesirable off-target editing and chromosomal translocations when present at high concentrations. Furthermore, small molecule inhibitors of RNA-guided endonucleases can be used to rapidly terminate constitutively active Cas9, following on-target gene-editing.

Small molecule inhibitors of RNA-guided endonucleases can also be used to regulate genome editing technologies in other organisms, including invertebrates, plants, and unicellular organisms (e.g., bacteria). Potential uses include regulating gene drives for entomological and agricultural uses. In addition, it is anticipated that Cas9 inhibitors will be valuable probes to understand the role of Cas9 in CRISPR-mediated bacterial immunity (e.g., spacer acquisition) (Nunez et al., Nature. 2015 Mar. 12; 519(7542):193-8; Heler et al., Nature 2015, 519, 199-202). Along similar lines, Cas9 inhibitors can be deployed for directed evolution of Cas9. It is hypothesized that Cas9 inhibitors will disrupt bacterial immunity against bacteriophages (or toxic DNA) by interfering with the CRISPR-Cas9-based immune surveillance system in bacteria. Akin to the development of antibiotic resistance, bacteria will be forced to evolve Cas9 protein. Accordingly, the inhibitors may also be used as an anti-infection agent.

Agents described herein, including analogs thereof, and/or agents discovered to have medicinal value using the methods described herein are useful as a drug for inhibiting RNA guided endonucleases (e.g., Cas9, Cpf1). For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms. Generally, amounts will be in the range of those used for other agents used in the treatment of disease.

The disclosed compounds may be administered alone (e.g., in saline or buffer) or using any delivery vehicles known in the art. For instance the following delivery vehicles have been described: Cochleates; Emulsomes; ISCOMs; Liposomes; Live bacterial vectors (e.g., *Salmonella, Escherichia coli, Bacillus* calmette-guerin, *Shigella, Lactobacillus*); Live viral vectors (e.g., Vaccinia, adenovirus, Herpes Simplex); Microspheres; Nucleic acid vaccines; Polymers; Polymer rings; Proteosomes; Sodium Fluoride; Transgenic plants; Virosomes; Virus-like particles. Other delivery vehicles are known in the art and some additional examples are provided below.

The disclosed compounds may be administered by any route known, such as, for example, orally, transdermally, intravenously, cutaneously, subcutaneously, nasally, intramuscularly, intraperitoneally, intracranially, and intracerebroventricularly.

In certain embodiments, disclosed compounds are administered at dosage levels greater than about 0.01 mg/kg, such as greater than about 0.01 mg/kg or greater than about 0.1 mg/kg. For example, the dosage level may be from about 0.001 mg/kg to about 50 mg/kg such as from about 0.01 mg/kg to about 25 mg/kg, from about 0.1 mg/kg to about 10 mg/kg, or from about 1 mg/kg to about 5 mg/kg of subject body weight per day, one or more times a day, to obtain the desired therapeutic effect. It will also be appreciated that dosages smaller than about 0.001 mg/kg or greater than about 50 mg/kg (for example about 50-100 mg/kg) can also be administered to a subject.

In one embodiment, the compound is administered once-daily, twice-daily, or three-times daily. In one embodiment, the compound is administered continuously (e.g., every day) or intermittently (e.g., 3-5 days a week). In another embodiment, administration could be on an intermittent schedule.

Further, administration less frequently than daily, such as, for example, every other day may be chosen. In additional embodiments, administration with at least 2 days between doses may be chosen. By way of example only, dosing may be every third day, bi-weekly or weekly. As another example, a single, acute dose may be administered. Alternatively, compounds can be administered on a non-regular basis e.g., whenever symptoms begin. For any compound described herein the effective amount can be initially determined from animal models.

Toxicity and efficacy of the compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices may have a greater effect when practicing the methods as disclosed herein. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage of the compounds disclosed herein for use in humans. The dosage of such agents lies within a range of circulating concentrations that include the $ED_{50}$ with little or no toxicity. The dosage may vary within this range depending upon the dosage form employed and the route of administration utilized. For any compound used in the disclosed methods, the effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography. In certain embodiments, pharmaceutical compositions may comprise, for example, at least about 0.1% of an active compound. In other embodiments, the active compound may comprise between about 2% to about 75% of the weight of the unit, or between about 25% to about 60%, for example, and any range derivable therein. Multiple doses of the compounds are also contemplated.

The formulations disclosed herein are administered in pharmaceutically acceptable solutions, which may routinely contain pharmaceutically acceptable concentrations of salt, buffering agents, preservatives, compatible carriers, and optionally other therapeutic ingredients.

For use in therapy, an effective amount of one or more disclosed compounds can be administered to a subject by any mode that delivers the compound(s) to the desired surface, e.g., mucosal, systemic. Administering the pharmaceutical composition of the present disclosure may be accomplished by any means known to the skilled artisan. Disclosed compounds may be administered orally, transdermally, intravenously, cutaneously, subcutaneously, nasally, intramuscularly, intraperitoneally, intracranially, or Inhibition of function and activity of Cas proteins.

Cas Proteins

The small molecule compounds herein may be used for modulating the activities and functions of Cas proteins in CRISPR-Cas systems.

In general, a CRISPR-Cas or CRISPR system as used herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. By "Protospacer adjacent motif (PAM)" is meant a nucleic acid sequence immediately adjacent the nucleic acid sequence targeted by an RNA guided endonuclease (e.g., Cas9, Cpf1). In certain embodiments, the PAM sequence is the Cas9 PAM sequence: 5'-NGG-3'.

In some embodiments, the PAM may be a 5' PAM (i.e., located upstream of 5' end of the protospacer). In other embodiments, the PAM may be a 3' PAM (i.e., located downstream of 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein His A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the (E≤-actin promoter, the phosphoglycerol kinase (PGK) promoter, and the EF1(E± promoter. An advantageous promoter is the promoter is U6.

The RNA-guided nucleases herein may be identified by their proximity to cas1 genes, for example, though not limited to, within the region 20 kb from the start of the cas1 gene and 20 kb from the end of the cas1 gene. In certain embodiments, the RNA-guided nuclease comprises at least one HEPN domain and at least 500 amino acids, and protein is naturally present in a prokaryotic genome within 20 kb upstream or downstream of a Cas gene or a CRISPR array.

In certain example embodiments, the CRISPR-Cas system may be a Class 2 CRISPR-Cas system. A Class 2 CRISPR-Cas system may be of a subtype, e.g., Type II-A, Type II-B, Type II-C, Type V-A, Type V-B, Type V-C, Type V-U, Type VI-A, Type VI-B, or Type VI-C CRISPR-Cas system. The definition and exemplary members of the CRISPR-Cas system include those described in Kira S. Makarova and Eugene V. Koonin, Annotation and Classification of CRISPR-Cas systems, Methods Mol Biol. 2015; 1311:47-75; and Sergey Shmakov et al., Diversity and evolution of class 2 CRISPR-Cas systems, Nat Rev Microbiol. 2017 March; 15 (3): 169-182.

In certain embodiments, the RNA-guided nucleases may be the nuclease in any CRISPR-Cas system, e.g., a Cas protein (interchangeably used as "CRISPR protein", "Cas effector", "CRISPR effector", "Cas"). Non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Cas12 (e.g., Cas12a, Cas12b, Cas12c, Cas12d), Cas13 (e.g., Cas13a, Cas13b, Cas13c, Cas13d), Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, CasX, Cas Y, Cas14, homologues thereof, or modified versions thereof.

For example, the Cas protein may be a Cas protein of class 2 CRISPR systems, including Type II, Type V and Type VI systems. In certain example embodiments, the Cas protein is Cas9, Cas12a, Cas12b, Cas12c, Cas12d, Cas13a, Cas13b, Cas13c, or Cas13d system. In some embodiments, the small molecule compounds can inhibit Cas9, including but not limited to SpCas9, SaCas9, StCas9 and other Cas9 orthologs. Similarly, the methods may inhibit Cas12, including but not limited to orthologs of Cas12a, Cas12b, and Cas12c, including FnCas12a. Moreover, the method may inhibit Cas13, including but not limited to orthologs of Cas13a, Cas13b, Cas13c, and Cas13d.

In some embodiments, the Cas protein may be a class 2 Type II Cas protein, e.g., Cas9. By "Cas9 (CRISPR associated protein 9)" is meant a polypeptide or fragment thereof having at least about 85% amino acid identity to NCBI Accession No. NP_269215 and having RNA binding activity, DNA binding activity, and/or DNA cleavage activity (e.g., endonuclease or nickase activity). "Cas9 function" can be defined by any of a number of assays including, but not limited to, fluorescence polarization-based nucleic acid bind assays, fluorescence polarization-based strand invasion assays, transcription assays, EGFP disruption assays, DNA cleavage assays, and/or Surveyor assays, for example, as described herein. By "Cas 9 nucleic acid molecule" is meant a polynucleotide encoding a Cas9 polypeptide or fragment thereof. An exemplary Cas9 nucleic acid molecule sequence is provided at NCBI Accession No. NC_002737. In some embodiments, disclosed herein are inhibitors of Cas9, e.g., naturally occurring Cas9 in *S. pyogenes* (SpCas9) or *S. aureus* (SaCas9), or variants thereof. Cas9 recognizes foreign DNA using Protospacer Adjacent Motif (PAM) sequence and the base pairing of the target DNA by the guide RNA (gRNA). The relative ease of inducing targeted strand breaks at any genomic loci by Cas9 has enabled efficient genome editing in multiple cell types and organisms. Cas9 derivatives can also be used as transcriptional activators/repressors.

In some embodiments, the Cas protein may be a class 2 Type V Cas protein, e.g., Cas12a (Cpf1), Cas12b (C2c1), Cas12c (C2c3), or Cas12k. By "Cpf1 (CRISPR associated protein Cpf1)" is meant a polypeptide or fragment thereof having at least about 85% amino acid identity to GenBank Accession No. AJI61006. 1 and having RNA binding activity, DNA binding activity, and/or DNA cleavage activity (e.g., endonuclease or nickase activity). "Cpf1 function" can be defined by any of a number of assays including, but not limited to, fluorescence polarization-based nucleic acid bind assays, fluorescence polarization-based strand invasion assays, transcription assays, EGFP disruption assays, DNA cleavage assays, and/or Surveyor assays, for example, as described herein. By "Cpf1 nucleic acid molecule" is meant a polynucleotide encoding a Cpf1 polypeptide or fragment thereof. An exemplary Cpf1 nucleic acid molecule sequence is provided at GenBank Accession No. CP009633, nucleotides 652838-656740.

In certain example embodiments, the RNA-guided nuclease is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Base Editing

The small molecule compounds may be used to modulate based editing systems. A base editing system may a Cas protein or a variant thereof (e.g., inactive or dead Cas) fused with a functional domains. The Cas protein may be a dead Cas protein or a Cas nickase protein. A base-editing system may comprise a deaminase (e.g., an adenosine deaminase or cytidine deaminase) fused with a Cas protein or a variant thereof. In certain examples, the system comprises a mutated form of an adenosine deaminase fused with a dead CRISPR-Cas or CRISPR-Cas nickase. The mutated form of the adenosine deaminase may have both adenosine deaminase and cytidine deaminase activities. Examples of base editing systems include those described in WO2019071048, WO2019084063, WO2019126716, WO2019126709, WO2019126762, WO2019126774, Cox DBT, et al., RNA editing with CRISPR-Cas13, Science. 2017 Nov. 24; 358 (6366):1019-1027; Abudayyeh O O, et al., A cytosine deaminase for programmable single-base RNA editing, Science 26 Jul. 2019: Vol. 365, Issue 6451, pp. 382-386; Gaudelli N M et al., Programmable base editing of A·T to G·C in genomic DNA without DNA cleavage, Nature volume 551, pages 464-471 (23 Nov. 2017); Komor A C, et al., Programmable editing of a target base in genomic DNA without double-stranded DNA cleavage. Nature. 2016 May 19; 533(7603):420-4.

Applications in Non-Animal Organisms and Animals

The small molecule compounds herein may be used to modulate the functions and activities of RNA-guided nuclease (e.g., Cas proteins), variants thereof, and fragments thereof in animals and non-animal organisms. In some examples, the animals and non-animal organisms may have been engineered to constitutively or inducibly express an RNA-guided nuclease (e.g., Cas protein). In some examples, the small molecule inhibitors herein may modulate the activities of the RNA-guided nucleases or their interaction with other molecules, e.g., their binding with target polynucleotides.

Applications in Non-Animal Organisms

The small molecule compounds herein can be used on non-animal organisms, such as plants and fungi. The small molecule inhibitors herein can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits.

The small molecule compounds herein may be used on plants. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, eucalyptus, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, papaya, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The small molecule compounds herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Plant cells and tissues for engineering include, without limitation, roots, stems, leaves, flowers, and reproductive structures, undifferentiated meristematic cells, parenchyma, collenchyma, sclerenchyma, xylem, phloem, epidermis, and germplasm. Thus, the methods and systems can be used over a broad range of plants, such as for example with dicotyledonous plants belonging to the orders Magnoliales, Illiciales, Laurales, Piperales, Aristochiales, Nymphaeales, Ranunculales, Papeverales, Sarraceniaceae, Trochodendrales, Hamamelidales, Eucommiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santalales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales, or with plants belonging to Gymnospermae, e.g those belonging to the orders Pinales, Ginkgoales, Cycadales, Araucariales, Cupressales and Gnetales.

The small molecule compounds herein can be used over a broad range of plant species, included in the non-limitative list of dicot, monocot or gymnosperm genera hereunder: *Atropa, Alseodaphne, Anacardium, Arachis, Beilschmiedia,*

*Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; and the genera *Allium, Andropogon, Eragrostis, Asparagus, Avena, Cynodon, Elaeis, Festuca, Festulolium, Hemerocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus,* and *Pseudotsuga*.

The small molecule compounds herein can also be used over a broad range of "algae" or "algae cells"; including for example algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: *Amphora, Anabaena, Ankistrodesmus, Botryococcus, Chaetoceros, Chlamydomonas, Chlorella, Chlorococcum, Cyclotella, Cylindrotheca, Dunaliella, Emiliana, Euglena, Haematococcus, Isochrysis*, Monochrysis, Monoraphidium, Nannochloris, *Nannochloropsis*, Navicula, Nephrochloris, Nephroselmis, *Nitzschia, Nodularia, Nostoc*, Ochromonas, Oocystis, *Oscillatoria, Pavlova, Phaeodactylum, Platymonas, Pleurochrysis, Porphyra, Pseudanabaena,* Pyramimonas, Stichococcus, *Synechococcus, Synechocystis, Tetraselmis, Thalassiosira,* and *Trichodesmium*.

The small molecule compounds herein can also be used over a broad range of fungi. As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell. As used herein, the term "yeast" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus,* or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis,* a.k.a. *Pichia* kudriavzevii and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella* isabellina).

Plant Cultures and Regeneration

In particular embodiments, plant cells which have a modified genome and that are produced or obtained may be treated with the small molecule inhibitors herein, and can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In particular embodiments, transformed or improved plants to be treated with the small molecule compounds as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using the Cpf1 enzyme whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, CA, 50-98 (1960)).

Generation of Plants with Enhanced Agronomic Traits

The small molecule compounds herein can be used to treat plants that are introduced with targeted double-strand or single-strand breaks and/or introduced gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the small molecule compounds herein is used to treat organisms that are introduced targeted double-strand breaks (DSB) in an endogenous DNA sequence. The DSB activates cellular DNA repair pathways, which can be harnessed to achieve desired DNA sequence modifications near the break site. This is of interest where the inactivation of endogenous genes can confer or contribute to a desired trait. In particular embodiments, homologous recombination with a template sequence is promoted at the site of the DSB, in order to introduce a gene of interest.

The small molecule compounds may be used to treat improved plants. Improved plants may have one or more desirable traits compared to the wildtype plant. The small molecule compounds herein may further modulate these traits. In particular embodiments, the plants, plant cells or plant parts obtained are transgenic plants, comprising an exogenous DNA sequence incorporated into the genome of all or part of the cells of the plant. In particular embodiments, non-transgenic genetically modified plants, plant parts or cells are obtained, in that no exogenous DNA sequence is incorporated into the genome of any of the plant cells of the plant. In such embodiments, the improved plants are non-transgenic. Where only the modification of an endogenous gene is ensured and no foreign genes are introduced or maintained in the plant genome, the resulting genetically modified crops contain no foreign genes and can thus basically be considered non-transgenic.

Modification of Polyploid Plants

Many plants are polyploid, which means they carry duplicate copies of their genomes-sometimes as many as six, as in wheat. The methods according to the present invention, which make use of the small molecule compounds can be "multiplexed" to affect all copies of a gene, or to target dozens of genes at once. For instance, in particular embodiments, the methods of the present invention are used to simultaneously ensure a loss of function mutation in different genes responsible for suppressing defenses against a disease. In particular embodiments, the methods of the present invention are used to simultaneously suppress the expression of the TaMLO-Al, TaMLO-Bl and TaMLO-Dl nucleic acid sequence in a wheat plant cell and regenerating a wheat plant therefrom, in order to ensure that the wheat plant is resistant to powdery mildew (see also WO2015109752).

Creating Male Sterile Plants

Hybrid plants typically have advantageous agronomic traits compared to inbred plants. However, for self-pollinating plants, the generation of hybrids can be challenging. In different plant types, genes have been identified which are important for plant fertility, more particularly male fertility. For instance, in maize, at least two genes have been identified which are important in fertility (Amitabh Mohanty International Conference on New Plant Breeding Molecular Technologies Technology Development And Regulation, Oct. 9-10, 2014, Jaipur, India; Svitashev et al. Plant Physiol. 2015 October; 169 (2): 931-45; Djukanovic et al. Plant J. 2013 December; 76 (5): 888-99). The small molecule compounds herein can be used to target genes required for male fertility so as to generate male sterile plants which can easily be crossed to generate hybrids. In particular embodiments, the system provided herein is used for targeted mutagenesis of the cytochrome P450-like gene (MS26) or the meganuclease gene (MS45) thereby conferring male sterility to the maize plant. Maize plants which are as such genetically altered can be used in hybrid breeding programs.

Increasing the Fertility Stage in Plants

In particular embodiments, the small molecule compounds herein are used to prolong the fertility stage of a plant such as of a rice plant. For instance, a rice fertility stage gene such as Ehd3 can be targeted in order to generate a mutation in the gene and plantlets can be selected for a prolonged regeneration plant fertility stage (as described in CN 104004782).

Regulating Fruit-Ripening

Ripening is a normal phase in the maturation process of fruits and vegetables. Only a few days after it starts it renders a fruit or vegetable inedible. This process brings significant losses to both farmers and consumers. In particular embodiments, the small molecule compounds herein are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil bacterium. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

Thus in particular embodiments, the small molecule compounds herein may be used to ensure one or more modifications of the genome of a plant cell such as described above, and regenerating a plant therefrom. In particular embodiments, the plant is a tomato plant.

Increasing Storage Life of Plants

In particular embodiments, the small molecule compounds herein are used to modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

The Use of the System to Ensure a Value Added Trait

In particular embodiments the small molecule compounds herein is used to produce nutritionally improved agricultural crops. In particular embodiments, the methods provided herein are adapted to generate "functional foods", i.e. a modified food or food ingredient that may provide a health benefit beyond the traditional nutrients it contains and/or "nutraceutical", i.e. substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Biofuel Production

The small molecule compounds herein may be used to modulate biofuel production in plants, fungi, and other organism, e.g., those have been engineered by expressing an RNA-guide nucleases. The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation.

Enhancing Plant Properties for Biofuel Production

In particular embodiments, the small molecule compounds herein are used to alter the properties of the cell wall in order to facilitate access by key hydrolyzing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in WO 2008064289 A2.

In particular embodiments, the small molecule compounds herein are used to produce plant mass that produces lower levels of acetic acid during fermentation (see also WO 2010096488). More particularly, the methods disclosed herein are used to generate mutations in homologs to CaslL to reduce polysaccharide acetylation.

Modifying Yeast for Biofuel Production

In particular embodiments, the small molecule compounds herein may be used to modulate Cas enzymes used for bioethanol production by recombinant micro-organisms. For instance, Cas can be used to engineer micro-organisms, such as yeast, to generate biofuel or biopolymers from fermentable sugars and optionally to be able to degrade plant-derived lignocellulose derived from agricultural waste as a source of fermentable sugars. More particularly, the invention provides methods whereby the Cas CRISPR complex is used to introduce foreign genes required for biofuel production into micro-organisms and/or to modify endogenous genes why may interfere with the biofuel synthesis. More particularly the methods involve introducing into a micro-organism such as a yeast one or more nucleotide sequence encoding enzymes involved in the conversion of pyruvate to ethanol or another product of interest. In particular embodiments the methods ensure the introduction of one or more enzymes which allows the micro-organism to degrade cellulose, such as a cellulase. In yet further embodiments, the Cas proteins may be those used to modify endogenous metabolic pathways which compete with the biofuel production pathway.

Modifying Algae and Plants for Production of Vegetable Oils or Biofuels

Transgenic algae or other plants such as rape may be useful in the production of vegetable oils or biofuels such as alcohols (especially methanol and ethanol), for instance. These may be engineered to express or overexpress high levels of oil or alcohols for use in the oil or biofuel industries.

According to particular embodiments of the invention, the system is used to generate lipid-rich diatoms which are useful in biofuel production.

In particular embodiments it is envisaged to specifically modify genes that are involved in the modification of the quantity of lipids and/or the quality of the lipids produced by the algal cell. Examples of genes encoding enzymes involved in the pathways of fatty acid synthesis can encode proteins having for instance acetyl-CoA carboxylase, fatty acid synthase, β-ketoacyl-acyl-carrier protein synthase III, glycerol-3-phospate deshydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid: diacylglycerol acyltransferase, phoshatidate phosphatase, fatty acid thioesterase such as palmitoyi protein thioesterase, or malic enzyme activities. In further embodiments it is envisaged to generate diatoms that have increased lipid accumulation. This can be achieved by targeting genes that decrease lipid catabolisation. Of particular interest for use in the methods of the present invention are genes involved in the activation of both triacylglycerol and free fatty acids, as well as genes directly involved in β-oxidation of fatty acids, such as acyl-CoA synthetase, 3-ketoacyl-CoA thiolase, acyl-CoA oxidase activity and phosphoglucomutase. The system and methods described herein can be used to specifically activate such genes in diatoms as to increase their lipid content.

Organisms such as microalgae are widely used for synthetic biology. Stovicek et al. (Metab. Eng. Comm., 2015; 2:13) describes genome editing of industrial yeast, for example, *Saccharomyces cerevisiae*, to efficiently produce robust strains for industrial production. Stovicek used a CRISPR-Cas9 system codon-optimized for yeast to simultaneously disrupt both alleles of an endogenous gene and knock in a heterologous gene. Cas9 and gRNA were expressed from genomic or episomal 2µ-based vector locations. The authors also showed that gene disruption efficiency could be improved by optimization of the levels of Cas9 and gRNA expression. Hlavová et al. (Biotechnol. Adv. 2015) discusses development of species or strains of microalgae using techniques such as CRISPR to target nuclear and chloroplast genes for insertional mutagenesis and screening. The methods of Stovicek and Hlavová may be applied to the Cas effector protein system of the present invention.

The use of system in the generation of micro-organisms capable of fatty acid production In particular embodiments, the methods of the invention are used for the generation of genetically engineered micro-organisms capable of the production of fatty esters, such as fatty acid methyl esters ("FAME") and fatty acid ethyl esters ("FAEE").

Typically, host cells can be engineered to produce fatty esters from a carbon source, such as an alcohol, present in the medium, by expression or overexpression of a gene encoding a thioesterase, a gene encoding an acyl-CoA synthase, and a gene encoding an ester synthase. Accordingly, the methods provided herein are used to modify a micro-organisms so as to overexpress or introduce a thioesterase gene, a gene encoding an acyl-CoA synthase, and a gene encoding an ester synthase. In particular embodiments, the thioesterase gene is selected from tesA, 'tesA, tesB, fat, fatB2, fatB3, fatA1, or fatA. In particular embodiments, the gene encoding an acyl-CoA synthase is selected from fadDJadK, BH3103, pfl-4354, EAV15023, fadD1, fadD2, RPC_4074, fadDD35, fadDD22, faa39, or an identified gene encoding an enzyme having the same properties. In particular embodiments, the gene encoding an ester synthase is a gene encoding a synthase/acyl-CoA: diacylglycerl acyltransferase from Simmondsia chinensis, Acinetobacter sp. ADP, Alcanivorax borkumensis, Pseudomonas aeruginosa, Fundibacter jadensis, Arabidopsis thaliana, or Alcaligenes eutrophus, or a variant thereof.

Additionally or alternatively, the small molecule compounds herein are used to decrease expression in said micro-organism of at least one of a gene encoding an acyl-CoA dehydrogenase, a gene encoding an outer membrane protein receptor, and a gene encoding a transcriptional regulator of fatty acid biosynthesis. In particular embodiments one or more of these genes is inactivated, such as by introduction of a mutation.

In particular embodiments, the gene encoding an acyl-CoA dehydrogenase is fadE. In particular embodiments, the gene encoding a transcriptional regulator of fatty acid biosynthesis encodes a DNA transcription repressor, for example, fabR.

Additionally or alternatively, said micro-organism is modified to reduce expression of at least one of a gene encoding a pyruvate formate lyase, a gene encoding a lactate dehydrogenase, or both. In particular embodiments, the gene encoding a pyruvate formate lyase is pflB. In particular embodiments, the gene encoding a lactate dehydrogenase is IdhA. In particular embodiments one or more of these genes is inactivated, such as by introduction of a mutation therein.

In particular embodiments, the micro-organism is selected from the genus Escherichia, Bacillus, Lactobacillus, Rhodococcus, Synechococcus, Synechocystis, Pseudomonas, Aspergillus, Trichoderma, Neurospora, Fusarium, Humicola, Rhizomucor, Kluyveromyces, Pichia, Mucor, Myceliophthora, Penicillium, Phanerochaete, Pleurotus, Trametes, Chrysosporium, Saccharomyces, Stenotrophomonas, Schizosaccharomyces, Yarrowia, or Streptomyces.

The small molecule compounds herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-1dh), L-lactate dehydrogenase (l-1dh), lactate 2-monooxygenase.

In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

The use of the small molecule compounds in the generation of improved xylose or cellobiose utilizing yeasts strains In particular embodiments, the small molecule compounds herein may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S., et al. (2011) Proc. Natl. Acad. Sci. USA 108(2):504-9 and Galazka, J. M., et al. (2010) Science 330(6000):84-6. Resulting libraries of double-stranded DNA molecules, each comprising a random mutation in such a selected gene could be co-transformed with the components of the system into a yeast strain (for instance S288C) and strains can be selected with enhanced xylose or cellobiose utilization capacity, as described in WO2015138855.

The use of the small molecule compounds in the generation of improved yeasts strains for use in isoprenoid biosynthesis Tadas Jakočiūnas et al. described the successful application of a multiplex CRISPR/Cas9 system for genome engineering of up to 5 different genomic loci in one transformation step in baker's yeast Saccharomyces cerevisiae (Metabolic Engineering Volume 28, March 2015, Pages 213-222) resulting in strains with high mevalonate production, a key intermediate for the industrially important isoprenoid biosynthesis pathway. In particular embodiments, the system may be applied in a multiplex genome engineering method as described herein for identifying additional high producing yeast strains for use in isoprenoid synthesis.

The use of the small molecule compounds in the generation of lactic acid producing yeasts strains In another embodiment, successful application of a multiplex system is encompassed. In analogy with Vratislav Stovicek et al. (Metabolic Engineering Communications, Volume 2, December 2015, Pages 13-22), improved lactic acid-producing strains can be designed and obtained in a single transformation event. In a particular embodiment, the system is used for simultaneously inserting the heterologous lactate dehydrogenase gene and disruption of two endogenous genes PDC1 and PDC5 genes.

Further applications of the small molecule compounds in plants

In particular embodiments, the small molecule compounds herein, can be used for visualization of genetic element dynamics. For example, the small molecule compounds may regulate the CRISPR imaging that can visualize either repetitive or non-repetitive genomic sequences, report telomere length change and telomere movements and monitor the dynamics of gene loci throughout the cell cycle (Chen et al., Cell, 2013). These methods may also be applied to plants.

Other applications of the small molecule compounds herein, is the targeted gene disruption positive-selection screening in vitro and in vivo (Malina et al., Genes and Development, 2013). These methods may also be applied to plants.

In particular embodiments, fusion of inactive Cas endonucleases with histone-modifying enzymes can introduce custom changes in the complex epigenome (Rusk et al., Nature Methods, 2014). The small molecule compounds may also be applied to plants.

In particular embodiments, the small molecule compounds herein, can be used to purify a specific portion of the chromatin and identify the associated proteins, thus elucidating their regulatory roles in transcription (Waldrip et al., Epigenetics, 2014). These methods may also be applied to plants.

In particular embodiments, the small molecule compounds can be used as a therapy for virus removal in plant systems as it is able to cleave both viral DNA and RNA. Previous studies in human systems have demonstrated the success of utilizing CRISPR in targeting the single strand RNA virus, hepatitis C (A. Price, et al., Proc. Natl. Acad. Sci, 2015) as well as the double stranded DNA virus, hepatitis B (V. Ramanan, et al., Sci. Rep, 2015).

In particular embodiments, the small molecule compounds may be used to alter genome complexity. In further particular embodiment, the small molecule compounds herein, can be used to disrupt or alter chromosome number and generate haploid plants, which only contain chromosomes from one parent. Such plants can be induced to undergo chromosome duplication and converted into diploid plants containing only homozygous alleles (Karimi-Ashtiyani et al., PNAS, 2015; Anton et al., Nucleus, 2014). These methods may also be applied to plants.

In particular embodiments, the small molecule compounds can be used for regulating self-cleavage. In these embodiments, the promotor of the Cas enzyme and gRNA can be a constitutive promotor and a second gRNA is introduced in the same transformation cassette, but controlled by an inducible promoter. This second gRNA can be designated to induce site-specific cleavage in the Cas gene in order to create a non-functional Cas. In a further particular embodiment, the second gRNA induces cleavage on both ends of the transformation cassette, resulting in the removal of the cassette from the host genome. This system offers a controlled duration of cellular exposure to the Cas enzyme and further minimizes off-target editing. Furthermore, cleavage of both ends of a CRISPR/Cas cassette can be used to generate transgene-free T0 plants with bi-allelic mutations (as described for Cas9 e.g. Moore et al., Nucleic Acids Research, 2014; Schaeffer et al., Plant Science, 2015). The methods of Moore et al. may be applied to the systems described herein.

Applications in Non-Human Animals

The small molecule compounds herein may be used on non-human animals, those expressing an RNA-guided nuclease (e.g., constitutively or inducibly). The inhibitors may regulate the functions and activities of the RNA-guided nucleases in the animals.

In an aspect, small molecule compounds may be used on a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The present invention may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation (discussed also elsewhere herein), and tumor development and will aid in developing therapies for human SCID patients. Lee et al., (Proc Natl Acad Sci USA. 2014 May 20; 111(20):7260-5) utilized a reporter-guided transcription activator-like effector nuclease (TALEN) system to generated targeted modifications of recombination activating gene (RAG) 2 in somatic cells at high efficiency, including some that affected both alleles. The Type V effector protein may be applied to a similar system.

The small molecule compounds herein may be used (e.g., with an RNA-guided nuclease) to create a platform to model a disease or disorder of an animal, in some embodiments a mammal, in some embodiments a human. In certain embodiments, such models and platforms are rodent based, in non-limiting examples rat or mouse. Such models and platforms can take advantage of distinctions among and comparisons between inbred rodent strains. In certain embodiments, such models and platforms primate, horse, cattle, sheep, goat, swine, dog, cat or bird-based, for example to directly model diseases and disorders of such animals or to create modified and/or improved lines of such animals. Advantageously, in certain embodiments, an animal based platform or model is created to mimic a human disease or disorder. For example, the similarities of swine to humans make swine an ideal platform for modeling human diseases. Compared to rodent models, development of swine models has been costly and time intensive. On the other hand, swine and other animals are much more similar to humans genetically, anatomically, physiologically and pathophysiologically. The small molecule compounds herein may be used to provide a high efficiency platform for targeted gene and genome editing, gene and genome modification and gene and genome regulation to be used in such animal platforms and models. Though ethical standards block development of human models and in many cases models based on non-human primates, the present invention is used with in vitro systems, including but not limited to cell culture systems, three dimensional models and systems, and organoids to mimic, model, and investigate genetics, anatomy, physiology and pathophysiology of structures, organs, and systems of humans. The platforms and models provide manipulation of single or multiple targets.

In certain embodiments, the present invention is applicable to disease models like that of Schomberg et al. (FASEB Journal, April 2016; 30(1): Suppl 571.1). For example, small molecule compounds herein may be used to regulate the CRISPR systems used herein. To model the inherited disease neurofibromatosis type 1 (NF-1) Schomberg used CRISPR-Cas9 to introduce mutations in the swine neurofibromin 1 gene by cytosolic microinjection of CRISPR/Cas9 components into swine embryos. CRISPR guide RNAs (gRNA) were created for regions targeting sites both upstream and downstream of an exon within the gene for targeted cleavage by Cas9 and repair was mediated by a specific single-stranded oligodeoxynucleotide (ssODN) template to introduce a 2500 bp deletion. The small molecule compounds herein may also used to engineer swine with specific NF-1 mutations or clusters of mutations, and further can be used to engineer mutations that are specific to or representative of a given human individual. The invention is similarly used to develop animal models, including but not limited to swine models, of human multigenic diseases. According to the invention, multiple genetic loci in one gene or in multiple genes are simultaneously targeted using multiplexed guides and optionally one or multiple templates.

The present invention is also applicable to modifying SNPs of other animals, such as cows. Tan et al. (Proc Natl Acad Sci USA. 2013 Oct. 8; 110(41):16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific gRNA sequences were cloned into the Church lab gRNA vector (Addgene ID: 41824) according to their methods (Mali P, et al. (2013) RNA-Guided Human Genome Engineering via Cas9. Science 339 (6121): 823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid.

Heo et al. (Stem Cells Dev. 2015 Feb. 1; 24(3):393-402. doi: 10.1089/scd.2014.0278. Epub 2014 Nov. 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of yamanaka factors and GSK3β and MEK inhibitor (2i) treatment. Heo et al. observed that these bovine iPSCs are highly similar to naïve pluripotent stem cells with regard to gene expression and developmental potential in teratomas. Moreover, CRISPR-Cas9 nuclease, which was specific for the bovine NANOG locus, showed highly efficient editing of the bovine genome in bovine iPSCs and embryos.

Livestock-Pigs

Viral targets in livestock may include, in some embodiments, porcine CD163, for example on porcine macrophages. CD163 is associated with infection (thought to be through viral cell entry) by PRRSv (Porcine Reproductive and Respiratory Syndrome virus, an arterivirus). Infection by PRRSv, especially of porcine alveolar macrophages (found in the lung), results in a previously incurable porcine syndrome ("Mystery swine disease" or "blue ear disease") that causes suffering, including reproductive failure, weight loss and high mortality rates in domestic pigs. Opportunistic infections, such as enzootic pneumonia, meningitis and ear oedema, are often seen due to immune deficiency through loss of macrophage activity. It also has significant economic and environmental repercussions due to increased antibiotic use and financial loss (an estimated $660m per year).

As reported by Kristin M Whitworth and Dr Randall Prather et al. (Nature Biotech 3434 published online 7 Dec. 2015) at the University of Missouri and in collaboration with Genus Plc, CD163 was targeted using CRISPR-Cas9 and the offspring of edited pigs were resistant when exposed to PRRSv. One founder male and one founder female, both of whom had mutations in exon 7 of CD163, were bred to produce offspring. The founder male possessed an 11-bp deletion in exon 7 on one allele, which results in a frameshift mutation and missense translation at amino acid 45 in domain 5 and a subsequent premature stop codon at amino acid 64. The other allele had a 2-bp addition in exon 7 and a 377-bp deletion in the preceding intron, which were predicted to result in the expression of the first 49 amino acids of domain 5, followed by a premature stop code at amino acid 85. The sow had a 7 bp addition in one allele that when translated was predicted to express the first 48 amino acids of domain 5, followed by a premature stop codon at amino acid 70. The sow's other allele was unamplifiable. Selected offspring were predicted to be a null animal (CD163−/−), i.e. a CD163 knock out.

Accordingly, in some embodiments, porcine alveolar macrophages may be targeted by the CRISPR protein and regulated by small molecule compounds herein. In some embodiments, porcine CD163 may be targeted by the CRISPR protein. In some embodiments, porcine CD163 may be knocked out through induction of a DSB or through insertions or deletions, for example targeting deletion or modification of exon 7, including one or more of those described above, or in other regions of the gene, for example deletion or modification of exon 5.

An edited pig and its progeny are also envisaged, for example a CD163 knock out pig. This may be for livestock, breeding or modelling purposes (i.e. a porcine model). Semen comprising the gene knock out is also provided.

CD163 is a member of the scavenger receptor cysteine-rich (SRCR) superfamily. Based on in vitro studies SRCR domain 5 of the protein is the domain responsible for unpackaging and release of the viral genome. As such, other members of the SRCR superfamily may also be targeted in order to assess resistance to other viruses. PRRSV is also a member of the mammalian arterivirus group, which also includes murine lactate dehydrogenase-elevating virus, simian hemorrhagic fever virus and equine arteritis virus. The arteriviruses share important pathogenesis properties, including macrophage tropism and the capacity to cause both severe disease and persistent infection. Accordingly, arteriviruses, and in particular murine lactate dehydrogenase-elevating virus, simian hemorrhagic fever virus and equine arteritis virus, may be targeted, for example through porcine CD163 or homologues thereof in other species, and murine, simian and equine models and knockout also provided.

Indeed, this approach may be extended to viruses or bacteria that cause other livestock diseases that may be transmitted to humans, such as Swine Influenza Virus (SIV) strains which include influenza C and the subtypes of influenza A known as H1N1, H1N2, H2N1, H3N1, H3N2, and H2N3, as well as pneumonia, meningitis and oedema mentioned above.

Generation of Models of Genetic and Epigenetic Conditions

The small molecule compounds herein may be used, e.g., with an RNA-guided nuclease, to create a plant, an animal or cell that may be used to model and/or study genetic or epigenetic conditions of interest, such as a through a model of mutations of interest or a disease model. In some embodiments, the models may be generated using the RNA-guided nuclease, and the characters of the models may be further modulated and controlled using the small molecule compounds herein.

As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of components of the system; and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the systems and methods herein on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models. An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The small molecule compounds herein may regulate the effects (e.g., binding, cleavage) of a CRISPR-complex on a target polynucleotide. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of the system herein can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592.

The target polynucleotide of the system may include a number of disease-associated genes and polynucleotides as well as signaling biochemical pathway-associated genes and polynucleotides as listed in U.S. provisional patent applications 61/736,527 and 61/748,427 respectively, both entitled SYSTEMS METHODS AND COMPOSITIONS FOR SEQUENCE MANIPULATION filed on Dec. 12, 2012 and Jan. 2, 2013, respectively, and PCT Application PCT/US2013/074667, entitled DELIVERY, ENGINEERING AND OPTIMIZATION OF SYSTEMS, METHODS AND COMPOSITIONS FOR SEQUENCE MANIPULATION AND THERAPEUTIC APPLICATIONS, filed Dec. 12, 2013, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Therapeutic Applications

The small molecule compounds herein may be used for treatment in a variety of diseases and disorders. The inhibitors may be used to modulate the function and activity of an RNA-guided nuclease (e.g., a Cas protein) used for treating a disease. For example, the inhibitors may be used for regulating the strength, efficacy, timing, dosage of the therapeutic RNA-guided nuclease.

In some cases, a small molecule compound herein may be administered to a subject concurrently with an RNA-guided nuclease. Alternatively or additionally, a small molecule inhibitor herein may be administered to a subject prior to the administration of an RNA-guided nuclease. Alternatively or additionally, a small molecule inhibitor herein may be administered to a subject after the administration of an RNA-guided nuclease. In some examples, the small molecule compounds herein are used for modulating CRISPR gene editing (e.g., by modulating Cas protein of the CRISPR system).

The small molecule compounds herein may be administered as one or more doses as needed. In some examples, the small molecule compounds may be administered as a single dose. In certain examples, the small molecule compounds may be administered as multiple doses, e.g., 2, 3, 4, 5, 6, 7, 8, 9, 10 or more doses. The multi-dose regime may be used to achieve optimal efficacy and/or temporal control of the activity and function of the RNA-guided nuclease.

Exemplary Therapies

The small molecule compounds herein may be used for treatment in a variety of diseases and disorders. The inhibitors may be used to modulate the function and activity of an RNA-guided nuclease (e.g., a Cas protein) used for treating a disease.

In embodiments, the small molecule compounds herein relates to a method for therapy in which cells are edited ex vivo by CRISPR to modulate at least one gene, with subsequent administration of the edited cells to a patient in need thereof. In some embodiments, the CRISPR editing involves knocking in, knocking out or knocking down expression of at least one target gene in a cell. In particular embodiments, the small molecule compounds herein can modulate CRISPR editing inserts an exogenous, gene, minigene or sequence, which may comprise one or more exons and introns or natural or synthetic introns into the locus of a target gene, a hot-spot locus, a safe harbor locus of the gene genomic locations where new genes or genetic elements can be introduced without disrupting the expression or regulation of adjacent genes, or correction by insertions or deletions one or more mutations in DNA sequences that encode regulatory elements of a target gene.

In embodiments, the treatment is for disease/disorder of an organ, including liver disease, eye disease, muscle disease, heart disease, blood disease, brain disease, kidney disease, or may comprise treatment for an autoimmune disease, central nervous system disease, cancer and other proliferative diseases, neurodegenerative disorders, inflammatory disease, metabolic disorder, musculoskeletal disorder and the like.

Particular diseases/disorders include achondroplasia, achromatopsia, acid maltase deficiency, adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangiectasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemia, Gaucher's disease, generalized gangliosidosis (e.g., GM1), hemochromatosis, the hemoglobin C mutation in the 6th codon of beta-globin (HbC), hemophilia, Huntington's disease, Hurler Syndrome, hypophosphatasia, Klinefelter syndrome, Krabbe's Disease, Langer-Giedion Syndrome, leukodystrophy, long QT syndrome, Marfan syndrome, Moebius syndrome, mucopolysaccharidosis (MPS), nail patella syndrome, nephrogenic diabetes insipidus, neurofibromatosis, Niemann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, and Wiskott-Aldrich syndrome.

In embodiments, the disease is associated with expression of a tumor antigen, e.g., a proliferative disease, a precancerous condition, a cancer, or a non-cancer related indication associated with expression of the tumor antigen, which may in some embodiments comprise a target selected from B2M, CD247, CD3D, CD3E, CD3G, TRAC, TRBC1, TRBC2, HLA-A, HLA-B, HLA-C, DCK, CD52, FKBPIA, CIITA, NLRC5, RFXANK, RFX5, RFXAP, or NR3C1, HAVCR2, LAG3, PDCD1, PD-L2, CTLA4, CEACAM (CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, or PTPN11 DCK, CD52, NR3C1, LILRB1, CD19; CD123; CD22; CD30; CD171; CS-1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRvIII); ganglioside G2 (GD2); ganglioside GD3 (aNeu5Ac (2-8) aNeu5Ac (2-3) bDGalp (1-4) bDGlcp (1-1) Cer); TNF receptor family member B cell maturation (BCMA); Tn antigen ((Tn Ag) or (GalNAca-Ser/Thr)); prostate-specific membrane antigen (PSMA); Receptor tyrosine kinase-like orphan receptor 1 (ROR1); Fms-Like Tyrosine Kinase 3 (FLT3); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); Lewis (Y) antigen; CD24; Platelet-derived growth factor receptor beta (PDGFR-beta); Stage-specific embryonic antigen-4 (SSEA-4); CD20; Folate receptor alpha; Receptor tyrosine-protein kinase ERBB2 (Her2/neu); n kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeu5Ac (2-3) bDGalp (1-4) bDGlcp (1-1) Cer); transglutaminase 5 (TGS5); high molecular weight-melanoma-associated antigen (HMWMAA); o-acetyl-GD2 ganglioside (OAcGD2); Folate receptor beta; tumor endothelial marker 1 (TEM1/CD248); tumor endothelial marker 7-related (TEM7R); claudin 6 (CLDN6); thyroid stimulating hormone receptor (TSHR); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY—BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ESO-1); Cancer/testis antigen 2 (LAGE-1a); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; surviving; telomerase; prostate carcinoma tumor antigen-1 (PCTA-1 or Galectin 8), melanoma antigen recognized by T cells 1 (MelanA or MART1); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP1B1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5

(FCRLS); and immunoglobulin lambda-like polypeptide 1 (IGLL1), CD19, BCMA, CD70, G6PC, Dystrophin, including modification of exon 51 by deletion or excision, DMPK, CFTR (cystic fibrosis transmembrane conductance regulator). In embodiments, the targets comprise CD70, or a Knock-in of CD33 and Knock-out of B2M. In embodiments, the targets comprise a knockout of TRAC and B2M, or TRAC B2M and PD1, with or without additional target genes. In certain embodiments, the disease is cystic fibrosis with targeting of the SCNN1A gene, e.g., the non-coding or coding regions, e.g., a promoter region, or a transcribed sequence, e.g., intronic or exonic sequence, targeted knock-in at CFTR sequence within intron 2, into which, e.g., can be introduced CFTR sequence that codes for CFTR exons 3-27; and sequence within CFTR intron 10, into which sequence that codes for CFTR exons 11-27 can be introduced.

In embodiments, the disease is Metachromatic Leukodystrophy, and the target is Arylsulfatase A, the disease is Wiskott-Aldrich Syndrome and the target is Wiskott-Aldrich Syndrome protein, the disease is Adreno leukodystrophy and the target is ATP-binding cassette DI, the disease is Human Immunodeficiency Virus and the target is receptor type 5-C—C chemokine or CXCR4 gene, the disease is Beta-thalassemia and the target is Hemoglobin beta subunit, the disease is X-linked Severe Combined ID receptor subunit gamma and the target is interelukin-2 receptor subunit gamma, the disease is Multisystemic Lysosomal Storage Disorder cystinosis and the target is cystinosin, the disease is Diamond-Blackfan anemia and the target is Ribosomal protein S19, the disease is Fanconi Anemia and the target is Fanconi anemia complementation groups (e.g. FNACA, FNACB, FANCC, FANCD1, FANCD2, FANCE, FANCF, RAD51C), the disease is Shwachman-Bodian-Diamond syndrome and the target is Shwachman syndrome gene, the disease is Gaucher's disease and the target is Glucocerebrosidase, the disease is Hemophilia A and the target is Antihemophiliac factor OR Factor VIII, Christmas factor, Serine protease, Factor Hemophilia B IX, the disease is Adenosine deaminase deficiency (ADA-SCID) and the target is Adenosine deaminase, the disease is GM1 gangliosidosis and the target is beta-galactosidase, the disease is Glycogen storage disease type II, Pompe disease, the disease is acid maltase deficiency acid and the target is alpha-glucosidase, the disease is Niemann-Pick disease, SMPDI-associated (Types Sphingomyelin phosphodiesterase 1 OR A and B) acid and the target is sphingomyelinase, the disease is Krabbe disease, globoid cell leukodystrophy and the target is Galactosylceramidase or galactosylceramide lipidosis and the target is galactocerebrosidase. Human leukocyte antigens DR-15, DQ-6, the disease is Multiple Sclerosis (MS) DRB1, the disease is Herpes Simplex Virus 1 or 2 and the target is knocking down of one, two or three of RS1, RL2 and/or LAT genes. In embodiments, the disease is an HPV associated cancer with treatment including edited cells comprising binding molecules, such as TCRs or antigen binding fragments thereof and antibodies and antigen-binding fragments thereof, such as those that recognize or bind human papilloma virus. The disease can be Hepatitis B with a target of one or more of PreC, C, X, PreS1, PreS2, S, P and/or SP gene(s).

In embodiments, the immune disease is severe combined immunodeficiency (SCID), Omenn syndrome, and in one aspect the target is Recombination Activating Gene 1 (RAG1) or an interleukin-7 receptor (IL7R). In particular embodiments, the disease is Transthyretin Amyloidosis (ATTR), Familial amyloid cardiomyopathy, and in one aspect, the target is the TTR gene, including one or more mutations in the TTR gene. In embodiments, the disease is Alpha-1 Antitrypsin Deficiency (AATD) or another disease in which Alpha-1 Antitrypsin is implicated, for example GvHD, Organ transplant rejection, diabetes, liver disease, COPD, Emphysema and Cystic Fibrosis, in particular embodiments, the target is SERPINA1.

In embodiments, the disease is primary hyperoxaluria, which, in certain embodiments, the target comprises one or more of Lactate dehydrogenase A (LDHA) and hydroxy Acid Oxidase 1 (HAO 1). In embodiments, the disease is primary hyperoxaluria type 1 (ph1) and other alanine-glyoxylate aminotransferase (agxt) gene related conditions or disorders, such as Adenocarcinoma, Chronic Alcoholic Intoxication, Alzheimer's Disease, Cooley's anemia, Aneurysm, Anxiety Disorders, Asthma, Malignant neoplasm of breast, Malignant neoplasm of skin, Renal Cell Carcinoma, Cardiovascular Diseases, Malignant tumor of cervix, Coronary Arteriosclerosis, Coronary heart disease, Diabetes, Diabetes Mellitus, Diabetes Mellitus Non-Insulin-Dependent, Diabetic Nephropathy, Eclampsia, Eczema, Subacute Bacterial Endocarditis, Glioblastoma, Glycogen storage disease type II, Sensorineural Hearing Loss (disorder), Hepatitis, Hepatitis A, Hepatitis B, Homocystinuria, Hereditary Sensory Autonomic Neuropathy Type 1, Hyperaldosteronism, Hypercholesterolemia, Hyperoxaluria, Primary Hyperoxaluria, Hypertensive disease, Inflammatory Bowel Diseases, Kidney Calculi, Kidney Diseases, Chronic Kidney Failure, leiomyosarcoma, Metabolic Diseases, Inborn Errors of Metabolism, Mitral Valve Prolapse Syndrome, Myocardial Infarction, Neoplasm Metastasis, Nephrotic Syndrome, Obesity, Ovarian Diseases, Periodontitis, Polycystic Ovary Syndrome, Kidney Failure, Adult Respiratory Distress Syndrome, Retinal Diseases, Cerebrovascular accident, Turner Syndrome, Viral hepatitis, Tooth Loss, Premature Ovarian Failure, Essential Hypertension, Left Ventricular Hypertrophy, Migraine Disorders, Cutaneous Melanoma, Hypertensive heart disease, Chronic glomerulonephritis, Migraine with Aura, Secondary hypertension, Acute myocardial infarction, Atherosclerosis of aorta, Allergic asthma, pineoblastoma, Malignant neoplasm of lung, Primary hyperoxaluria type I, Primary hyperoxaluria type 2, Inflammatory Breast Carcinoma, Cervix carcinoma, Restenosis, Bleeding ulcer, Generalized glycogen storage disease of infants, Nephrolithiasis, Chronic rejection of renal transplant, Urolithiasis, pricking of skin, Metabolic Syndrome X, Maternal hypertension, Carotid Atherosclerosis, Carcinogenesis, Breast Carcinoma, Carcinoma of lung, Nephronophthisis, Microalbuminuria, Familial Retinoblastoma, Systolic Heart Failure Ischemic stroke, Left ventricular systolic dysfunction, Cauda Equina Paraganglioma, Hepatocarcinogenesis, Chronic Kidney Diseases, Glioblastoma Multiforme, Non-Neoplastic Disorder, Calcium Oxalate Nephrolithiasis, Ablepharon-Macrostomia Syndrome, Coronary Artery Disease, Liver carcinoma, Chronic kidney disease stage 5, Allergic rhinitis (disorder), Crigler Najjar syndrome type 2, and Ischemic Cerebrovascular Accident. In certain embodiments, treatment is targeted to the liver. In embodiments, the gene is AGXT, with a cytogenetic location of 2q37.3 and the genomic coordinate are on Chromosome 2 on the forward strand at position 240,868,479-240,880,502.

Treatment can also target collagen type vii alpha 1 chain (col7a1) gene related conditions or disorders, such as Malignant neoplasm of skin, Squamous cell carcinoma, Colorectal Neoplasms, Crohn Disease, Epidermolysis Bullosa, Indirect Inguinal Hernia, Pruritus, Schizophrenia, Dermatologic disorders, Genetic Skin Diseases, Teratoma, Cockayne-Touraine Disease, Epidermolysis Bullosa Acquisita, Epidermolysis Bullosa Dystrophica, Junctional Epidermolysis Bullosa, Hallopeau-Siemens Disease, Bullous Skin Diseases, Agenesis of corpus callosum, Dystrophia unguium, Vesicular Stomatitis, Epidermolysis Bullosa With Congenital Localized Absence Of Skin And Deformity Of Nails, Juvenile Myoclonic Epilepsy, Squamous cell carcinoma of esophagus, Poikiloderma of Kindler, pretibial Epidermolysis bullosa, Dominant dystrophic epidermolysis bullosa albopapular type (disorder), Localized recessive dystrophic epidermolysis bullosa, Generalized dystrophic epidermolysis bullosa, Squamous cell carcinoma of skin, Epidermolysis Bullosa Pruriginosa, Mammary Neoplasms, Epidermolysis Bullosa Simplex Superficialis, Isolated Toenail Dystrophy, Transient bullous dermolysis of the newborn, Autosomal Recessive Epidermolysis Bullosa Dystrophica Localisata Variant, and Autosomal Recessive Epidermolysis Bullosa Dystrophica Inversa.

In embodiments, the disease is acute myeloid leukemia (AML), targeting Wilms Tumor I (WTI) and HLA expressing cells. In embodiments, the therapy is T cell therapy, as described elsewhere herein, comprising engineered T cells with WTI specific TCRs. In certain embodiments, the target is CD157 in AML.

In embodiments, the disease is a blood disease. In certain embodiments, the disease is hemophilia, in one aspect the target is Factor XI. In other embodiments, the disease is a hemoglobinopathy, such as sickle cell disease, sickle cell trait, hemoglobin C disease, hemoglobin C trait, hemoglobin S/C disease, hemoglobin D disease, hemoglobin E disease, a thalassemia, a condition associated with hemoglobin with increased oxygen affinity, a condition associated with hemoglobin with decreased oxygen affinity, unstable hemoglobin disease, methemoglobinemia. Hemostasis and Factor X and XII deficiencies can also be treated. In embodiments, the target is BCL11A gene (e.g., a human BCL11a gene), a BCL11a enhancer (e.g., a human BCL11a enhancer), or a HPFH region (e.g., a human HPFH region), beta globulin, fetal hemoglobin, γ-globin genes (e.g., HBG1, HBG2, or HBG1 and HBG2), the erythroid specific enhancer of the BCL11A gene (BCL11Ae), or a combination thereof.

In embodiments, the target locus can be one or more of RAC, TRBC1, TRBC2, CD3E, CD3G, CD3D, B2M, CIITA, CD247, HLA-A, HLA-B, HLA-C, DCK, CD52, FKBPIA, NLRC5, RFXANK, RFX5, RFXAP, NR3C1, CD274, HAVCR2, LAG3, PDCD1, PD-L$_2$, HCF2, PAI, TFPI, PLAT, PLAU, PLG, RPOZ, F7, F8, F9, F2, F5, F10, F11, F12, F13A1, F13B, STAT1, FOXP3, IL2RG, DCL-REIC, ICOS, MHC2TA, GALNS, HGSNAT, ARSB, RFXAP, CD20, CD81, TNFRSF13B, SEC23B, PKLR, IFNG, SPTB, SPTA, SLC4A1, EPO, EPB42, CSF2 CSF3, VFW, SERPINA1, CTLA4, CEACAM (e.g., CEACAM-1, CEACAM-3 and/or CEACAM-5), VISTA, BTLA, TIGIT, LAIR1, CD160, 2B4, CD80, CD86, B7-H3 (CD113), B7-H4 (VTCN1), HVEM (TNFRSF14 or CD107), KIR, A2aR, MHC class I, MHC class II, GAL9, adenosine, and TGF beta, PTPN11, and combinations thereof. In embodiments, the target sequence within the genomic nucleic acid sequence at Chrl 1:5,250,094-5,250,237, —strand, hg38; Chrl 1:5,255,022-5,255,164, —strand, hg38; nondeletional HPFH region; Chrl 1:5,249,833 to Chrl 1:5,250,237, —strand, hg38; Chrl 1:5,254,738 to Chrl 1:5,255, 164, —strand, hg38; Chrl 1:5,249,833-5,249,927, —strand, hg3; Chrl 1:5,254,738-5,254,851, —strand, hg38; Chrl 1:5,250, 139-5,250,237, —strand, hg38.

In embodiments, the disease is associated with high cholesterol, and regulation of cholesterol is provided, in some embodiments, regulation is affected by modification in the target PCSK9. Other diseases in which PCSK9 can be implicated, and thus would be a target for the systems and methods described herein include Abetalipoproteinemia, Adenoma, Arteriosclerosis, Atherosclerosis, Cardiovascular Diseases, Cholelithiasis, Coronary Arteriosclerosis, Coronary heart disease, Non-Insulin-Dependent Diabetes Mellitus, Hypercholesterolemia, Familial Hypercholesterolemia, Hyperinsulinism, Hyperlipidemia, Familial Combined Hyperlipidemia, Hypobetalipoproteinemia, Chronic Kidney Failure, Liver diseases, Liver neoplasms, melanoma, Myocardial Infarction, Narcolepsy, Neoplasm Metastasis, Nephroblastoma, Obesity, Peritonitis, Pseudoxanthoma Elasticum, Cerebrovascular accident, Vascular Diseases, Xanthomatosis, Peripheral Vascular Diseases, Myocardial Ischemia, Dyslipidemias, Impaired glucose tolerance, Xanthoma, Polygenic hypercholesterolemia, Secondary malignant neoplasm of liver, Dementia, Overweight, Hepatitis C, Chronic, Carotid Atherosclerosis, Hyperlipoproteinemia Type Ha, Intracranial Atherosclerosis, Ischemic stroke, Acute Coronary Syndrome, Aortic calcification, Cardiovascular morbidity, Hyperlipoproteinemia Type lib, Peripheral Arterial Diseases, Familial Hyperaldosteronism Type II, Familial hypobetalipoproteinemia, Autosomal Recessive Hypercholesterolemia, Autosomal Dominant Hypercholesterolemia 3, Coronary Artery Disease, Liver carcinoma, Ischemic Cerebrovascular Accident, and Arteriosclerotic cardiovascular disease NOS. In embodiments, the treatment can be targeted to the liver, the primary location of activity of PCSK9.

In embodiments, the disease or disorder is Hyper IGM syndrome or a disorder characterized by defective CD40 signaling. In certain embodiments, the insertion of CD40L exons are used to restore proper CD40 signaling and B cell class switch recombination. In particular embodiments, the target is CD40 ligand (CD40L)-edited at one or more of exons 2-5 of the CD40L gene, in cells, e.g., T cells or hematopoietic stem cells (HSCs).

In embodiments, the disease is merosin-deficient congenital muscular dystrophy (mdcmd) and other laminin, alpha 2 (lama2) gene related conditions or disorders. The therapy can be targeted to the muscle, for example, skeletal muscle, smooth muscle, and/or cardiac muscle. In certain embodiments, the target is Laminin, Alpha 2 (LAMA2) which may also be referred to as Laminin-12 Subunit Alpha, Laminin-2 Subunit Alpha, Laminin-4 Subunit Alpha 3, Merosin Heavy Chain, Laminin M Chain, LAMM, Congenital Muscular Dystrophy and Merosin. LAMA2 has a cytogenetic location of 6q22.33 and the genomic coordinate are on Chromosome 6 on the forward strand at position 128,883, 141-129,516, 563. In embodiments, the disease treated can be Merosin-Deficient Congenital Muscular Dystrophy (MDCMD), Amyotrophic Lateral Sclerosis, Bladder Neoplasm, Charcot-Marie-Tooth Disease, Colorectal Carcinoma, Contracture, Cyst, Duchenne Muscular Dystrophy, Fatigue, Hyperopia, Renovascular Hypertension, melanoma, Mental Retardation, Myopathy, Muscular Dystrophy, Myopia, Myositis, Neuromuscular Diseases, Peripheral Neuropathy, Refractive Errors, Schizophrenia, Severe mental retardation (I.Q. 20-34), Thyroid Neoplasm, Tobacco Use Disorder, Severe Combined Immunodeficiency, Synovial Cyst, Adenocarcinoma of lung (disorder), Tumor Progression, Strawberry nevus of skin, Muscle degeneration, Microdontia (disorder), Walker-Warburg congenital muscular dystrophy, Chronic Periodontitis, Leukoencephalopathies, Impaired cognition, Fukuyama Type Congenital Muscular Dystrophy, Scleroatonic muscular dystrophy, Eichsfeld type congenital muscular dystrophy, Neuropathy, Muscle eye brain disease, Limb-Muscular Dystrophies, Girdle, Congenital muscular dystrophy (disorder), Muscle fibrosis, cancer recurrence, Drug Resistant Epilepsy, Respiratory Failure, Myxoid cyst, Abnormal breathing, Muscular dystrophy congenital merosin negative, Colorectal Cancer, Congenital Muscular Dystrophy due to Partial LAMA2 Deficiency, and Autosomal Dominant Craniometaphyseal Dysplasia.

In certain embodiments, the target is an AAVS1 (PPPIR12C), an ALB gene, an Angptl3 gene, an ApoC3 gene, an ASGR2 gene, a CCR5 gene, a FIX (F9) gene, a G6PC gene, a Gys2 gene, an HGD gene, a Lp (a) gene, a Pcsk9 gene, a Serpinal gene, a TF gene, and a TTR gene. Assessment of efficiency of HDR/NHEJ mediated knock-in of cDNA into the first exon can utilize cDNA knock-in into "safe harbor" sites such as: single-stranded or double-stranded DNA having homologous arms to one of the following regions, for example: ApoC3 (chr11:116829908-116833071), Angptl3 (chr1:62,597,487-62,606,305), Serpinal (chr14:94376747-94390692), Lp (a) (chr6:160531483-160664259), Pcsk9 (chr1:55,039,475-55,064,852), FIX (chrX:139,530,736-139,563,458), ALB (chr4:73,404,254-73,421,411), TTR (chr1 8:31,591,766-31,599,023), TF (chr3:133,661,997-133,779,005), G6PC (chr17:42,900,796-42,914,432), Gys2 (chr12:21,536,188-21,604,857), AAVS1 (PPP1R12C) (chr19:55,090,912-55,117,599), HGD (chr3:120,628,167-120,682,570), CCR5 (chr3:46,370,854-46,376,206), or ASGR2 (chr17:7,101,322-7,114,310).

In one aspect, the target is superoxide dismutase 1, soluble (SOD1), which can aid in treatment of a disease or disorder associated with the gene. In particular embodiments, the disease or disorder is associated with SOD1, and can be, for example, Adenocarcinoma, Albuminuria, Chronic Alcoholic Intoxication, Alzheimer's Disease, Amnesia, Amyloidosis, Amyotrophic Lateral Sclerosis, Anemia, Autoimmune hemolytic anemia, Sickle Cell Anemia, Anoxia, Anxiety Disorders, Aortic Diseases, Arteriosclerosis, Rheumatoid Arthritis, Asphyxia Neonatorum, Asthma, Atherosclerosis, Autistic Disorder, Autoimmune Diseases, Barrett Esophagus, Behcet Syndrome, Malignant neoplasm of urinary bladder, Brain Neoplasms, Malignant neoplasm of breast, Oral candidiasis, Malignant tumor of colon, Bronchogenic Carcinoma, Non-Small Cell Lung Carcinoma, Squamous cell carcinoma, Transitional Cell Carcinoma, Cardiovascular Diseases, Carotid Artery Thrombosis, Neoplastic Cell Transformation, Cerebral Infarction, Brain Ischemia, Transient Ischemic Attack, Charcot-Marie-Tooth Disease, Cholera, Colitis, Colorectal Carcinoma, Coronary Arteriosclerosis, Coronary heart disease, Infection by Cryptococcus neoformans, Deafness, Cessation of life, Deglutition Disorders, Presenile dementia, Depressive disorder, Contact Dermatitis, Diabetes, Diabetes Mellitus, Experimental Diabetes Mellitus, Insulin-Dependent Diabetes Mellitus, Non-Insulin-Dependent Diabetes Mellitus, Diabetic Angiopathies, Diabetic Nephropathy, Diabetic Retinopathy, Down Syndrome, Dwarfism, Edema, Japanese Encephalitis, Toxic Epidermal Necrolysis, Temporal Lobe Epilepsy, Exanthema, Muscular fasciculation, Alcoholic Fatty Liver, Fetal Growth Retardation, Fibromyalgia, Fibrosarcoma, Fragile X Syndrome, Giardiasis, Glioblastoma, Glioma, Headache, Partial Hearing Loss, Cardiac Arrest, Heart failure, Atrial Septal Defects, Helminthiasis, Hemochromatosis, Hemolysis (disorder), Chronic Hepatitis, HIV Infections, Huntington Disease, Hypercholesterolemia, Hyperglycemia, Hyperplasia, Hypertensive disease, Hyperthyroidism, Hypopituitarism, Hypoproteinemia, Hypotension, natural Hypothermia, Hypothyroidism, Immunologic Deficiency Syndromes, Immune System Diseases, Inflammation, Inflammatory Bowel Diseases, Influenza, Intestinal Diseases, Ischemia, Kearns-Sayre syndrome, Keratoconus, Kidney Calculi, Kidney Diseases, Acute Kidney Failure, Chronic Kidney Failure, Polycystic Kidney Diseases, leukemia, Myeloid Leukemia, Acute Promyelocytic Leukemia, Liver Cirrhosis, Liver diseases, Liver neoplasms, Locked-In Syndrome, Chronic Obstructive Airway Disease, Lung Neoplasms, Systemic Lupus Erythematosus, Non-Hodgkin Lymphoma, Machado-Joseph Disease, Malaria, Malignant neoplasm of stomach, Animal Mammary Neoplasms, Marfan Syndrome, Meningomyelocele, Mental Retardation, Mitral Valve Stenosis, Acquired Dental Fluorosis, Movement Disorders, Multiple Sclerosis, Muscle Rigidity, Muscle Spasticity, Muscular Atrophy, Spinal Muscular Atrophy, Myopathy, Mycoses, Myocardial Infarction, Myocardial Reperfusion Injury, Necrosis, Nephrosis, Nephrotic Syndrome, Nerve Degeneration, nervous system disorder, Neuralgia, Neuroblastoma, Neuroma, Neuromuscular Diseases, Obesity, Occupational Diseases, Ocular Hypertension, Oligospermia, Degenerative polyarthritis, Osteoporosis, Ovarian Carcinoma, Pain, Pancreatitis, Papillon-Lefevre Disease, Paresis, Parkinson Disease, Phenylketonuria, Pituitary Diseases, Pre-Eclampsia, Prostatic Neoplasms, Protein Deficiency, Proteinuria, Psoriasis, Pulmonary Fibrosis, Renal Artery Obstruction, Reperfusion Injury, Retinal Degeneration, Retinal Diseases, Retinoblastoma, Schistosomiasis, Schistosomiasis mansoni, Schizophrenia, Scrapie, Seizures, Age-related cataract, Compression of spinal cord, Cerebrovascular accident, Subarachnoid Hemorrhage, Progressive supranuclear palsy, Tetanus, Trisomy, Turner Syndrome, Unipolar Depression, Urticaria, Vitiligo, Vocal Cord Paralysis, Intestinal Volvulus, Weight Gain, HMN (Hereditary Motor Neuropathy) Proximal Type I, Holoprosencephaly, Motor Neuron Disease, Neurofibrillary degeneration (morphologic abnormality), Burning sensation, Apathy, Mood swings, Synovial Cyst, Cataract, Migraine Disorders, Sciatic Neuropathy, Sensory neuropathy, Atrophic condition of skin, Muscle Weakness, Esophageal carcinoma, Lingual-Facial-Buccal Dyskinesia, Idiopathic pulmonary hypertension, Lateral Sclerosis, Migraine with Aura, Mixed Conductive-Sensorineural Hearing Loss, Iron deficiency anemia, Malnutrition, Prion Diseases, Mitochondrial Myopathies, MELAS Syndrome, Chronic progressive external ophthalmoplegia, General Paralysis, Premature aging syndrome, Fibrillation, Psychiatric symptom, Memory impairment, Muscle degeneration, Neurologic Symptoms, Gastric hemorrhage, Pancreatic carcinoma, Pick Disease of the Brain, Liver Fibrosis, Malignant neoplasm of lung, Age related macular degeneration, Parkinsonian Disorders, Disease Progression, Hypocupremia, Cytochrome-c Oxidase Deficiency, Essential Tremor, Familial Motor Neuron Disease, Lower Motor Neuron Disease, Degenerative myelopathy, Diabetic Polyneuropathies, Liver and Intrahepatic Biliary Tract Carcinoma, Persian Gulf Syndrome, Senile Plaques, Atrophic, Frontotemporal dementia, Semantic Dementia, Common Migraine, Impaired cognition, Malignant neoplasm of liver, Malignant neoplasm of pancreas, Malignant neoplasm of prostate, Pure Autonomic Failure, Motor symptoms, Spastic, Dementia, Neurodegenerative Disorders, Chronic Hepatitis C, Guam Form Amyotrophic Lateral Sclerosis, Stiff limbs, Multisystem disorder, Loss of scalp hair, Prostate carcinoma, Hepatopulmonary Syndrome, Hashimoto Disease, Progressive Neoplastic Disease, Breast Carcinoma, Terminal illness, Carcinoma of lung, Tardive Dyskinesia, Secondary malignant neoplasm of lymph node, Colon Carcinoma, Stomach Carcinoma, Central neuroblastoma, Dissecting aneurysm of the thoracic aorta, Diabetic macular edema, Microalbuminuria, Middle Cerebral Artery Occlusion, Middle Cerebral Artery Infarction, Upper motor neuron signs, Frontotemporal Lobar Degeneration, Memory Loss, Classical phenylketonuria, CADASIL Syndrome, Neurologic Gait Disorders, Spinocerebellar Ataxia Type 2, Spinal Cord Ischemia, Lewy Body Disease, Muscular Atrophy, Spinobulbar, Chromosome 21 monosomy, Thrombocytosis, Spots on skin, Drug-Induced Liver Injury, Hereditary Leber Optic Atrophy, Cerebral Ischemia, ovarian neoplasm, Tauopathies, Macroangiopathy, Persistent pulmonary hypertension, Malignant neoplasm of ovary, Myxoid cyst, Drusen, Sarcoma, Weight decreased, Major Depressive Disorder, Mild cognitive disorder, Degenerative disorder, Partial Trisomy, Cardiovascular morbidity, hearing impairment, Cognitive changes, Ureteral Calculi, Mammary Neoplasms, Colorectal Cancer, Chronic Kidney Diseases, Minimal Change Nephrotic Syndrome, Non-Neoplastic Disorder, X-Linked Bulbo-Spinal Atrophy, Mammographic Density, Normal Tension Glaucoma Susceptibility To Finding, Vitiligo-Associated Multiple Autoimmune Disease Susceptibility 1 (Finding), Amyotrophic Lateral Sclerosis And/Or Frontotemporal Dementia 1, Amyotrophic Lateral Sclerosis 1, Sporadic Amyotrophic Lateral Sclerosis, monomelic Amyotrophy, Coronary Artery Disease, Transformed migraine, Regurgitation, Urothelial Carcinoma, Motor disturbances, Liver carcinoma, Protein Misfolding Disorders, TDP-43 Proteinopathies, Promyelocytic leukemia, Weight Gain Adverse Event, Mitochondrial cytopathy, Idiopathic pulmonary arterial hypertension, Progressive cGVHD, Infection, GRN-related frontotemporal dementia, Mitochondrial pathology, and Hearing Loss.

In particular embodiments, the disease is associated with the gene ATXN1, ATXN2, or ATXN3, which may be targeted for treatment. In some embodiments, the CAG repeat region located in exon 8 of ATXN1, exon 1 of ATXN2, or exon 10 of the ATXN3 is targeted. In embodiments, the disease is spinocerebellar ataxia 3 (sca3), sca1, or sca2 and other related disorders, such as Congenital Abnormality, Alzheimer's Disease, Amyotrophic Lateral Sclerosis, Ataxia, Ataxia Telangiectasia, Cerebellar Ataxia, Cerebellar Diseases, Chorea, Cleft Palate, Cystic Fibrosis, Mental Depression, Depressive disorder, Dystonia, Esophageal Neoplasms, Exotropia, Cardiac Arrest, Huntington Disease, Machado-Joseph Disease, Movement Disorders, Muscular Dystrophy, Myotonic Dystrophy, Narcolepsy, Nerve Degeneration, Neuroblastoma, Parkinson Disease, Peripheral Neuropathy, Restless Legs Syndrome, Retinal Degeneration, Retinitis Pigmentosa, Schizophrenia, Shy-Drager Syndrome, Sleep disturbances, Hereditary Spastic Paraplegia, Thromboembolism, Stiff-Person Syndrome, Spinocerebellar Ataxia, Esophageal carcinoma, Polyneuropathy, Effects of heat, Muscle twitch, Extrapyramidal sign, Ataxic, Neurologic Symptoms, Cerebral atrophy, Parkinsonian Disorders, Protein S Deficiency, Cerebellar degeneration, Familial Amyloid Neuropathy Portuguese Type, Spastic syndrome, Vertical Nystagmus, Nystagmus End-Position, Antithrombin III Deficiency, Atrophic, Complicated hereditary spastic paraplegia, Multiple System Atrophy, Pallidoluysian degeneration, Dystonia Disorders, Pure Autonomic Failure, Thrombophilia, Protein C, Deficiency, Congenital Myotonic Dystrophy, Motor symptoms, Neuropathy, Neurodegenerative Disorders, Malignant neoplasm of esophagus, Visual disturbance, Activated Protein C Resistance, Terminal illness, Myokymia, Central neuroblastoma, Dyssomnias, Appendicular Ataxia, Narcolepsy-Cataplexy Syndrome, Machado-Joseph Disease Type I, Machado-Joseph Disease Type II, Machado-Joseph Disease Type III, Dentatorubral-Pallidoluysian Atrophy, Gait Ataxia, Spinocerebellar Ataxia Type 1, Spinocerebellar Ataxia Type 2, Spinocerebellar Ataxia Type 6 (disorder), Spinocerebellar Ataxia Type 7, Muscular Spinobulbar Atrophy, Genomic Instability, Episodic ataxia type 2 (disorder), Bulbo-Spinal Atrophy X-Linked, Fragile X Tremor/Ataxia Syndrome, Thrombophilia Due to Activated Protein C Resistance (Disorder), Amyotrophic Lateral Sclerosis 1, Neuronal Intranuclear Inclusion Disease, Hereditary Antithrombin Iii Deficiency, and Late-Onset Parkinson Disease.

In embodiments, the disease is associated with expression of a tumor antigen-cancer or non-cancer related indication, for example acute lymphoid leukemia, diffuse large B cell lymphoma, follicular lymphoma, chronic lymphocytic leukemia, Hodgkin lymphoma, non-Hodgkin lymphoma. In embodiments, the target can be TET2 intron, a TET2 intron-exon junction, a sequence within a genomic region of chr4.

In embodiments, neurodegenerative diseases can be treated. In particular embodiments, the target is Synuclein, Alpha (SNCA). In certain embodiments, the disorder treated is a pain related disorder, including congenital pain insensitivity, Compressive Neuropathies, Paroxysmal Extreme Pain Disorder, High grade atrioventricular block, Small Fiber Neuropathy, and Familial Episodic Pain Syndrome 2. In certain embodiments, the target is Sodium Channel, Voltage Gated, Type X Alpha Subunit (SCNIOA).

In certain embodiments, hematopoietic stem cells and progenitor stem cells are edited, including knock-ins. In particular embodiments, the knock-in is for treatment of lysosomal storage diseases, glycogen storage diseases, mucopolysaccharoidoses, or any disease in which the secretion of a protein will ameliorate the disease. In one embodiment, the disease is sickle cell disease (SCD). In another embodiment, the disease is β-thalassemia.

In certain embodiments, the T cell or NK cell is used for cancer treatment and may include T cells comprising the recombinant receptor (e.g. CAR) and one or more phenotypic markers selected from CCR7+, 4-1BB+ (CD137+), TIM3+, CD27+, CD62L+, CD127+, CD45RA+, CD45RO—, t-betl'w, IL-7Ra+, CD95+, IL-2RP+, CXCR3+ or LFA-1+. In certain embodiments the editing of a T cell for caner immunotherapy comprises altering one or more T-cell expressed gene, e.g., one or more of FAS, BID, CTLA4, PDCD1, CBLB, PTPN6, B2M, TRAC and TRBC gene. In some embodiments, editing includes alterations introduced into, or proximate to, the CBLB target sites to reduce CBLB gene expression in T cells for treatment of proliferative diseases and may include larger insertions or deletions at one or more CBLB target sites. T cell editing of TGFBR2 target sequence can be, for example, located in exon 3, 4, or 5 of the TGFBR2 gene and utilized for cancers and lymphoma treatment.

Cells for transplantation can be edited and may include allele-specific modification of one or more immunogenicity genes (e.g., an HLA gene) of a cell, e.g., HLA-A, HLA-B, HLA-C, HLA-DRB1, HLA-DRB3/4/5, HLA-DQ, and HLA-DP MiHAs, and any other MHC Class I or Class II genes or loci, which may include delivery of one or more matched recipient HLA alleles into the original position(s) where the one or more mismatched donor HLA alleles are located, and may include inserting one or more matched recipient HLA alleles into a "safe harbor" locus. In an embodiment, the method further includes introducing a chemotherapy resistance gene for in vivo selection in a gene.

Methods and systems can target Dystrophia Myotonica-Protein Kinase (DMPK) for editing, in particular embodiments, the target is the CTG trinucleotide repeat in the 3' untranslated region (UTR) of the DMPK gene. Disorders or diseases associated with DMPK include Atherosclerosis, Azoospermia, Hypertrophic Cardiomyopathy, Celiac Disease, Congenital chromosomal disease, Diabetes Mellitus, Focal glomerulosclerosis, Huntington Disease, Hypogonadism, Muscular Atrophy, Myopathy, Muscular Dystrophy, Myotonia, Myotonic Dystrophy, Neuromuscular Diseases, Optic Atrophy, Paresis, Schizophrenia, Cataract, Spinocerebellar Ataxia, Muscle Weakness, Adrenoleukodystrophy, Centronuclear myopathy, Interstitial fibrosis, myotonic muscular dystrophy, Abnormal mental state, X-linked Charcot-Marie-Tooth disease 1, Congenital Myotonic Dystrophy, Bilateral cataracts (disorder), Congenital Fiber Type Disproportion, Myotonic Disorders, Multisystem disorder, 3-Methylglutaconic aciduria type 3, cardiac event, Cardiogenic Syncope, Congenital Structural Myopathy, Mental handicap, Adrenomyeloneuropathy, Dystrophia myotonica 2, and Intellectual Disability.

In embodiments, the disease is an inborn error of metabolism. The disease may be selected from Disorders of Carbohydrate Metabolism (glycogen storage disease, G6PD deficiency), Disorders of Amino Acid Metabolism (phenylketonuria, maple syrup urine disease, glutaric acidemia type 1), Urea Cycle Disorder or Urea Cycle Defects (carbamoyl phosphate synthase I deficiency), Disorders of Organic Acid Metabolism (alkaptonuria, 2-hydroxyglutaric acidurias), Disorders of Fatty Acid Oxidation/Mitochondrial Metabolism (Medium-chain acyl-coenzyme A dehydrogenase deficiency), Disorders of Porphyrin metabolism (acute intermittent porphyria), Disorders of Purine/Pyrimidine Metabolism (Lesch-Nyhan syndrome), Disorders of Steroid Metabolism (lipoid congenital adrenal hyperplasia, congenital adrenal hyperplasia), Disorders of Mitochondrial Function (Kearns-Sayre syndrome), Disorders of Peroxisomal function (Zellweger syndrome), or Lysosomal Storage Disorders (Gaucher's disease, Niemann-Pick disease).

In embodiments, the target can comprise Recombination Activating Gene 1 (RAG1), BCL11 A, PCSK9, laminin, alpha 2 (lama2), ATXN3, alanine-glyoxylate aminotransferase (AGXT), collagen type vii alpha 1 chain (COL7a1), spinocerebellar ataxia type 1 protein (ATXN1), Angiopoietin-like 3 (ANGPTL3), Frataxin (FXN), Superoxidase Dismutase 1, soluble (SOD1), Synuclein, Alpha (SNCA), Sodium Channel, Voltage Gated, Type X Alpha Subunit (SCN10A), Spinocerebellar Ataxia Type 2 Protein (ATXN2), Dystrophia Myotonica-Protein Kinase (DMPK), beta globin locus on chromosome 11, acyl-coenzyme A dehydrogenase for medium chain fatty acids (ACADM), long-chain 3-hydroxyl-coenzyme A dehydrogenase for long chain fatty acids (HADHA), acyl-coenzyme A dehydrogenase for very long-chain fatty acids (ACADVL), Apolipoprotein C3 (APOCIII), Transthyretin (TTR), Angiopoietin-like 4 (ANGPTL4), Sodium Voltage-Gated Channel Alpha Subunit 9 (SCN9A), Interleukin-7 receptor (IL7R), glucose-6-phosphatase, catalytic (G6PC), haemochromatosis (HFE), SERPINA1, C9ORF72, β-globin, dystrophin, γ-globin.

In certain embodiments, the disease or disorder is associated with Apolipoprotein C3 (APOCIII), which can be targeted for editing. In embodiments, the disease or disorder may be Dyslipidemias, Hyperalphalipoproteinemia Type 2, Lupus Nephritis, Wilms Tumor 5, Morbid obesity and spermatogenic, Glaucoma, Diabetic Retinopathy, Arthrogryposis renal dysfunction cholestasis syndrome, Cognition Disorders, Altered response to myocardial infarction, Glucose Intolerance, Positive regulation of triglyceride biosynthetic process, Renal Insufficiency, Chronic, Hyperlipidemias, Chronic Kidney Failure, Apolipoprotein C—III Deficiency, Coronary Disease, Neonatal Diabetes Mellitus, Neonatal, with Congenital Hypothyroidism, Hypercholesterolemia Autosomal Dominant 3, Hyperlipoproteinemia Type III, Hyperthyroidism, Coronary Artery Disease, Renal Artery Obstruction, Metabolic Syndrome X, Hyperlipidemia, Familial Combined, Insulin Resistance, Transient infantile hypertriglyceridemia, Diabetic Nephropathies, Diabetes Mellitus (Type 1), Nephrotic Syndrome Type 5 with or without ocular abnormalities, and Hemorrhagic Fever with renal syndrome.

In certain embodiments, the target is Angiopoietin-like 4 (ANGPTL4). Diseases or disorders associated with ANGPTL4 that can be treated include ANGPTL4 is associated with dyslipidemias, low plasma triglyceride levels, regulator of angiogenesis and modulate tumorigenesis, and severe diabetic retinopathy. both proliferative diabetic retinopathy and non-proliferative diabetic retinopathy.

In embodiments, editing can be used for the treatment of fatty acid disorders. In certain embodiments, the target is one or more of ACADM, HADHA, ACADVL. In embodiments, the targeted edit is the activity of a gene in a cell selected from the acyl-coenzyme A dehydrogenase for medium chain fatty acids (ACADM) gene, the long-chain 3-hydroxyl-coenzyme A dehydrogenase for long chain fatty acids (HADHA) gene, and the acyl-coenzyme A dehydrogenase for very long-chain fatty acids (ACADVL) gene. In one aspect, the disease is medium chain acyl-coenzyme A dehydrogenase deficiency (MCADD), long-chain 3-hydroxyl-coenzyme A dehydrogenase deficiency (LCHADD), and/or very long-chain acyl-coenzyme A dehydrogenase deficiency (VLCADD).

Adoptive Cell Therapies

The small molecule compounds herein may modulate RNA-guided nuclease that modifies cells for adoptive therapies. Aspects of the invention accordingly involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32:189-225; Rosenberg and Restifo, 2015, Adoptive cell transfer as personalized immunotherapy for human cancer, Science Vol. 348 no. 6230 pp. 62-68; and, Restifo et al., 2015, Adoptive immunotherapy for cancer: harnessing the T cell response. Nat. Rev. Immunol. 12 (4): 269-281; and Jenson and Riddell, 2014, Design and implementation of adoptive therapy with chimeric antigen receptor-modified T cells. Immunol Rev. 257 (1): 127-144). Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD35 or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD32; see U.S. Pat. Nos. 8,911,993; 8,916,381; 8,975,071; 9,101,584; 9,102,760; 9,102,761). Third-generation CARs include a combination of costimulatory endodomains, such a CD32-chain, CD97, GDI 1a-CD18, CD2, ICOS, CD27, CD154, CDS, OX40, 4-1BB, or CD28 signaling domains (for example scFv-CD28-4-1BB-CD35 or scFv-CD28-OX40-CD32; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARS, for example using 2nd generation antigen-specific CARs signaling through CD35 and either CD28 or CD137. Viral vectors may for example include vectors based on HIV, SV40, EBV, HSV or BPV.

Cells that are targeted for transformation, and can be treated by the small molecule compounds herein, may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to threat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction). Dosing in CAR T cell therapies may for example involve administration of from 106 to 109 cells/kg, with or without a course of lymphodepletion, for example with cyclophosphamide.

In one embodiment, the treatment can be administered into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. Dosing in CAR T cell therapies may for example involve administration of from 106 to 109 cells/kg, with or without a course of lymphodepletion, for example with cyclophosphamide. The cells or population of cells can be administrated in one or more doses. In another embodiment, the effective number of cells are administrated as a single dose. In another embodiment, the effective number of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective number of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6:95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28 (6): 1107-15 (2010)).

In a further refinement of adoptive therapies, genome editing with a system as described herein may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18):3853). For example, immunoresponsive cells may be edited to delete expression of some or all of the class of HLA type II and/or type I molecules, or to knockout selected genes that may inhibit the desired immune response, such as the PD1 gene.

Cells may be edited using any system and method of use thereof as described herein. Systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V (D) J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL1ORA, IL1ORB, HMOX2, IL6R, IL6ST, EIF2AK4, CSK, PAGI, SITI, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R.I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

In some embodiments, the invention described herein relates to a method for adoptive immunotherapy, in which T cells are edited ex vivo by CRISPR to modulate at least one gene and subsequently administered to a patient in need thereof. In some embodiments, the CRISPR editing comprising knocking-out or knocking-down the expression of at least one target gene in the edited T cells. In some embodiments, in addition to modulating the target gene, the T cells are also edited ex vivo by CRISPR to (1) knock-in an exogenous gene encoding a chimeric antigen receptor (CAR) or a T-cell receptor (TCR), (2) knock-out or knock-down expression of an immune checkpoint receptor, (3) knock-out or knock-down expression of an endogenous TCR, (4) knock-out or knock-down expression of a human leukocyte antigen class I (HLA-I) proteins, and/or (5) knock-out or knock-down expression of an endogenous gene encoding an antigen targeted by an exogenous CAR or TCR.

In some embodiments, the T cells are contacted ex vivo with an adeno-associated virus (AAV) vector encoding a CRISPR effector protein, and a guide molecule comprising a guide sequence hybridizable to a target sequence, a tracr mate sequence, and a tracr sequence hybridizable to the tracr mate sequence. In some embodiments, the T cells are contacted ex vivo (e.g., by electroporation) with a ribonucleoprotein (RNP) comprising a CRISPR effector protein complexed with a guide molecule, wherein the guide molecule comprising a guide sequence hybridizable to a target sequence, a tracr mate sequence, and a tracr sequence hybridizable to the tracr mate sequence. See Rupp et al., Scientific Reports 7:737 (2017); Liu et al., Cell Research 27:154-157 (2017). In some embodiments, the T cells are contacted ex vivo (e.g., by electroporation) with an mRNA encoding a CRISPR effector protein, and a guide molecule comprising a guide sequence hybridizable to a target sequence, a tracr mate sequence, and a tracr sequence hybridizable to the tracr mate sequence. See Eyquem et al., Nature 543:113-117 (2017). In some embodiments, the T cells are not contacted ex vivo with a lentivirus or retrovirus vector.

In some embodiments, the small molecule compounds herein may modulate the editing of T cells ex vivo by CRISPR to knock-in an exogenous gene encoding a CAR, thereby allowing the edited T cells to recognize cancer cells based on the expression of specific proteins located on the cell surface. In some embodiments, T cells are edited ex vivo by CRISPR to knock-in an exogenous gene encoding a TCR, thereby allowing the edited T cells to recognize proteins derived from either the surface or inside of the cancer cells. In some embodiments, the method comprising providing an exogenous CAR-encoding or TCR-encoding sequence as a donor sequence, which can be integrated by homology-directed repair (HDR) into a genomic locus targeted by a CRISPR guide sequence. In some embodiments, targeting the exogenous CAR or TCR to an endogenous TCR α constant (TRAC) locus can reduce tonic CAR signaling and facilitate effective internalization and re-expression of the CAR following single or repeated exposure to antigen, thereby delaying effector T-cell differentiation and exhaustion. See Eyquem et al., Nature 543:113-117 (2017).

In some embodiments, the small molecule compounds herein may modulate the editing T cells ex vivo by CRISPR to block one or more immune checkpoint receptors to reduce immunosuppression by cancer cells. In some embodiments, T cells are edited ex vivo by CRISPR to knock-out or knock-down an endogenous gene involved in the programmed death-1 (PD-1) signaling pathway, such as PD-1 and PD-L$_1$. In some embodiments, T cells are edited ex vivo by CRISPR to mutate the Pdcd1 locus or the CD274 locus. In some embodiments, T cells are edited ex vivo by CRISPR using one or more guide sequences targeting the first exon of PD-1. See Rupp et al., Scientific Reports 7:737 (2017); Liu et al., Cell Research 27:154-157 (2017).

In some embodiments, the small molecule compounds herein may modulate the editing T cells ex vivo by CRISPR to eliminate potential alloreactive TCRs to allow allogeneic adoptive transfer. In some embodiments, T cells are edited ex vivo by CRISPR to knock-out or knock-down an endogenous gene encoding a TCR (e.g., an αβ TCR) to avoid graft-versus-host-disease (GVHD). In some embodiments, T cells are edited ex vivo by CRISPR to mutate the TRAC locus. In some embodiments, T cells are edited ex vivo by CRISPR using one or more guide sequences targeting the first exon of TRAC. See Liu et al., Cell Research 27:154-157 (2017). In some embodiments, the method comprises use of CRISPR to knock-in an exogenous gene encoding a CAR or a TCR into the TRAC locus, while simultaneously knocking-out the endogenous TCR (e.g., with a donor sequence encoding a self-cleaving P2A peptide following the CAR cDNA). See Eyquem et al., Nature 543:113-117 (2017). In some embodiments, the exogenous gene comprises a promoter-less CAR-encoding or TCR-encoding sequence which is inserted operably downstream of an endogenous TCR promoter.

In some embodiments, the small molecule compounds herein may modulate the editing T cells ex vivo by CRISPR to knock-out or knock-down an endogenous gene encoding an HLA-I protein to minimize immunogenicity of the edited T cells. In some embodiments, T cells are edited ex vivo by CRISPR to mutate the beta-2 microglobulin (B2M) locus. In some embodiments, T cells are edited ex vivo by CRISPR using one or more guide sequences targeting the first exon of B2M. See Liu et al., Cell Research 27:154-157 (2017). In some embodiments, the method comprises use of CRISPR to knock-in an exogenous gene encoding a CAR or a TCR into the B2M locus, while simultaneously knocking-out the endogenous B2M (e.g., with a donor sequence encoding a self-cleaving P2A peptide following the CAR cDNA). See Eyquem et al., Nature 543:113-117 (2017). In some embodiments, the exogenous gene comprises a promoter-less CAR-encoding or TCR-encoding sequence which is inserted operably downstream of an endogenous B2M promoter.

In some embodiments, the small molecule compounds herein may modulate the editing T cells ex vivo by CRISPR to knock-out or knock-down an endogenous gene encoding an antigen targeted by an exogenous CAR or TCR. In some embodiments, the T cells are edited ex vivo by CRISPR to knock-out or knock-down the expression of a tumor antigen selected from human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (DI) (see WO2016/011210). In some embodiments, the T cells are edited ex vivo by CRISPR to knock-out or knock-down the expression of an antigen selected from B cell maturation antigen (BCMA), transmembrane activator and CAML Interactor (TACI), or B-cell activating factor receptor (BAFF-R), CD38, CD138, CS-1, CD33, CD26, CD30, CD53, CD92, CD100, CD148, CD150, CD200, CD261, CD262, or CD362 (see WO2017/011804).

Xenotransplantation

The small molecule compounds herein may modulate RNA-guided DNA nucleases that are adapted to be used to provide modified tissues for transplantation. For example, RNA-guided DNA nucleases may be used to knockout, knockdown or disrupt selected genes in an animal, such as a transgenic pig (such as the human heme oxygenase-1 transgenic pig line), for example by disrupting expression of genes that encode epitopes recognized by the human immune system, e.g., xenoantigen genes. Candidate porcine genes for disruption may for example include α(1,3)-galactosyltransferase and cytidine monophosphate-N-acetyl-neuraminic acid hydroxylase genes (see PCT Patent Publication WO 2014/066505). In addition, genes encoding endogenous retroviruses may be disrupted, for example the genes encoding all porcine endogenous retroviruses (see Yang et al., 2015, Genome-wide inactivation of porcine endogenous retroviruses (PERVs), Science 27 Nov. 2015: Vol. 350 no. 6264 pp. 1101-1104). In addition, RNA-guided DNA nucleases may be used to target a site for integration of additional genes in xenotransplant donor animals, such as a human CD55 gene to improve protection against hyperacute rejection.

General Gene Therapy Considerations

Examples of disease-associated genes and polynucleotides AMD disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex of the present invention. Examples of disease-associated genes and polynucleotides are listed in Tables 3 and 4. Examples of signaling biochemical pathway-associated genes and polynucleotides are listed in Table 5.

TABLE 3

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |

TABLE 3-continued

| DISEASE/DISORDERS | GENE(S) |
|---|---|
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3crl; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 4

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, |

TABLE 4-continued

| | |
|---|---|
| | TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN; CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular / Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tphl Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, |

TABLE 4-continued

GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

TABLE 5

| CELLULAR FUNCTION | GENES |
| --- | --- |
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; H5P90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TS22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; |

TABLE 5-continued

| CELLULAR FUNCTION | GENES |
|---|---|
| | ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1 GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |

TABLE 5-continued

| CELLULAR FUNCTION | GENES |
| --- | --- |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |

TABLE 5-continued

| CELLULAR FUNCTION | GENES |
|---|---|
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |

TABLE 5-continued

| CELLULAR FUNCTION | GENES |
|---|---|
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition | IRAK1; MYD88; TRAF6; PPARA; RXRA; ABCA1; MAPK8; ALDH1A1; GSTP1; MAPK9; ABCB1; TRAF2; |

TABLE 5-continued

| CELLULAR FUNCTION | GENES |
|---|---|
| of RXR Function | TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RP56KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |

TABLE 5-continued

| CELLULAR FUNCTION | GENES |
|---|---|
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dabl; unc-86 (Pou4f1 or Brn3a); Numb; Rein |

Embodiments of the applications of the small molecule compounds also include those related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011-Medical). Specific aspects of tandem repeat sequences have been found to be responsible for more than twenty human diseases (New insights into repeat instability: role of RNA·DNA hybrids. McIvor E I, Polak U, Napierala M. RNA Biol. 2010 September-October; 7 (5): 551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

Gene Drives

The small molecule compounds herein may be used to modulate gene drives, e.g., in cells and organisms. For example, the inhibitors may inhibit or reverse the function of the gene drives. Genes drives may include RNA-guided gene drives, for example in systems analogous to gene drives described in PCT Patent Publication WO 2015/

105928. Systems of this kind may for example provide methods for altering eukaryotic germline cells, by introducing into the germline cell a nucleic acid sequence encoding an RNA-guided DNA nuclease and one or more guide RNAs. The guide RNAs may be designed to be complementary to one or more target locations on genomic DNA of the germline cell. The nucleic acid sequence encoding the RNA guided DNA nuclease and the nucleic acid sequence encoding the guide RNAs may be provided on constructs between flanking sequences, with promoters arranged such that the germline cell may express the RNA guided DNA nuclease and the guide RNAs, together with any desired cargo-encoding sequences that are also situated between the flanking sequences. The flanking sequences will typically include a sequence which is identical to a corresponding sequence on a selected target chromosome, so that the flanking sequences work with the components encoded by the construct to facilitate insertion of the foreign nucleic acid construct sequences into genomic DNA at a target cut site by mechanisms such as homologous recombination, to render the germline cell homozygous for the foreign nucleic acid sequence. In this way, gene-drive systems are capable of introgressing desired cargo genes throughout a breeding population (Gantz et al., 2015, Highly efficient Cas9-mediated gene drive for population modification of the malaria vector mosquito Anopheles stephensi, PNAS 2015, published ahead of print Nov. 23, 2015, doi: 10.1073/pnas.1521077112; Esvelt et al., 2014, Concerning RNA-guided gene drives for the alteration of wild populations eLife 2014; 3:e03401). In select embodiments, target sequences may be selected which have few potential off-target sites in a genome. Targeting multiple sites within a target locus, using multiple guide RNAs, may increase the cutting frequency and hinder the evolution of drive resistant alleles. Truncated guide RNAs may reduce off-target cutting. Paired nickases may be used instead of a single nuclease, to further increase specificity. Gene drive constructs may include cargo sequences encoding transcriptional regulators, for example to activate homologous recombination genes and/or repress non-homologous end-joining. Target sites may be chosen within an essential gene, so that non-homologous end-joining events may cause lethality rather than creating a drive-resistant allele. The gene drive constructs can be engineered to function in a range of hosts at a range of temperatures (Cho et al. 2013, Rapid and Tunable Control of Protein Stability in Caenorhabditis elegans Using a Small Molecule, PLOS ONE 8(8): e72393. doi: 10.1371/journal.pone.0072393).

Modulation Gene Editing Mechanisms

The small molecule inhibitor herein may be administered to cells or organisms at doses effective to impact gene editing outcomes, e.g., to control the gene editing mechanisms via NHEJ or HDR.

The activity of NHEJ and HDR DSB repair varies significantly by cell type and cell state. NHEJ is not highly regulated by the cell cycle and is efficient across cell types, allowing for high levels of gene disruption in accessible target cell populations. In contrast, HDR acts primarily during S/G2 phase, and is therefore restricted to cells that are actively dividing, limiting treatments that require precise genome modifications to mitotic cells [Ciccia, A. & Elledge, S. J. Molecular cell 40, 179-204 (2010); Chapman, J. R., et al. Molecular cell 47, 497-510 (2012)].

The small molecule compounds may affect the gene editing mechanisms by modulating the function and activity of the RNA-guided nuclease involved in the gene editing. The efficiency of correction via HDR may be controlled by the epigenetic state or sequence of the targeted locus, or the specific repair template configuration (single vs. double stranded, long vs. short homology arms) used [Hacein-Bey-Abina, S., et al. The New England journal of medicine 346, 1185-1193 (2002); Gaspar, H. B., et al. Lancet 364, 2181-2187 (2004); Beumer, K. J., et al. G3 (2013)]. The relative activity of NHEJ and HDR machineries in target cells may also affect gene correction efficiency, as these pathways may compete to resolve DSBs [Beumer, K. J., et al. Proceedings of the National Academy of Sciences of the United States of America 105, 19821-19826 (2008)]. HDR also imposes a delivery challenge not seen with NHEJ strategies, as it requires the concurrent delivery of nucleases and repair templates. In practice, these constraints have so far led to low levels of HDR in therapeutically relevant cell types. Clinical translation has therefore largely focused on NHEJ strategies to treat disease, although proof-of-concept preclinical HDR treatments have now been described for mouse models of haemophilia B and hereditary tyrosinemia [Li, H., et al. Nature 475, 217-221 (2011); Yin, H., et al. Nature biotechnology 32, 551-553 (2014)].

Kits

The present compositions, e.g., compounds and/or pharmaceutical formulations, may be assembled into kits or pharmaceutical systems. The kits can include instructions for the treatment regime, reagents, equipment (test tubes, reaction vessels, needles, syringes, etc.) and standards for calibrating or conducting the treatment. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

The container means of the kits will generally include at least one vial, test tube, flask, bottle, or other container means, into which a component may be placed, and preferably, suitably aliquoted. Where there is more than one component in the kit, the kit also will generally contain additional containers into which the additional components may be separately placed. However, various combinations of components may be comprised in a container. The kits of the present invention also will typically include a means for packaging the component containers in close confinement for commercial sale. Such packaging may include injection or blow-molded plastic containers into which the desired component containers are retained.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The present application also provides aspects and embodiments as set forth in the following numbered Statements:

Statement 1. A compound having the structure of Formula (I):

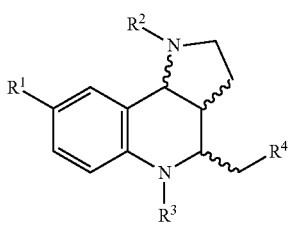

wherein $R^1$ is independently selected from alkynyl or aryl;

$R^2$ is independently selected from -$L_1$-X or -$L_1$-R;

$R^3$ is independently selected from hydrogen, —X, —R, -$L_2$-X, or -$L_2$-R;

$R^4$ is —(CH$_2$)—OH; where $L_1$ is independently selected from —CO— or —S(O)$_2$—;

$L_2$ is independently selected from —(CH$_2$)$_n$—, —(CH$_2$)$_n$—C(O)O—, —(CH$_2$)$_n$—C(O)—NH—, —C(O)—NH—(CH$_2$)$_n$—, —(CH$_2$)$_n$—NH—C(O)—, —(CH$_2$)$_n$—NH—SO$_2$—, —NH—SO$_2$—(CH$_2$)$_n$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—$R^{L2}$—, —$R^{L2}$—C(O)—O—, —$R^{L2}$—NH—C(O)—(CH$_2$)$_n$—, —$R^{L2}$—NH—S(O)$_2$—(CH$_2$)$_n$—, —S—, —S(O)—, or —S(O)$_2$—, wherein n is independently at each occurrence 0, 1, 2, 3, 4, 5, or 6;

X is independently selected from hydrogen, CN, OH, CF$_3$, COOH, OR, OR, NR$_2$, or halogen;

$R^{L2}$ is independently selected from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I, or a combination thereof; and R is independently selected from $C_{1-12}$ hydrocarbons, optionally substituted with one or more groups X and/or with 1-10 heteroatoms selected from O, S, N, P, F, Cl, Br, I, or a combination thereof.

Statement 2. The compound of statement 1, wherein the $L_1$ is —S(O)$_2$—.

Statement 3. The compound of statement 1 or 2, wherein the R in $R^2$ is benzyl.

Statement 4. The compound of any one of the proceeding statements having the structure:

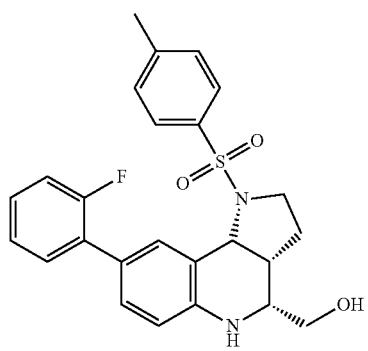

or

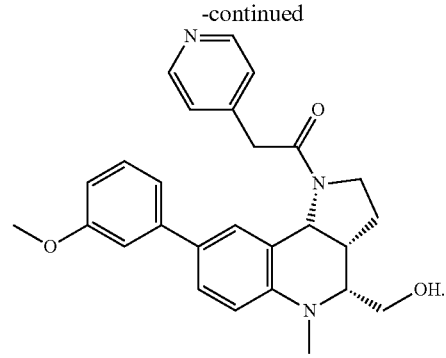

Statement 5. The compound of any one of the proceeding statements having the structure:

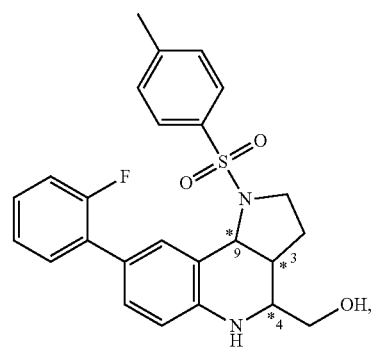 [SMILES: Cc1ccc(S(=O)(=O)N2CCC3C(CO)Nc4ccc(-c5ccccc5F)cc4C32)cc1]

wherein the structure has a stereochemistry of (3aR, 4R, 9bR).

Statement 6. The compound of any one of the proceeding statements having the structure:

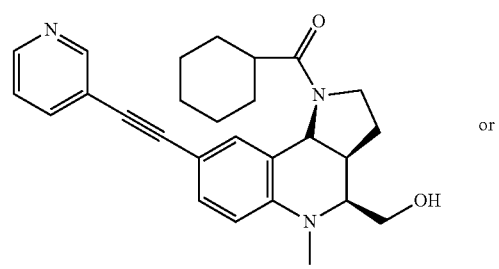

or

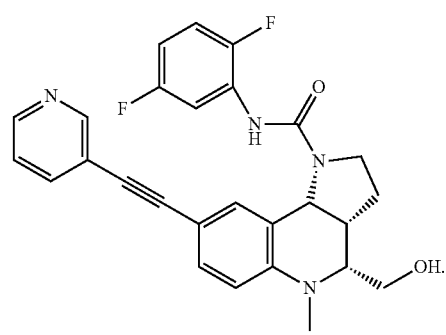

Statement 7. A compound of Formula 1A, 1B, 1C, or 1D:

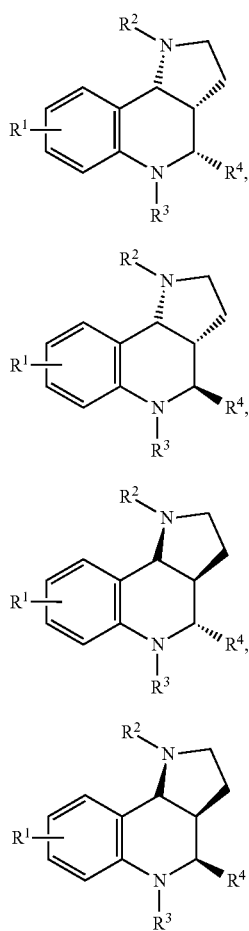

wherein $R^1$ is independently selected from alkynyl or aryl;
$R^2$ is independently selected from $-L_1$-X or $-L_1$-R;
$R^3$ is independently selected from hydrogen, —X, —R, $-L_2$-X, or $-L_2$-R;
$R^4$ is —(CH$_2$)—OH; where
$L_1$ is independently selected from —CO— or —S(O)$_2$—;
$L_2$ is independently selected from —(CH$_2$)$_n$—, —(CH$_2$)$_n$—C(O)O—, —(CH$_2$)$_n$—C(O)—NH—, —C(O)—NH—(CH$_2$)$_n$—, —(CH$_2$)$_n$—NH—C(O)—, —(CH$_2$)$_n$—NH—SO$_2$—, —NH—SO$_2$—(CH$_2$)$_n$—, —(CH$_2$)$_n$—SO$_2$—NH—, —(CH$_2$)$_n$—SO$_2$, —(CH$_2$)$_n$—SO$_2$—NH—C(O)—, —(CH$_2$)$_n$—R$^{L2}$—, —R$^{L2}$—C(O)—O—, —R$^{L2}$—NH—C(O)—(CH$_2$)$_n$—, —R$^{L2}$—NH—S(O)$_2$—(CH$_2$)$_n$—, —S—, —S(O)—, or —S(O)$_2$—, wherein n is independently at each occurrence 0, 1, 2, 3, 4, 5, or 6;
X is independently selected from hydrogen, CN, OH, CF$_3$, COOH, OR, OR, NR$_2$, or halogen;
$R^{L2}$ is independently selected at each occurrence from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I, or a combination thereof; and
R is independently selected from $C_{1-12}$ hydrocarbons, optionally substituted with one or more groups X and/or with 1-10 heteroatoms selected from O, S, N, P, F, Cl, Br, I, or a combination thereof.

Statement 8. The compound of statement 7, wherein the $L_1$ is —S(O)$_2$—.

Statement 9. The compound of statement 7 or 8, wherein the R in $R^2$ is benzyl.

Statement 10. A method of inhibiting an activity of an RNA-guided endonuclease, the method comprising contacting the RNA-guided endonuclease with the compound of any one of statements 1-9.

Statement 11. The method of statement 10, wherein the compound inhibits the activity of an RNA-guided endonuclease reversibly.

Statement 12. The method of statement 10 or 11, wherein the method is performed in vitro.

Statement 13. The method of any one of statements 10-12, wherein the method is performed in vivo.

Statement 14. The method of any one of statements 10-13, wherein the method is performed in a cell.

Statement 15. The method of statement 14, wherein the cell is a germline cell.

Statement 16. The method of statement 14, wherein the cell is a prokaryotic cell.

Statement 17. The method of statement 16, wherein the prokaryotic cell is a bacterium.

Statement 18. The method of statement 14, wherein the cell is a eukaryotic cell.

Statement 19. The method of statement 18, wherein the eukaryotic cell is a human cell, a mammalian cell, an insect cell, a plant cell, or a yeast cell.

Statement 20. The method of statement 14, wherein the cell is in an organism.

Statement 21. The method of statement 20, wherein the organism is a human, mammal, vertebrate, invertebrate, insect, or plant.

Statement 22. The method of any one of statements 10-21, wherein the RNA-guided endonuclease is Cas9.

Statement 23. The method of statement 22, wherein the RNA-guided endonuclease is *Streptococcus pyogenes* Cas9 or a variant thereof.

Statement 24. A method of treating a subject, comprising:
administering an RNA-guided endonuclease-RNA complex or a reagent causing expression of the RNA-guided endonuclease-RNA complex to the subject; and administering an effective amount of a compound of any one of statements 1-9.

Statement 25. A pharmaceutical formulation comprising the compound of any one of statements 1-9 and a pharmaceutically acceptable carrier.

Statement 26. A kit comprising the compound of any one of statements 1-9.

Statement 27. The use of a compound of any one of statements 1-9 for the preparation of a medicament for the treatment of a disease or condition.

Statement 28. A compound of any one of statements 1-9 for use as a medicament.

The invention is further described in the following examples, which do not limit the scope of the invention described in the claims.

EXAMPLES

Example 1—a High-Throughput Platform to Identify Small-Molecule Inhibitors of CRISPR-Cas9

The precision control of CRISPR-Cas9-based technologies, which is needed for several applications, can be accomplished using anti-CRISPR molecules. Here, Applicants report a generalizable platform that provided the first synthetic anti-CRISPRs of S. pyogenes Cas9 (SpCas9) that are miniature (<500 Da), cell-permeable, reversible, and stable under physiological conditions. Applicants developed a suite of high-throughput assays for SpCas9, including a primary screening assay for SpCas9 binding to the protospacer adjacent motif (PAM). Next, Applicants used these assays to screen a structurally diverse collection of natural-product-like small molecules to identify compounds that disrupt the SpCas9-DNA interaction. Using these synthetic anti-CRISPR small molecules, Applicants demonstrated dose and temporal control of SpCas9 and catalytically-impaired SpCas9 technologies, including transcription activation. Applicants also identified a pharmacophore for SpCas9 inhibition by systematically varying the structure and stereochemistry of the inhibitors. These studies established a platform for rapid identification of synthetic, miniature, cell-permeable, and reversible inhibitors against both SpCas9 and next-generation CRISPR-associated nucleases.

SpCas9 is a programmable RNA-guided DNA endonuclease from S. pyogenes that has allowed the facile introduction of genomic alterations. The complex of SpCas9 and guide RNA (gRNA) recognizes substrate sequence via a protospacer adjacent motif (PAM) sequence and base-pairing of the target DNA with gRNA (Chen and Doudna, 2017). The ease of targeting catalytically impaired SpCas9 to any genomic locus has resulted in transformative technologies (Komor et al., 2016a; Wang et al., 2016). For example, the fusion of catalytically inactive SpCas9 (dCas9) to transcriptional activators or repressors has enabled gene transcription and repression; fusion of catalytically impaired SpCas9 to base-modifying enzymes has allowed base conversion (e.g., C→T) at specific genomic sites; dCas9-GFP fusion has made imaging genomic loci possible; and dCas9-acetyl-transferases or deacetylases fusion has enabled epigenome editing.

The need for precision control of wildtype and engineered SpCas9 over the dimensions of dose and time has created a demand for anti-CRISPR molecules (Nunez et al., 2016). SpCas9 is being developed as a gene therapy agent for multiple pathologies, including HIV, vision disorders, muscular dystrophy, and hereditary disorders (Cox et al., 2015; Fellmann et al., 2017). Dose and temporal controls, which are desired for therapeutic agents, are important for SpCas9, as off-target effects and chromosomal translocations are observed at elevated activity (Davis et al., 2015; Frock et al., 2015; Fu et al., 2013; Hsu et al., 2013; Maji et al., 2017; Pattanayak et al., 2014; Pattanayak et al., 2013a; Tsai et al., 2015). Further, temporal control is important because most delivery systems use constitutively active SpCas9, and this activity needs to be terminated following on-target editing in some cases (Frock et al., 2015; Fu et al., 2013; Hsu et al., 2013; Pattanayak et al., 2014; Pattanayak et al., 2013a; Shing et al., 2017; Tsai et al., 2015).

SpCas9 inhibitors may be useful in several other contexts. First, in germline editing, restriction of SpCas9 activity to a narrow temporal window is important, as persistent activity in dividing cells contributes to mosaicism (Wang et al., 2013; Yen et al., 2014). Indeed, timely SpCas9 degradation reduced mosaicism in non-human primate embryos (Tu et al., 2017). Second, an SpCas9 inhibitor may be useful in the context of gene drives that propagate lethal traits (Champer et al., 2016; Esvelt et al., 2014; Gantz and Bier, 2016). Here, temporarily switching off gene drives by inhibiting SpCas9 may allow facile animal husbandry and population expansion of mosquitoes for field studies (Hammond and Galizi, 2016). Further, dose and temporal control of gene drives in a laboratory setting may allow precision population control and propel our understanding of the limits of this technology. Third, inhibition of SpCas9-mediated toxicity to helper cells can enable efficient packaging of SpCas9 in adeno-associated virus (AAV) for delivery (Neve et al., 2005). Fourth, SpCas9 inhibitors may help allay dual-use concerns from a biosafety perspective in the use of SpCas9 in disease modeling (Wegrzyn et al., 2017). Fifth, SpCas9 inhibitors may propel the fundamental understanding of the biological functions of endogenous SpCas9 and allow application of immune response-based selection pressure on bacteria to evolve new CRISPR-based systems. Finally, dCas9-based technologies, including base editing, may benefit from the dose and temporal control.

While several protein-based anti-CRISPR molecules have been reported (Hynes et al., 2017; Pawluk et al., 2016a; Pawluk et al., 2016b; Rauch et al., 2017; Shing et al., 2017), Applicants focused on small-molecule-based SpCas9 inhibitors, as they complement the protein-based anti-CRISPR in multiple ways. For example, small-molecule inhibitors can be cell-permeable, reversible, proteolytic stable, and non-immunogenic, while protein-based anti-CRISPRs can be highly potent, since they possess a greater number of SpCas9 binding sites. Unlike genetic methods used to express protein-based anti-CRISPRs, small-molecule inhibitors exhibit fast kinetics, inhibiting enzymic activity in as little as a few minutes (Weiss et al., 2007), and allow precise temporal control. Small molecules can be synthesized on a large scale at low cost, with little batch-to-batch variability. Pharmacologic inhibition of intracellular proteins is usually accomplished using small molecules. Notwithstanding these advantages, the identification of small-molecule inhibitors of SpCas9 is challenging for multiple reasons. First, inhibitor identification may need robust, orthogonal, sensitive, high-throughput, miniature, and inexpensive SpCas9 assays. Second, SpCas9 is a single turnover enzyme that holds on to its substrate with picomolar affinity throughout the biochemical reaction (Sternberg et al., 2014), adding to the challenge of developing such high-throughput assays. Third, the inhibition of SpCas9 activity requires inactivation of two nuclease domains. Fourth, SpCas9 possesses novel protein folds, limiting the ability to leverage existing rational design approaches (Nishimasu et al., 2014). Finally, SpCas9 is a DNA-binding protein, a class of targets that are often deemed chemically intractable (Koehler, 2010).

Here, Applicants describe a platform for rapid identification and validation of small-molecule inhibitors of SpCas9. Applicants developed a suite of high-throughput assays for SpCas9 activity, including a fluorescence polarization-based primary screening assay for SpCas9-PAM interaction. Using this primary screening assay, Applicants sampled a set of small-molecule libraries derived from diversity-oriented synthesis (DOS) (Schreiber, 2000) to identify specific libraries enriched for screening hits. A focused screen of the enriched libraries resulted in the identification of BRD0539 as a SpCas9 inhibitor. Applicants validated the activity of BRD0539 in multiple biochemical and cell-based assays, and demonstrated target engagement by BRD0539 in cells. Furthermore, BRD0539 is stable in human plasma and reversibly inhibits SpCas9. Finally, Applicants performed structure-activity and stereochemistry-activity relationship studies for BRD0539 to identify the pharmacophore required for SpCas9 inhibition. In these studies, rapid identification of cell-permeable, reversible, synthetic anti-CRISPR molecules for contemporary and emerging CRISPR-associated nucleases were achieved.

Results
Development of High-Throughput Primary and Secondary Assays.

Primary assay for SpCas9-PAM binding. Applicants focused on targeting the SpCas9-PAM interaction for several reasons. Mutating the PAM binding site renders SpCas9 inactive (Kleinstiver et al., 2015a), and disrupting PAM binding has been exploited by numerous anti-CRISPR proteins. Further, SpCas9 has a low affinity for the PAM sequence, which can be effectively blocked by small molecules. Applicants used fluorescence polarization (FP) to monitor the interaction between SpCas9 and a fluorophore-labeled PAM-containing DNA oligonucleotide (Lundblad et al., 1996). The binding of a PAM-rich DNA to a much larger SpCas9:gRNA complex may lower DNA's tumbling rate, with a concomitant increase in anisotropy (FIG. 1A). However, the low-affinity SpCas9-PAM interaction creates a challenge in developing robust binding assays, as the interaction is not strong enough to make a sustained, measurable change in the anisotropy that is detectable over background. To overcome this challenge, Applicants employed a DNA sequence bearing multiple PAM sites (henceforth called 12PAM-DNA) that would increase the association between the DNA and the SpCas9. The DNA sequences are shown in Table 6.

TABLE 6

List of oligonucleotides used in this study

| Sequence name | Sequences (5'→3') |
|---|---|
| 0PAM top | AGCTGCATAACGCGAAAAAATATATTTATCTGCTTGATCTTCAAA TGTTGTATTGTTT/36-FAM/ (SEQ ID NO: 3) |
| 0PAM bottom | AAACAATACAACATTTGAAGATCAAGCAGATAAATATATTTTTC GCGTTATGCAGCT (SEQ ID NO: 4) |
| 2PAM top | AGCTGCATAACGCGAAAAAATATATTTATCTGGTTGATCTCCAAA TGTTGTATTGTTT/36-FAM/ (SEQ ID NO: 5) |
| 2PAM bottom | AAACAATACAACATTTGGAGATCAACCAGATAAATATATTTTTC GCGTTATGCAGCT (SEQ ID NO: 6) |
| 4PAM top | AGCTGCATAACGCGGGAAAATCCATTTATCTGCTTGATCTTCGGA TGTTCCATTGTTT/36-FAM/ (SEQ ID NO: 7) |
| 4PAM bottom | AAACAATGGAACATCCGAAGATCAAGCAGATAAATGGATTTTCC CGCGTTATGCAGCT (SEQ ID NO: 8) |
| 8PAM top | GGCTGCACCACGCGGGAAAATCCATTTAGGTGCTTCCTCTTCGGA TGTTCCATTGTTT/36-FAM/ (SEQ ID NO: 9) |
| 8PAM bottom | AAACAATGGAACATCCGAAGAGGAAGCACCTAAATGGATTTTCC CGCGTGGTGCAGCC (SEQ ID NO: 10) |
| 12PAM top | GGCTGGACCACGCGGGAAAATCCACCTAGGTGGTTCCTCTTCGGA TGTTCCATCCTTT/36-FAM/ (SEQ ID NO: 11) |
| 12PAM bottom | AAAGGATGGAACATCCGAAGAGGAACCACCTAGGTGGATTTTCC CGCGTGGTCCAGCC (SEQ ID NO: 12) |
| 0PAM competitor top | AGCTGCATAACGCGAAAAAATATATTTATCTGCTTGATCTTCAAA TGTTGTATTGTTT (SEQ ID NO: 13) |
| 0PAM competitor bottom | AAACAATACAACATTTGAAGATCAAGCAGATAAATATATTTTTC GCGTTATGCAGCT (SEQ ID NO: 14) |
| 2PAM competitor top | AGCTGCATAACGCGAAAAAATATATTTATCTGGTTGATCTCCAAA TGTTGTATTGTTT (SEQ ID NO: 15) |
| 2PAM competitor bottom | AAACAATACAACATTTGGAGATCAACCAGATAAATATATTTTTC GCGTTATGCAGCT (SEQ ID NO: 16) |
| 4PAM competitor top | AGCTGCATAACGCGGGAAAATCCATTTATCTGCTTGATCTTCGGA TGTTCCATTGTTT (SEQ ID NO: 17) |
| 4PAM competitor bottom | AAACAATGGAACATCCGAAGATCAAGCAGATAAATGGATTTTCC CGCGTTATGCAGCT (SEQ ID NO: 18) |
| 8PAM competitor top | GGCTGCACCACGCGGGAAAATCCATTTAGGTGCTTCCTCTTCGGA TGTTCCATTGTTT (SEQ ID NO: 19) |

TABLE 6-continued

List of oligonucleotides used in this study

| Sequence name | Sequences (5'→3') |
|---|---|
| 8PAM competitor bottom | AAACAATGGAACATCCGAAGAGGAAGCACCTAAATGGATTTTCC CGCGTGGTGCAGCC (SEQ ID NO: 20) |
| 12PAM competitor top | GGCTGGACCACGCGGGAAAATCCACCTAGGTGGTTCCTCTTCGGA TGTTCCATCCTTT (SEQ ID NO: 21) |
| 12PAM competitor bottom | AAAGGATGGAACATCCGAAGAGGAACCACCTAGGTGGATTTTCC CGCGTGGTCCAGCC (SEQ ID NO: 22) |
| RC_Biotin-0PAM | CAATACAACATTTGAAGATCAAGCAGATAAATATATTTTTTCGCG TTATGCAGCT (SEQ ID NO: 23) |
| Biotin-2PAM | /5Biosg/AGCTGCATAACGCGAAAAAATATATTTATCTGGTTGATCT CCAAATGTTGTATTG (SEQ ID NO: 24) |
| RC_Biotin-2PAM | CAATACAACATTTGGAGATCAACCAGATAAATATATTTTTTCGCG TTATGCAGCT (SEQ ID NO: 25) |
| Biotin-4PAM | /5Biosg/AGCTGCATAACGCGGGAAAATCCATTTATCTGCTTGATCT TCGGATGTTCCATTG (SEQ ID NO: 26) |
| RC_Biotin-4PAM | CAATGGAACATCCGAAGATCAAGCAGATAAATGGATTTTCCCGC GTTATGCAGCT (SEQ ID NO: 27) |
| Biotin-8PAM | /5Biosg/AAACAATGGAACATCCGAAGAGGAAGCACCTAAATGGAT TTTCCCGCGTGGTGCAGCC (SEQ ID NO: 28) |
| RC_Biotin-8PAM | GGCTGCACCACGCGGGAAAATCCATTTAGGTGCTTCCTCTTCGGA TGTTCCATTGTTT (SEQ ID NO: 29) |
| eGFP1 Surveyor fwd | GAGGAGCTGTTCACCGGG (SEQ ID NO: 30) |
| eGFP1 Surveyor rev | GCATGGACGAGCTGTACAAG (SEQ ID NO: 31) |
| eGFP1 NGS fwd | ACACTCTTTCCCTACACGACGCTCTTCCGATCTNNNNACGTAAAC GGCCACAAGTTC (SEQ ID NO: 32) |
| eGFP1 NGS rev | TGGAGTTCAGACGTGTGCTCTTCCGATCTGTCGTCCTTGAAGAAG ATGGTG (SEQ ID NO: 33) |

The binding of SpCas9:gRNA to 12PAM-DNA resulted in a dose-dependent increase in FP (FIG. 1B). Applicants confirmed the PAM-dependence of SpCas9:gRNA and 12PAM-DNA interactions in competition experiments using unlabeled DNA sequences containing a varying number of PAM sites. The decrease in FP of 12PAM-DNA correlated with the density of PAM sites on the competitor DNA (FIG. 1C) as well as with the concentration of the competitor DNA. Next, Applicants used differential scanning fluorimetry, which detected ligand-induced changes in protein stability (Niesen et al., 2007). The melting temperature of the SpCas9:gRNA complex increased with the number of PAM sites in the DNA sequence (FIG. 1D). Finally, using biolayer interferometry (BLI) (Richardson et al., 2016), Applicants found increased affinity of SpCas9:gRNA towards DNA sequences containing more PAM sites (FIG. 1E, Table 6).

Secondary assays for cell-based SpCas9 activity. Applicants developed several cell-based, orthogonal, and high-throughput assays of SpCas9 activity with gain- or loss-of-signal. Applicants used a U2OS.eGFP.PEST cell line in which eGFP knockout by SpCas9 leads to loss of fluorescence (Fu et al., 2013; Kleinstiver et al., 2015a); the percentage of eGFP-negative cells correlated with SpCas9 activity. Using automated imaging and counting of eGFP-positive cells, Applicants adapted this eGFP-disruption assay in a 96-well or 384-well format with a Z'=0.9 or 0.8, respectively (FIGS. 1F, 1I and FIGS. 5A, 5D) (Zhang et al., 1999). In a second fluorescence-based assay, Applicants used HEK293T cells expressing a single plasmid construct (Cas9-mKate2-gRNA) encoding both SpCas9 and gRNA components, along with their red fluorescent protein target mKate2 (FIGS. 1G and 5B) (Moore et al., 2015). Applicants quantified the SpCas9-triggered loss of mKate signal using automated microscopy, yielding an assay with Z'=0.5 in a 96-well format. These two assays, when deployed for inhibitor identification, were gain-of-signal assays which had a lower probability of false positives. Applicants complemented these assays with a loss-of-signal, non-homologous end joining (NHEJ) assay in which cells were transfected with two plasmids in an equimolar ratio: one plasmid expresses out-of-frame eGFP downstream of mCherry, separated by a stop codon, while the other plasmid expresses SpCas9 and a gRNA that could target the stop codon linker, bringing the eGFP gene in-frame (Nguyen et al., 2016a). In this assay, SpCas9-mediated DNA cleavage induced eGFP expression, affording an assay with a Z'=0.4 in a 96-well format (FIGS. 1H, 1I, and FIGS. 5C, 5D). Unlike the mKate2 assay, Applicants used mCherry expression in this assay to normalize for transfection efficiency.

Small-molecule screening and identification of enriched libraries. The initial primary screen focused on a 2,652-membered performance-diverse compound collection (Wawer et al., 2014) containing 2,240 small molecules from commercial libraries and 412 from libraries derived from DOS. All screening hits in this experiment were DOS compounds. Indeed, DOS libraries of natural-product like compounds have performed well against microbial targets (corner et al., 2014a; corner et al., 2014b; Dandapani et al., 2012; Dandapani and Marcaurelle, 2010; Kato et al., 2016; Marcaurelle and Johannes, 2008; Schreiber, 2000). However, screening all available 100,000 DOS compounds, across 32 libraries, would be inefficient, as compounds within a single library are structurally similar, and may perform similarly in assays. Instead, Applicants employed a computational approach to assemble 9,549 compounds, a DOS "informer set", which maximally represents the structural diversity across all DOS compounds (FIGS. 5A-5E, Table 7).

TABLE 7

List of hit compounds from the primary screening of DOS informer set

| Entry | Library | Compound | Entry | Library | Compound |
|---|---|---|---|---|---|
| 1 | Pictet Spengler | BRD-K98710661 | 2 | Povarov | BRD-K45172940 |
|   |   | BRD-K82078087 |   |   | BRD-K73159484 |
|   |   | BRD-K58043445 |   |   | BRD-K41660079 |
|   |   | BRD-K50953983 |   |   | BRD-K08465510 |
|   |   | BRD-K13559434 | 3 | Spirocyclic Azetidine | BRD-K71274172 |
|   |   | BRD-K13624944 |   |   | BRD-K38801421 |
|   |   | BRD-K16126971 |   |   | BRD-K27533033 |
|   |   | BRD-K17663482 |   |   | BRD-K27251656 |
|   |   | BRD-K20315727 | 4 | Benzofuran | BRD-K46473681 |
|   |   | BRD-K25585643 |   |   | BRD-K69233724 |
|   |   | BRD-K37174007 |   |   | BRD-K51998640 |
|   |   | BRD-K38586507 | 5 | Buchwald azetidine | BRD-K58999025 |
|   |   | BRD-K66340791 |   |   | BRD-K53373965 |
|   |   | BRD-K78486523 | 6 | Oxazocane | BRD-K80496944 |
|   |   | BRD-K79962460 |   |   | BRD-K22080587 |
|   |   | BRD-K27398156 | 7 | Biaryl | BRD-K59918754 |
|   |   | BRD-K11689127 | 8 | Tan/Linear amine | BRD-K11068374 |
|   |   | BRD-K81227048 | 9 | RCM | BRD-K62179699 |
|   |   | BRD-K56569077 | 10 | Monocyclic Ester | BRD-K41355839 |
|   |   | BRD4K27882424 | 11 | SnAr 8-ortho | BRD-K63688927 |
|   |   | BRD-K47512679 |   |   | BRD-K15985619 |
|   |   | BRD-K69073942 |   |   |   |
|   |   | BRD-K63684048 |   |   |   |
|   |   | BRD-K91907713 | 12 | Tricyclic Glycal | BRD-K24427624 |
|   |   | BRD-K62473389 |   |   |   |
|   |   | BRD-K74704013 |   |   |   |

Applicants screened the DOS informer set using the FP assay (FIG. 2A), employing 12PAM-DNA lacking a fluorophore as a positive control. Screening hits, which lowered the fluorescence polarization signal by >30 compared to the DMSO vehicle-control distribution, were grouped by library to assess enrichment (FIG. 2B, Table 8). Members of the Pictet-Spengler, spirocyclic azetidine, and Povarov, libraries (corner et al., 2015; Gerard et al., 2012) yielded screening hit rates >1%.

Table 8 NMR parameters used for analysis of BRD7087 binding to SpCas9:gRNA complex. The binding study of BRD7087 to SpCas9:gRNA complex was analyzed based on the method described by Shortridge et. al. The linewidth (LW) increases with increasing SpCas9:gRNA concentration, as expected. Peak intensity values were used to measure the fractional occupancy using the equation Fractional Occupancy=$(1-I_{bound}/I_0)$, where $I_0$ is the intensity of the peak with no protein in the sample. The peak area remains relatively constant, as expected for a fixed concentration of ligand.

TABLE 8

RAW DATA EXTRACTED FROM SPECTRA

| [BRD7087], (μM) | [SpCas9:gRNA], (μM) | LW (Hz) | Peak Intensity | Peak Area | Fractional Occupancy |
|---|---|---|---|---|---|
| 50 | 0 | 4.1 | 572470.95 | 3151271.718 | 0 |
| 50 | 0.75 | 4.3 | 497630.81 | 2968891.536 | 0.130731769 |
| 50 | 1.0 | 4.6 | 468481.06 | 2999269.636 | 0.181650947 |
| 50 | 1.25 | 5.3 | 398322.72 | 2964107.303 | 0.304204484 |
| 50 | 1.5 | 5.9 | 375769.97 | 3176044.761 | 0.343599933 |
| 50 | 1.75 | 6.3 | 342640.49 | 3020022.312 | 0.401470957 |

Biochemical and cellular validation of the Povarov scaffold. Applicants chose not to pursue the spirocyclic azetidine library, as the compounds lowered FP of 12PAM-DNA in the absence of SpCas9:gRNA. Screening of additional members of the Pictet-Spengler and Povarov libraries using the FP assay, and subsequent counter-screening, revealed that most Pictet-Spengler compounds, but not Povarov compounds, exhibited significant fluorescent background, and the hits from the Pictet-Spengler library were also cytotoxic (FIG. 2C and FIG. 6A). As such, before embarking on activity-guided structure optimization in cells, Applicants decided to validate the binding and inhibitory activity of the Povarov scaffold using small molecules BRD7087, BRD5779, and their biotinylated analog, BRD3539 (FIG. 6B). Biolayer Interferometry studies using BRD3539 and SpCas9:gRNA complex suggested a dissociation constant of 0.7 μM (FIGS. 2D and 6C). No detectable binding was observed in the absence of the Povarov scaffold or in the presence of 10-fold excess of biotin (FIGS. 6D, 6E). After confirming that BRD7087 was soluble up to 75 μM in PBS (FIGS. 6F, 6G), Applicants used 19F NMR spectroscopy to validate the binding of BRD7087 to SpCas9:gRNA. Applicants observed a differential line broadening of the 19F signal upon titration with SpCas9:gRNA (FIG. 2E, Table 9 and FIG. 6H), with significant broadening occurring at protein concentrations as low as 0.75 μM (67-fold excess of BRD7087), indicating tight binding.

TABLE 9

Hit list from the screening of 641 structural analogs of BRD7087 in the eGFP-disruption assay in U2OS.eGFP.PEST cells. Compounds that showed higher activity than BRD7087 are listed.

| No | Compound | Inhibition activity Rep 1 | Rep 2 | Average Inhibition activity |
|---|---|---|---|---|
| 1 | BRD-K89354425 | 85.4 | 78.7 | 82.0 |
| 2 | BRD-K81763433 | 82.2 | 74.9 | 78.6 |
| 3 | BRD-K17890048 | 84.1 | 68.7 | 76.4 |
| 4 | BRD-K81261525 | 71.3 | 77.4 | 74.3 |
| 5 | BRD-K67297693 | 64.3 | 80.1 | 72.2 |
| 6 | BRD-K20055065 | 67.5 | 73.9 | 70.7 |
| 7 | BRD-K92041481 | 57.8 | 78.8 | 68.3 |
| 8 | BRD-K39870434 | 53.7 | 82.5 | 68.1 |
| 9 | BRD-K71200053 | 54.6 | 80.6 | 67.6 |
| 10 | BRD-K31513357 | 59.8 | 73.6 | 66.7 |
| 11 | BRD-K05104277 | 71.6 | 58.4 | 65.0 |
| 12 | BRD-K18296007 | 69.6 | 59.7 | 64.7 |
| 13 | BRD-K46446619 | 63.4 | 65.9 | 64.6 |
| 14 | BRD-K76160539 | 61.0 | 67.4 | 64.2 |
| 15 | BRD-K58893765 | 67.8 | 57.4 | 62.6 |
| 16 | BRD-K14474387 | 56.1 | 66.4 | 61.3 |
| 17 | BRD-K60987574 | 59.5 | 62.2 | 60.9 |
| 18 | BRD-K12807496 | 50.9 | 70.7 | 60.8 |
| 19 | BRD-K16827616 | 76.4 | 44.6 | 60.5 |
| 20 | BRD-A34097118 | 50.1 | 70.1 | 60.1 |
| 21 | BRD-K43330291 | 68.2 | 50.4 | 59.3 |
| 22 | BRD-K11943259 | 53.0 | 64.6 | 58.8 |
| 23 | BRD-K56594357 | 55.8 | 59.9 | 57.9 |
| 24 | BRD-K63155325 | 63.0 | 52.1 | 57.6 |
| 25 | BRD-K29966477 | 50.1 | 64.8 | 57.5 |
| 26 | BRD-K94204229 | 47.5 | 66.6 | 57.0 |
| 27 | BRD-K82266131 | 51.7 | 62.1 | 56.9 |
| 28 | BRD-K26627503 | 47.5 | 66.3 | 56.9 |
| 29 | BRD-K49114971 | 49.0 | 63.1 | 56.1 |
| 30 | BRD-K92333822 | 53.1 | 57.1 | 55.1 |
| 31 | BRD-K39647256 | 51.3 | 58.4 | 54.9 |
| 32 | BRD-K11970601 | 59.0 | 50.0 | 54.5 |
| 33 | BRD-K51395794 | 46.5 | 61.3 | 53.9 |
| 34 | BRD-K95820322 | 47.6 | 59.4 | 53.5 |
| 35 | BRD-K77165899 | 47.0 | 59.9 | 53.5 |
| 36 | BRD-K69451415 | 56.2 | 50.6 | 53.4 |
| 37 | BRD-K83829793 | 61.0 | 45.2 | 53.1 |
| 38 | BRD-K53346571 | 49.1 | 56.3 | 52.7 |
| 39 | BRD-K17925790 | 52.6 | 50.8 | 51.7 |
| 40 | BRD-K40448176 | 52.1 | 51.2 | 51.6 |
| 41 | BRD-K70808105 | 47.4 | 55.6 | 51.5 |
| 42 | BRD-K04388421 | 49.1 | 53.3 | 51.2 |
| 43 | BRD-K79906422 | 51.3 | 50.9 | 51.1 |
| 44 | BRD-K11385710 | 55.7 | 46.5 | 51.1 |
| 45 | BRD-K09759494 | 51.1 | 50.7 | 50.9 |
| 46 | BRD-K22244182 | 57.2 | 43.4 | 50.3 |
| 47 | BRD-K80765942 | 50.5 | 49.6 | 50.0 |
| 48 | BRD-K72901141 | 53.2 | 45.9 | 49.5 |
| 49 | BRD-K18260949 | 49.8 | 49.1 | 49.5 |
| 50 | BRD-K03427362 | 48.3 | 50.6 | 49.4 |
| 51 | BRD-K98925777 | 53.6 | 45.2 | 49.4 |
| 52 | BRD-K90247032 | 47.6 | 51.1 | 49.3 |
| 53 | BRD-K35104316 | 54.2 | 44.1 | 49.1 |
| 54 | BRD-K31090697 | 46.0 | 49.9 | 48.0 |
| 55 | BRD-K88933335 | 47.8 | 43.7 | 45.7 |
| 56 | BRD-K83261893 | 47.1 | 44.3 | 45.7 |
| 57 | BRD-K83448282 | 46.7 | 44.6 | 45.7 |
| 58 | BRD-K47320872 | 44.5 | 45.7 | 45.1 |

Applicants confirmed that BRD7087 and BRD5779 were non-cytotoxic (FIG. 6I, 6J), demonstrated dose-dependent inhibition of SpCas9 in the eGFP-disruption assay (FIGS. 2F and 6K, 6L), and found BRD7087 to inhibit SpCas9 up to ~44% at 10 μM, without either affecting eGFP expression (FIG. 6M) or inducing notable auto-fluorescence (FIG. 6N). BRD7087 and BRD5779 showed a dose-dependent inhibition of SpCas9 in both the mKate2 disruption (FIG. 6O, 6P) and NHEJ assays (FIG. 6Q). Since BRD7087 and BRD5779 alter PAM binding, they may inhibit technologies using catalytically impaired SpCas9, including transcription activation and base editing. Dose-dependent inhibition of dCas9-based transcription activation of HBG1, but not of the control gene, was observed using BRD7087 and BRD5779, attaining ~60% inhibition of transcriptional activation at 20 µM (FIG. 2G and FIG. 6R). Both compounds also inhibited C→T conversion of EMX1 gene using SpCas9 (A840H)-cytidine deaminase conjugate (BE3) (Komor et al., 2016b; Rees et al., 2017a), with close to a two-fold reduction in C→T conversion at 20 µM (FIG. 6S).

Figure 3I:
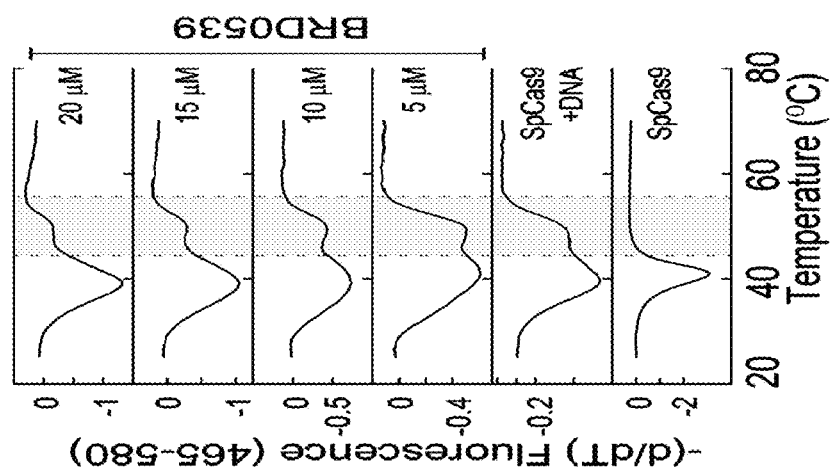
Figure 3H:
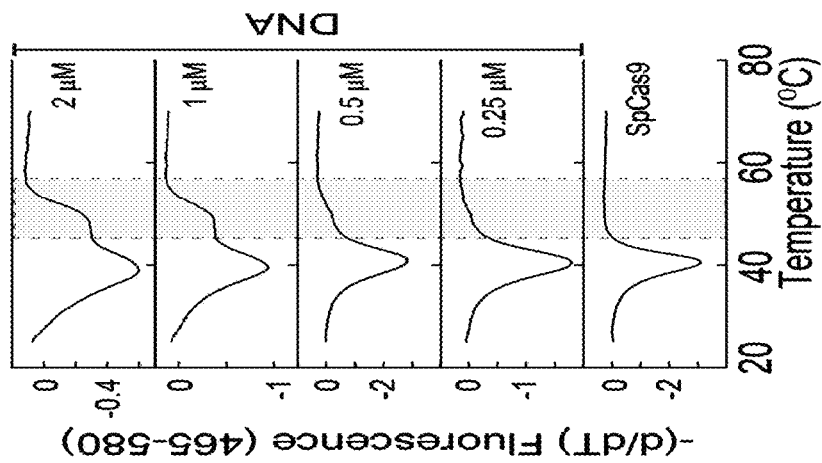
Figure 3K:
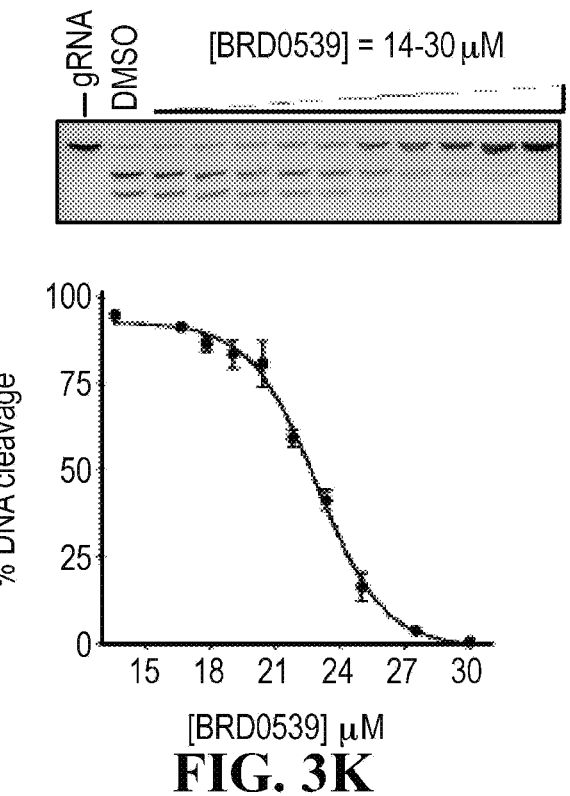
(FIG. 3K) Inhibition of SpCas9 nuclease activity by BRD0539 in a DNA cleavage assay. SpCas9:gRNA (5 nM) was incubated with BRD0539 at the indicated concentrations for 30 min at room temperature followed by addition of linear DNA substrate (2783 bp, puc57) and incubated for additional 30 min at 37° C. Error bars represent ±s.d. across technical replicates (n=2).
Figure 3L:
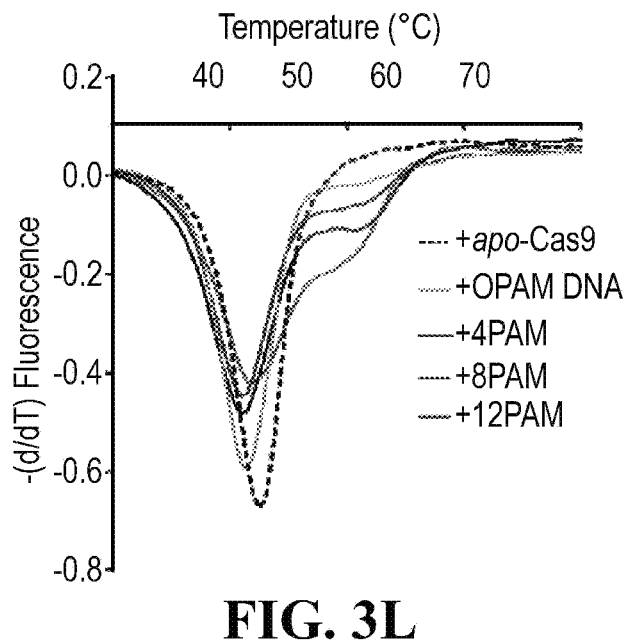
(FIG. 3L) Differential scanning fluorimetry studies of apo-SpCas9 interaction with DNA. SpCas9 (1 μM) was incubated with DNA (2 μM) bearing an increasing number of PAM sequence (0-12 PAM). Data are for one of the three biological replicates.
Figure 3M:
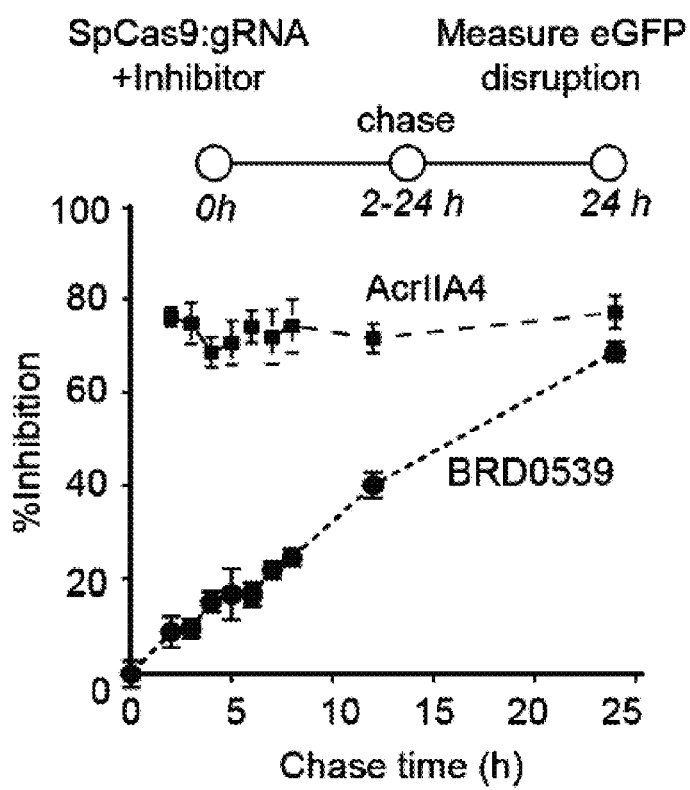
(FIG. 3M) Reversibility of BRD0539- or AcrIIA4-mediated inhibition of SpCas9 in U2OS.eGFP.PEST cells in the eGFP-disruption assay. Cells were nucleofected with either SpCas9 or a preformed SpCas9:gRNA ribonucleoprotein complex or the SpCas9:gRNA:AcrIIA4 ternary complex with an eGFP gene targeting guide and then were incubated with either DMSO or 15 μM of BRD0539 followed by a pulse-chase over 2-24 h before imaging. Error bars represent ±s.d. across technical replicates (n=2) of two biological replicates.
Figure 7D:
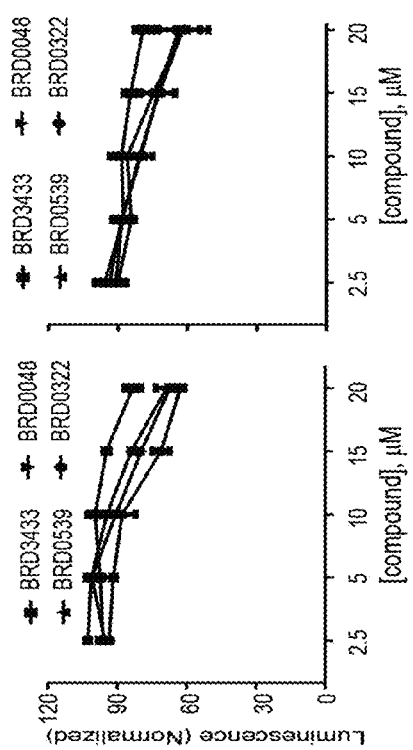
(FIG. 7D) Cell viability of U2OS.eGFP.PEST and HEK293FT cells in the presence of small molecules. Cell viability was determined by measurement of ATP content of U2OS.eGFP.PEST and HEK293FT cells upon incubation with compounds (5, 10, 15, and 20 μM) for 24 h. Error bars represent ±s.d. across technical replicates (n=3).
Figure 7E:
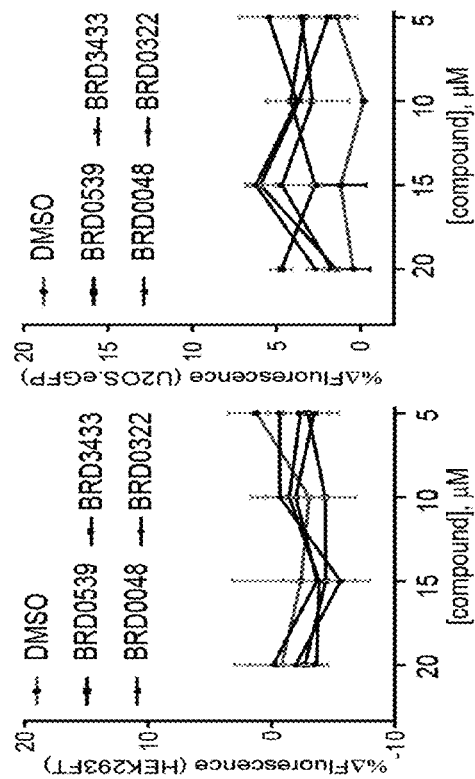
(FIG. 7E) Cell viability of U2OS.eGFP.PEST and HEK293FT cells in the presence of small molecules. Cell viability was determined by measurement of ATP content of U2OS.eGFP.PEST and HEK293FT cells upon incubation with compounds (5, 10, 15, and 20 μM) for 48 h. Error bars represent ±s.d. across technical replicates (n=3).
Figure 7F:
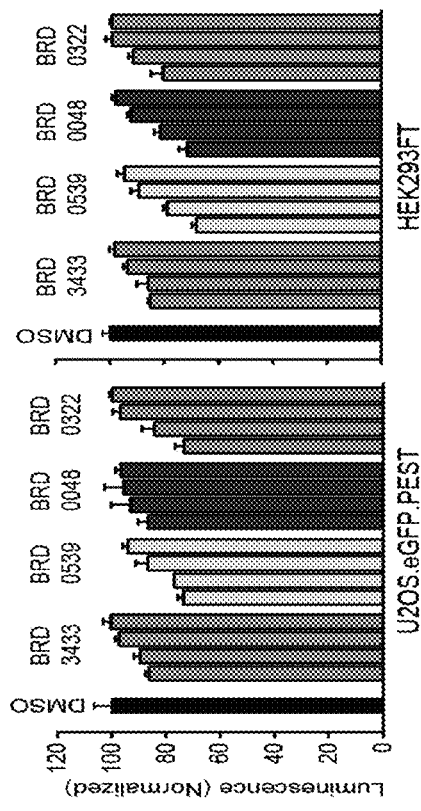
(FIG. 7F) Cell viability of human islets and bone-marrow stroma cells in the presence of small molecules. Cell viability was determined by measurement of ATP content of human islets and bone-marrow stroma cells upon incubation with compounds (5, 10, 15, and 20 μM) for 48 h. Error bars represent ±s.d. across technical replicates (n=3).
Figure 7G:
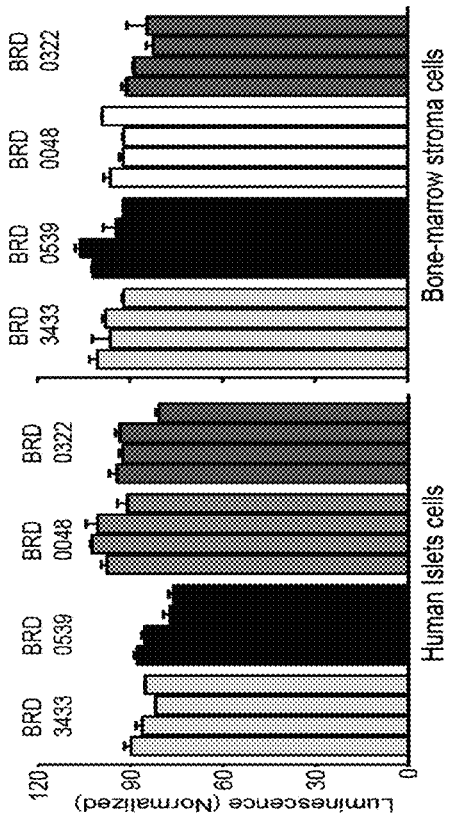
(FIG. 7G) Auto-fluorescence of HEK293FT and U2OS.eGFP.PEST cells treated with the inhibitors in the eGFP-disruption assay. Cells were imaged in the GFP channel with the same exposure time as that used for the eGFP disruption assay. Small molecule-treated cells showed a maximum of ~5% auto-fluorescent population, indicating no significant contribution of auto-fluorescence. Error bars represent ±s.d. across technical replicates (n=4).
Figure 7H:
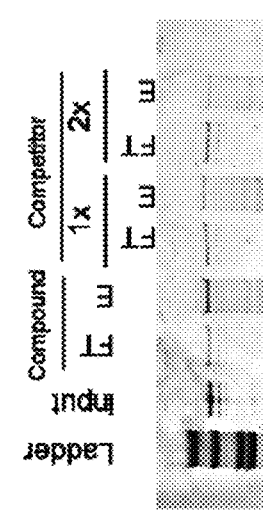
(FIG. 7H) Bio-layer interferometry binding plots for BRD3433-biotin and SpCas9: gRNA complex. BLI experiment was performed using 1 μM BRD3433-biotin on streptavidin sensors followed by association with different concentration of SpCas9:gRNA complex and subsequent dissociation. Response data were plotted along Y-axis and concentration of SpCas9:gRNA complex was plotted along X-axis.
Figure 7I:
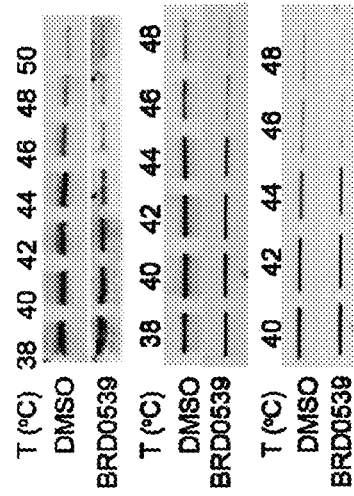
(FIG. 7I) Steady-state analysis of the BLI binding results to determine the dissociation constant. A global 2:1 (small molecule:protein) model was used to plot the steady state and determine the binding constant.
Figure 7O:
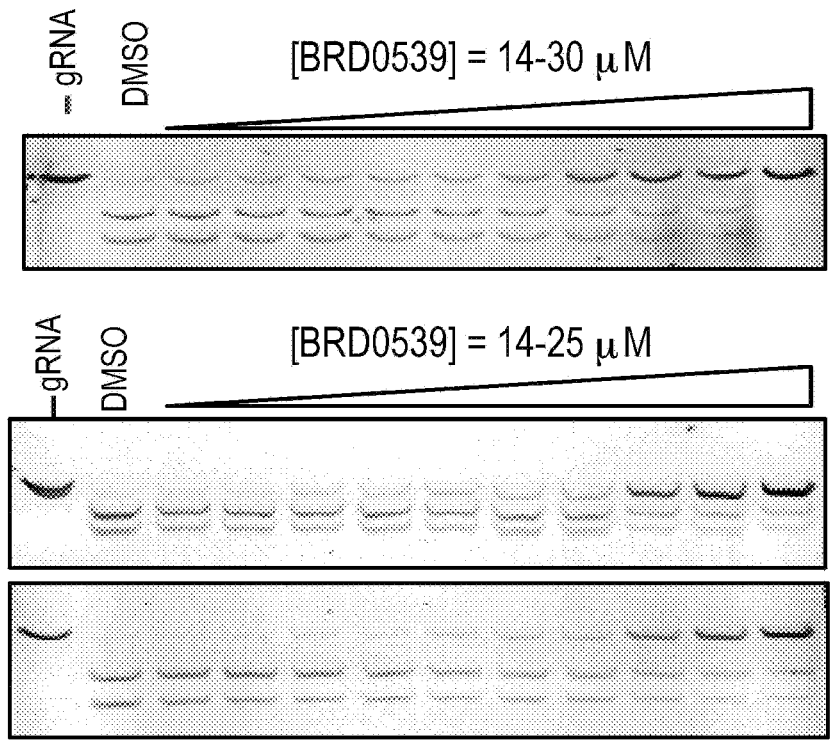
(FIG. 7O) Inhibition of SpCas9 by BRD0539 in a DNA cleavage assay. SpCas9:gRNA (5 nM) was incubated with BRD0539 at the indicated concentrations (14-30 μM) for 30 min at room temperature followed by addition of substrate DNA (2783 bp, puc57) and incubated for additional 30 min at 37° C.
Figure 8A:
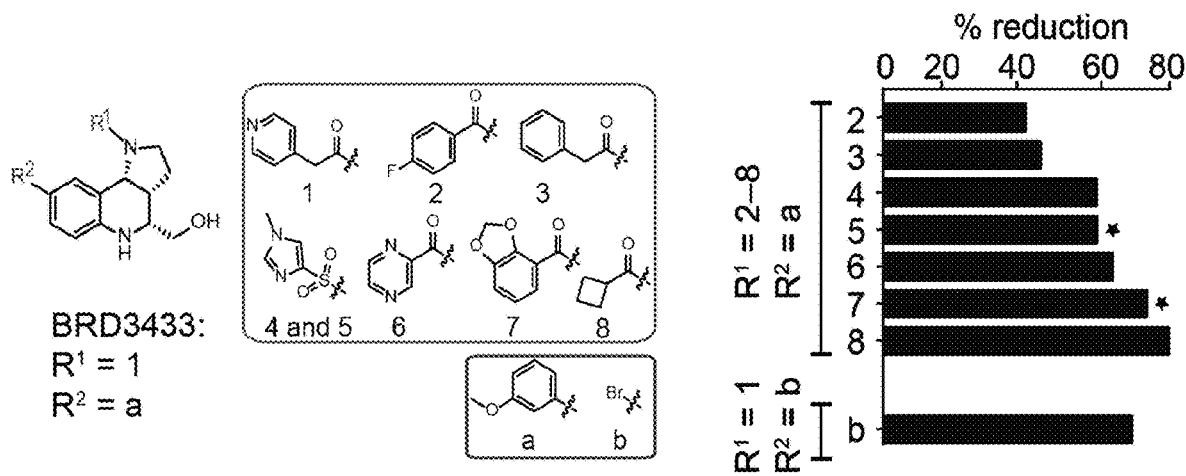
FIGS. 8A-8H—Structure-activity analysis and inhibition of dCas9-based transcriptional upregulation.
Figure 8B:
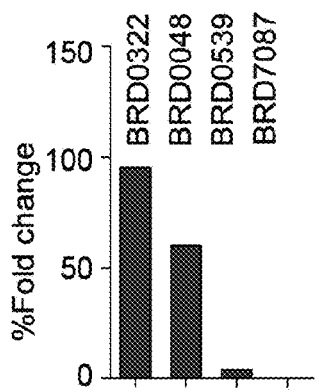
Figure 8C:
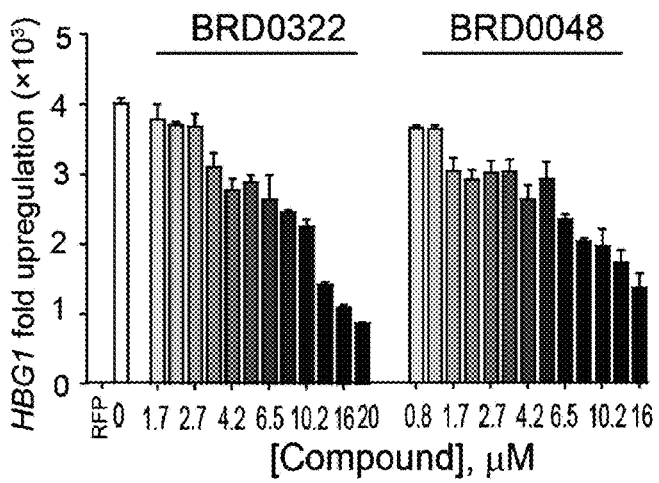
Figure 8D:
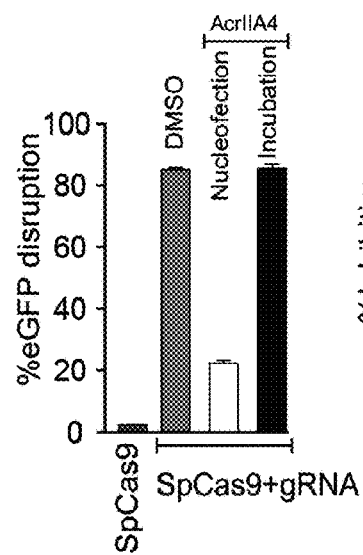
Figure 8E:
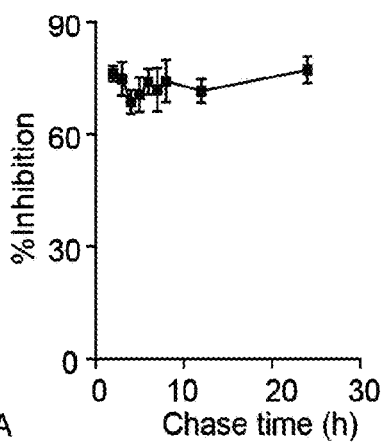
Figure 8F:
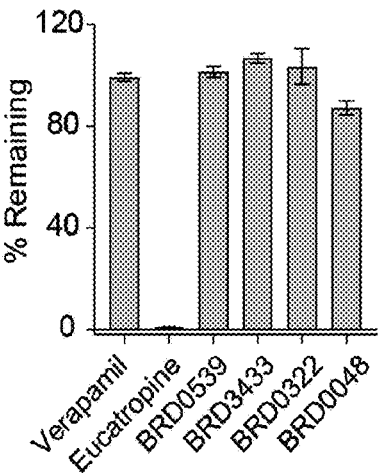

Cell-based activity-guided structure optimization identifies BRD0539 as a potent SpCas9 inhibitor. Upon biochemical and cellular validation of the Povarov scaffold, Applicants sought to improve the potencies of the identified SpCas9 inhibitors in mammalian cells. To this end, Applicants tested 640 structural analogs of BRD7087 (either synthesized or available from the Broad Institute) at 15 µM in the cell-based eGFP-disruption assay. Several compounds possessed greater potency than BRD7087 (FIG. 3A, Table 9). Our hit-triage workflow involved prioritizing compounds based on the absence of cytotoxicity, and the presence of dose-dependent inhibition in the eGFP-disruption assay when SpCas9 is provided to cells as a ribonucleoprotein complex or as a plasmid. From these studies, BRD0539 and BRD3433 emerged as top performers with a 1.8-fold improvement in potency over BRD7087 with a 1.8-fold improvement in potency over BRD7087 in the eGFP-disruption assay (FIGS. 3B-D and 7A) and an apparent EC50 of 11 µM. To confirm that these SpCas9 inhibitions were independent of the DNA repair mechanisms or the optical readout, HiBiT assay was performed (Schwinn et al., 2018a). While the eGFP-disruption assay is a fluorescence-based assay involving error-prone DNA repair, the HiBiT assay involves SpCas9 mediated homology-directed tagging of GAPDH with a short peptide, which produces luminescence upon complementation with a subunit derived from nanoluciferase (FIG. 3E). Both compounds exhibited dose-dependent inhibition of SpCas9 in the HiBiT assay. Both compounds inhibited SpCas9 in a dose-dependent manner in a luminescence-based HiBiT assay (Schwinn et al., 2018b), where SpCas9 mediates the tagging of GAPDH with a luminescent peptide, a split nanoluciferase (FIG. 3E). The inhibitory activity of BRD0539 was further confirmed using fluorescent-activated sorting of eGFP cells (FIG. 7B), real-time monitoring of eGFP-disruption, surveyor assay, and next-generation sequencing of the eGFP locus (FIGS. 7C and 3F). Applicants noted that while BRD0539 is cell permeable, protein-based anti-CRISPRs (e.g., AcrIIA4) are not and require delivery methods like nucleofection (FIG. 8D). To demonstrate reversible inhibition of SpCas9 by BRD0539, Applicants performed eGFP-disruption experiments, wherein cells were treated with short pulses of BRD0539 followed by treatment with inhibitor-free media. The cells with media swap at an earlier time point had lower levels of eGFP-disruption, suggesting reversible inhibition by BRD0539 (FIG. 3H). In contrast, the SpCas9 inhibition by AcrIIA4 was irreversible (FIG. 3H). Applicants confirmed binding of the identified compounds to SpCas9:gRNA using BLI (FIGS. 7H, 7I) following the aforementioned protocol. BRD0539 exhibited a dose-dependent inhibition (apparent $IC_{50=22}$ µM) in an in vitro DNA cleavage assay, even when the concentration of SpCas9 (5 nM) was much higher than typically present in cells (FIGS. 3M and 7O). Finally, Applicants confirmed that none of the compounds were auto-fluorescent in cells, none were cytotoxic to multiple cell lines and primary cells (FIGS. 7G, 7D, 7E, and 7F), and all were stable in human plasma (FIG. 8F) (Di et al., 2005).

Figure 7J:
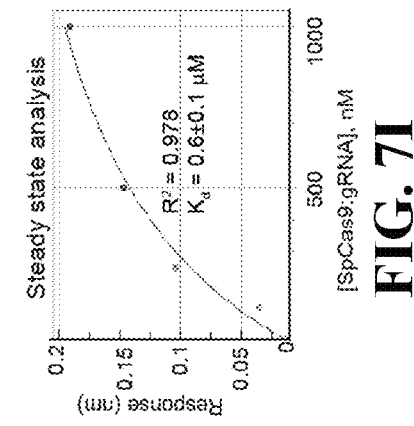
(FIG. 7J) Pull-down study of SpCas9 by biotinylated BRD3433. Representative gel electrophoretic image showing compound mediated enrichment of SpCas9 in the eluent (E). A competition with unlabeled BRD3433 showed a reduction in the SpCas9 enrichment in the eluent with a concomitant increase in the flow through (FT).
Figure 7K:
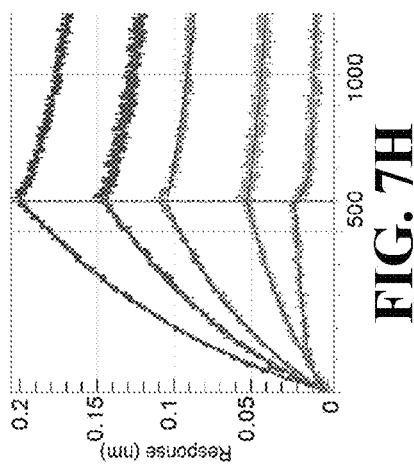
(FIG. 7K) Differential scanning fluorimetry assay plots showing the formation of a more stable SpCas9 complex (shaded region) upon binding with the increasing concentration (0.25, 0.5, 1, and 2 μM) of 8PAM DNA. Error bars represent ±s.d. across technical replicates (n=2).
Figure 7L:
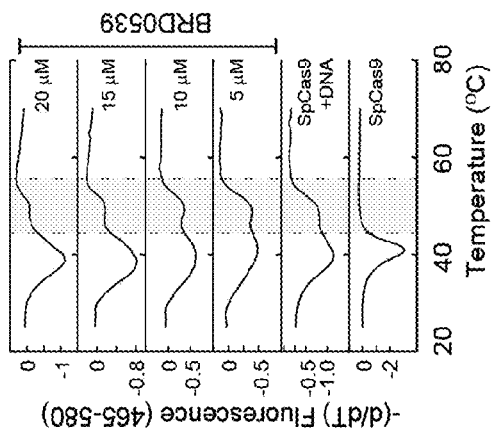
(FIG. 7L) Differential scanning fluorimetry assay plots depicting the destabilization of SpCas9:8PAM DNA (1 μM: 2 μM) complexes (shaded region) upon incubation with an increasing concentration (5, 10, 15, and 20 μM) of BRD0539. Error bars represent ±s.d. across technical replicates (n=2).
Figure 7M:
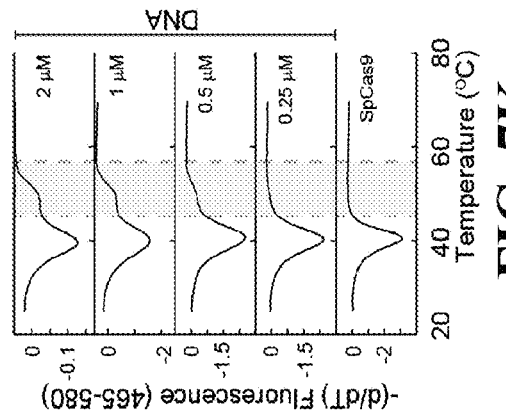
(FIG. 7M) Representative immunoblots of cellular thermal shift assay (CETSA) for SpCas9 in WM793 melanoma cells in the absence or presence of BRD0539. Stably SpCas9 expressing WM793 cells were incubated with 15 μM BRD0539 for 24 h before performing CETSA and analyzed by Western blot.
Figure 7N:
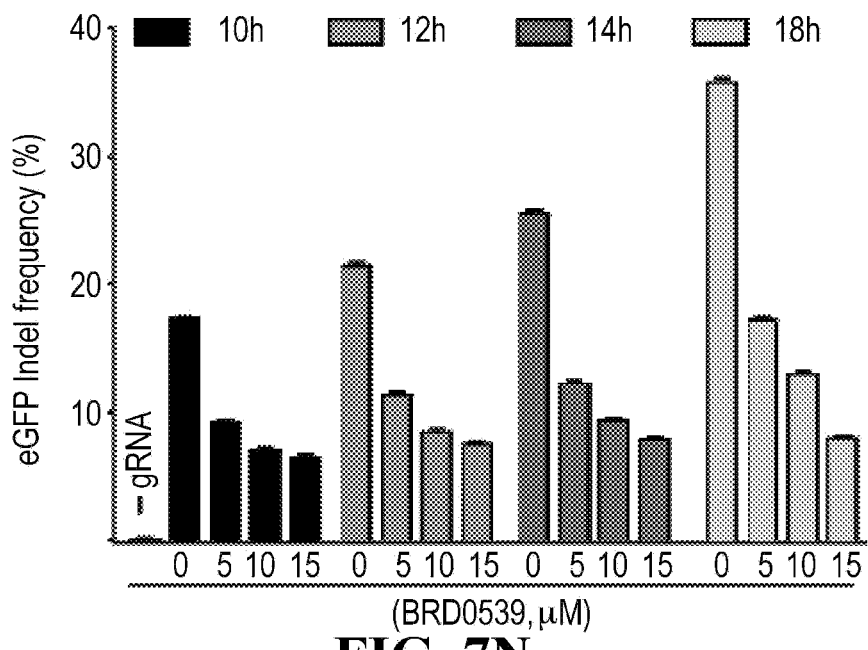
(FIG. 7N) Next-generation sequencing analysis of eGFP indicating dose and time-dependent inhibition of SpCas9 by BRD0539 in U2OS.eGFP.PEST cells. Cells were nucleofected with either SpCas9 or preformed SpCas9:gRNA ribonucleoprotein complex targeting the eGFP gene and incubated with BRD0539 at the indicated concentrations for 10, 12, 14, and 18 h before harvesting genomic DNA. Error bars represent ±s.d. across technical replicates (n=2) of two biological replicates.

Applicants confirmed the binding of these compounds to SpCas9:gRNA using BLI (FIGS. 7H, 7I) following the aforementioned protocol and a pulldown and competition experiment (FIG. 7J). BRD0539 exhibited a dose-dependent inhibition (apparent $IC_{50=22}$ µM) in an in vitro DNA cleavage assay even when the concentration of SpCas9 (5 nM) was much higher than those typically present in cells (FIGS. 3M and 7O).

Figure 7P:
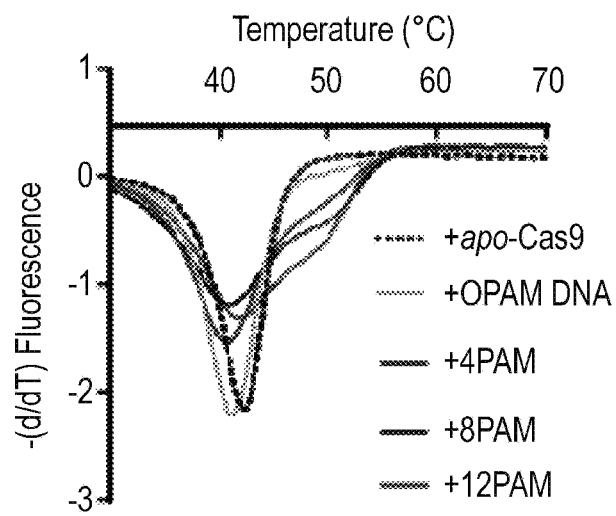
(FIG. 7P) Biological replicate data of differential scanning fluorimetry studies of apo-SpCas9 interaction with DNA. SpCas9 (1 μM) was incubated with DNA (2 μM) bearing an increasing number of PAM sequence (0-12 PAM).
Figure 7Q:
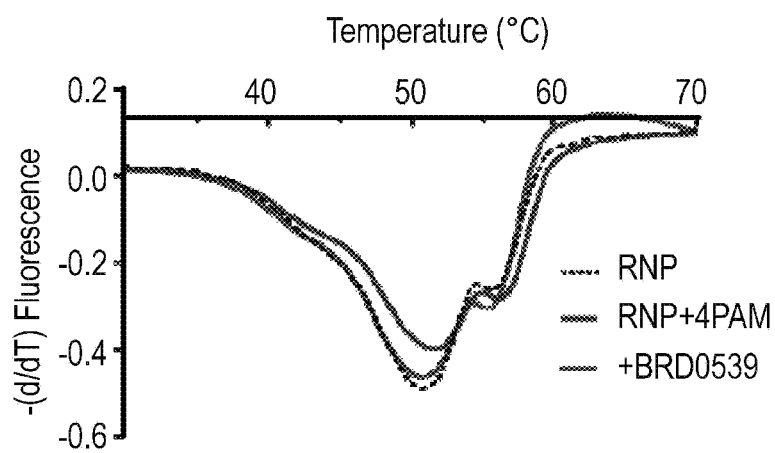

Applicants confirmed disruption of SpCas9:DNA interactions by BRD0539 using DSF. Briefly, the melting curves of apo-SpCas9 suggested the presence of DNA bound state upon the addition of DNA with increasing number of PAM sequences (0-12 PAM, FIGS. 3N and 7P) or increasing concentration of 8PAM DNA (FIGS. 3H and 7K). BRD0539 dose-dependently blocked the formation of the DNA bound state (FIGS. 3I and 7L). The SpCas9:gRNA exhibited a multiphasic melting signature which was altered upon addition of DNA containing PAM sequences. BRD0539 impaired the perturbation induced by the 4 PAM DNA (FIG. 7Q).

Finally, to confirm target engagement by BRD0539 in cells, Applicants used the cellular thermal shift assay (CETSA, cellular version of the DSF assay) (Martinez Molina et al., 2013; Martinez Molina and Nordlund, 2016). Since SpCas9:DNA interactions increase the melting temperature of SpCas9 (FIGS. 1D, 3H), disruption of such interactions by BRD0539 should lower the melting temperature of SpCas9. Indeed, Applicants observed ~2.5° C. lowering in the melting temperature of SpCas9 in cells treated with BRD0539 (FIGS. 3J and 7M).

Figure 4D:
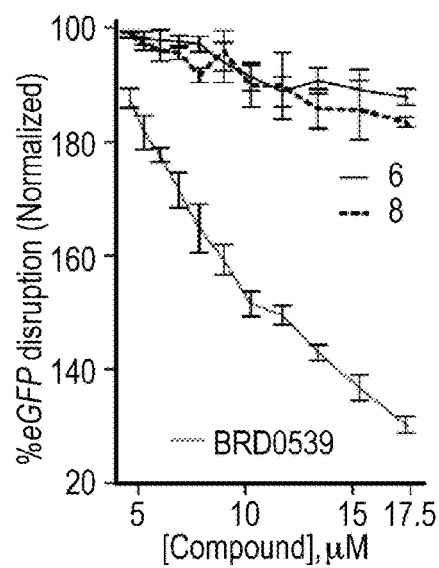
Figure 4E:
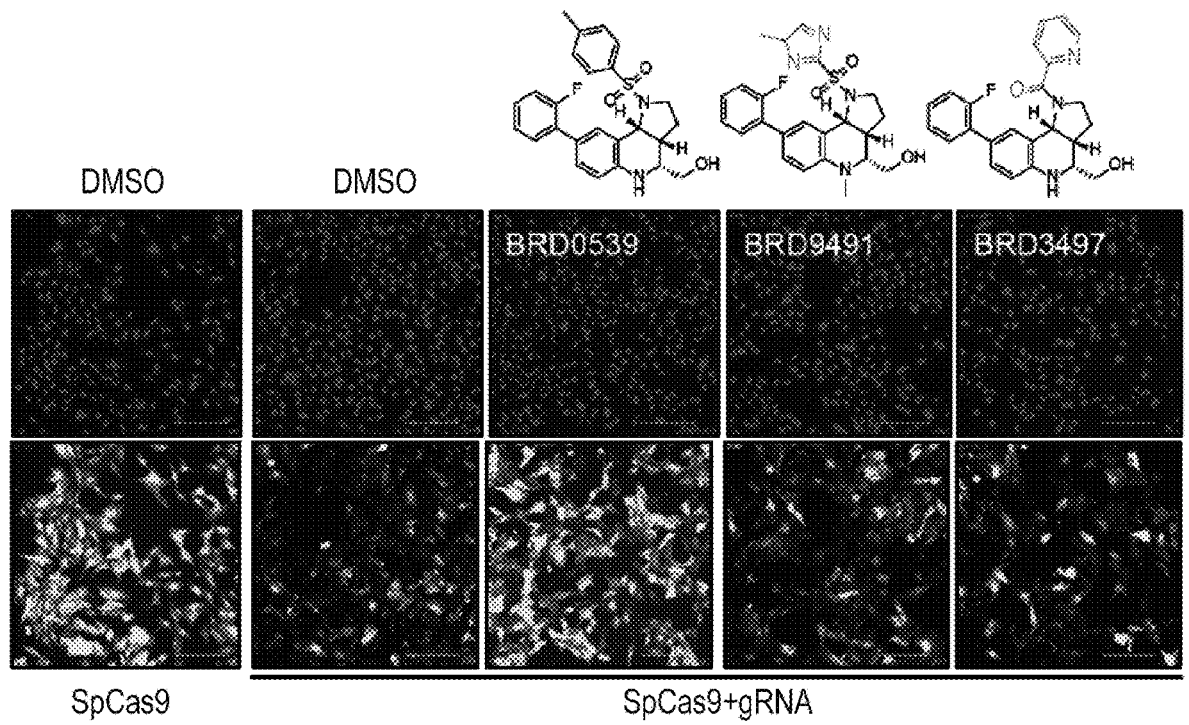
Figure 4F:
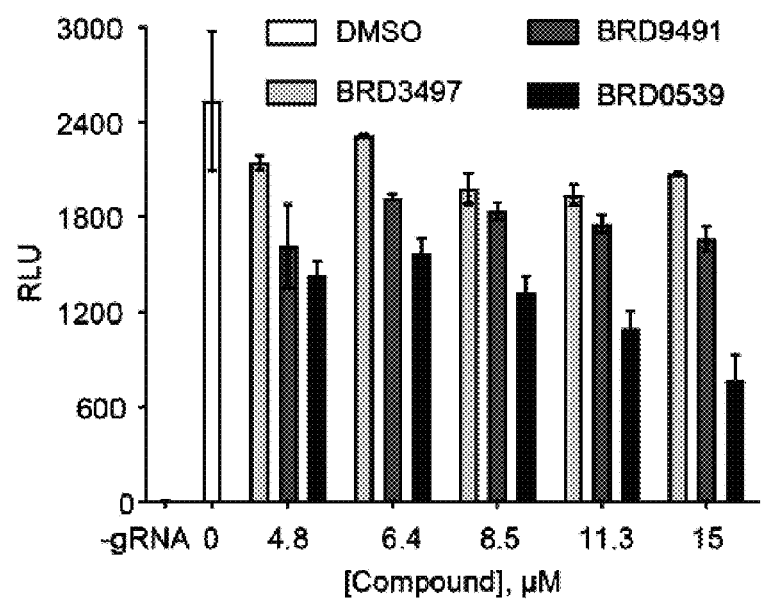
Figure 5A:
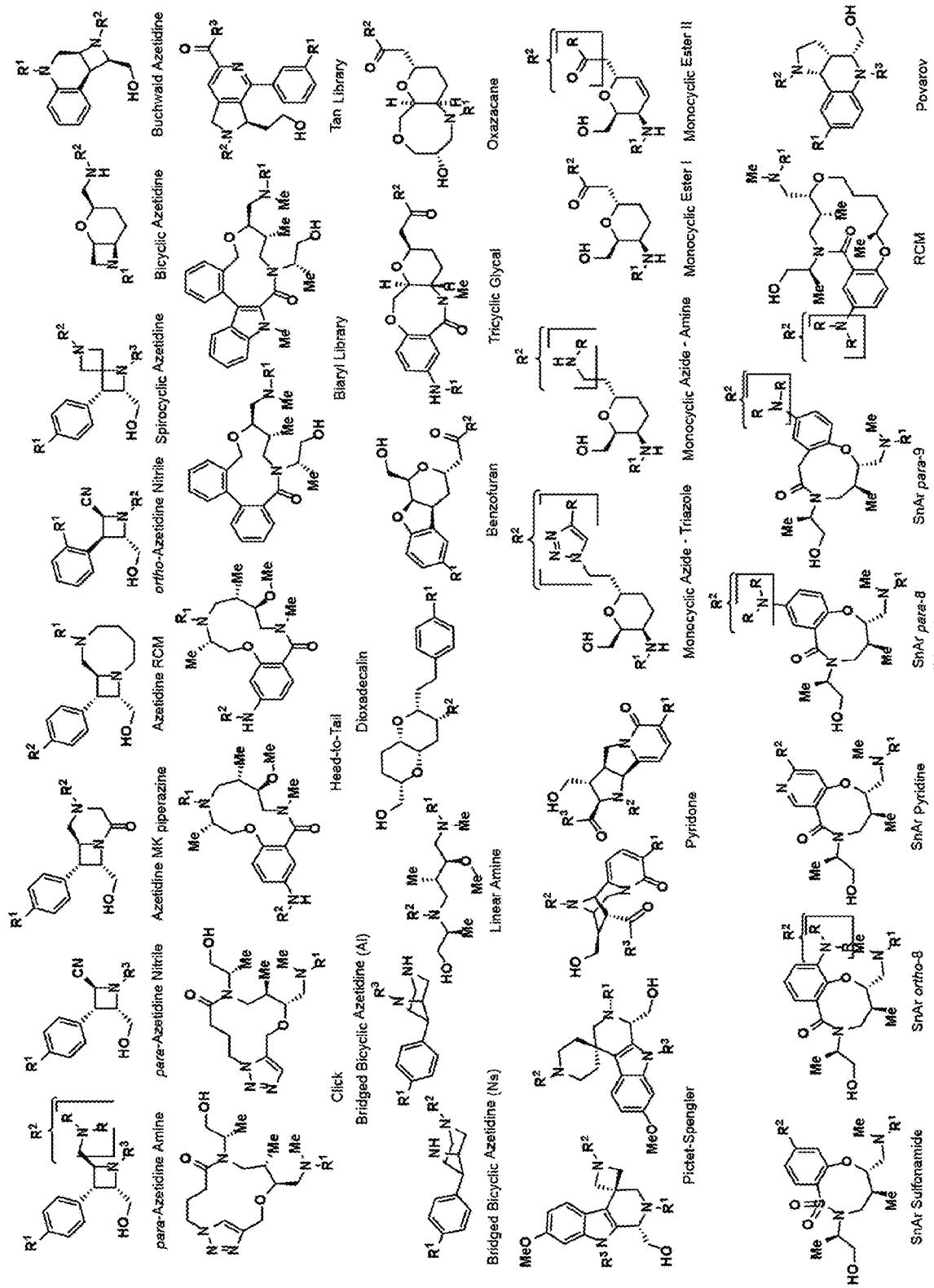

Structure-activity relationship of BRD0539. To identify the pharmacophore of BRD0539, Applicants examined the activities of structural analogs that differed in $R^1$ or $R^2$ groups but not both (FIG. 4A). Keeping $R^2$=a and varying $R^1$ showed that sulfonamides (1-4) are more potent than amides (5-7), perhaps because a sulfonamide can accept two hydrogen bonds while an amide can accept one. Interestingly, minor changes on $R^1$ significantly alter potencies—while 1, 2, or 3 have similar bond connectivity except for the nature of substituent at the para-position, the replacement of methyl (1) with fluoro (2) or methoxyl (3) decreases activity by 18% and 20%, respectively. Furthermore, alteration of the position of the methyl group from para-(1) to meta-(4) resulted in a 47% reduction of activity. Introducing heteroatoms on the rings (5-8) failed to improve potency—the compound with R1=8 was virtually inactive. Keeping R1=1 and varying $R^2$ groups showed that the use of alkynyl spacers (b or d) lowers inhibitory activity, which was also observed for an alkenyl moiety. Substitution of relatively small 2-fluoro-(a) with larger 3-N,N-dimethyl-carbamoyl-(c) also led to the loss of activity. Applicants compared the activity of BRD0539 at 12 different dose points in the eGFP-disruption assay with that of BRD3497 and BRD9419, which have a 4-methyl-imidazole or a 2-keto-pyridyl group, respectively, in place of the p-tolyl group in BRD0539. While BRD0539 showed dose-dependent inhibitory activity, BRD3497 and BRD9419 barely inhibited SpCas9 (FIG. 4D, 4E). The lower inhibitory activity of BRD3497 and BRD9419 was apparent in the HiBiT assay, as well, where BRD0539 showed a greater than two-fold higher activity. (FIG. 4F).

Figure 8G:
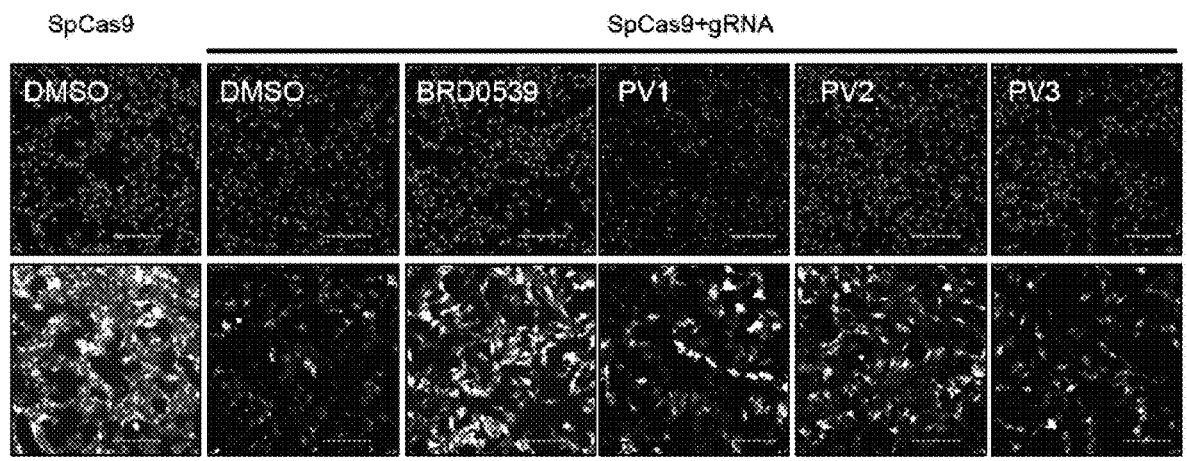

In addition to the aforementioned structure-activity relationship, Applicants determined the stereochemical structure-activity relationship for BRD0539 by testing the activities of four stereoisomers in the eGFP-disruption assay (FIGS. 4B and 8G). Interestingly, among the four stereoisomers, BRD0539 with RRR stereochemistry was the most potent. Finally, Applicants observed a strong structure-activity relationship with BRD3433 as well. Keeping $R^2$=a and systematically varying $R^1$ showed that the size and nature of the $R^1$ rings are important: 6-membered rings (1, 2, or 3) are better than 5-membered rings (4 or 5), 4-membered rings (8) or a fused-ring system (7) (FIG. 8A). Further, compounds with aryl rings at R1 were better inhibitors than those with an aliphatic rings—the compound with R1=8 was virtually inactive. In contrast to BRD0539, the introduction of heteroatom on the ring improves potency (R1=1 vs. R1=3). Finally, replacement of aryl ring with bromine led to a drastic 78% reduction in activity.

Figure 10A:
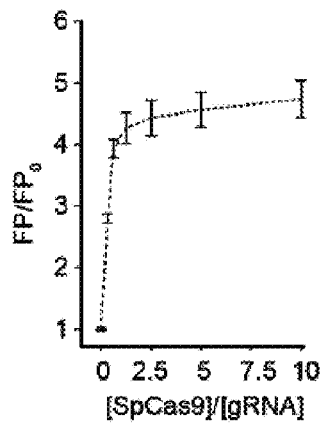
Figure 10B:
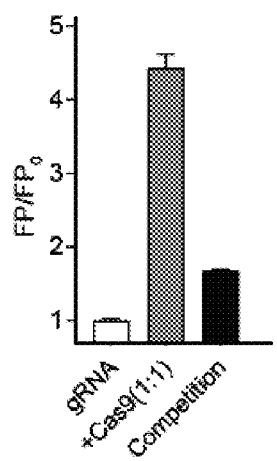
Figure 10C:
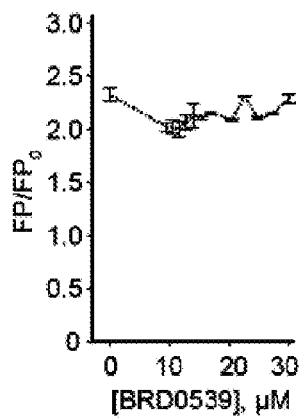
Figure 11:
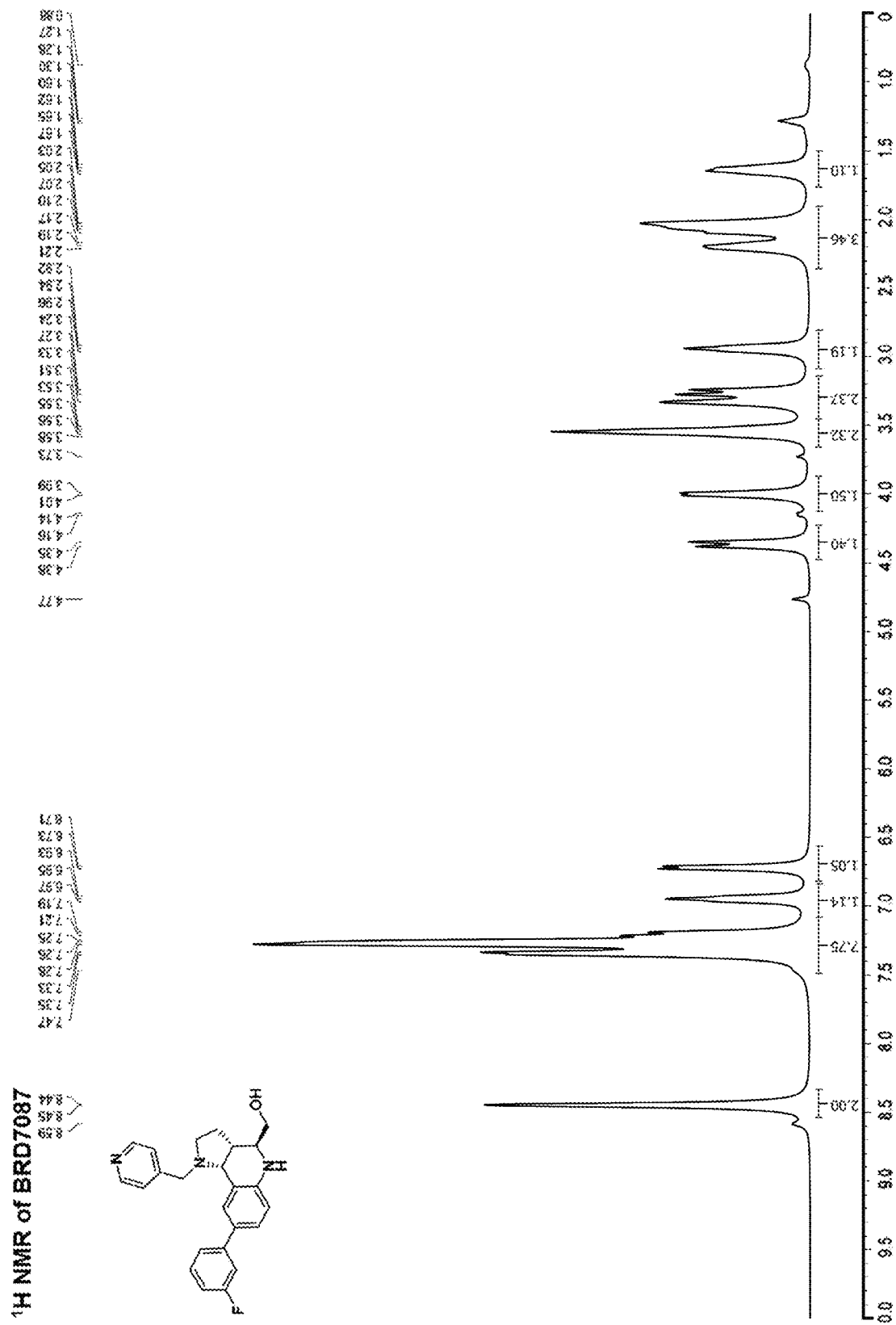
Figure 12:
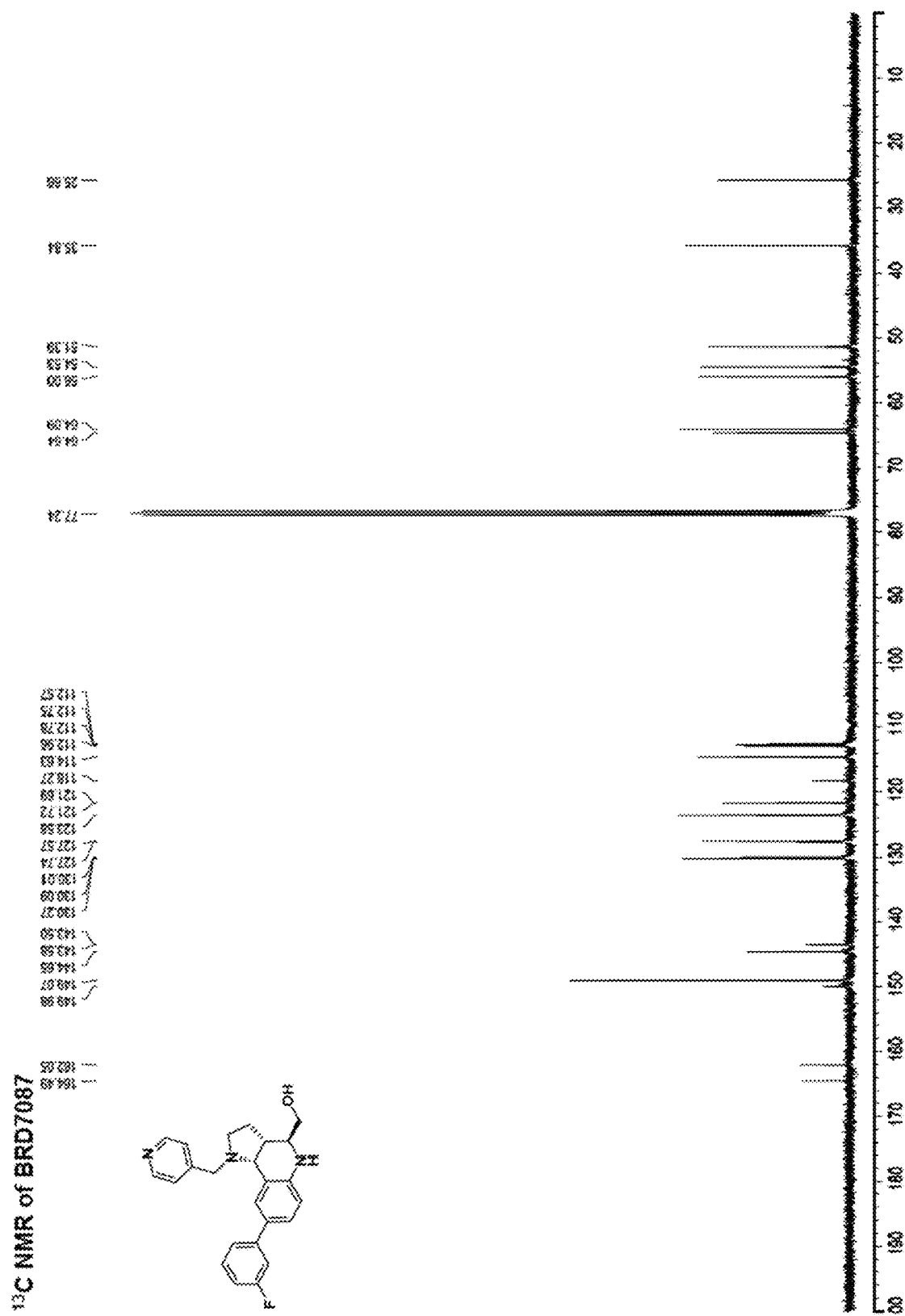
Figure 14:
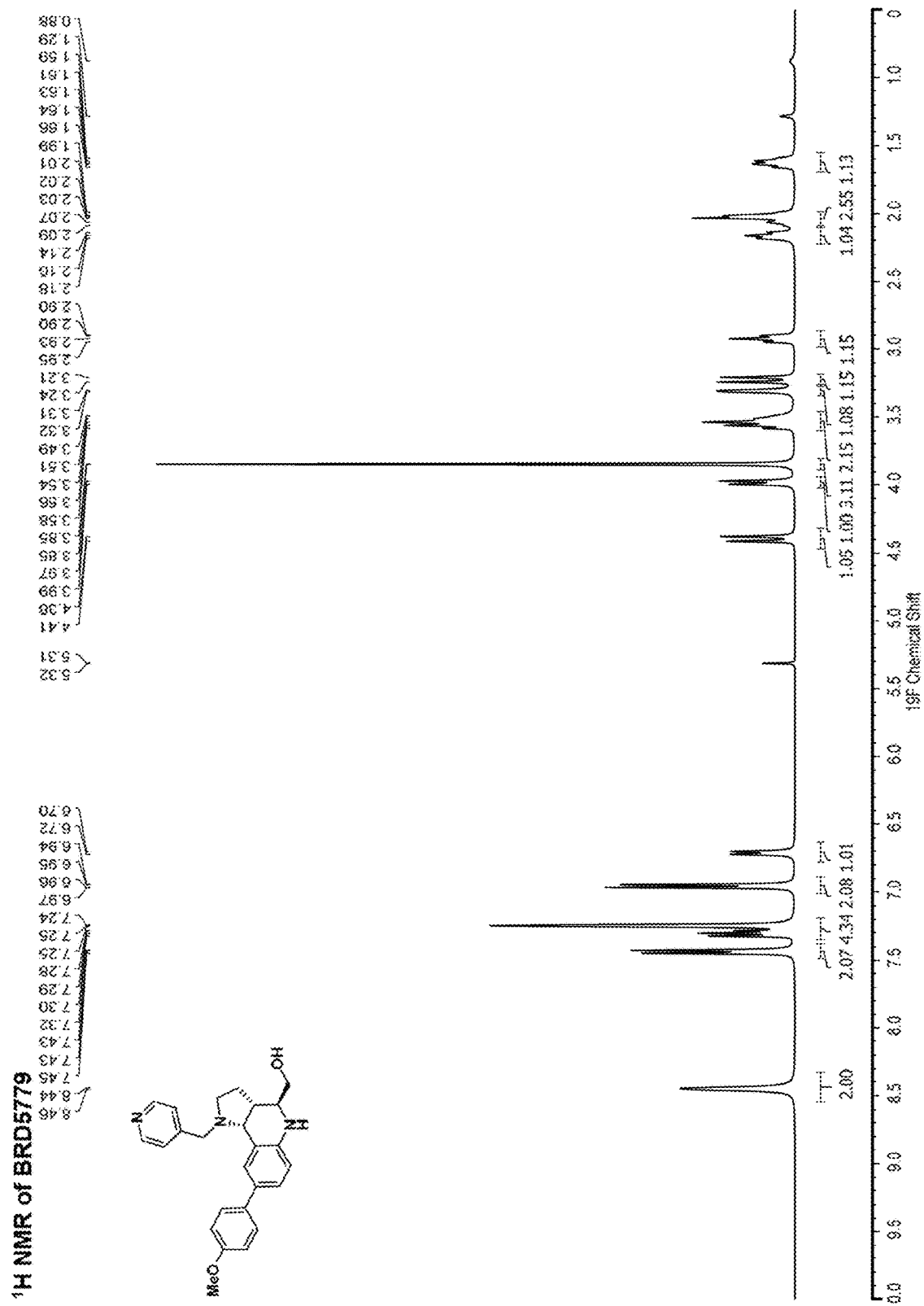
Figure 15:
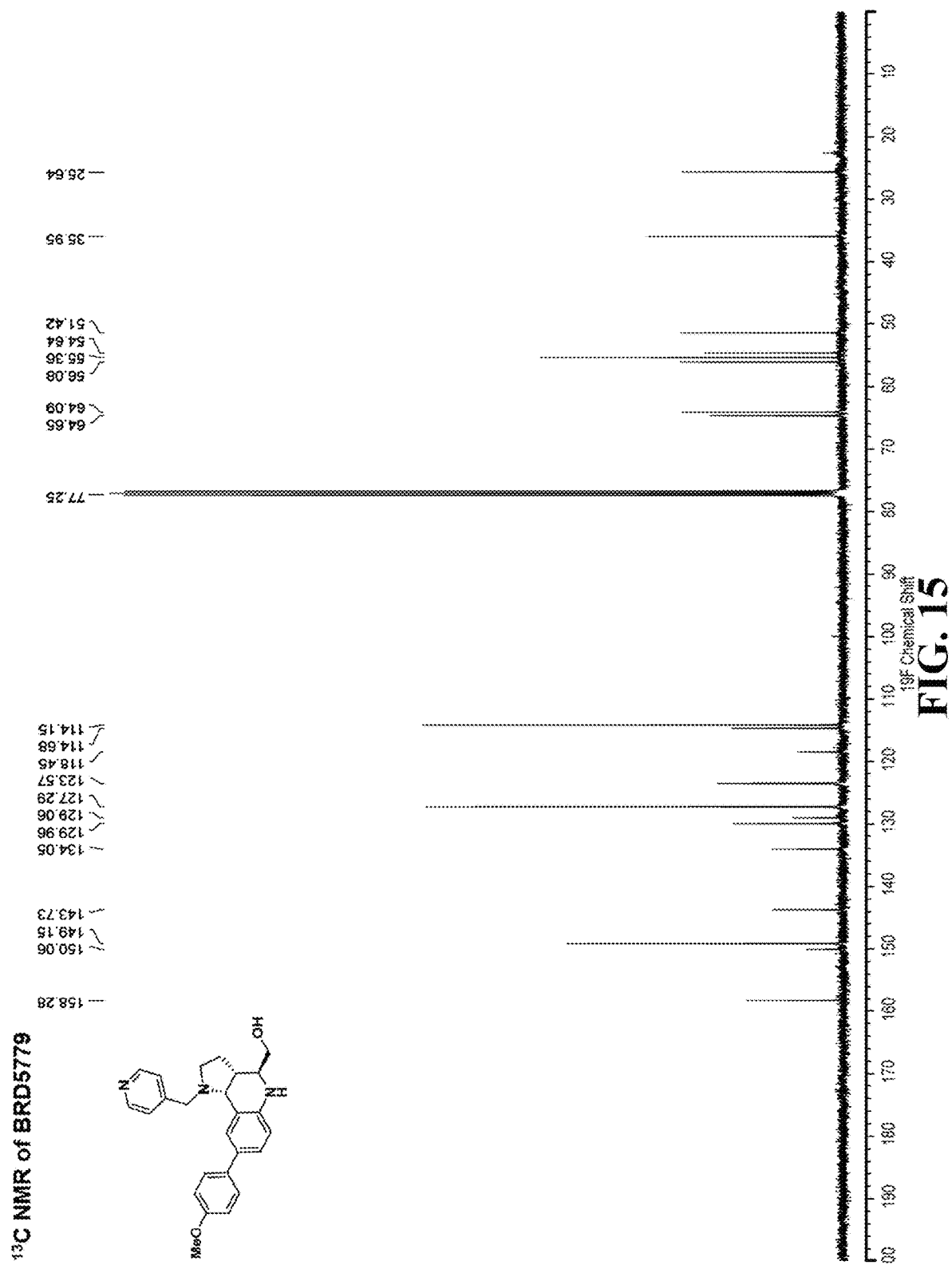
Figure 16:
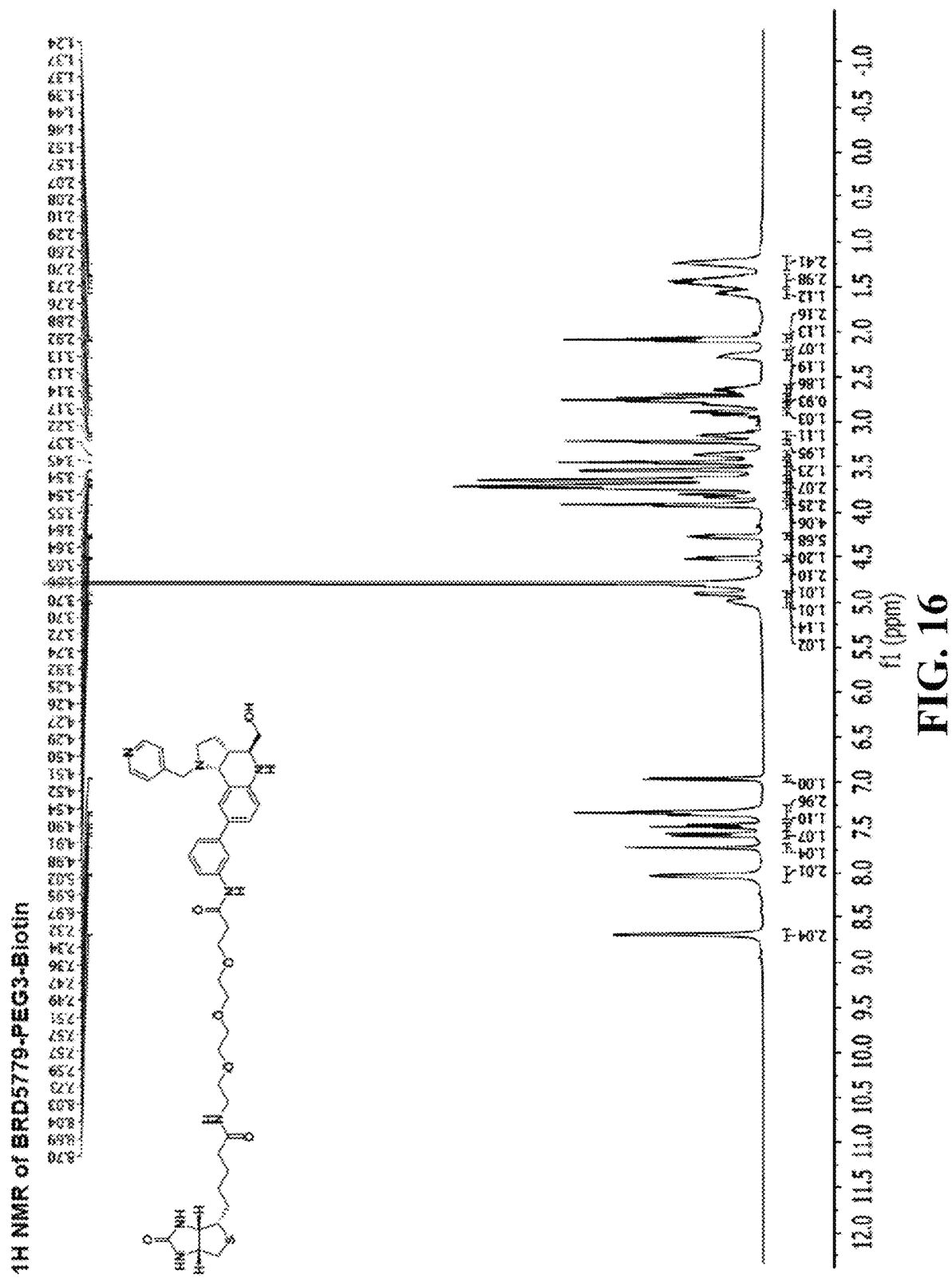
Figure 18:
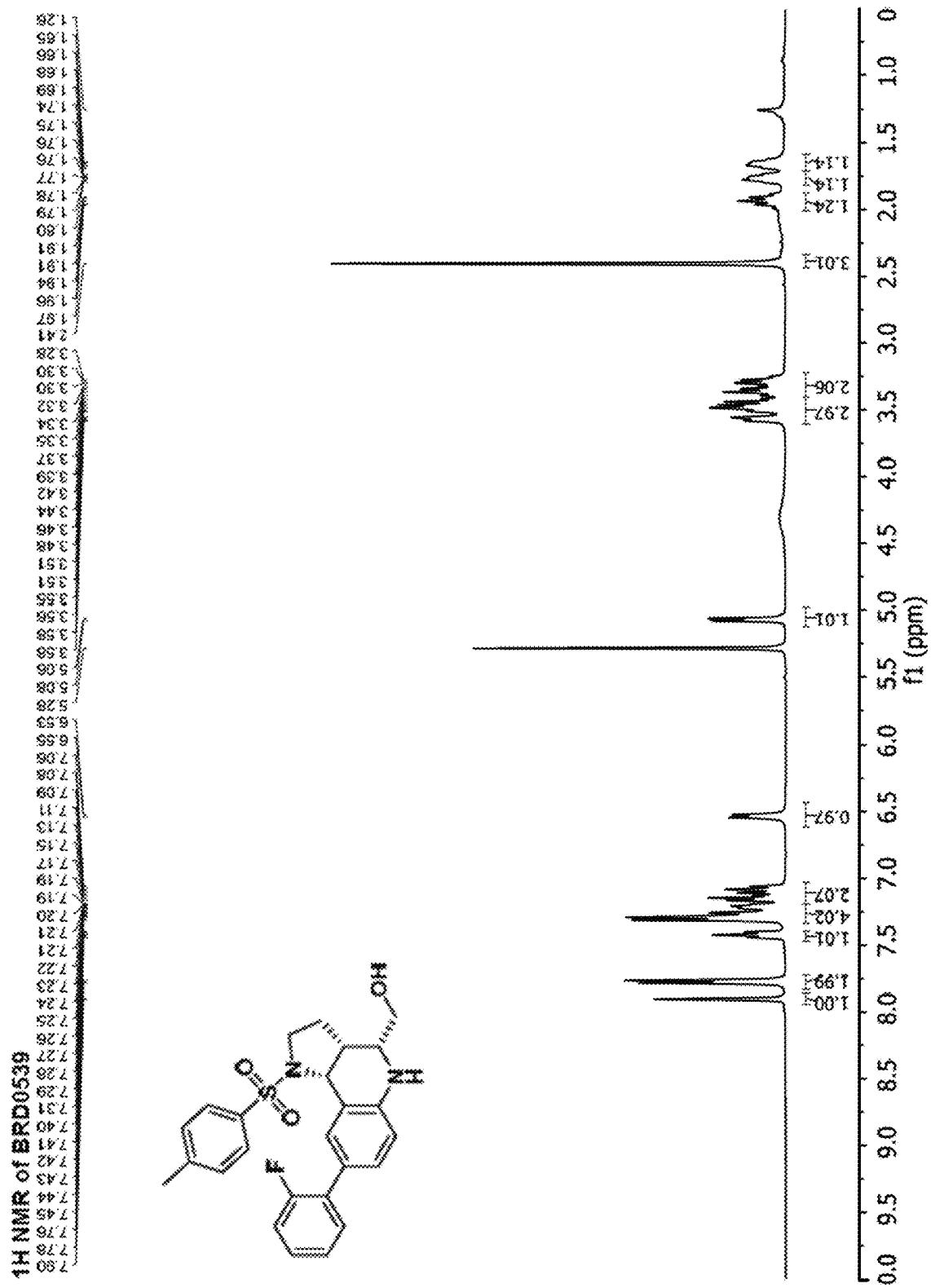
Figure 19:
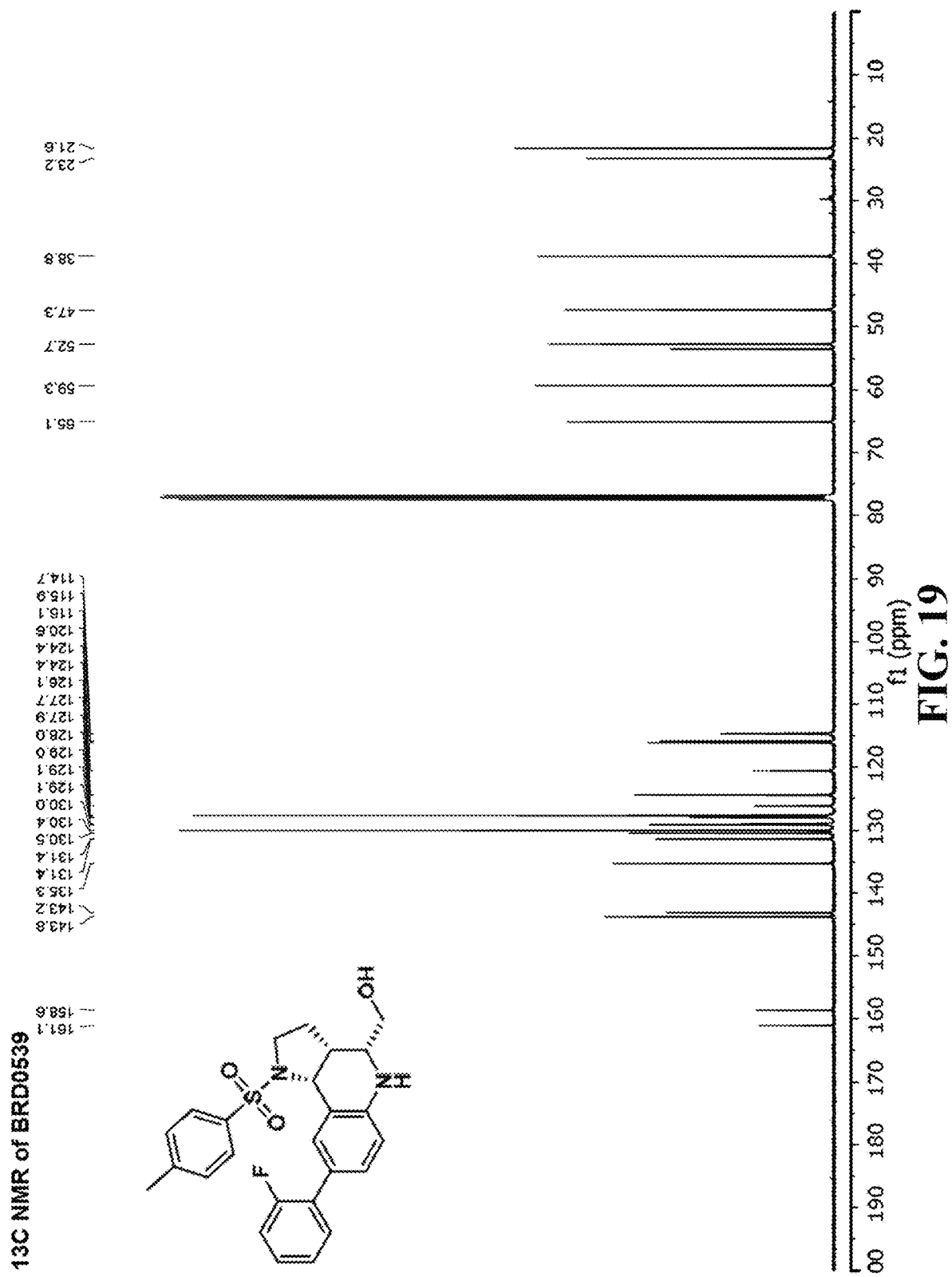
Figure 20:
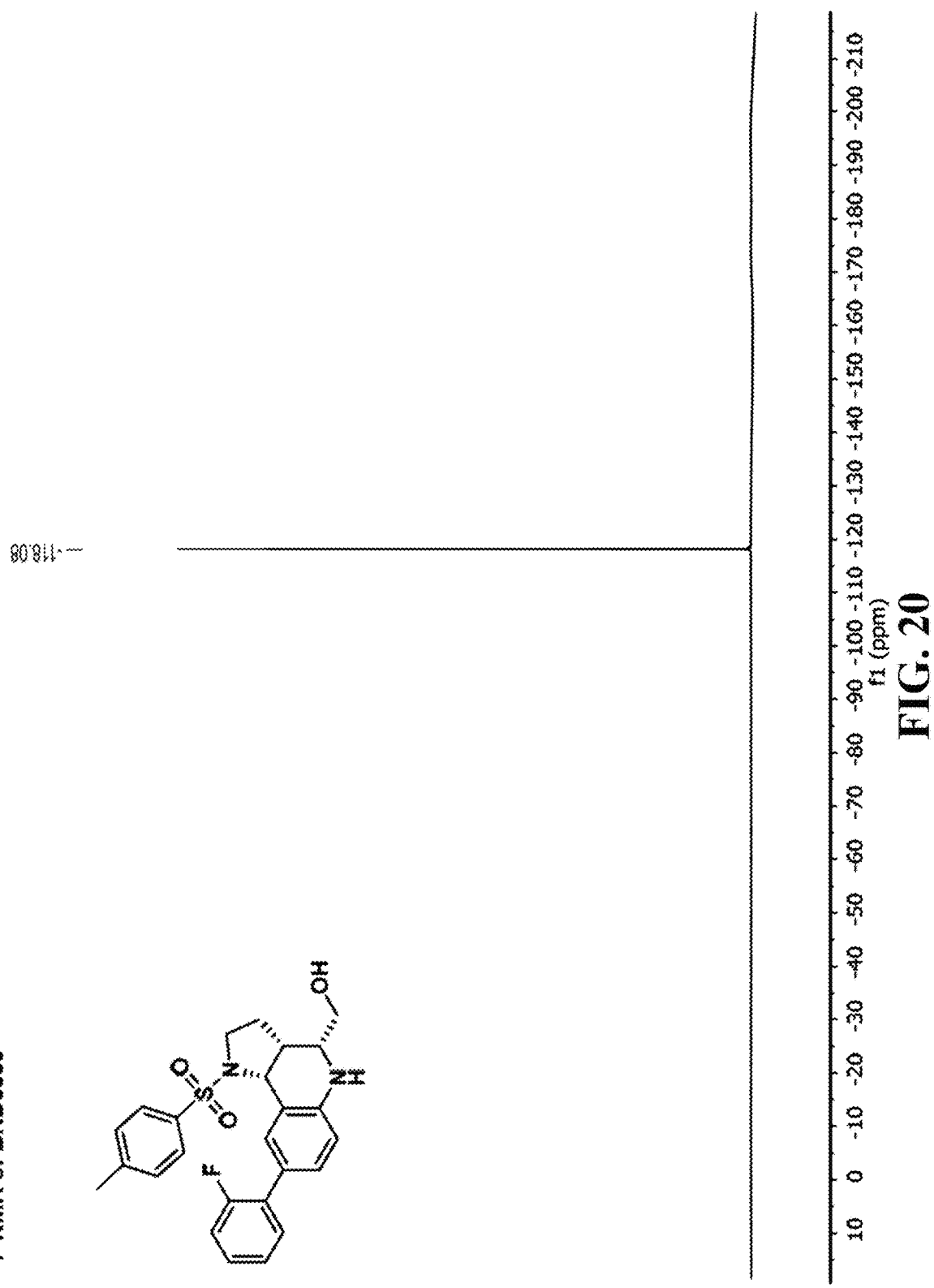
Figure 21:
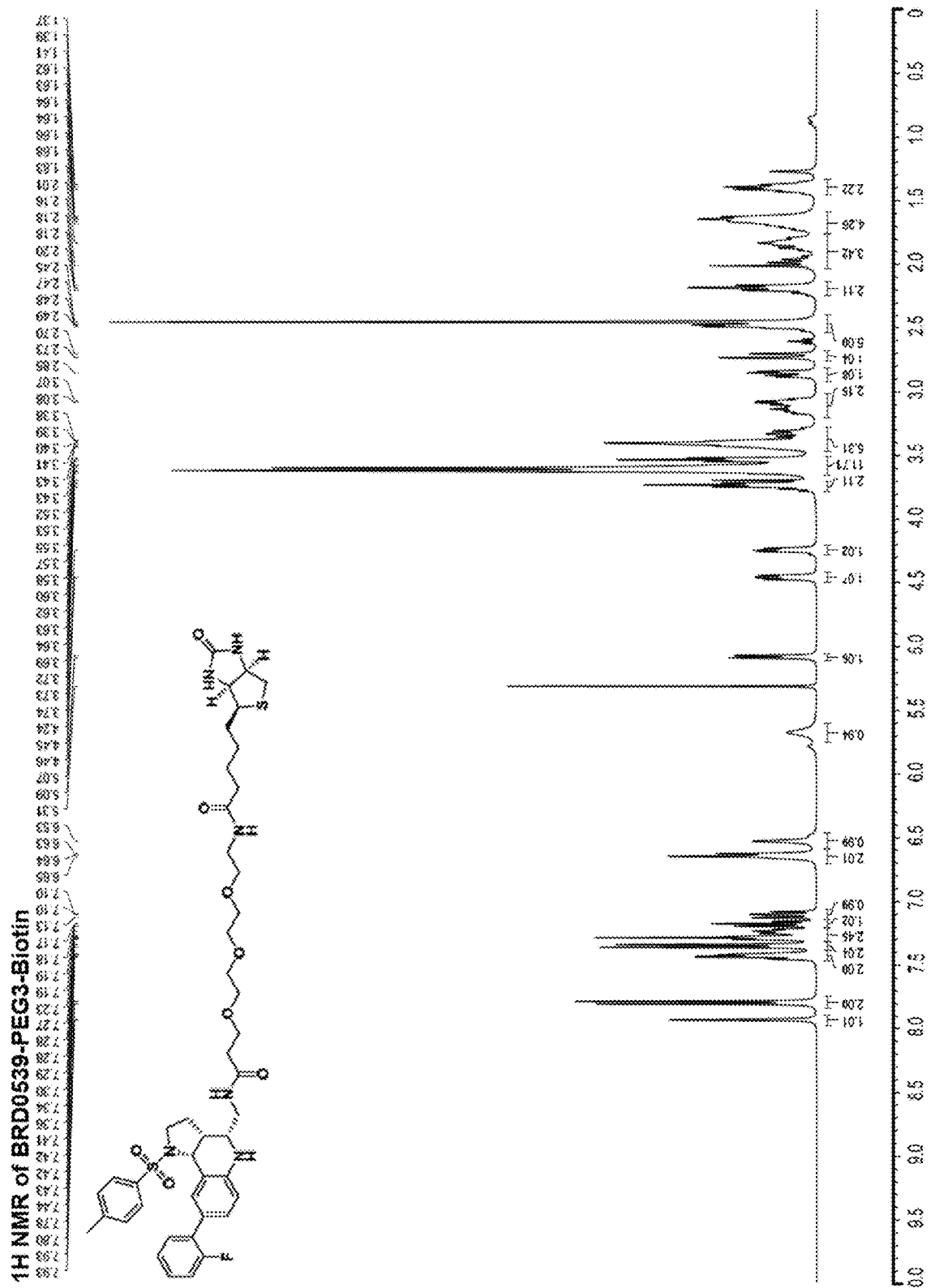
Figure 22:
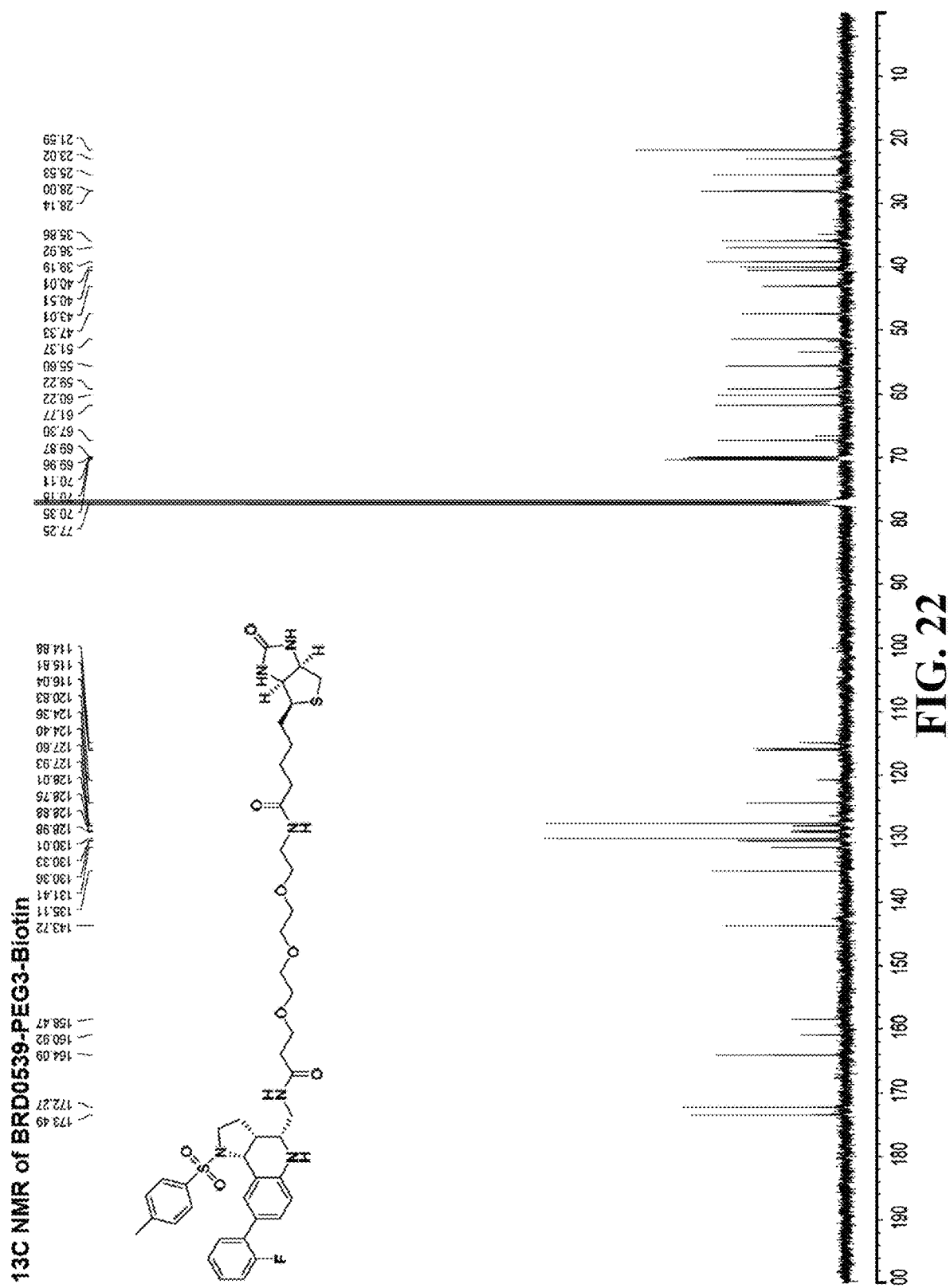
Figure 23:
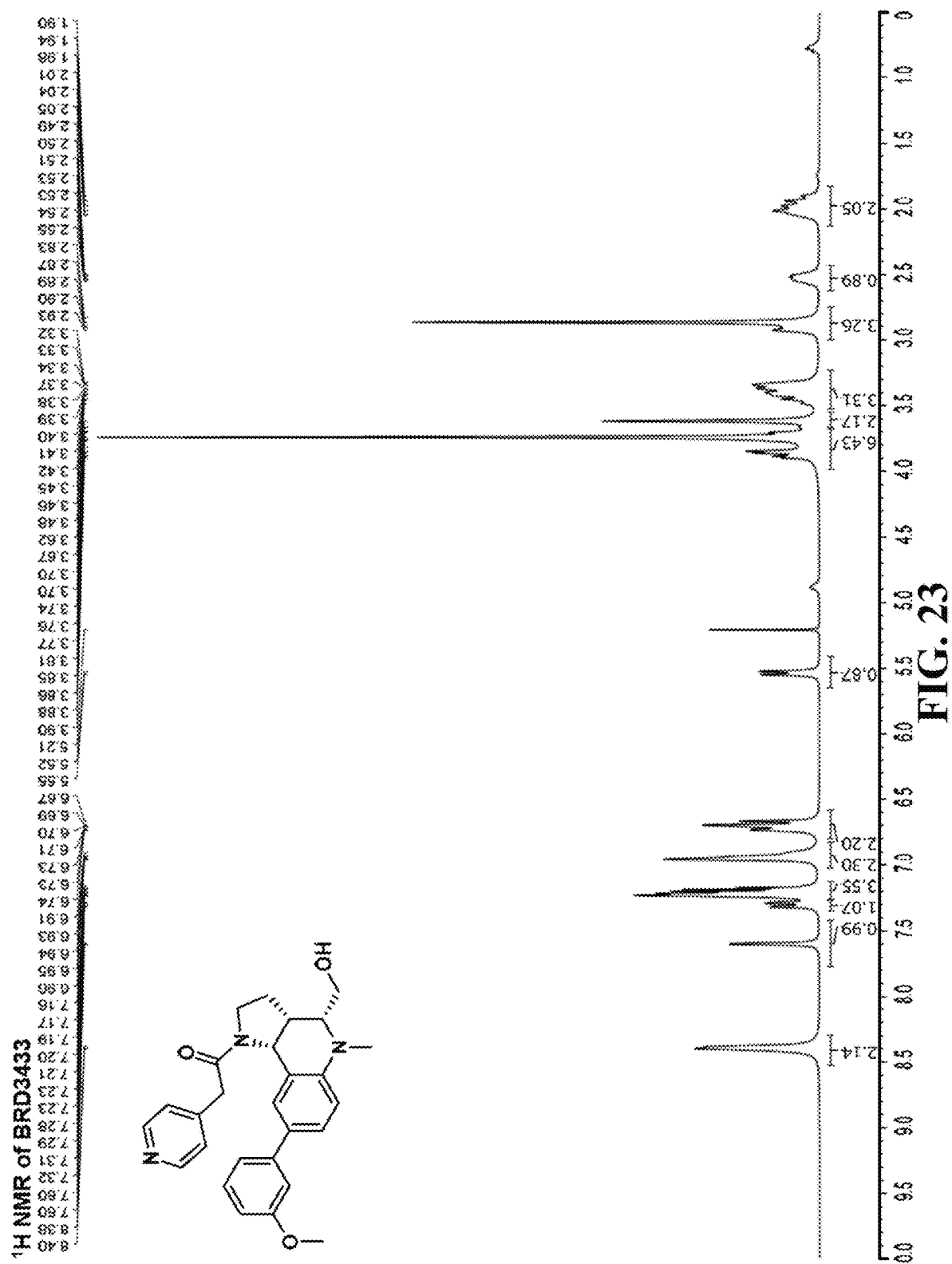
Figure 24:
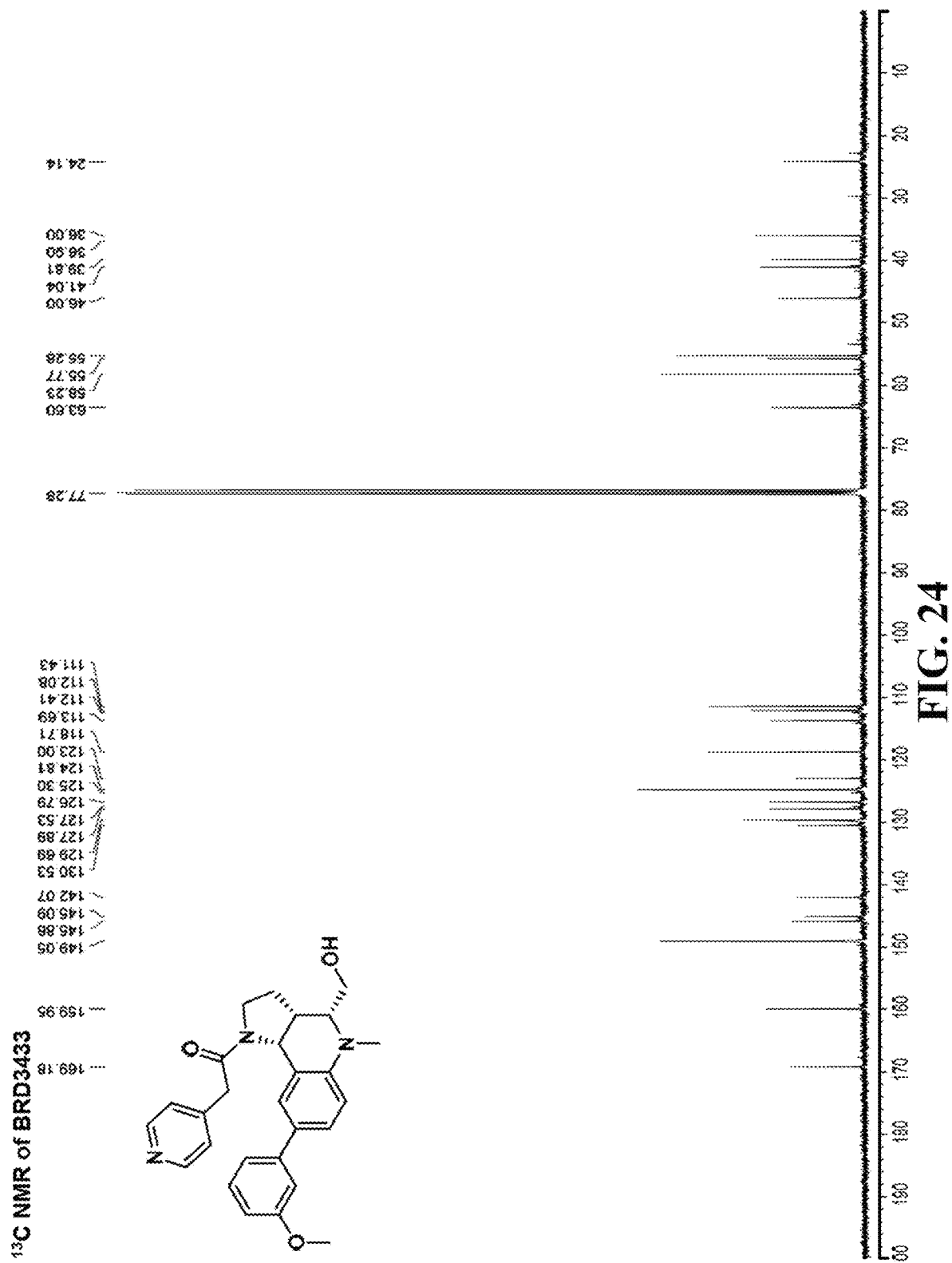
Figure 25:
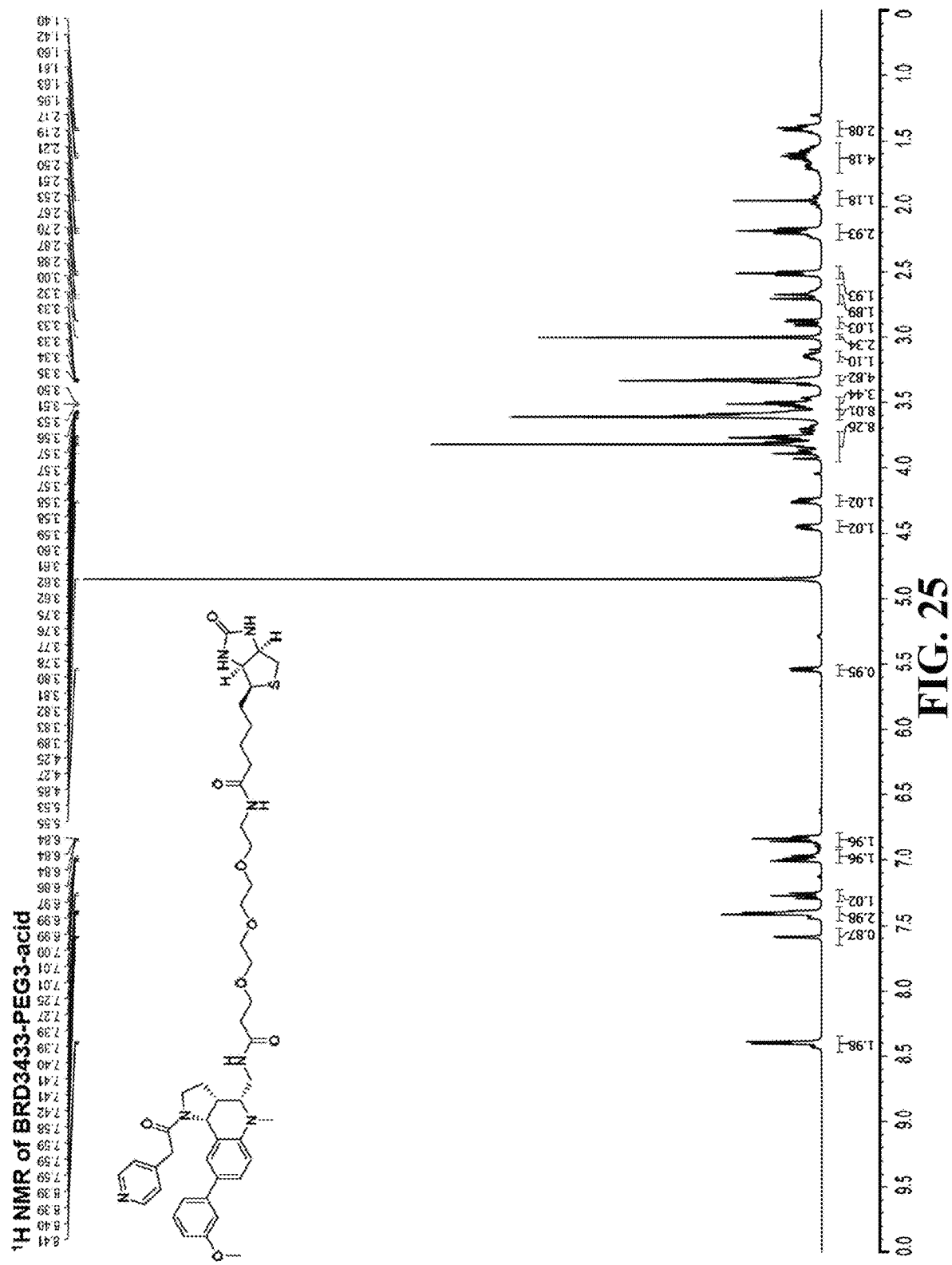
Figure 26:
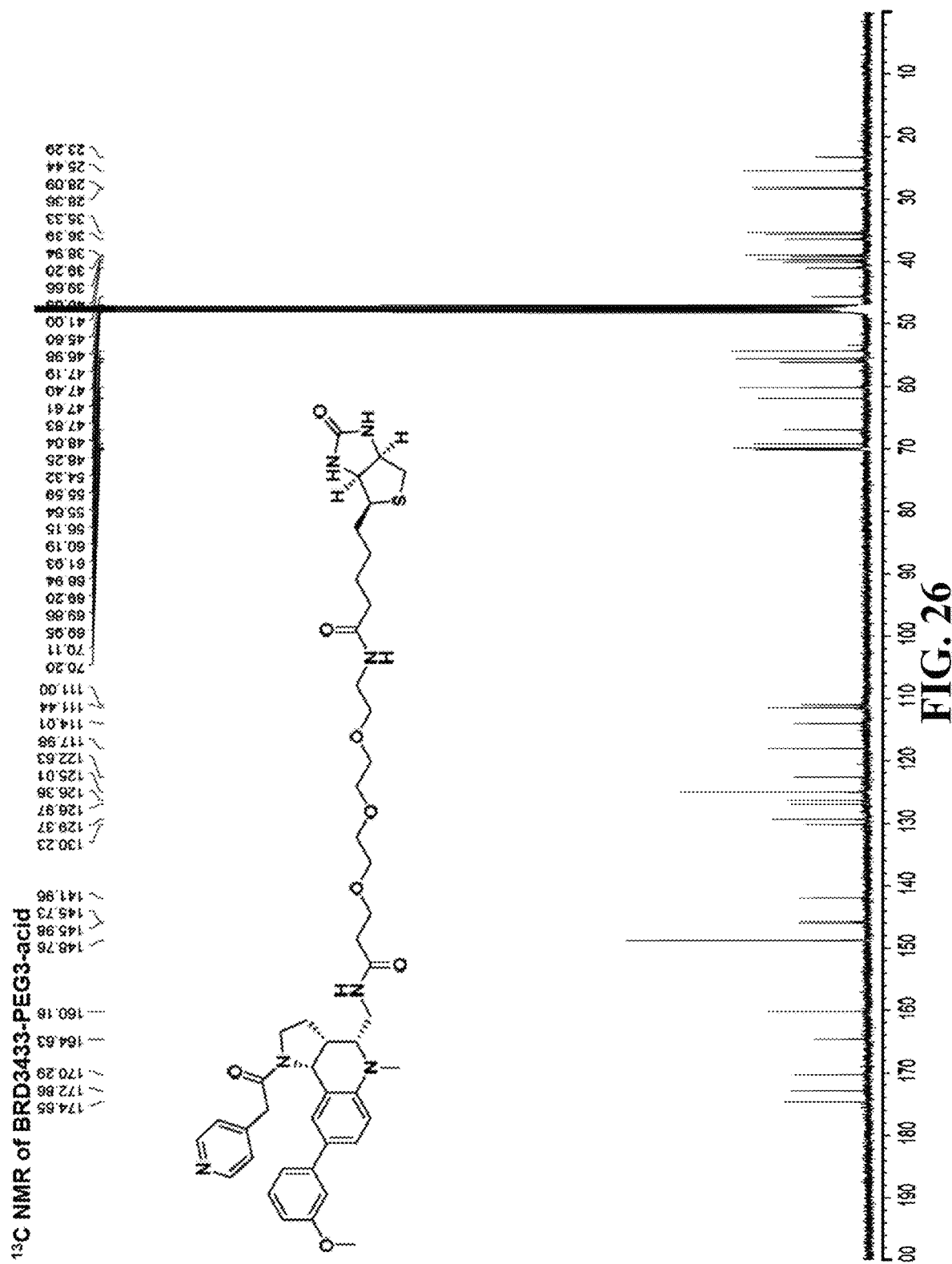
Figure 27:
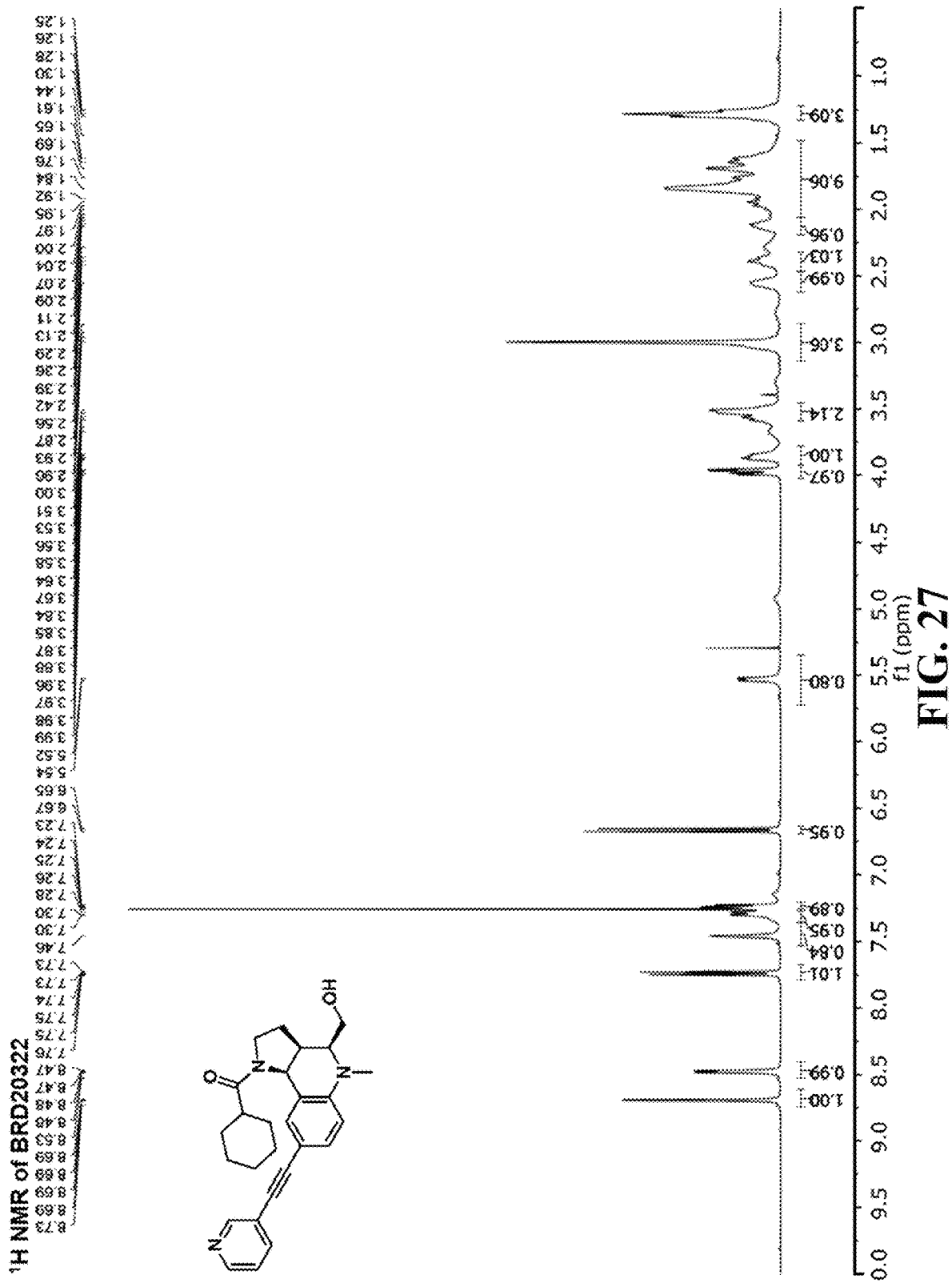
Figure 28:
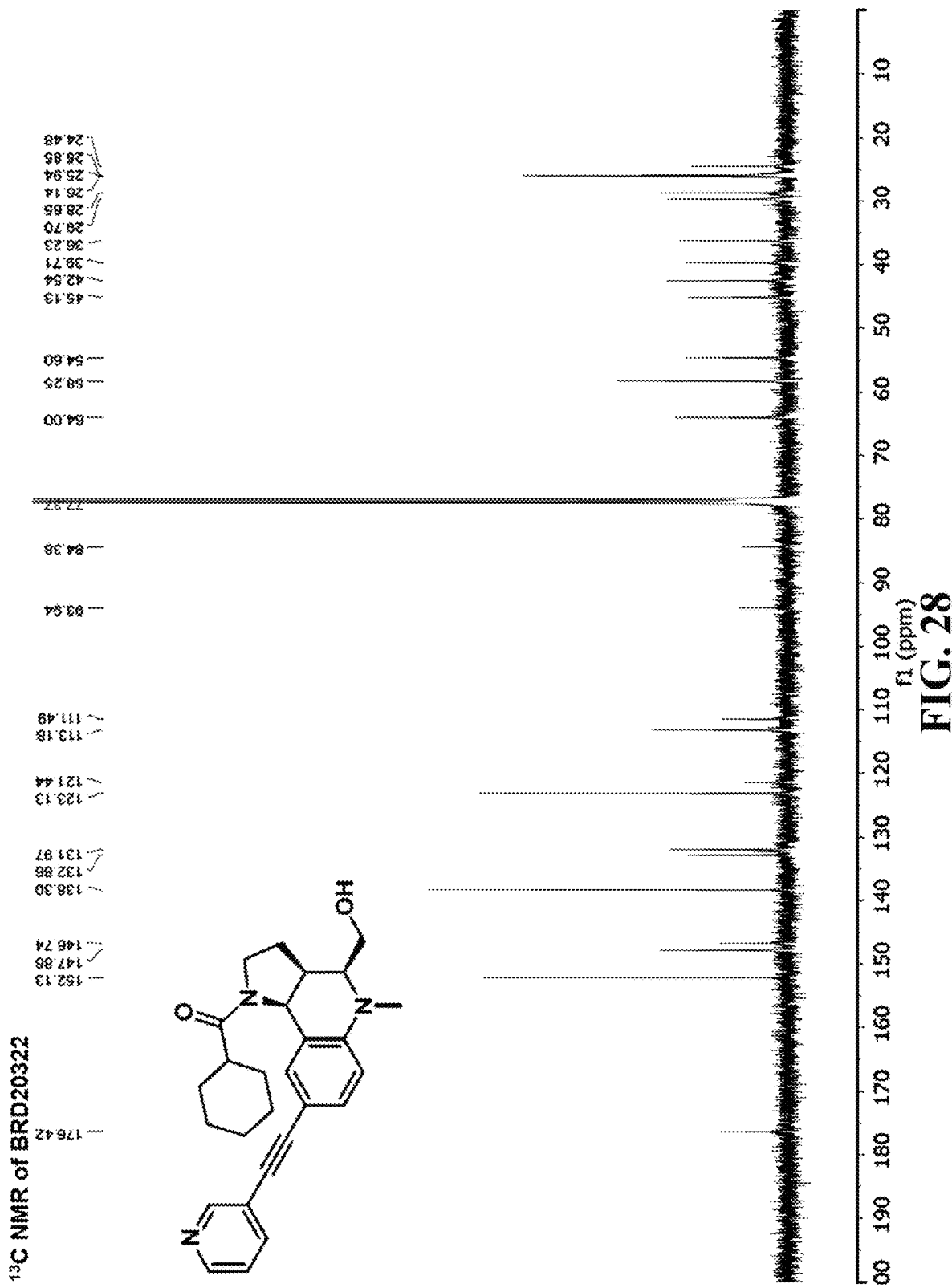
Figure 29:
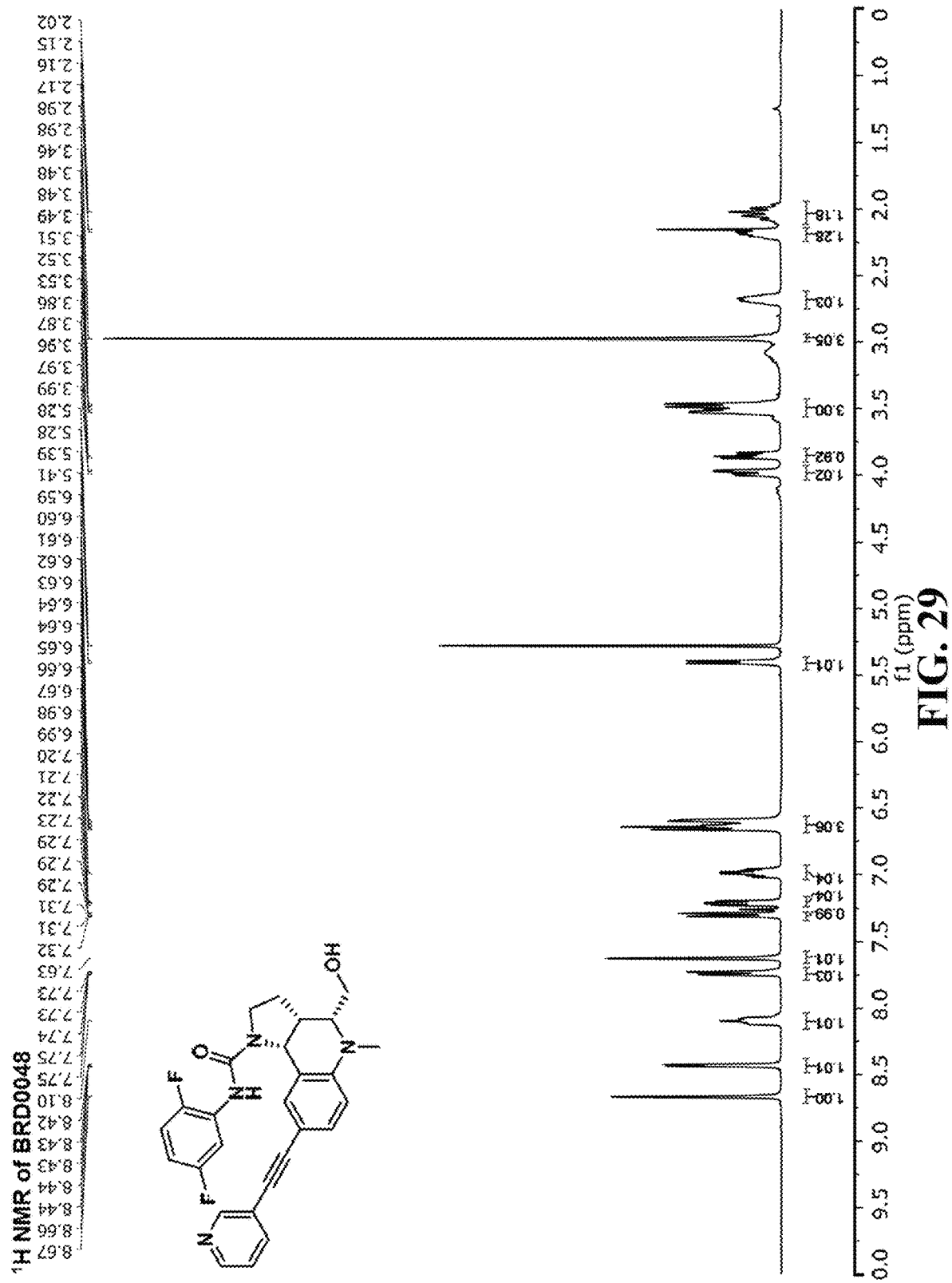
Figure 30:
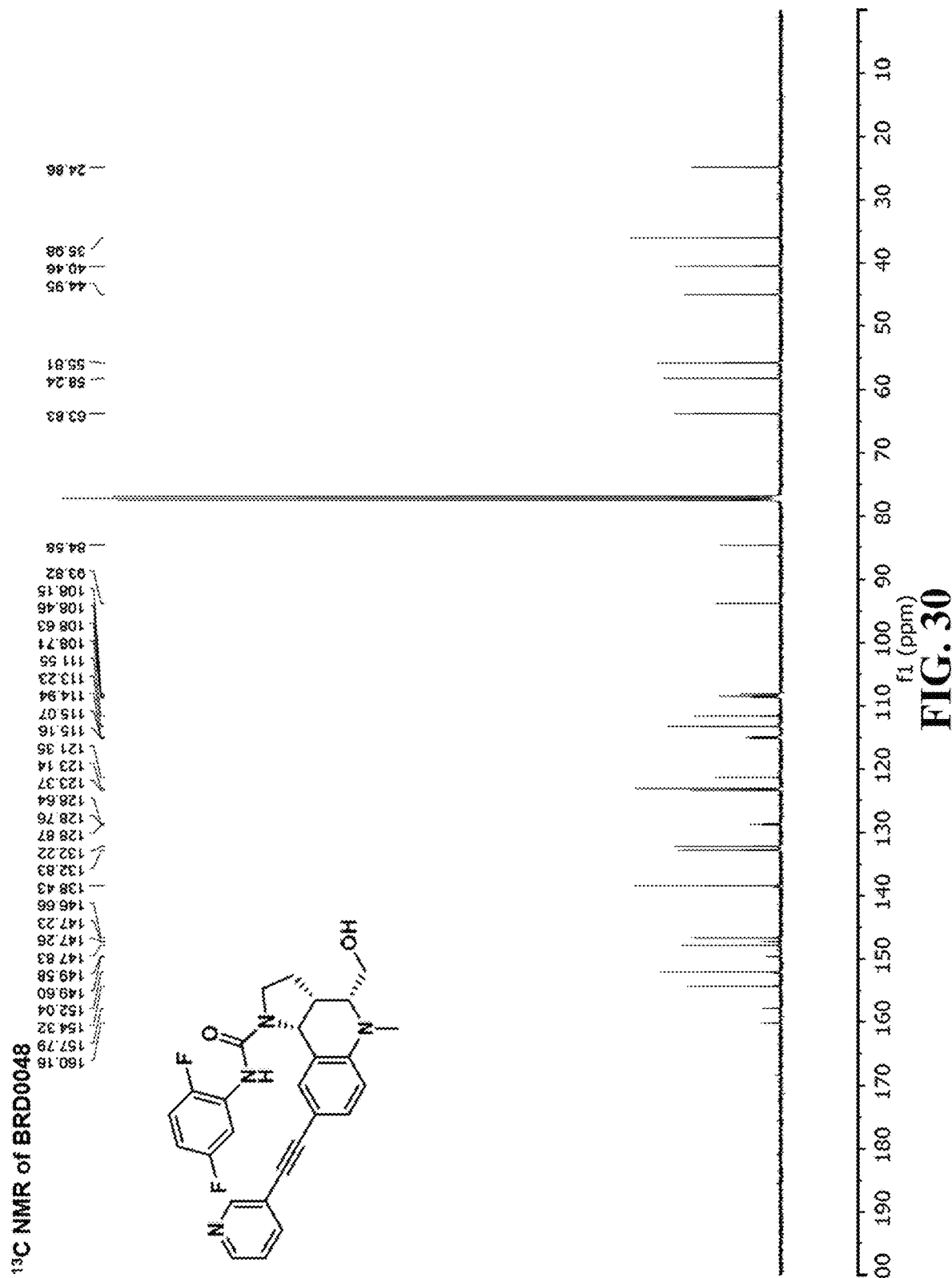

Mechanism of inhibition and specificity of BRD0539. To determine if BRD0539 disrupted the binding of gRNA to SpCas9, Applicants developed and utilized a fluorescence polarization assay for SpCas-gRNA binding. Applicants monitored the binding of FITC-crRNA:tracrRNA to SpCas9 using fluorescence polarization, observing a sharp increase in the polarization signal upon the addition of SpCas9 to the gRNA (FIG. 10A). While the addition of unlabeled competitor gRNA (1 equiv.) caused a drop in polarization signal (FIG. 10B), the addition of BRD0539 did not perturb the polarization signal suggesting that BRD0539 does not interfere with the SpCas9:gRNA interaction (FIG. 10C).

Next, Applicants examined if BRD0539 disrupted the interactions of SpCas9 with DNA using DSF. Briefly, the melting curves of SpCas9 lacking the guide RNA (apo-SpCas9) suggested the presence of a DNA-bound state upon the addition of DNA with increasing numbers of PAM sequences (0-12 PAM, FIG. 7P) or an increasing concentration of 8PAM DNA (FIG. 7K). BRD0539 dose-dependently blocked the formation of the DNA-bound state in a dose-dependent fashion (FIG. 7L). The SpCas9:gRNA exhibited a multiphasic melting signature that was altered upon the addition of DNA that contained PAM sequences. BRD0539 impaired the perturbation induced by the 4PAM DNA (FIG. 7Q).

Figure 8H:
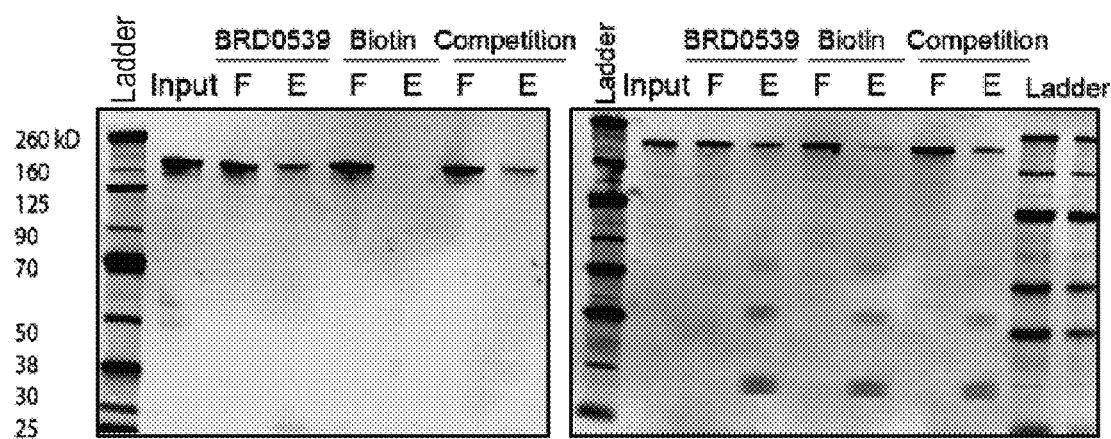

Finally, to confirm target engagement by BRD0539 in cells, Applicants used the cellular thermal shift assay (CE-TSA), a cellular version of the DSF assay (Martinez Molina et al., 2013; Martinez Molina and Nordlund, 2016). Since SpCas9:DNA interactions increase the melting temperature of SpCas9, disrupting such interactions by BRD0539 should lower the melting temperature of SpCas9, and Applicants observed ~2.5° C. lowering in cells treated with BRD0539 (FIGS. 3L and 7M). The interaction between BRD0539 and SpCas9 was further confirmed by pulldown studies in which biotinylated BRD0539 was able to pulldown SpCas9 from WM793-SpCas9 cell lysate (FIGS. 10D and 8H), while no notable non-specific protein pulldown was observed (Supplementary item 5, Mendeley). Finally, while BRD0539 was able to inhibit SpCas9 in the eGFP-disruption assay, BRD0539 was unable to inhibit FnCpf1, a structurally different CRISPR-associated nuclease, in the same assay, further highlighting the specificity of BRD0539 (FIG. 10E).

Figure 9A:
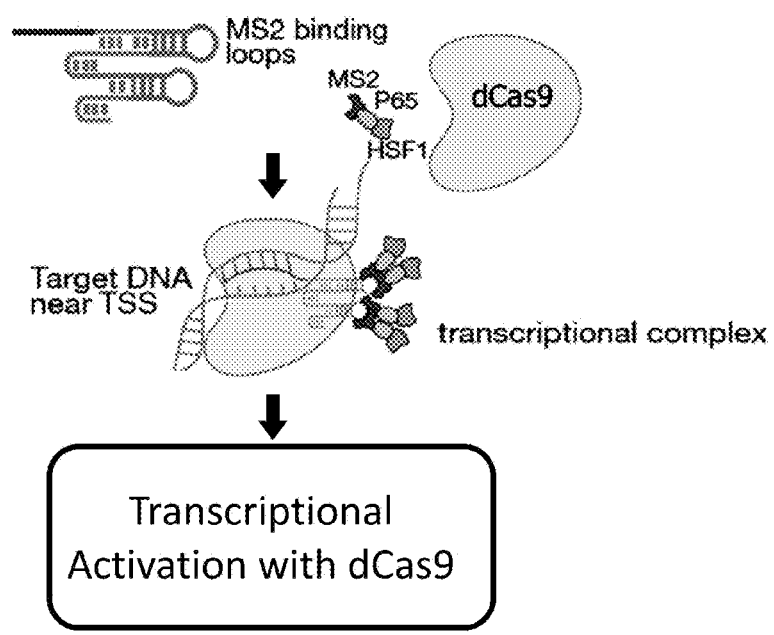
FIGS. 9A-9B—Screening of potential inhibitors of dCas9-based transcription upregulation.
Figure 9B:
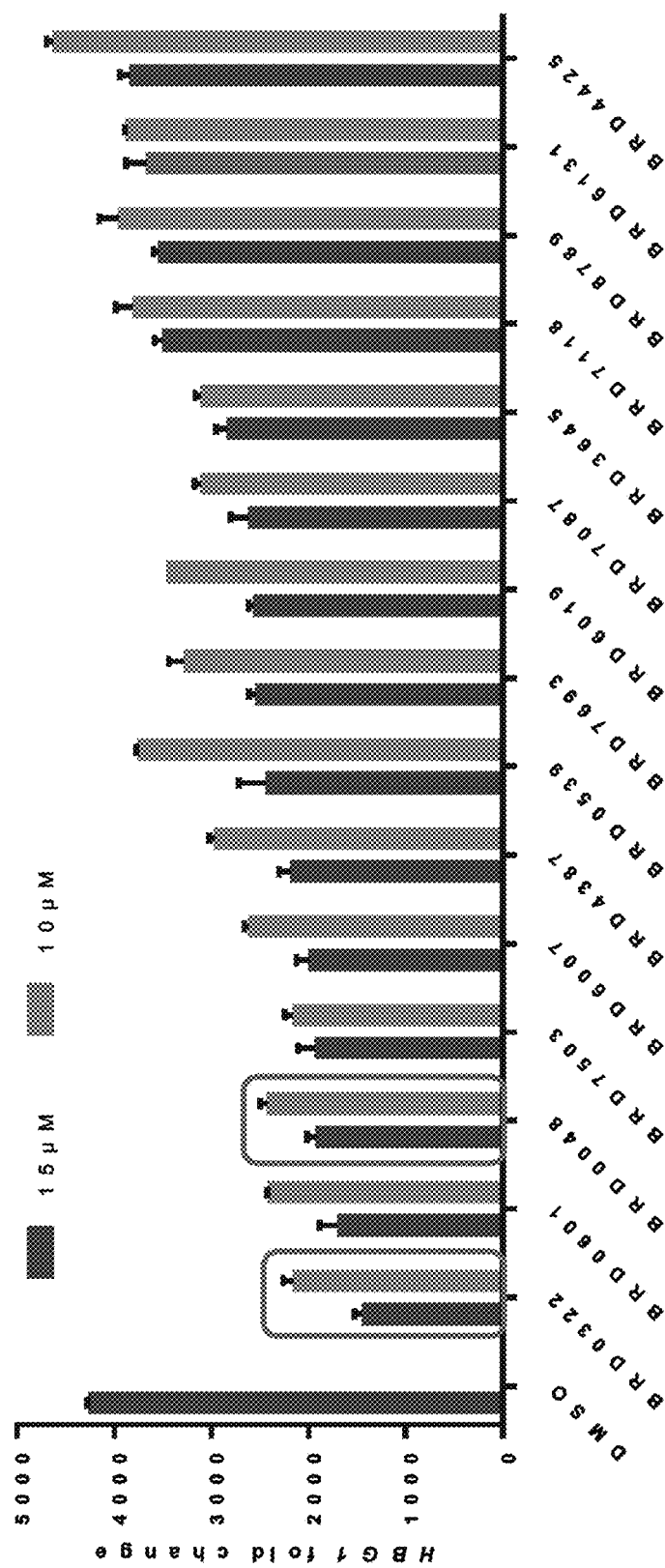

Inhibition of the dCas9-based transcription-activation complex. After optimizing the inhibition of the nuclease activity of SpCas9:gRNA complex, Applicants sought to optimize for inhibition of the transcriptional activation complex, which consists of dCas9:gRNA and transcription-activating SAM domains (Konermann et al., 2015a) that are recruited by the gRNA. Our hit-triage workflow was similar to those for the nuclease activity and involved prioritizing compounds based on the absence of cytotoxicity and the presence of dose-dependent inhibition of transcriptional activation in cells. Various compounds were screened by testing their effects on dCas9-based HBG1 transcription regulation (FIGS. 9A and 9B). While the nuclease inhibitors identified above also blocked transcription (FIG. 8B), BRD20322 and BRD0048 emerged as most potent inhibitors of the transcription activation complex, showing a dose-dependent inhibition with an EC50 of 12.2 µM and 9 µM, with BRD20322 inhibiting 89% of the transcription at 20 µM (FIG. 4C and FIG. 8C). None of the inhibitors altered expression of control genes.

The example shows a workflow for the rapid identification of small-molecule inhibitors of SpCas9, and demonstrates the utility of this workflow by identifying novel examples of small-molecule inhibitors of SpCas9. The screening strategy involved disrupting PAM binding by SpCas9, followed by demonstrating activity in multiple mammalian cell lines, using gene or protein delivery. Further, Applicants demonstrated inhibition of SpCas9 nuclease activity and transcription activation. Thus, these inhibitors were effective against both wild-type and engineered SpCas9 in mammalian cells with multiple delivery modes, including delivery of ribonucleoprotein complex. The inhibitor identification methodology was rapid and cost-effective, involving testing only ~15,000 compounds to identify potent SpCas9 inhibitors. The availability of high-throughput assays and a screening workflow may propel the rapid discovery of highly potent inhibitors, not only for SpCas9 but also for next-generation CRISPR-associated nucleases. The small-molecule inhibitors may complement the protein-based anti-CRISPRs in many ways. The small-molecule inhibitors complement protein-based anti-CRISPRs in being cell-permeable (FIG. 8D), reversible (FIG. 8E), stable in human plasma (FIG. 8F) and resistant to proteases (Di et al., 2005).

The methods herein may be used for not only the identification of inhibitors for next-generation CRISPR systems and understanding their mode of inhibition, but also the application of such inhibitors. For example, Applicants are interested in determining if disruption of CRISPR-based immunity by our SpCas9 inhibitors will induce bacteria to evolve new CRISPR systems. Here, the rapid, reversible, and dose-controlled SpCas9 inhibition by small molecules is particularly relevant, given the highly dynamic nature of the molecular warfare between phage and bacteria. Applicants note that the presence of multiple defense systems within bacteria has hampered efforts for developing phages as next-generation antibiotics. Development of small-molecule inhibitors of these defense systems may provide an approach for species-selective disruption of the immune system while leaving beneficial bacteria unaffected, and such studies may lay the foundation for precision anti-infectives. In another application, SpCas9-mediated germline editing creates mosaic mutations in the embryo with different mutations in different cell types in the same animal, and our inhibitors may reduce mosaicism (Tu et al., 2017; Wang et al., 2013; Yen et al., 2014). Such mosaic mutations are quite extensive in zebrafish, and additional crosses are required to dilute mosaicism in small animals. In large animals (e.g., non-human primates), where sexual maturity takes multiple years, mosaic mutations are a major obstacle to obtain genetically modified animals. Restricting the half-life of SpCas9 was shown to reduce mosaicism, but the reported method involved fusion of SpCas9 to a constitutively active degron without precise temporal control. The inhibitors may allow precision dose and temporal control of SpCas9 activity in these ex vivo germline editing experiments. Similarly, temporarily switching off SpCas9 in germ cells of mosquitoes bearing lethal gene drive constructs may allow facile population expansion of mosquitoes.

The methods may also be used for identification of the binding site of the identified inhibitors and understanding the mechanism of action. For example, the reported inhibitors may operate by directly competing with the NGG PAM or bind to an allosteric site. Mechanism-of-action studies will involve single-molecule biophysics experiments to examine the effects of the inhibitor on the conformational change of SpCas9 during the catalytic cycle. The dependence of inhibitory activity on the compound stereochemistry points to the specific nature of interactions between the inhibitors and the SpCas9:gRNA complex. Further, the subtle structural variation between inhibitors that block SpCas9:gRNA complex from those that inhibit dCas9:gRNA:SAM complex also points to specific interactions; identifying these interactions via structural studies will be key towards mechanistic understanding.

Multiple lines of evidence point to the specific nature of interactions between the inhibitors and the SpCas9:gRNA complex. Small perturbations to the structure or even the stereochemistry of BRD0539 causes loss of inhibitory activity and FnCpf1 remain uninhibited by BRD0539. Further, the subtle structural variation between inhibitors that block SpCas9:gRNA complex from those that inhibit dCas9:gRNA:SAM complex for transcription activation also points to specific interactions. The ability of identified inhibitor BRD0539 to block the formation of the DNA-bound state indicates that the reported inhibitors could either operate by directly competing with the NGG PAM or bind to an allosteric site. Identifying the binding pocket of the inhibitors via structural may be useful for mechanistic understanding of the aforementioned observations as well as potency improvement of the inhibitors. Mechanism-of-action studies involving single-molecule biophysics experiments to examine the effects of the inhibitor on the conformational change of SpCas9 during the catalytic cycle will also provide valuable insight and may explain the molecular mechanism of disruption of DNA binding as suggested by DSF studies. The DSF studies confirm the presence of flexible conformation of apo-SpCas9 that shows a preference for DNA sequences with PAM sequences (FIG. 10D). Apo-SpCas9 binds to DNA with an affinity of 25 nM (Sternberg et al., 2014) and high-speed atomic force microscopy studies suggest the presence of a flexible conformation in solution (Shibata et al., 2017) as opposed to closed conformation observed in crystal structures.

Many anti-CRISPR proteins operate by inhibiting both nuclease and PAM binding, pointing to possible synergies between these two modes of inhibition. Identification of small-molecule inhibitors of the nuclease activity presents similar assay development challenges, which Applicants have overcome. The methods may also be used for identification of nuclease inhibitors and exploration of possible synergies between the two classes of inhibitors. The inhibitors are nontoxic to mammalian cells, and do not alter transcription and translation of housekeeping genes. Finally, in many applications, degradation of SpCas9 may be needed. For example, a recent study shows the existence of antibodies against SpCas9 in humans (Charlesworth et al., 2018) and the SpCas9-specific immune response is construed as a bottleneck in the development of therapeutic applications of SpCas9. Reducing the half-life of SpCas9 may reduce the severity of immune response. Proteolysis targeting chimeras (PROTACs) are heterobifunctional small molecules containing a target protein binder and a ubiquitin ligase binder joined by a linker (Bondeson et al., 2018; Lai and Crews, 2017). A PROTAC formed by joining our inhibitor to the ubiquitin ligase binder, can recruit ubiquitin ligase to SpCas9, promoting ubiquitination and proteasomal degradation of SpCas9. Furthermore, PROTACs are catalytic and may require lower dose as they operate by "event-driven pharmacology" as opposed to inhibitors that are stoichiometric and operate by "occupancy driven pharmacology."

Other embodiments the identification of inhibitors for next-generation CRISPR systems and understanding their mode of inhibition as well as the application of such inhibitors. The timely and partial inhibition (~50%) of SpCas9 reduced off-target editing for several genes, including a five-fold reduction for β-globin (HBB)-targeting gRNA that is of therapeutic interest for sickle cell disease (Shin et al., 2017). Partial inhibition of SpCas9 by BRD0539 together with its cellular permeability, reversibility, and plasma stability should afford a facile method for reducing the off-target activity of SpCas9.

Together, our studies point to the utility of invocation of chemical biology-based approaches for genome editing and functional genomics studies using CRISPR-based systems.

Methods

*Escherichia coli* Rosetta (DE3)

*E. coli* Rosetta (DE3) cells were used for protein expression for in vitro and cellular studies. Cells were grown at 37° C. (unless otherwise indicated) in Terrific Broth (TB) medium supplemented with 25 mg/mL kanamycin for plasmid maintenance.

*Escherichia coli* BL21 (DE3)

This strain was used for recombinant anti-CRISPR protein expression for cellular studies. Cells were grown at 37° C. (unless otherwise indicated) in LB medium supplemented with 100 mg/mL ampicillin for plasmid maintenance.

Cell culture. All cells were cultured at 37° C. in a humidified 5% $CO_2$ atmosphere. HEK293T cells (ATCC) used in transcriptional activation, NHEJ, and mCherry-disruption assays were cultured in Dulbecco's modified Eagle's medium (Life Technologies) supplemented with 10% fetal bovine serum (Sigma Aldrich) and 1×penicillin/streptomycin/glutamax (Life Technologies). U2OS.eGFP.PEST cells stably integrated with an eGFP-.PEST fusion gene were maintained in Dulbecco's modified Eagle's medium (Life Technologies) supplemented 10% FBS, with 1×penicillin/streptomycin/glutamax (Life Technologies) and 400 μg/mL G418 (selection antibiotic). WM793 cells were cultured in RPMI1640 media supplemented with 10% FBS, 1× penicillin/streptomycin/glutamax (Life Technologies). Human islet cells were maintained in CMRL 1066 containing 10% fetal bovine serum, 1×penicillin/streptomycin/glutamax (Life Technologies) and 1 mM sodium pyruvate and cultivated at 37° C. with 5% $CO_2$ in a humidified atmosphere. Human bone marrow-derived mesenchymal stem cells (hMSC) were cultured in DMEM (Life Technologies) supplemented with 10% fetal bovine serum (Sigma Aldrich) and 1×penicillin/streptomycin/glutamax (Life Technologies). Cells were continuously maintained at <90% confluency. All cell lines were sourced commercially or were functionally validated. Cells were periodically tested for mycoplasma contamination using the MycoAlert PLUS Mycoplasma Detection Kit (Lonza).

SpCas9 expression and purification. SpCas9 was expressed and purified following a previously reported protocol (Pattanayak et al., 2013b).

In vitro transcription of gRNA. Linear DNA fragments containing the T7 RNA polymerase promoter sequence upstream of the desired 20 bp gRNA protospacer and the gRNA backbone were generated by PCR (Q5 Hot Start MasterMix, New England Biolabs) using primers forward:

(SEQ ID NO: 34)
5'-TAATACGACTCACTATAGGGAGTCCGAGCAGAAGAAGAAGTTTTAG
AGCTAGAAATAGCA-3' and reverse:

(SEQ ID NO: 35)
5'-AAAAAAAGCACCGACTCGGTGCCAC-3' and concentrated on minelute columns (Qiagen). gRNA was transcribed with the HiScribe T7 High Yield RNA Synthesis Kit (New England Biolabs) at 37° C. for 14-16 h with 400 ng of linear template per 20 µl reaction. gRNA was purified using the MEGAClear Transcription Clean Up Kit (Thermo Fisher), according to the manufacturer's instructions. Purified gRNAs were stored in aliquots at −80° C.

Fluorescence polarization (FP) assay. The fluorescence polarization assay was performed in a 384-well plate (Corning 3575) format using a total reaction volume of 30 µL. A 58 base-pair ds DNA with a FITC-label (Nex 490 nm; Nem 525 nm) at 3'-end and 12 PAM (NGG) sequences distributed throughout its length was used as the DNA template (Table 10). A 25 nM FITC-labeled 12PAM DNA was titrated against increasing concentration of SpCas9:gRNA (1:1.2) complex in a 20 mM Tris-HCl buffer (150 mM KCl, 5 mM MgCl$_2$, 1 mM DTT, pH 7.5). The fluorescence polarization signal was measured using a microplate reader (PerkinElmer, En Vision). Error bars represent ±s.d. across technical replicates (n=3). The Z'-factor for the FP-assay was calculated using the equation, $$Z'=1-(3(\sigma_1+\sigma_2))/(|\mu_1-\mu_2|) \tag{1}$$

Where $\sigma_1$ and $\sigma_2$ are the standard deviations of the DMSO control population and the SpCas9:gRNA control population, respectively. $\mu_1$ and $\mu_2$ are the mean FP for DMSO controls and SpCas9:gRNA controls, respectively.

Fluorescence polarization competition assay. In a 384-well plate (Corning 3575), 25 nM FITC-labeled 12PAM DNA was incubated with 50 nM SpCas9:gRNA (1:1.2) complex in the presence and absence of unlabeled DNA (Table 10) in excess (10- and 50-fold) in a 20 mM Tris-HCl buffer (150 mM KCl, 5 mM MgCl$_2$, 1 mM DTT, pH 7.5). FP was measured using a microplate reader (PerkinElmer, EnVision). The number of PAM sequence in the unlabeled competitor DNA was varied from 0, 4, 8, and 12. Error bars represent ±s.d. across technical replicates (n=3).

Differential scanning fluorimetry (DSF). Protein melting experiments were performed in a 384-well format using a 6 µL reaction volume in a LightCycler 480 instrument. A 3.7 µM SpCas9:gRNA (1:1.2) was incubated with equimolar concentration of DNA with different PAM density (0, 4, 8, and 12; Table 10) for 15 min in 20 mM Tris-HCl buffer (150 mM KCl, 5 mM MgCl$_2$, 1 mM DTT, pH 7.5). 2 µL of 50×SYPRO® Orange (Invitrogen) was then added before running the melting cycle with a temperature gradient of 4.8° C./min. Experiments were performed in triplicate and data were processed using Roche LightCycler® 480 Protein Melting software. Error bars represent ±s.d. across technical replicates (n=3).

Bio-layer interferometry (BLI). DNA-SpCas9 interactions were probed using BLI experiments in an Octet Red384 (Pall ForteBio) instrument. Experiments were performed in a 96-well format with 180 µL reaction volume using biotinylated ds DNA and streptavidin sensors. 300 nM of biotinylated DNA with different PAM density (0, 2, 4, and 8, Table 10) were loaded onto the sensors for 180 s in 20 mM Tris buffer (100 mM KCl, 5 mM MgCl$_2$, 1 mM DTT, 0.01% Tween, 50 µg/mL heparin, pH 7.5). Excess DNA was washed off for 60 s in reaction buffer followed by association with 200 nM of SpCas9-gRNA (1:1.2) for 300 s. The complex was then allowed to dissociate for 3600 s in the reaction buffer. Response curves were normalized against the reference sensor without SpCas9:gRNA.

mKate2-disruption assay. Approximately 8,000 cells/well were seeded in a 96-well plate 24 h before transient transfection with 100 ng of either CgRNA (Addgene Plasmid #64955) or T1gRNA (Addgene Plasmid #62717) plasmids using Lipofectamine 2000 (Life Technologies). Transfected cells were allowed to grow in the indicated amount of small molecule or DMSO for 24 h. Cells were then fixed using 4% paraformaldehyde and imaged with the HCS NuclearMask™ Blue Stain (Life Technologies) as the nuclear counter-staining agent. Imaging was performed with an ImageXpress Micro automated microscope (Molecular Devices) at 20× magnification under two excitation channels (blue and red) with 9 acquisition sites per well. Images were analyzed using the MetaXpress software to determine the % mKate2 positive cells and data was plotted using GraphPad Prism 6. The Z'-value was calculated following the formula: $Z'=1-(3(\sigma_1+\sigma_2))/(|\mu_1-\mu_2|)$ where $\sigma_1$ and $\sigma_2$ are the standard deviations of CgRNA transfected wells and T1gRNA transfected wells respectively. $\mu_1$ and $\mu_2$ are the mean % RFP$^+$ cell population for CgRNA transfected wells and T1gRNA transfected wells, respectively.

NHEJ assay. Approximately 8,000 cells/well were seeded in a 96-well plate 24 h before transient transfection with a total 100 ng of DN66 (mCherry—TAG—GFP reporter) and DN78 (SpCas9 and gRNA) plasmids (1:1) using Lipofectamine 2000 (Life Technologies) (Nguyen et al., 2016b). Transfected cells were incubated with the indicated amount of small molecule or DMSO for 24 h. Cells were then fixed using 4% paraformaldehyde and imaged with the HCS NuclearMask™ Blue Stain (Life Technologies) as the nuclear counter-staining agent. Imaging was performed with an ImageXpress Micro automated microscope (Molecular Devices) at 4× magnification under three excitation channels (blue, green and red) with 9 acquisition sites per well. Images were analyzed in the MetaXpress software to determine the % NHEJ and the data were plotted using GraphPad Prism 6. The Z'-value was calculated following the formula: $Z'=1-(3(\sigma_1+\sigma_2))/(|\mu_1-\mu_2|)$ where $\sigma_1$ and $\sigma_2$ are the standard deviations of DN66 transfected wells and (DN66+DN78) transfected wells respectively. $\mu_1$ and $\mu_2$ are the mean % GFP cell population for DN66 transfected wells and (DN66+DN78) transfected wells respectively.

Primary assay for compound screening. The compound library screening was performed in two steps. Initially, the DOS informer set was screened in the FP-based assay to identify the libraries enriched for hits. Then, the specific enriched libraries were also screened at greater depth using the same assay. The screening assay was performed in a 384-well plate format with a total reaction volume of 30 µL. Initially, 25 µL of 60 nM SpCas9 was transferred to all wells of the 384-well plate except for the positive-control wells. 25 µL of a solution containing 60 nM SpCas9 and 300 nM unlabeled 12PAM DNA was transferred to the positive-control wells. In the next step, 25 nL DMSO alone or 10 mM compounds in DMSO were transferred to the reaction mixture and incubated for 30 min at room temperature. Next, a 5 µL solution containing 360 nM gRNA and 150 nM FAM-labeled 12PAM DNA was added and incubated for 15 min at room temperature before measuring the fluorescence polarization signal with a microplate reader (Envision, PerkinElmer). Compounds were screened in duplicate and data were processed to calculate the Z-score $((x-\mu)/\sigma)$ values and plotted in Spotfire analysis software (TIBCO). Hit compounds (Z-score >3) were clustered according to the class of compound, and a hit-rate plot was generated. The entire specific libraries of the enriched ones were then screened in the same FP assay.

Counter-screening assay. Counter-screening was performed in a similar format as followed in the compound-screening assay. In a 384-well plate, a 30 µL of 25 nM FAM-labeled 12PAM DNA was transferred to each well. Next, 25 nL of either DMSO or compound in DMSO were transferred and incubated for 30 min before measuring fluorescence polarization signal with a microplate reader (Envision, PerkinElmer). The change in the FP signal was calculated in percentile and plotted against compounds' average Z-score values obtained from the original compound-screening assay. Compounds that resulted in a >3σ change in the primary assay, but did not alter the FP-signal by >10% in the counter-screen assay, were selected as hits. A structure-based similarity search was also performed, and compounds with >0.8 Tanimoto similarity using ECFP6 fingerprints were included in the hit list.

Compound-SpCas9 interaction in BLI. The experiments were performed in a 96-well format with 180 µL reaction volume using BRD3539 and streptavidin sensors. 1 µM of the biotinylated compound was loaded onto the sensors for 180 s in 20 mM Tris buffer (100 mM KCl, 5 mM $MgCl_2$, 1 mM DTT, 0.01% Tween, pH 7.4). Compound-loaded sensors were then allowed to associate with different concentrations of the SpCas9:gRNA complex (0.15-1 µM) for 300 s, followed by dissociation in reaction buffer. The reference sensor was loaded with compound and allowed to associate and dissociate in reaction buffer alone. Response curves were fitted with a 2:1 stoichiometric model and a global fit steady-state analysis was performed using manufacturer's protocol. Experiments were performed in triplicate.

Competition experiments were performed using biotin-linker fragment. In this experiment, streptavidin sensors were pre-incubated with 10 µM of biotin-linker for 10 min before dipping into a solution of either 1 µM BRD7087-biotin or reaction buffer alone. Sensors were then allowed to associate with different concentration of SpCas9:gRNA complex (0.15-1 µM) or buffer alone.

NMR binding assay. All samples were prepared with 50 µM BRD7087 in 20 mM Tris buffer (pH 7.4) with varying concentrations of SpCas9:gRNA in a 3 mm NMR tube. Experiments were performed on a 600 MHZ ($^{19}F$: 564.71 MHZ) Bruker Avance III NMR spectrometer equipped with a 5 mm QCI-F CryoProbe and a SampleJet for automated sample handling. To acquire spectra, a standard one-pulse $^{19}F$ experiment with WALTZ-16 for proton decoupling during acquisition, a 5 second recycle delay, and 256 scans were used. All spectra were recorded at 280 K. NMR data were apodized with a 1 Hz exponential function prior to Fourier transformation. All spectra were baseline corrected, and peak widths and intensities were extracted using the automated line-fitting feature provided with the MNova software package.

SpCas9 nuclease activity in eGFP-disruption assay. Approximately 200,000 U2OS.eGFP-PEST cells were nucleofected following two different methods either by nucleofecting plasmids or RNP using the SE Cell Line 4D-Nucleofector™ X Kit (Lonza) according to the manufacturer's protocol. In the plasmid nucleofection method, cells were nucleofected either with 440 ng of SpCas9 (Addgene Plasmid #43861) or 400 ng of SpCas9 along with 40 ng of sgRNA (pFYF1320 eGFP Site #1, Addgene Plasmid #47511). Cells nucleofected only with SpCas9-expressing plasmid were used as the transfection control. In the RNP nucleofection method, either 20 mmol SpCas9 or 20 pmol preformed SpCas9:gRNA (eGFP Site #1) complex were nucleofected. Approximately 20,000 transfected cells/well were plated in 4 replicates in a 96-well plate (Corning® 3904). Cells were incubated with the indicated amount of compound or DMSO for 24 h post transfection. A DMSO solution of compound (20 mM) was resuspended in the 10% FBS containing growth media and thoroughly mixed before adding to the cells. Cells were then fixed using 4% paraformaldehyde and imaged with the HCS Nuclear-Mask™ Blue Stain (Life Technologies) as the nuclear counter-staining agent. Imaging was performed with an ImageXpress Micro automated microscope (Molecular Devices) at 10× magnification under three excitation channels (blue, green and red) acquiring nine sites per well. Images were analyzed using MetaXpress software and data were plotted using GraphPad Prism 6.

The Z'-value was calculated using the equation (1), where $\sigma_1$ and $\sigma_2$ are the standard deviations of DMSO control and SpCas9:gRNA control respectively. $\mu_1$ and $\mu_2$ are the mean % $GFP^-$ cell population for DMSO control and SpCas9:gRNA control, respectively.

Western blot analysis. U2OS.eGFP.PEST cells stably expressing eGFP were treated with small molecules for 24 h at 37° C. prior to harvesting the cells. Cell suspensions were centrifuged at 1000×g for 5 min and cells were resuspended in RIPA total cell lysis buffer (Abcam) and incubated at 4° C. for 10 min. The cell suspensions were then vortexed for 10 min at 4° C. followed by centrifugation at 16,000×g for 15 min at 4° C. The supernatant was transferred to a fresh tube and processed for Western blotting.

Western blotting was performed following SDS-PAGE gel electrophoresis. In a typical experimental protocol, 40 µg of normalized proteins were electrophoresed on a 4-12% Bis/Tris gel. The protein bands were transferred to a PVDF membrane and probed with primary anti-GFP antibody (Cell Signaling #2956). Anti-actin antibody (Sigma) was used as a protein loading control.

Base-Editing Experiments.

BE3 expression and purification. BE3 was expressed and purified as previously reported (Rees et al., 2017b). BL21 Star (DE3)-competent *E. coli* cells were transformed with plasmids encoding the bacterial codon-optimized base editor with a $His_6$ N-terminal purification tag. A single colony was grown overnight in 2xYT broth containing 50 µg ml$^{-1}$ kanamycin at 37° C. The cells were diluted 1:400 into 4 L of the same media and grown at 37° C. until $OD_{600}$=0.70–0.75. The cultures were incubated on ice for 3 h and protein expression was induced with 1 mM isopropyl-β-D-1-thiogalactopyranoside (GoldBio). Expression was sustained for 16-18 h with shaking at 18° C. The subsequent purification steps were carried out at 4° C. Cells were collected by centrifugation and resuspended in cell collection buffer (100 mM tris(hydroxymethyl)-aminomethane (Tris)-HCl, pH 8.0, 1 M NaCl, 20% glycerol, 5 mM tris(2-carboxyethyl) phosphine (TCEP; GoldBio), 0.4 mM phenylmethane sulfonyl fluoride (Sigma-Aldrich) and 1 EDTA-free protease inhibitor pellet (Roche)). Cells were lysed by sonication (6 min total, 3 s on, 3 s off) and the lysate cleared by centrifugation at 25,000 g (20 min).

The cleared lysate was incubated with His-Pur nickel-nitrilotriacetic acid (nickel-NTA) resin with rotation at 4° C. for 90 min. The resin was washed twice with 15 column volumes of cell collection buffer before bound protein was eluted with elution buffer (100 mM tris(hydroxymethyl)-aminomethane (Tris)-HCl, pH 8.0, 0.5 M NaCl, 20% glycerol, 5 mM TCEP (GoldBio), 200 mM imidazole). The resulting protein fraction was further purified on a 5 ml Hi-Trap HP SP (GE Healthcare) cation exchange column using an Akta Pure FPLC. Protein-containing fractions were concentrated using a column with a 100 kDa cutoff (Millipore) centrifuged at 3,000 g, and the concentrated solution was sterile-filtered through a 22 µm polyvinylidene difluoride membrane (Millipore). After sterile filtration, proteins were quantified with Reducing Agent Compatible Bicinchoninic acid assay (Pierce Biotechnology), snap-frozen in liquid nitrogen and stored in aliquots at −80° C.

Analysis of base-edited sequences. Nucleotide frequencies were analyzed using a previously described MATLAB script (Komor et al., 2016b). Briefly, the reads were aligned to the reference sequence via the Smith-Waterman algorithm. Base calls with Q-scores below 30 were replaced with a placeholder nucleotide (N). This quality threshold results in nucleotide frequencies with an expected theoretical error rate of 1 in 1,000. To distinguish small molecule-induced inhibition of C→T editing from artefactual C→T editing, Applicants compared the sequencing reads from cells treated with base-editor in the presence of small molecule to the sequencing reads from base-edited cells not exposed to small molecule. A Student's two-tailed t-test was used to determine if inhibition of C→T editing by small-molecule is statistically significant with P<0.05 as the threshold.

In vitro transcription of gRNA. Linear DNA fragments containing the T7 RNA polymerase promoter sequence upstream of the desired 20 bp gRNA protospacer and the gRNA backbone were generated by PCR (Q5 Hot Start MasterMix, New England Biolabs) using primers forward:

(SEQ ID NO: 36)
AAAAGCACCGACTCGGTGCCACTTTTTCAAGTTGATAACGGACTAGCCT
TATTTTAACTTGCTATTTCTAGCTCTAAAAC-3' and reverse primer:

(SEQ ID NO: 37)
5'-TAATACGACTCACTATAGCTATAGGACGCGACCGAAAGTTTTAGAG
CTAGAAAT-3'.

gRNA was transcribed with the HiScribe T7 High Yield RNA Synthesis Kit (New England Biolabs) at 37° C. for 16 h with 150 ng of linear template per 20 µl reaction. gRNA was purified using the MEGAClear Transcription Clean Up Kit (Thermo Fisher), according to the manufacturer's instructions. Purified gRNAs were stored in aliquots at −80° C.

Protein transfection of base editor BE3 into HEK293T cells. HEK293T cells were seeded on 48-well BioCoat poly-D-lysine plates (Corning) in 250 µL of antibiotic-free medium and transfected at ~70% confluency. Prior to protein transfection, cells were incubated with BRD7087 or BRD5779 at the indicated concentrations for 2-3 h. BE3 protein was incubated with 1.1× molar excess of EMX1-targeting sgRNA at a final concentration ratio of 200 nM: 220 nM (based on a total well volume of 275 µL). The complex was mixed with the small molecules for five minutes, incubated with 1.5 µL Lipofectamine 2000 (Thermo Fisher) and transfected according to the manufacturer's protocol plasmid delivery. The cells and ribonucleoprotein complex were incubated with compounds at final concentrations of 1.25 µM, 2.5 µM, 5 µM, 10 µM or 20 µM.

Purifications and sequencing of genomic DNA. Transfected cells were harvested after 72 h in 50 µL of lysis buffer (10 mM Tris-HCl pH 8.0, 0.05% SDS, 25 µg/mL proteinase K) and incubated at 37° C. for 1 h. Cell lysates were heated at 85° C. for 15 min to denature proteinase K. For the first PCR, genomic DNA was amplified to the top of the linear range using Phusion Hot Start II DNA polymerase (New England Biolabs) according to the manufacturer's instructions. For all amplicons, the PCR protocol used was an initial heating step for 1 min at 98° C. followed by an optimized number of amplification cycles (10 s at 98° C., 20 s at 68° C., 15 s at 72° C.). qPCR was performed to determine the optimal number of cycles for each amplicon. Amplified DNA was purified using RapidTip2 (Diffinity Genomics) and barcoded with a further PCR. Sequencing adapters and dual-barcoding sequences are based on the TruSeq Indexing Adapters (Illumina). Barcoded samples were pooled and purified by gel extraction (Qiagen) before quantification using the Qubit dsDNA HS Kit (Thermo Fisher) and qPCR (KAPA BioSystems) according to the manufacturer's instructions. Sequencing of pooled samples was performed using a single-end read from 260 to 300 bases (MiSeq, Illumina) according to the manufacturer's instructions.

Transcription Assays.

gRNA cloning. The plasmid for guide RNA targeting the HBG1 gene was constructed by cloning a 20 nucleotide long spacer sequence into the gRNA (MS2) cloning backbone plasmid (Addgene #61424) by using the Golden Gate cloning protocol (Dahlman et al., 2015; Konermann et al., 2015b). Briefly, 100 µM of the forward and reverse oligonucleotides (SEQ ID NO: 38)
(5'-CACCGGGCAAGGCTGGCCAACCCAT-3' and (SEQ ID NO: 39)
5'-AAACATGGGTTGGCCAGCCTTGCC-3', respectively) were phosphorylated and annealed in presence of T4 ligase buffer (NEB) and T4 PNK (NEB) in a thermal cycler using the following conditions: 37° C. for 30 min, 95° C. for 5 min followed by ramp to 25° C. at 5° C./min. The annealed oligonucleotides were then mixed with the sgRNA (MS2) backbone and subjected to digestion using restriction enzyme Bbs/(Fermentas FD) and ligation using T7 ligase (Enzymatics) in a thermal cycler using the following conditions: 37° C. for 5 min, 20° C. for 5 min, repeated for 15 cycles. 2 µL of the golden gate reaction was transformed into DH5 alpha cells (NEB) and plated on ampicillin containing LB plates. Plasmids were extracted and sequenced to confirm cloning of spacer into the gRNA (MS2) backbone.

Transcription activation experiments and quantitative RT-PCR analyses. HEK293FT cells were maintained in high glucose DMEM with glutamax (Life Technologies) and supplemented with 10% FBS (Life Technologies), 1% penicillin-streptomycin (Life Technologies) and 1 mM sodium pyruvate (Life Technologies). For transcription activation experiments, 20,000 cells/well were plated in a poly D-lysine-coated 96-well plate. The cells were transiently transfected with a 1:1:1 mass ratio of the dCas9 plasmid, MS2-P65-HSF1 effector plasmid and the sgRNA plasmid targeting the HBG1 gene or an RFP control plasmid. A total of 0.3 µg plasmid DNA was transfected using Lipofectamine 2000 (Life Technologies) according to manufacturer's protocol. Immediately after transfection, the cells were treated with an appropriate dose of the small-molecule inhibitors. A DMSO solution of compound (20 mM) was resuspended in the 10% FBS containing growth media and thoroughly mixedbefore adding to the cells. After 48 h the cells were lysed and 5 µL of the cell lysate was used to perform reverse transcription using the RevertAid RT Reverse Transcription Kit (Thermo Fischer Scientific) as described by Joung J. et al. qPCR reactions were performed to quantify RNA expression using the TaqMan probes (Life Technologies, HBG1/HBG2: Hs00361131_g1, ACTB: Hs01060665_g1) and TaqMan Fast Advanced Master Mix (Life Technologies) in 5 µL multiplexed reactions and 384-well format using the LightCycler 480 Instrument II (Roche). For each sample, four technical replicates were performed. Data were analyzed using the LightCycler 480 software (Roche) by the $\Delta\Delta C_t$ method: $C_t$ values for the gene of interest (HBG1) were normalized to Ct values for the housekeeping gene (ACTB), and fold-changes in the expression level of gene of interest were normalized to RFP-transfected control. The data is reported as mean±S.E.M. for technical replicates.

sgRNA cloning for HiBiT assay. The plasmid for guide RNA targeting the C-terminus of GAPDH gene was constructed by cloning a 20 nucleotide-long spacer into the SpCas9 sgRNA backbone plasmid (BPK1520, Addgene #65777). (Kleinstiver et al., 2015b). Briefly, 10 µM of the forward and reverse oligonucleotides (SEQ ID NO: 40)
(5'-CACCGGTCCAGGGGTCTTACTCCT-3' and (SEQ ID NO: 41))
5'-AAACAGGAGTAAGACCCCTGGACC-3' were phosphorylated and annealed in the presence of T4 ligase buffer (NEB) and T4 PNK (NEB) in a thermal cycler using the following conditions: 37° C. for 60 min, 95° C. for 5 min followed by ramp to 10° C. at 5° C./min. 3 µg of the sgRNA backbone plasmid was digested using BsmBI (NEB) and CIP (NEB) at 55° C. for 16 h. The cut plasmid was isolated by gel extraction. A 0.5 µM of the annealed oligonucleotides were then ligated with 40 ng of the BsmBI digested backbone by incubation at 24° C. for 30 min in the presence of T4 DNA ligase (NEB). 5 µL of the ligation reaction was transformed into DH5 alpha cells (NEB) and plated on ampicillin-containing LB plates. Plasmids were extracted and sequenced to confirm cloning of spacer into the sgRNA backbone.

HiBiT assay. For SpCas9 expression in cells, the previously described JDS246 plasmid was used (Kleinstiver et al., 2015b). ssODN donor DNA template with the HiBiT tag was purchased as single-stranded Ultramer DNA Oligonucleotides (IDT) and resuspended to 40 µM in nuclease-free water. For the assay, $2 \times 10^5$ cells were co-transfected with 300 ng Cas9 plasmid, 75 ng sgRNA plasmid and 100 ng ssODN using the DN-100 program of Lonza 4D nucleofector according to the manufacturer's protocols. For negative controls, either the sgRNA plasmid or the ssODN was omitted. 20,000 transfected cells were plated in each well of a 96-well plate (Corning 3904). Immediately after transfection, cells were treated with varying concentrations of BRD0539 or BRD3433 and incubated at 37° C. with 5% $CO_2$. 24 h after transfection, the cells were washed once with PBS and kept in 80 µL PBS. An equal volume of the Nano-Glo HiBiT Lytic Reagent (Promega N3030), consisting of Nano-Glo HiBiT Lytic Buffer, Nano-Glo HiBiT Lytic Substrate, and LgBiT Protein, was added according to the manufacturer's protocol, and cells were incubated for 10 min at ambient temperature with shaking at 600 rpm (Schwinn et al., 2018a). The cells were then incubated for an additional 10 min without shaking at room temperature to allow equilibration of the HiBiT and LgBiT in the lysate. The lysate was then transferred to a white plate (Corning 3990) and luminescence was measured using an Envision plate reader (Perkin-Elmer) with 1 s of integration time.

Surveyor nuclease assay. U2OS.eGFP.PEST cells were nucleofected either with either 20 mmol SpCas9 or 20 pmol preformed SpCas9:gRNA (EGFP Site #1) complex. Approximately 160,000 nucleofected cells/well were plated in a 12-well plate. Cells were incubated with the indicated amount of compound or DMSO for 18 h post nucleofection. The cells were then harvested and genomic DNA was isolated using the QuickExtract™ DNA extraction kit (Epicentre). Genomic DNA was subjected to PCR using primers (Fwd:
(SEQ ID NO: 42)
GAGGAGCTGTTCACC GGG and Rev:

(SEQ ID NO:43))
CTTGTACAGCTCGTCCATGC corresponding to 702 bp in the eGFP(1) gene segment and the amplicons were purified by the QIAQuick PCR purification kit. The isolated amplicons were then normalized and annealed following a quick-annealing protocol (ramp 0.03° C./s). The normalized amplicons were then incubated with Surveyor nuclease S (Surveyor Mutation Detection Kits, IDT) at 42° C. for 1 h. The samples were then analyzed by running on a TBE gel and the cleavage bands were visualized by staining with SYBR Gold. The inhibition of SpCas9 activity was observed with the decrease in the indel band intensity in the presence of small molecules.

Next-generation sequencing. $2 \times 10^5$ U2OS.eGFP.PEST cells were nucleofected with either 20 pmol SpCas9 or 20 pmol preformed SpCas9:gRNA ribonucleoprotein complex. Approximately, $1 \times 10^6$ cells per well in a 12-well format were plated in the absence or presence of the compound at the indicated concentration in two biological replicates. Cells were harvested at 10, 12, 14, and 18 h and genomic DNA was extracted using the QuickExtract™ DNA extraction solution (Epicentre) by incubating the cells at 65° C. for 15 min, 68° C. for 15 min and 98° C. for 10 min. Next-generation sequencing samples were prepared in a two-step PCR (Supplementary Table 10) following a reported protocol. In the first step, PCR was performed using primers that amplified the target eGFP genomic loci of interest and also introduced an adapter priming sequence for the second-step PCR. The second-step PCR attached Illumina P5 adapters with barcodes, after which PCR products were isolated via two-step gel purification protocol. DNA concentrations were determined using the Qubit® dsDNA HS Assay Kit (Life Technologies) and sequencing of pooled samples was performed using a single-end read from 280 bases using the MiSeq Reagent Kit v2 300 (Illumina) according to the manufacturer's protocol. The % indel frequencies were calculated by analyzing the demultiplexed sequence files using MATLAB.

In vitro DNA cleavage assay. Inhibition of SpCas9 nuclease activity was assessed in an in vitro DNA cleavage assay with a linearized substrate plasmid DNA. A 94 µL of preformed SpCas9:gRNA (5.3 nM) was incubated with a 3 µL DMSO solution of BRD0539 at the indicated concentrations (13.6-25 µM) for 30 min at room temperature followed by addition of 3 µL of 33.3 nM substrate DNA and incubation for additional 30 min at 37° C. The reaction was quenched by the addition of 2 µL of Proteinase K (Qiagen) for 10 min and then analyzed by 1% agarose gel and visualized by SYBR Gold (Thermofisher). The bands were quantified by Image J and plotted in GraphPad Prism.

In vitro pull-down assay. Pull-down of SpCas9 by biotinylated compound was performed by incubating a preformed SpCas9:gRNA complex with biotin-compound pre-loaded streptavidin magnetic beads. Initially, a 5 µM biotin compound was incubated with 120 µL streptavidin magnetic bead suspension for 30 min in 1× Cas9 activity buffer (20 mM Tris-HCl buffer, 150 mM KCl, 5 mM $MgCl_2$, 1 mM DTT, pH 7.5). Next, beads were collected and washed with buffer twice and resuspended in 120 µL of 1× Cas9 activity buffer and distributed in 6 different tubes. A 0.3 µM of 480 µL of preformed SpCas9:gRNA complex were added to each tube along with the unlabeled BRD3433 compound (5 µM and 10 µM) in the competition experiment. The tubes were incubated at 4° C. for 12 h before collecting the beads and washed with 500 µL 1× Cas9 activity buffer. The beads were resuspended in 1× SDS gel loading buffer and denatured at 98° C. for 10 min. The samples were analyzed by electrophoresis followed by staining with Coomassie for 15 min before imaging.

Cellular Thermal Shift Assay (CETSA). Approximately 1× 106 cells pre-incubated with either DMSO or 15 µM BRD0539 for 24 h were resuspended in PBS and transferred to 200 µL PCR tubes. The suspended cells were heated to a different temperature for 3 min followed by lysis in 100 µL RIPA buffer containing protease inhibitors at 4° C. for 30 min. The clear cell lysate was collected by centrifuging the suspensions at 20,000×g for 20 min. The supernatant was transferred to a fresh tube and processed for Western blotting. Western blotting was performed using SDS-PAGE. In a typical experiment, 10 µg of proteins were electrophoresed on a 4-12% Bis-Tris gel and proteins were transferred to a PVDF membrane and probed with primary anti-SpCas9 antibody (abcam #ab191468). The membrane was imaged and bands were quantified using the LI-COR Odyssey imaging system. The CETSA curves were fitted with the equation, $y=(U-L)/(1+e^{(-(A/T-1)B)})+L$ where, U and L are the upper and lower asymptotes, A is a half-way temperature, and B controls the slope of the sigmoid; temperature T is expressed in K. After the fitting, the data were re-normalized by dividing by U and the Tm was calculated using the formula $Tm=AB/(B+log(1-2L/U))$.

AcrIIA activity assay. Ribonucleoprotein (RNP) was prepared by incubating SpCas9 (10 pmol) with eGFP targeting gRNA (12 pmol) for 10 min at room temperature. AcrIIA4 (50 pmol) was added to the RNP and the mixture was incubated for 5 min at room temperature. Approximately 2×10$^5$ U2OS.eGFP-PEST cells were nucleofected with the RNP or RNP-AcrIIA4 mixture using the SE Cell Line 4D-Nucleofector X Kit (Lonza) according to the manufacturer's protocol. Approximately 2×10$^4$ transfected cells were seeded in a well of a 96-well plate (Corning 3904) and incubated with indicated amounts of AcrIIA4 protein for 48 h. Cells were fixed with 4% paraformaldehyde, and nuclei were stained with HCS NuclearMask Blue Stain (Life Technologies). Imaging was performed using an ImageXpress Micro Automated High Content Microscope (Molecular Devices) at 4× magnification under two excitation channels (blue, green) with nine acquisition sites per well. Images were analyzed using the MetaXpress software.

Disruption of SpCas9-DNA interaction by BRD0539. Protein melting experiments were performed in a 384-well format using a 6 µL reaction volume in a LightCycler 480 instrument. For DNA binding assay, 1 µM SpCas9 (1 µM) was incubated with indicated amount of 8PAM DNA (0.25, 0.5, 1, and 2 µM) for 15 min in a 20 mM Tris-HCl buffer (150 mM KCl, 5 mM $MgCl_2$, 1 mM DTT, pH 7.5). For inhibition assay, SpCas9 (1 µM) or SpCas9:gRNA (1 µM) was incubated with indicated amount of either BRD0539 or equivalent amount of DMSO for 15 min in a 20 mM Tris-HCl buffer (150 mM KCl, 5 mM $MgCl_2$, 1 mM DTT, pH 7.5). Next, a 8PAM DNA (2 µM) was added to each of the reaction and incubated for additional 15 min followed by addition of 1 µL of 100×SYPRO® Orange (Invitrogen) before running the melting cycle with a temperature gradient of 4.8° C./min. Experiments were performed in duplicate and data were processed using Roche LightCycler® 480 Protein Melting software.

Reversible inhibition of SpCas9 by BRD0539. Reversal of BRD0539-mediated inhibition of SpCas9 was performed in the eGFP-disruption assay where 2×10$^5$ U2OS.eGFP.PEST cells were nucleofected with preformed SpCas9:gRNA complex as previously discussed. Approximately 22,000 transfected cells/well were plated in 4 replicates in a 96-well plate (Corning® 3904) along with 15 µM of BRD0539 or DMSO. For AcrIIA4 reversibility experiment, a preformed SpCas9:gRNA (10 pmol) was incubated with AcrIIA4 (5×) for 10 min and then nucleofected to U2OS.eGFP.PEST cells following the aforementioned protocol. The media were swapped with the fresh media containing no BRD0539/AcrIIA4 at the indicated time point (2-24 h) and the cells were allowed to grow until 24 h post-nucleofection. Cells were then fixed using 4% paraformaldehyde and imaged with the HCS Nuclear-Mask™ Blue Stain (Life Technologies) as the nuclear counter-staining agent. Imaging was performed with an ImageXpress Micro automated microscope (Molecular Devices) at 10× magnification under three excitation channels (blue, green and red) acquiring nine sites per well. Images were analyzed using MetaXpress software and data were plotted using GraphPad Prism 6.

Plasma stability assay. Human plasma stability of the compounds was performed following a reported protocol (Di et al., 2005). BRD0539 (5 µM) was incubated with 50% human plasma (K2 EDTA, BioreclamationIVT) in PBS for 5 h in triplicate. Eucatropine (Aldrich) and verapamil (Acros) were included as the positive and negative control, respectively. The samples were analyzed by UPLC-MS (AB Sciex 4500 with Waters Acquity FTN) with compounds detected by SIR detection on a single quadrupole mass spectrometer. All integration and analysis were performed using DiscoveryQuant software.

Quantification and Statistical Analysis

In vitro assays: In vitro biochemical assay data were analyzed using specific equations mentioned in the individual method.

Fluorescence imaging: Fluorescence images were analyzed by inbuilt MetaXpress software. Standard deviations were calculated either manually in excel or auto-generated in GraphPad Prism from the raw values.

Genome editing efficiency: Base-editing or indel frequencies were calculated following a reported protocol (Komor et al., 2016b).

Chemical Synthesis and Characterizations

Reagents and Instrumentation. All reagents were purchased and used as received from commercial sources without further purification. Reactions were performed in bottom flasks stirred with Teflon®-coated magnetic stir bars. Moisture- and air-sensitive reactions were performed with Schlenk technique under a dry nitrogen/argon atmosphere. Moisture- and air-sensitive liquids or solutions were transferred via nitrogen-flushed syringes. As necessary, organic solvents were degassed by bubbling nitrogen/argon through the liquid. Reaction progress were monitored by thin layer chromatography (TLC) and ultra-performance liquid chromatography mass spectrometry (UPLC-MS). The microwave reactions were performed in a Biotage single-mode microwave reactor with a power of 0 to 400 W.

Chromatography. Flash column chromatography was performed by using silica gel (60 Å mesh, 20-40 µm) on Teledyne Isco CombiFlash Rf system. Analytical TLC was performed using Merck Silica gel 60 F254 pre-coated plates (0.25 mm), illumination at 254 nm allowed for visualization of UV active materials, phosphomolybdic Acid (PMA) staining solution was used for visualization of UV inactive material. UPLC-MS was performed on a Waters ACQUITY UPLC I-Class PLUS System with ACQUITY SQ Detector 2.

Spectroscopy Data. Nuclear magnetic resonance (NMR) spectra were recorded on a Bruker 400 Spectrometer ($^1$H NMR, 400 MHz; 13C, 100 MHz; Dept-135 Carbon, 100 MHz; $^{19}$F NMR, 376 MHZ) at the Broad Institute of MIT and Harvard. Chemical shifts are reported in parts per million (ppm) relative to the solvent used. NMR solvents were purchased from Cambridge Isotope Laboratories, Inc., and NMR data were obtained in $CDCl_3$ or DMSO-$d_6$. Data for 1H NMR are reported as follows: chemical shift value in ppm, multiplicity (s=singlet, d=doublet, t=triplet, dd=double doublet, and m=multiplet), integration value, and coupling constant value in Hz. Enantio Excess were determined by supercritical fluid chromatography (SFC) on a Waters UPC2 convergence chromatography system connected to a QDa single quadrupole mass spectrometer with Chiralcel AD-H, AS-H, IC, and OD-H columns. Tandem liquid chromatography mass spectrometry (LCMS) was performed on a Waters 2795 separations module with a 3100 mass detector. High-resolution mass-spectra (HRMS) were acquired on an Agilent 1290 Infinity separations module coupled to a 6230 time-of-flight (TOF) mass detector operating in ESI$^+$ or ESI$^-$ mode at the Mass Spectrometry Facility at Harvard University. "Find-by-Formula" feature in the MassHunter Qalitative Analysis Vb.06.00 was used to confirm the recorded mass values, which are averages of three independent measurements.

Asymmetric Povarov Reaction. Urea cocatalysts were prepared as described by Jacobsen et al., spectroscopy data matched with a previous report (K. L. Tan, E. N. Jacobsen, *Angew. Chem. Int. Ed.* 2007, 46, 1315-1317.). Asymmetric Povarov reaction was performed as described by Jacobsen et al., spectroscopy data and enantiomeric excess of hexahydropyrroloquinoline product was matched with previous reports (H. Xu, H. Zhang, E. N. Jacobsen, Nat. Protoc. 2014, 9, 1860-1866; B. Gerald, M. W. O'Shea, E. Donckele, S. Kesavan, L. B. Akella, H. Xu, E. N. Jacobsen, L. S. Marcaurelle, *ACS Comb. Sci.* 2012, 14, 621-630).

General Procedure A: Microwave-Assisted Suzuki cross-coupling reactions. A Biotage microwave reaction vial was charged with the hexahydropyrroloquinoline substrate, phenylboronic acid (1.2 equiv.), potassium phosphate (1.8 M solution, 2.0 equiv.), XPhos-Pd-G2 (5% mol), and DMF. The vial was subjected to irradiation for 30 min at 60° C. The reaction mixture was then cooled to room temperature and dilute with ethyl acetate, then wash with lithium chloride solution and water, dried over sodium sulfate, filtered and solvent removed by vacuum to give crude product. Crude residue was purified by column chromatography on silica gel eluting with hexane/ethyl acetate or dichloromethane/methanol.

General Procedure B: Microwave-Assisted Sonogashira cross-coupling reactions. A Biotage microwave reaction vial was charged with the hexahydropyrroloquinoline substrates (1.0 equiv.), alkynes (5.0 equiv.), 1,4-diazabicyclo[2.2.2]octane (5.0 equiv.), XPhos-Pd-G3 (10% mol), and DMF. The vial was subjected to microwave irradiation for 1 h at 90° C. The reaction mixture was then cooled to room temperature and dilute with ethyl acetate, then wash with lithium chloride solution and water, dry with sodium sulfate, filter and solvent removed by vacuum to give crude product. Crude residue was purified by column chromatography on silica gel eluting with hexane/ethyl acetate or dichloromethane/methanol.

General Procedure C: N-capping with Aldehyde. After Cbz-/Boc-deprotection, the substrate (1.0 equiv.) was dissolved in anhydrous DCM, 4-pyridinecarboxyaldehyde (1.5 equiv.) and acetic acid (2.0 equiv.) were added subsequently, followed by addition of $NaBH(OAc)_3$ (3.0 equiv.) portion wisely. The reaction mixture was stirred at room temperature for three hours to reach the complete consumption of starting material. The reaction mixture was then diluted with DCM, quenched with a saturated $NaHCO_3$ aqueous solution, and extracted with DCM. Organic layers were combined, washed with brine, dried over anhydrous $Na_2SO_4$, filtered, and concentrated in vacuo to give a crude residue, which was purified by flash column chromatography on silica gel eluting with hexane and ethyl acetate (or dichloromethane and methanol).

General Procedure D: N-capping with Sulfonyl Chlorides/Isocyanates. After Boc-deprotection, substrate was dissolved in anhydrous DCM followed by addition of 2,6-lutidine (3.0 equiv) and then desired sulfonyl chloride/isocyanate (2.0 equiv). The reaction was allowed to stir at room temperature for two hours to reach the complete consumption of starting material. The reaction mixture was then diluted with DCM, quenched with saturated $NaHCO_3$ aqueous solution, and extracted with DCM. Organic layers were combined, washed with brine, dried over anhydrous $Na_2SO_4$, filtered, and concentrated in vacuo to give a crude residue, which was purified by flash column chromatography on silica gel eluting with hexane and ethyl acetate (or dichloromethane and methanol).

General Procedure E: N-capping with Acid. After Boc-deprotection, substrate and desired acid (2.0) was dissolved in anhydrous DMF followed by addition of PyBoP (3 equiv) and DIPEA (5 equiv). The reaction was allowed to stir at room temperature for 1 h to reach the complete consumption of starting material. The reaction mixture was then diluted with ethyl acetate, organic layer was washed with lithium chloride solution and water, dried over anhydrous $Na_2SO_4$, filtered, and concentrated in vacuo to give a crude residue, which was purified by flash column chromatography on silica gel eluting with hexane and ethyl acetate (or dichloromethane and methanol).

Synthesis of BRD7087 and BRD5779.

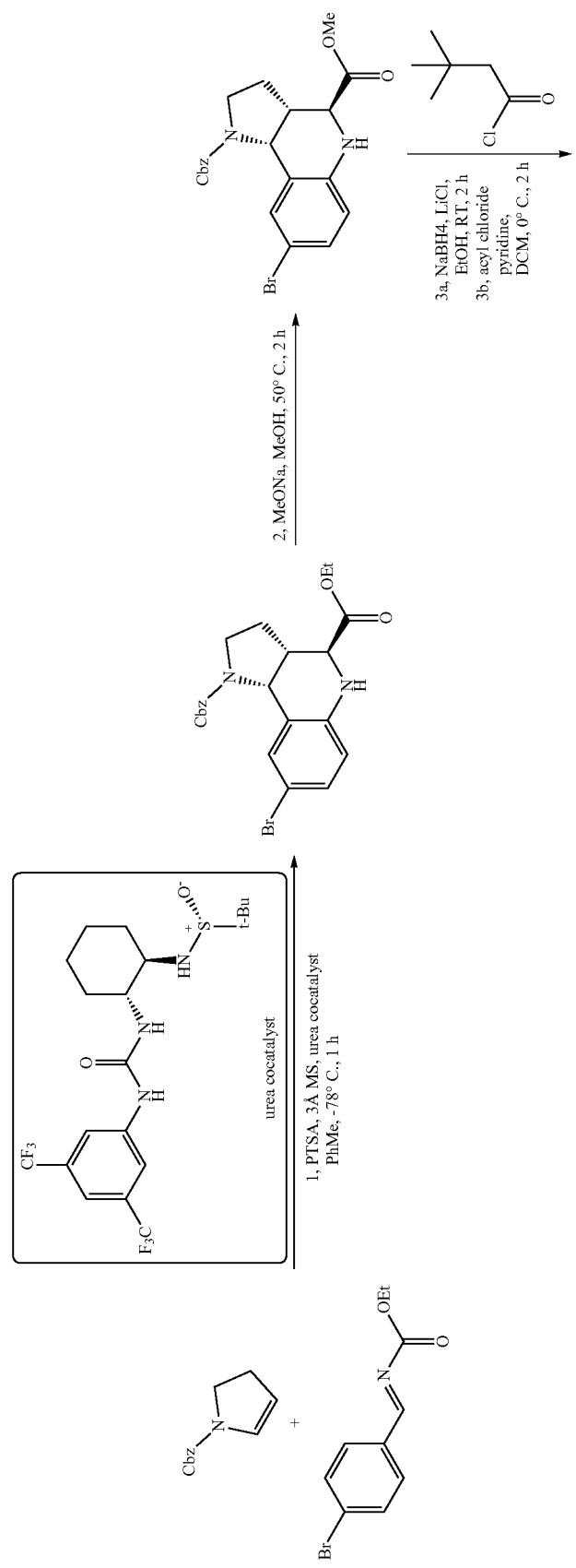

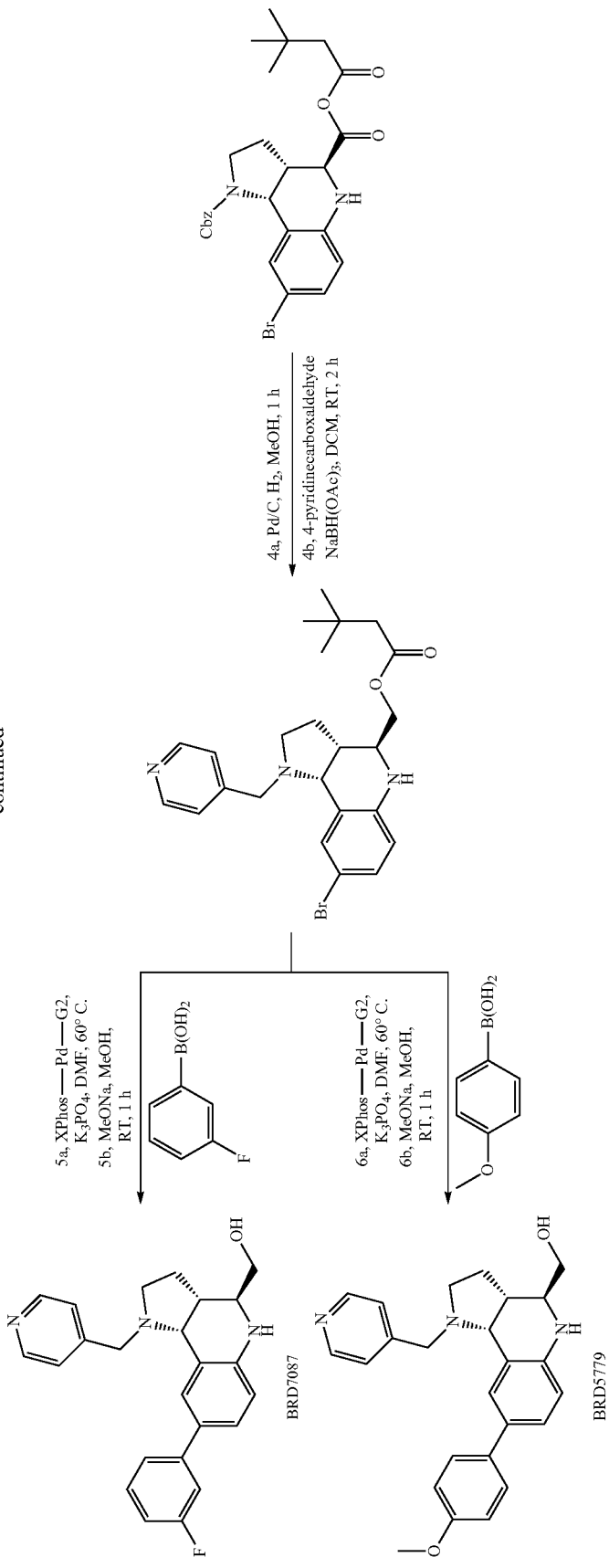

((3aR,4S,9bR)-8-(3-Fluorophenyl)-1-(pyridin-4-ylmethyl)-2,3,3a,4,5,9b-hexahydro-1H-pyrrolo[3,2-c]quinolin-4-yl) methanol (BRD7087) and ((3aR,4S,9bR)-8-(4-Methoxyphenyl)-1-(pyridin-4-ylmethyl)-2,3,3a,4,5,9b-hexahydro-1H-pyrrolo[3,2-c]quinolin-4-yl) methanol (BRD5779) were prepared as described in Scheme 1 and General Procedure A and C.

BRD7087. $^1$H NMR (400 MHZ, CDCl$_3$): δ 8.45 (d, 2H, J=4.8 Hz), 7.35 (d, 2H, J=8.2 Hz), 7.28-7.25 (m, 4H), 7.21 (d, 1H), 6.97 (t, 1H, J=8.6 Hz), 6.73 (d, 1H, J=8.4 Hz), 4.38 (d, 1H, J=13.8 Hz), 4.01 (d, 1H, J=8.6 Hz), 3.56-3.53 (m, 2H), 3.33 (s, 1H), 3.27 (d, 1H, J=13.8 Hz), 2.97-2.93 (m, 1H), 2.21-2.19 (m, 1H), 2.10-2.03 (m, 2H), 1.65-1.62 (m, 1H); $^{13}$C NMR (100 MHZ, CDCl$_3$): δ 164.5, 162.1 (d, $^1J_{C,F}$=243.4 Hz), 150.0, 149.1, 144.7, 143.6, 143.5 (d, $^3J_{C,F}$=7.8 Hz), 130.3, 130.1, 130.0 (d, $^3J_{C,F}$=8.8 Hz), 127.8, 127.6, 123.6, 121.7 (d, $^4J_{C,F}$=2.8 Hz), 118.3, 114.6, 113.0, 112.8 (d, $^2J_{C,F}$=21.8 Hz), 112.8, 112.6 (d, $^2J_{C,F}$=21.0 Hz), 64.7, 64.1, 56.0, 54.5, 51.4, 35.8, 25.7; $^{19}$F NMR (376 MHz, CDCl$_3$): δ −113.5; HRMS (ESI, m/z): calcd for C$_{24}$H$_{24}$FN$_3$O (M+H)$_+$: 390.1982, found: 390.1976.

BRD5779. $^1$H NMR (400 MHZ, CDCl$_3$): δ 8.46 (d, 2H, J=4.9 Hz), 7.44 (d, 2H, J=8.2 Hz), 7.33 (d, 1H, J=8.2 Hz), 7.25-7.24 (m, 3H), 6.97 (d, 2H, J=8.2 Hz), 6.74 (d, 1H, J=8.2 Hz), 4.41 (d, 1H, J=13.8 Hz), 3.99 (d, 1H, J=9.6 Hz), 3.85 (s, 3H), 3.59 (d, 1H, J=9.6 Hz), 3.53-3.51 (m, 1H), 3.32 (s, 1H), 3.25 (d, 1H, J=13.8 Hz), 2.97 (t, 1H, J=9.2 Hz), 2.20-2.18 (m, 1H), 2.10-2.05 (m, 2H), 1.66-1.62 (m, 1H); $^{13}$C NMR (101 MHZ, CDCl$_3$): δ 158.3, 149.9, 149.2, 143.7, 134.0, 130.0, 129.3, 127.3, 123.6, 118.5, 114.8, 114.2, 64.7, 64.1, 56.1, 55.4, 54.5, 51.4, 35.9, 25.7; HRMS (ESI, m/z): calcd for C$_{25}$H$_{27}$N$_3$O$_2$ (M+H)$_+$: 402.2182, found: 402.2172.

Synthesis of BRD3539-PEG-Biotin.

Scheme 2. Synthesis of BRD3539.
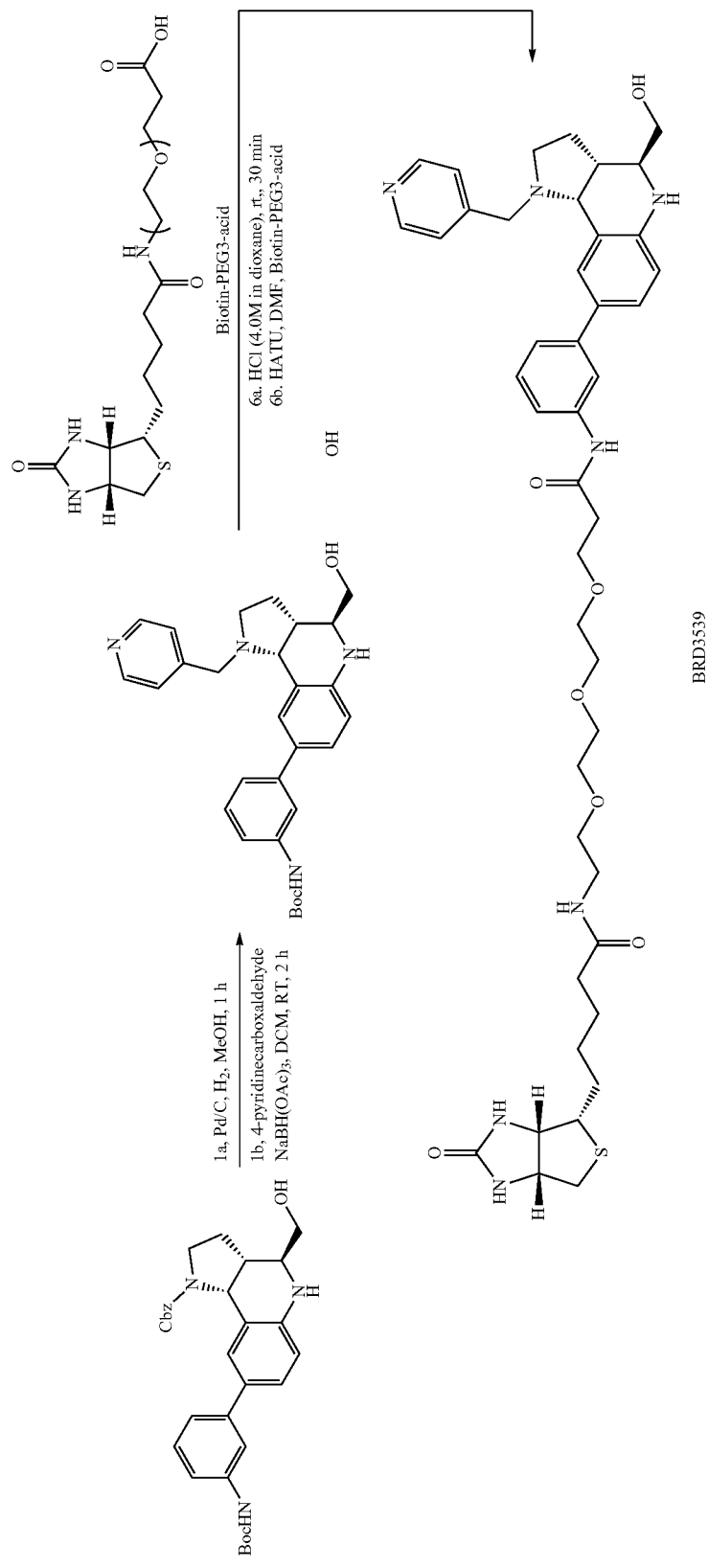

N-(2-(2-(2-(3-((3-((3aR,4S,9bR)-4-(Hydroxymethyl)-1-(pyridin-4-ylmethyl)-2,3,3a,4,5,9b-hexahydro-1H-pyrrolo[3,2-c]quinolin-8-yl)phenyl)amino)-3-oxopropoxy) ethoxy) ethoxy)ethyl)-5-((3aS,4S,6aR)-2-oxohexahydro-1H-thieno[3,4-d]imidazol-4-yl) pentanamide (BRD3539) was prepared as described in Scheme 2 and General Procedure A and C. The resulting residue was purified through preparative HPLC to afford the desired biotinylated product BRD3539.

BRD3539. $^1$H NMR (400 MHZ, $D_2O$): δ 8.70 (d, 2H, J=5.8 Hz), 8.04 (d, 2H, J=5.8 Hz), 7.73 (s, 1H), 7.59 (d, 1H, J=8.4 Hz), 7.51 (t, 1H, J=8.0 Hz), 7.36-7.32 (m, 3H), 6.98 (d, 1H, J=8.4 Hz), 5.02 (d, 1H, J=14.0 Hz), 4.91 (d, 1H, J=6.8 Hz), 4.54 (dd, 1H, J=8.8 and 5.0 Hz), 4.29 (dd, 1H, J=8.8 and 5.0 Hz), 3.94 (t, 2H, J=5.9 Hz), 3.84 (ddd, 1H, J=12.0, 3.0 and 1.5 Hz), 3.75-3.69 (m, 6H), 3.66-3.62 (m, 4H), 3.55-3.53 (m, 2H), 3.47 (t, 2H, J=5.4 Hz), 3.39-3.34 (m, 1H), 3.23 (t, 2H, J=5.2 Hz), 3.18-3.13 (m, 1H), 2.92 (dd, 1H, J=13.2 and 5.0 Hz), 2.81-2.79 (m, 1H), 2.77 (t, 2H, J=5.8 Hz), 2.73 (d, 1H, J=13.2 Hz), 2.67-2.62 (m, 1H), 2.30-2.24 (m, 1H), 2.11 (t, 2H, J=7.2 Hz), 1.61-1.54 (m, 1H), 1.50-1.39 (m, 3H), 1.28-1.20 (m, 2H); $^{13}$C NMR (101 MHZ, $D_2O$): δ 176.6, 173.0, 165.2, 151.0, 145.6, 141.7, 140.0, 137.8, 130.0, 130.0, 129.8, 129.1, 127.7, 122.6, 119.8, 118.6, 116.6, 111.0, 69.8, 69.7, 69.6, 69.4, 68.8, 66.7, 62.3, 62.0, 60.2, 55.4, 55.3, 53.5, 39.7, 38.8, 36.9, 35.7, 35.3, 27.9, 27.6, 26.5, 25.1; HRMS (ESI, m/z): calcd for $C_{43}H_{58}N_7O_7S$ $(M+H)_+$: 816.4118, found: 816.4103.

Synthesis of BRD0539.

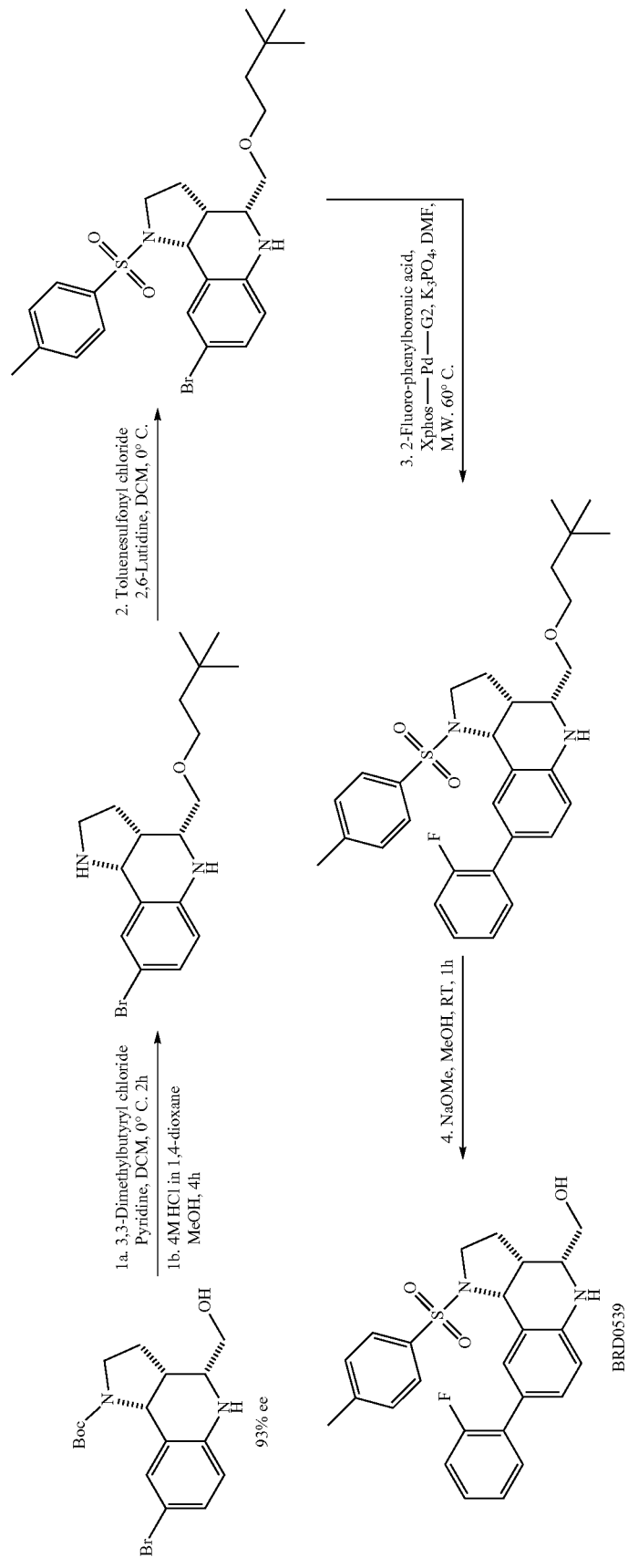
Scheme 3. Synthesis of BRD0539.

((3aR,4R,9bR)-8-(2-fluorophenyl)-1-tosyl-2,3,3a,4,5,9b-hexahydro-1H-pyrrolo[3,2-c]quinolin-4-yl) methanol (BRD0539) was prepared as described in Scheme 3 and General Procedure A and D.

BRD0539. $^1$H NMR (400 MHZ, Chloroform-d) δ 7.90 (s, 1H), 7.77 (d, J=7.8 Hz, 2H), 7.42 (td, J=7.9, 2.0 Hz, 1H), 7.34-7.19 (m, 4H), 7.18-7.04 (m, 2H), 6.54 (d, J=8.3 Hz, 1H), 5.07 (d, J=7.2 Hz, 1H), 3.61-3.41 (m, 3H), 3.40-3.20 (m, 2H), 2.41 (s, 3H), 2.01-1.87 (m, 1H), 1.83-1.71 (m, 1H), 1.66 (dt, J=13.5, 7.5 Hz, 1H); $^{13}$C NMR (101 MHZ, CDCl$_3$) δ 159.8 (d, J=246.5 Hz), 143.8, 143.2, 135.3, 131.4 (d, J=2.5 Hz), δ 130.5 (d, J=3.7 Hz), 130.0, δ 129.1 (d, J=4.6 Hz), δ 128.0 (d, J=8.1 Hz), 127.7, 126.1, 8124.4 (d, J=3.6 Hz), 120.6, 116.1, 115.9, 114.7, 65.1, 59.3, 52.7, 47.3, 38.8, 23.2, 21.6; 19F NMR (376 MHZ, CDCl$_3$): δ −118.1; HRMS (ESI, m/z): calcd for C$_{25}$H$_{26}$FN$_2$O$_3$S (M+H)$_+$: 453.1643, found: 453.1643.

Scheme: Synthesis of BRD0539-PEG3-Biotin.

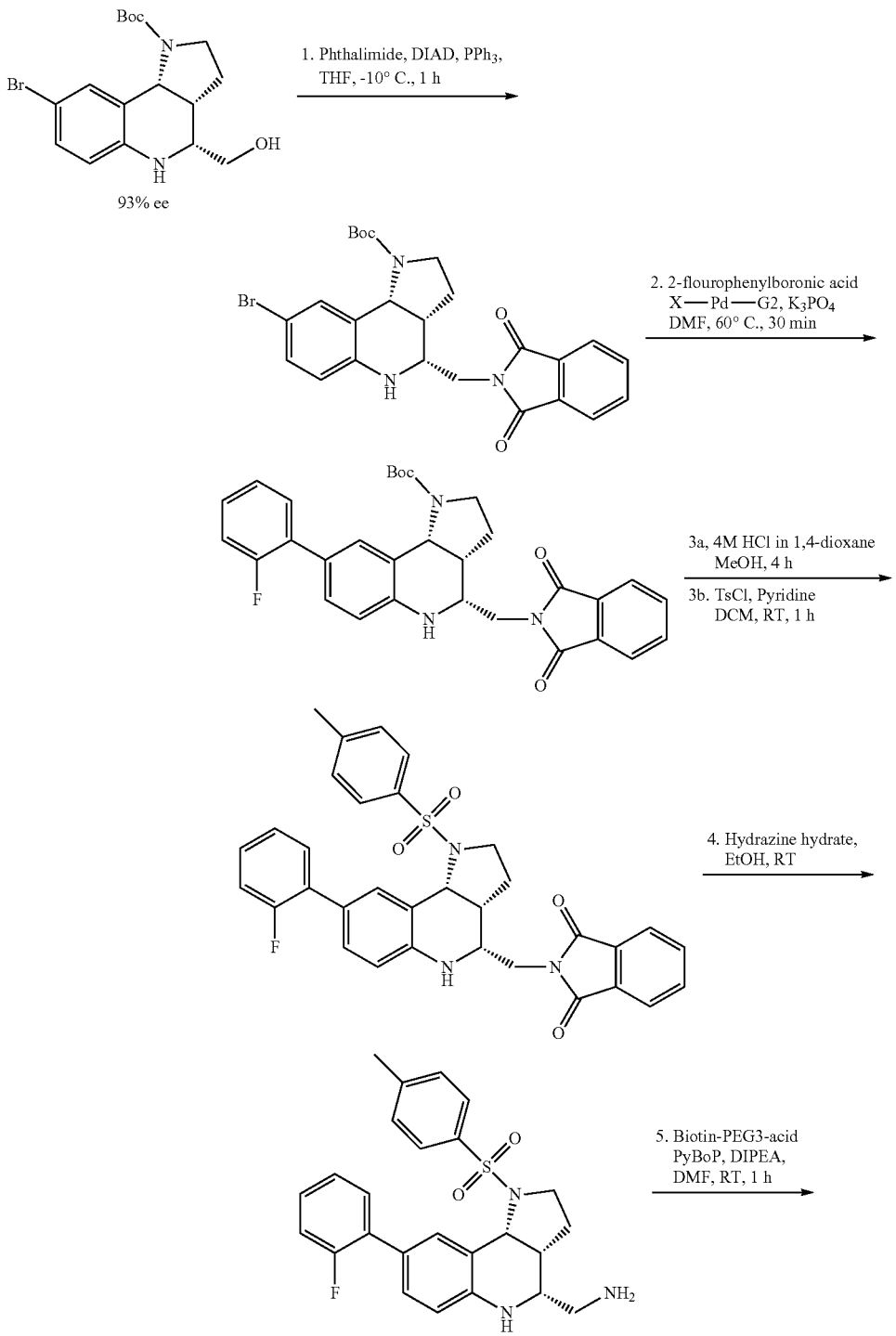

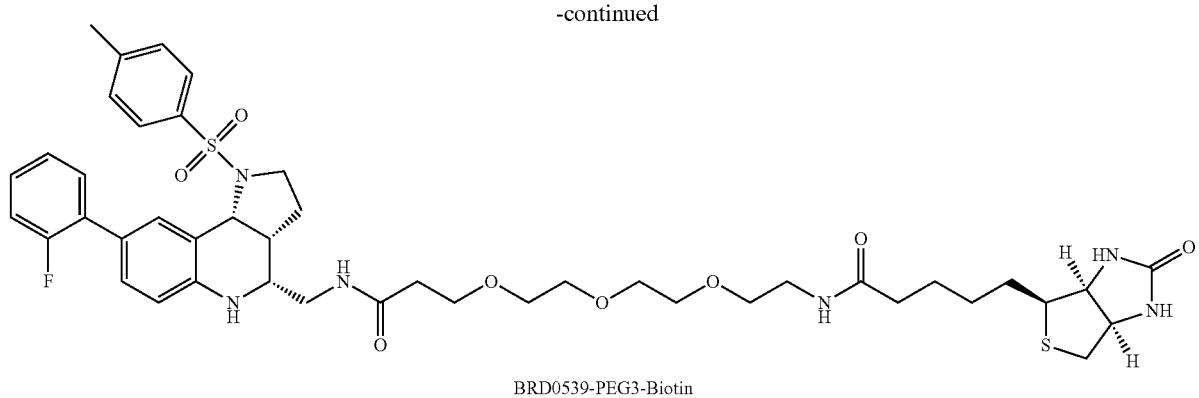

BRD0539-PEG3-Biotin

Scheme: Synthesis of BRD0539-PEG3-Biotin.

N-(1-((3aR,4R,9bR)-8-(2-fluorophenyl)-1-tosyl-2,3,3a,4,5,9b-hexahydro-1H-pyrrolo[3,2-c]quinolin-4-yl)-3-oxo-6,9,12-trioxa-2-azatetradecan-14-yl)-5-((3aS,4S,6aR)-2-oxo-hexahydro-1H-thieno[3,4-d]imidazol-4-yl) pentanamide (BRD0539-PEG3-Biotin) was prepared as described in Scheme 4 and General Procedure A and D.

BRD0539-PEG3-Biotin. $^1$H NMR (400 MHZ, Chloroform-d) δ 7.93 (d, J=2.0 Hz, 1H), 7.79 (d, J=8.1 Hz, 2H), 7.47-7.38 (m, 2H), 7.35 (d, J=8.0 Hz, 2H), 7.31-7.21 (m, 2H), 7.17 (td, J=7.5, 1.4 Hz, 1H), 7.10 (ddd, J=9.6, 8.1, 1.4 Hz, 1H), 6.65 (t, J=7.5 Hz, 2H), 6.53 (s, 1H), 5.67 (s, 1H), 5.08 (d, J=6.8 Hz, 1H), 4.46 (dd, J=7.8, 4.7 Hz, 1H), 4.24 (dd, J=7.8, 4.6 Hz, 1H), 3.75 (dt, J=12.0, 6.2 Hz, 2H), 3.66-3.50 (m, 12H), 3.46-3.27 (m, 5H), 3.11 (dd, J=8.0, 5.1 Hz, 2H), 2.86 (dd, J=12.8, 4.9 Hz, 1H), 2.72 (d, J=12.8 Hz, 1H), 2.47 (d, J=14.3 Hz, 5H), 2.24-2.14 (m, 2H), 2.03-1.77 (m, 3H), 1.76-1.59 (m, 4H), 1.40 (h, J=7.5 Hz, 2H); $^{13}$C NMR (101 MHz, CDCl$_3$) δ 173.5, 172.3, 164.1, 160.9, 158.5 (d, J=246.5 Hz), 143.7, 135.1, 131.4 (d, J=2.5 Hz), 130.4 (d, J=3.7 Hz), 130.3, 130.0, 129.0, 128.9, 128.8, 128.0, 127.9 (d, J=8.1 Hz), 127.6, 124.4, 124.4 (d, J=3.6 Hz), 120.8, 116.0, 115.8, 114.9, 77.3, 70.4, 70.2, 70.1, 70.0, 69.9, 67.3, 61.8, 60.2, 59.2, 55.6, 51.4, 47.3, 43.0, 40.5, 40.0, 39.2, 36.9, 35.9, 28.1, 28.0, 25.5, 23.0, 21.6; $^{19}$F NMR (376 MHz, CDCl$_3$): δ −118.2.

Synthesis of BRD3433.

Scheme 4. Synthesis of BRD3433.
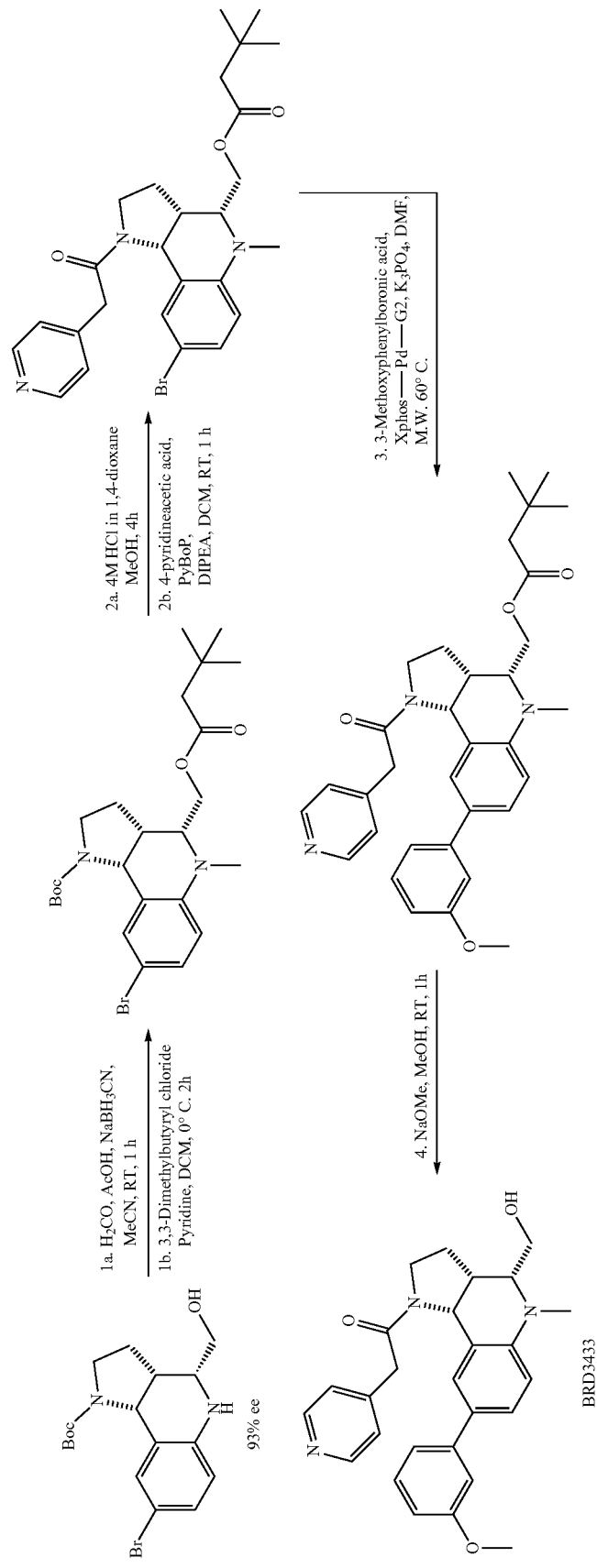

1-((3aS,4R,9bR)-4-(hydroxymethyl)-8-(3-methoxyphenyl)-5-methyl-2,3,3a,4,5,9b-hexahydro-1H-pyrrolo[3,2-c]quinolin-1-yl)-2-(pyridin-4-yl) ethan-1-one (BRD3433) was prepared as described in Scheme 4 and General Procedure A and E.

BRD3433. $^1$H NMR (400 MHZ, Chloroform-d) δ 8.49 (d, J=5.1 Hz, 2H), 7.70 (s, 1H), 7.44-7.25 (m, 4H), 7.04 (d, J=6.2 Hz, 2H), 6.80 (dd, J=15.5, 8.4 Hz, 2H), 5.63 (d, J=7.0 Hz, 1H), 3.96 (dt, J=13.7, 6.8 Hz, 2H), 3.84 (s, 4H), 3.71 (s, 2H), 3.49 (tdd, J=26.6, 18.2, 11.2 Hz, 3H), 3.00 (d, J=24.8 Hz, 3H), 2.62 (h, J=5.9, 5.3 Hz, 1H), 2.24-1.89 (m, 2H); 13C NMR (101 MHZ, CDCl$_3$) δ 169.2, 160.0, 149.1, 145.9, 145.1, 142.1, 130.5, 129.7, 127.9, 127.5, 126.8, 125.3, 124.8, 123.0, 118.7, 113.7, 112.4, 112.1, 111.4, 77.3, 63.6, 58.2, 55.8, 55.3, 46.0, 41.0, 39.8, 36.9, 36.0, 24.1; HRMS (ESI, m/z): calcd for $C_{27}H_{30}N_3O_3$ (M+H)+: 443.2209, found: 443.2211.

Synthesis of BRD3433-PEG3-Biotin.

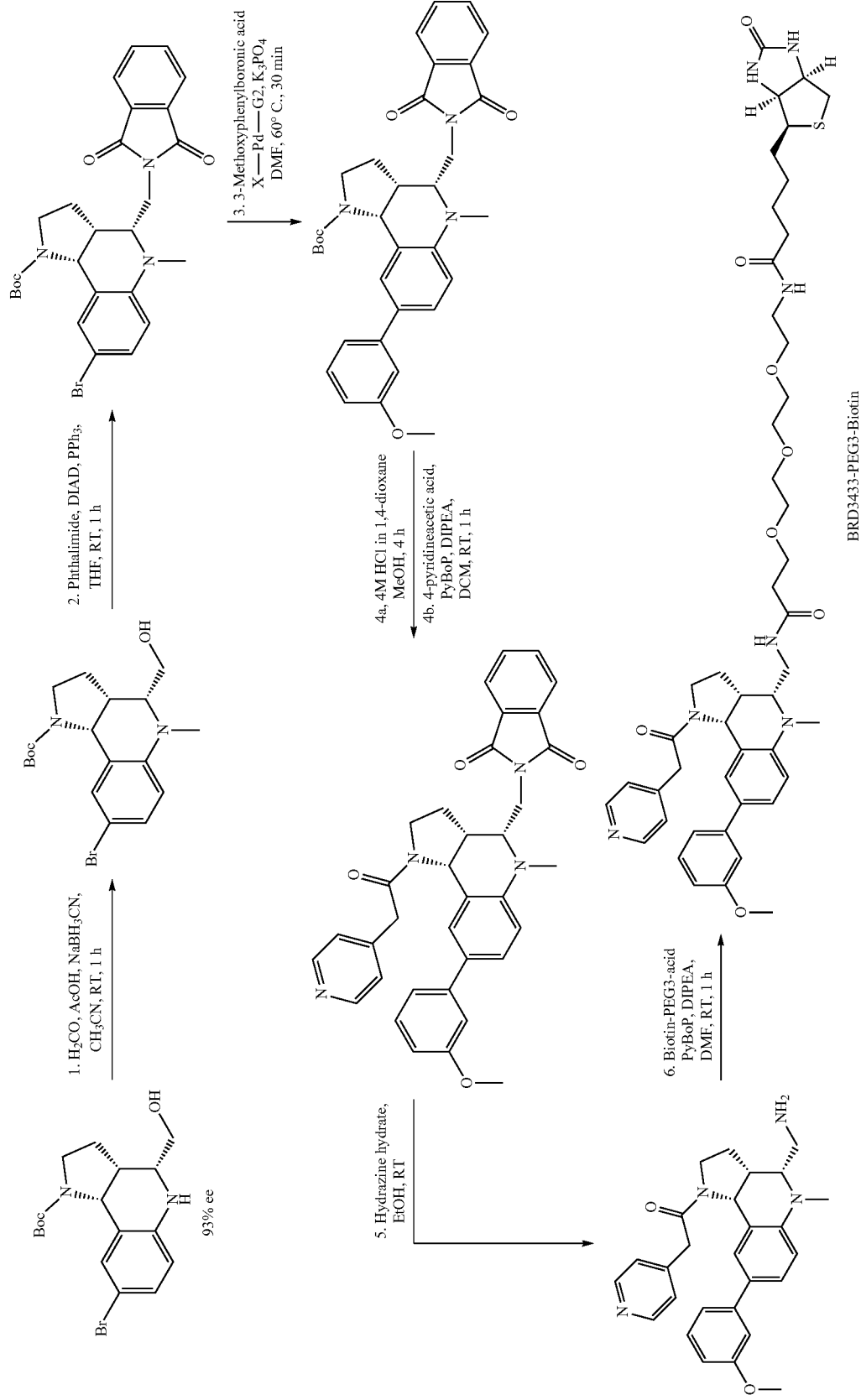

N-(1-((3aS,4R,9bR)-8-(3-methoxyphenyl)-5-methyl-1-(2-(pyridin-4-yl) acetyl)-2,3,3a,4,5,9b-hexahydro-1H-pyrrolo[3,2-c]quinolin-4-yl)-3-oxo-6,9,12-trioxa-2-azatetradecan-14-yl)-5-((3aS,4S,6aR)-2-oxohexahydro-1H-thieno[3,4-d]imidazol-4-yl) pentanamide (BRD3433-PEG3-Biotin) was prepared as described in Scheme 5 and General Procedure A and E.

BRD3433-PEG3-Biotin. $^1$H NMR (400 MHZ, MeOD) δ 8.45-8.31 (m, 1H), 7.63-7.55 (m, 1H), 7.45-7.32 (m, 2H), 7.27 (t, J=7.9 Hz, 1H), 7.05-6.92 (m, 1H), 6.88-6.78 (m, 1H), 5.54 (d, J=6.9 Hz, 1H), 4.85 (s, 4H), 4.48-4.41 (m, 1H), 4.25 (dd, J=7.9, 4.5 Hz, 1H), 3.95-3.84 (m, 1H), 3.82 (s, 2H), 3.77 (t, J=6.0 Hz, 2H), 3.65-3.55 (m, 5H), 3.54-3.43 (m, 2H), 3.42-3.18 (m, 3H), 3.15 (ddd, J=8.9, 5.9, 4.4 Hz, 1H), 3.00 (s, 2H), 2.89 (dd, J=12.7, 5.0 Hz, 1H), 2.69 (d, J=12.6 Hz, 1H), 2.51 (t, J=5.9 Hz, 1H), 2.19 (t, J=7.4 Hz, 2H), 1.95 (s, 1H), 1.64 (dtd, J=28.5, 14.4, 13.6, 7.1 Hz, 3H), 1.40 (dd, J=9.4, 5.9 Hz, 1H); $^{13}$C NMR (101 MHZ, MeOD) δ 174.7, 172.9, 170.3, 164.6, 160.2, 148.8, 146.0, 145.7, 142.0, 130.2, 129.4, 127.0, 126.4, 125.0, 122.6, 118.0, 114.0, 111.4, 111.0, 70.2, 70.1, 70.0, 69.9, 69.2, 66.9, 61.9, 60.2, 56.2, 55.6, 55.6, 54.3, 48.3, 48.0, 47.8, 47.6, 47.4, 47.2, 47.0, 45.6, 41.0, 40.1, 39.7, 39.2, 38.9, 36.4, 35.3, 28.4, 28.1, 25.4, 23.3; HRMS (ESI, m/z): calcd for $C_{46}H_{61}N_7O_8SNa$ $(M+Na)_+$: 894.4195, found: 894.4189.

Synthesis of BRD0322.

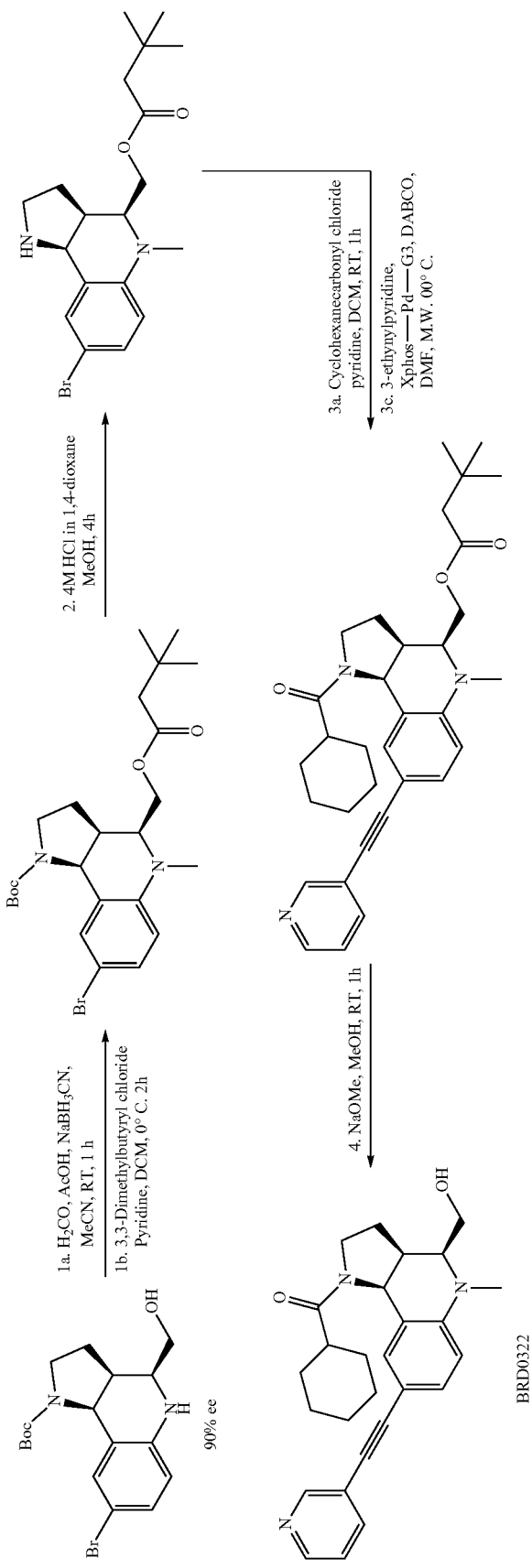

Cyclohexyl((3aR,4S,9bS)-4-(hydroxymethyl)-5-methyl-8-(pyridin-3-ylethynyl)-2,3,3a,4,5,9b-hexahydro-1H-pyrrolo[3,2-c]quinolin-1-yl) methanone (BRD0322) was prepared as described in Scheme 6 and General Procedure B and D.

BRD20322. $^1$H NMR (400 MHZ, Chloroform-d) δ 8.74-8.61 (m, 1H), 8.48 (dd, J=4.9, 1.7 Hz, 1H), 7.74 (dt, J=7.8, 1.9 Hz, 1H), 7.46 (s, 1H), 6.66 (d, J=8.7 Hz, 1H), 5.53 (d, J=6.8 Hz, 1H), 3.98 (dd, J=11.2, 4.2 Hz, 1H), 3.93-3.78 (m, 1H), 3.54 (dd, J=21.4, 8.8 Hz, 2H), 3.00 (s, 2H), 2.56 (s, 1H), 2.39 (t, J=11.7 Hz, 1H), 2.19-2.06 (m, 1H), 2.06-1.49 (m, 9H), 1.28 (t, J=9.4 Hz, 3H); $^{13}$C NMR (101 MHZ, CDCl$_3$) δ 176.4, 152.1, 147.9, 146.7, 138.3, 132.9, 132.0, 123.1, 121.4, 113.2, 111.5, 93.9, 4, 77.4, 64.0, 58.3, 54.6, 45.1, 42.5, 39.7, 36.2, 29.7, 28.7, 26.1, 25.9, 25.9, 24.5; HRMS (ESI, m/z): calcd for $C_{27}H_{31}N_3O_2Na$ (M+H)$^+$: 452.2308, found: 452.2315.

Synthesis of BRD0048.

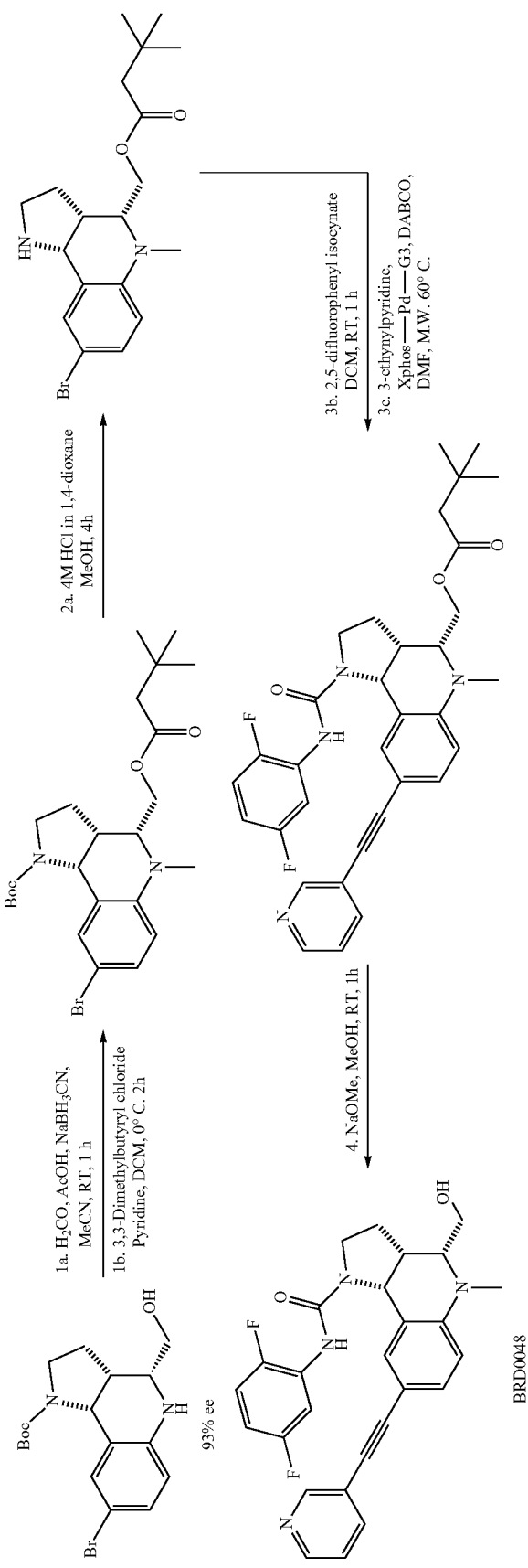

(3aS,4R,9bR)—N-(2,5-difluorophenyl)-4-(hydroxymethyl)-5-methyl-8-(pyridin-3-ylethynyl)-2,3,3a,4,5,9b-hexahydro-1H-pyrrolo[3,2-c]quinoline-1-carboxamide (BRD0048) was prepared as described in Scheme 7 and General Procedure B and D.

BRD0048. $^1$H NMR (400 MHZ, Chloroform-d) δ 8.67 (d, J=2.2 Hz, 1H), 8.43 (dd, J=4.9, 1.8 Hz, 1H), 8.10 (ddd, J=10.4, 6.2, 2.8 Hz, 1H), 7.74 (dq, J=7.9, 1.8 Hz, 1H), 7.63 (s, 1H), 7.30 (dt, J=8.7, 1.7 Hz, 1H), 7.26-7.16 (m, 1H), 7.05-6.91 (m, 1H), 6.70-6.51 (m, 3H), 5.40 (d, J=7.1 Hz, 1H), 3.98 (dd, J=11.4, 4.4 Hz, 1H), 3.85 (dd, J=11.3, 5.7 Hz, 1H), 3.57-3.42 (m, 3H), 2.98 (d, J=1.4 Hz, 3H), 2.75-2.61 (m, 1H), 2.25-2.14 (m, 1H), 2.12-1.93 (m, 1H); $^{13}$C NMR (101 MHZ, CDCl$_3$) δ 157.8 (d, J=238.95 Hz), 154.3, 152.0, 147.8, 147.2 (d, J=236.5 Hz), 146.7, 138.4, 132.8, 132.2, 128.6 (t, J=24.0 Hz), 123.4, 123.1, 121.4, 114.8 (dd, J=22.5 Hz), 113.2, 111.6, 108.5 (dd, J=25.9 Hz), 108.2 (d, J=30.3 Hz), 93.8, 84.6, 63.8, 58.2, 55.8, 45.0, 40.5, 36.0, 24.9; 19F NMR (376 MHZ, CDCl$_3$): δ −138.6, −113.3; HRMS (ESI, m/z): calcd for C$_{27}$H$_{24}$F$_2$N$_4$O$_2$Na (M+Na)$^+$: 497.1760, found: 497.1780. Small Molecule Characterization Information BRD7087. $^1$H NMR (400 MHZ, CDCl$_3$): δ 8.45 (d, 2H, J=4.8 Hz), 7.35 (d, 2H, J=8.2 Hz), 7.28-7.25 (m, 4H), 7.21 (d, 1H), 6.97 (t, 1H, J=8.6 Hz), 6.73 (d, 1H, J=8.4 Hz), 4.38 (d, 1H, J=13.8 Hz), 4.01 (d, 1H, J=8.6 Hz), 3.56-3.53 (m, 2H), 3.33 (s, 1H), 3.27 (d, 1H, J=13.8 Hz), 2.97-2.93 (m, 1H), 2.21-2.19 (m, 1H), 2.10-2.03 (m, 2H), 1.65-1.62 (m, 1H).

$^{13}$C NMR (100 MHz, CDCl$_3$): δ 164.5, 162.1 (d, $^1J_{C,F}$=243.4 Hz), 150.0, 149.1, 144.7, 143.6, 143.5 (d, $^3J_{C,F}$=7.8 Hz), 130.3, 130.1, 130.0 (d, $^3J_{C,F}$=8.8 Hz), 127.8, 127.6, 123.6, 121.7 (d, $^4J_{C,F}$=2.8 Hz), 118.3, 114.6, 113.0, 112.8 (d, $^2J_{C,F}$=21.8 Hz), 112.8, 112.6 (d, $^2J_{C,F}$=21.0 Hz), 64.7, 64.1, 56.0, 54.5, 51.4, 35.8, 25.7.

$^{19}$F NMR (376 MHZ, CDCl$_3$): δ −113.5.

HRMS (ESI, m/z): calcd for C$_{24}$H$_{24}$FN$_3$O (M+H)$^+$: 390.1982, found: 390.1976.

BRD5779. $^1$H NMR (400 MHz, CDCl$_3$): δ 8.46 (d, 2H, J=4.9 Hz), 7.44 (d, 2H, J=8.2 Hz), 7.33 (d, 1H, J=8.2 Hz), 7.25-7.24 (m, 3H), 6.97 (d, 2H, J=8.2 Hz), 6.74 (d, 1H, J=8.2 Hz), 4.41 (d, 1H, J=13.8 Hz), 3.99 (d, 1H, J=9.6 Hz), 3.85 (s, 3H), 3.59 (d, 1H, J=9.6 Hz), 3.53-3.51 (m, 1H), 3.32 (s, 1H), 3.25 (d, 1H, J=13.8 Hz), 2.97 (t, 1H, J=9.2 Hz), 2.20-2.18 (m, 1H), 2.10-2.05 (m, 2H), 1.66-1.62 (m, 1H).

$^{13}$C NMR (100 MHz, CDCl$_3$): δ 158.3, 149.9, 149.2, 143.7, 134.0, 130.0, 129.3, 127.3, 123.6, 118.5, 114.8, 114.2, 64.7, 64.1, 56.1, 55.4, 54.5, 51.4, 35.9, 25.7.

HRMS (ESI, m/z): calcd for C$_{25}$H$_{27}$N$_3$O$_2$ (M+H)$^+$: 402.2182, found: 402.2172.

BRD3539. $^1$H NMR (400 MHz, D$_2$O): δ 8.70 (d, 2H, J=5.8 Hz), 8.04 (d, 2H, J=5.8 Hz), 7.73 (s, 1H), 7.59 (d, 1H, J=8.4 Hz), 7.51 (t, 1H, J=8.0 Hz), 7.36-7.32 (m, 3H), 6.98 (d, 1H, J=8.4 Hz), 5.02 (d, 1H, J=14.0 Hz), 4.91 (d, 1H, J=6.8 Hz), 4.54 (dd, 1H, J=8.8 and 5.0 Hz), 4.29 (dd, 1H, J=8.8 and 5.0 Hz), 3.94 (t, 2H, J=5.9 Hz), 3.84 (ddd, 1H, J=12.0, 3.0 and 1.5 Hz), 3.75-3.69 (m, 6H), 3.66-3.62 (m, 4H), 3.55-3.53 (m, 2H), 3.47 (t, 2H, J=5.4 Hz), 3.39-3.34 (m, 1H), 3.23 (t, 2H, J=5.2 Hz), 3.18-3.13 (m, 1H), 2.92 (dd, 1H, J=13.2 and 5.0 Hz), 2.81-2.79 (m, 1H), 2.77 (t, 2H, J=5.8 Hz), 2.73 (d, 1H, J=13.2 Hz), 2.67-2.62 (m, 1H), 2.30-2.24 (m, 1H), 2.11 (t, 2H, J=7.2 Hz), 1.61-1.54 (m, 1H), 1.50-1.39 (m, 3H), 1.28-1.20 (m, 2H).

$^{13}$C NMR (100 MHz, D$_2$O): δ 176.6, 173.0, 165.2, 151.0, 145.6, 141.7, 140.0, 137.8, 130.0, 130.0, 129.8, 129.1, 127.7, 122.6, 119.8, 118.6, 116.6, 111.0, 69.8, 69.7, 69.6, 69.4, 68.8, 66.7, 62.3, 62.0, 60.2, 55.4, 55.3, 53.5, 39.7, 38.8, 36.9, 35.7, 35.3, 27.9, 27.6, 26.5, 25.1. HRMS (ESI, m/z): calcd for C$_{43}$H$_{58}$N$_7$O$_7$S (M+H)$^+$: 816.4118, found: 816.4103.

BRD0539. $^1$H NMR (400 MHz, Chloroform-d) δ 7.90 (s, 1H), 7.77 (d, J=7.8 Hz, 2H), 7.42 (td, J=7.9, 2.0 Hz, 1H), 7.34-7.19 (m, 4H), 7.18-7.04 (m, 2H), 6.54 (d, J=8.3 Hz, 1H), 5.07 (d, J=7.2 Hz, 1H), 3.61-3.41 (m, 3H), 3.40-3.20 (m, 2H), 2.41 (s, 3H), 2.01-1.87 (m, 1H), 1.83-1.71 (m, 1H), 1.66 (dt, J=13.5, 7.5 Hz, 1H).

$^{13}$C NMR (101 MHz, CDCl$_3$) δ 159.8 (d, J=246.5 Hz), 143.8, 143.2, 135.3, 131.4 (d, J=2.5 Hz), δ 130.5 (d, J=3.7 Hz), 130.0, δ 129.1 (d, J=4.6 Hz), δ 128.0 (d, J=8.1 Hz), 127.7, 126.1, δ 124.4 (d, J=3.6 Hz), 120.6, 116.1, 115.9, 114.7, 65.1, 59.3, 52.7, 47.3, 38.8, 23.2, 21.6.

$^{19}$F NMR (376 MHZ, CDCl$_3$): δ −118.1.

HRMS (ESI, m/z): calcd for C$_{25}$H$_{26}$FN$_2$a$_3$S (M+H)$^+$: 453.1643, found: 453.1643.

BRD3433. $^1$H NMR (400 MHZ, Chloroform-d) δ 8.49 (d, J=5.1 Hz, 2H), 7.70 (s, 1H), 7.44-7.25 (m, 4H), 7.04 (d, J=6.2 Hz, 2H), 6.80 (dd, J=15.5, 8.4 Hz, 2H), 5.63 (d, J=7.0 Hz, 1H), 3.96 (dt, J=13.7, 6.8 Hz, 2H), 3.84 (s, 4H), 3.71 (s, 2H), 3.49 (tdd, J=26.6, 18.2, 11.2 Hz, 3H), 3.00 (d, J=24.8 Hz, 3H), 2.62 (h, J=5.9, 5.3 Hz, 1H), 2.24-1.89 (m, 2H).

$^{13}$C NMR (101 MHz, CDCl$_3$) δ 169.18, 159.95, 149.05, 145.86, 145.09, 142.07, 130.53, 129.69, 127.89, 127.53, 126.79, 125.30, 124.81, 123.00, 118.71, 113.69, 112.41, 112.08, 111.43, 77.28, 63.60, 58.23, 55.77, 55.28, 46.00, 41.04, 39.81, 36.90, 36.00, 24.14. HRMS (ESI, m/z): calcd for C$_{27}$H$_{30}$N$_3$O$_3$ (M+H)+: 443.2209, found: 443.2211.

BRD3433-PEG3-Biotin. $^1$H NMR (400 MHz, MeOD) δ 8.45-8.31 (m, 1H), 7.63-7.55 (m, 1H), 7.45-7.32 (m, 2H), 7.27 (t, J=7.9 Hz, 1H), 7.05-6.92 (m, 1H), 6.88-6.78 (m, 1H), 5.54 (d, J=6.9 Hz, 1H), 4.85 (s, 4H), 4.48-4.41 (m, 1H), 4.25 (dd, J=7.9, 4.5 Hz, 1H), 3.95-3.84 (m, 1H), 3.82 (s, 2H), 3.77 (t, J=6.0 Hz, 2H), 3.65-3.55 (m, 5H), 3.54-3.43 (m, 2H), 3.42-3.18 (m, 3H), 3.15 (ddd, J=8.9, 5.9, 4.4 Hz, 1H), 3.00 (s, 2H), 2.89 (dd, J=12.7, 5.0 Hz, 1H), 2.69 (d, J=12.6 Hz, 1H), 2.51 (t, J=5.9 Hz, 1H), 2.19 (t, J=7.4 Hz, 2H), 1.95 (s, 1H), 1.64 (dtd, J=28.5, 14.4, 13.6, 7.1 Hz, 3H), 1.40 (dd, J=9.4, 5.9 Hz, 1H).

$^{13}$C NMR (101 MHz, MeOD) δ 174.65, 172.86, 170.29, 164.63, 160.16, 148.76, 145.98, 145.73, 141.96, 130.23, 129.37, 126.97, 126.36, 125.01, 122.63, 117.98, 114.01, 111.44, 111.00, 70.20, 70.11, 69.95, 69.86, 69.20, 66.94, 61.93, 60.19, 56.15, 55.64, 55.59, 54.32, 48.25, 48.04, 47.83, 47.61, 47.40, 47.19, 46.98, 45.60, 41.00, 40.05, 39.66, 39.20, 38.94, 36.39, 35.33, 28.36, 28.09, 25.44, 23.29.

HRMS (ESI, m/z): calcd for C$_{46}$H$_{61}$N$_7$O$_2$SNa (M+Na)+: 894.4195, found: 894.4189.

BRD0322. $^1$H NMR (400 MHZ, Chloroform-d) δ 8.74-8.61 (m, 1H), 8.48 (dd, J=4.9, 1.7 Hz, 1H), 7.74 (dt, J=7.8, 1.9 Hz, 1H), 7.46 (s, 1H), 6.66 (d, J=8.7 Hz, 1H), 5.53 (d, J=6.8 Hz, 1H), 3.98 (dd, J=11.2, 4.2 Hz, 1H), 3.93-3.78 (m, 1H), 3.54 (dd, J=21.4, 8.8 Hz, 2H), 3.00 (s, 2H), 2.56 (s, 1H), 2.39 (t, J=11.7 Hz, 1H), 2.19-2.06 (m, 1H), 2.06-1.49 (m, 9H), 1.28 (t, J=9.4 Hz, 3H).

$^{13}$C NMR (101 MHZ, CDCl$_3$) δ 176.4, 152.1, 147.9, 146.7, 138.3, 132.9, 132.0, 123.1, 121.4, 113.2, 111.5, 93.9, 4, 77.4, 64.0, 58.3, 54.6, 45.1, 42.5, 39.7, 36.2, 29.7, 28.7, 26.1, 25.9, 25.9, 24.5.

HRMS (ESI, m/z): calcd for C$_{27}$H$_{31}$N$_3$O$_2$Na (M+H)$^+$: 452.2308, found: 452.2315.

BRD0048. $^1$H NMR (400 MHZ, Chloroform-d) δ 8.67 (d, J=2.2 Hz, 1H), 8.43 (dd, J=4.9, 1.8 Hz, 1H), 8.10 (ddd, J=10.4, 6.2, 2.8 Hz, 1H), 7.74 (dq, J=7.9, 1.8 Hz, 1H), 7.63 (s, 1H), 7.30 (dt, J=8.7, 1.7 Hz, 1H), 7.26-7.16 (m, 1H), 7.05-6.91 (m, 1H), 6.70-6.51 (m, 3H), 5.40 (d, J=7.1 Hz, 1H), 3.98 (dd, J=11.4, 4.4 Hz, 1H), 3.85 (dd, J=11.3, 5.7 Hz, 1H), 3.57-3.42 (m, 3H), 2.98 (d, J=1.4 Hz, 3H), 2.75-2.61 (m, 1H), 2.25-2.14 (m, 1H), 2.12-1.93 (m, 1H).

$^{13}$C NMR (101 MHz, CDCl$_3$) δ 157.8 (d, J=238.95 Hz), 154.3, 152.0, 147.8, 147.2 (d, J=236.5 Hz), 146.7, 138.4, 132.8, 132.2, 128.6 (t, J=24.0 Hz), 123.4, 123.1, 121.4, 114.8 (dd, J=22.5 Hz), 113.2, 111.6, 108.5 (dd, J=25.9 Hz), 108.2 (d, J=30.3 Hz), 93.8, 84.6, 63.8, 58.2, 55.8, 45.0, 40.5, 36.0, 24.9.

$^{19}$F NMR (376 MHZ, CDCl$_3$): δ −138.6, −113.3.

HRMS (ESI, m/z): calcd for C$_{27}$H$_{24}$F$_2$N$_4$O$_2$Na (M+Na)$^+$: 497.1760, found: 497.1780.

FIGS. 11-31 show NMR characterization of the compounds.

Figure 32A:
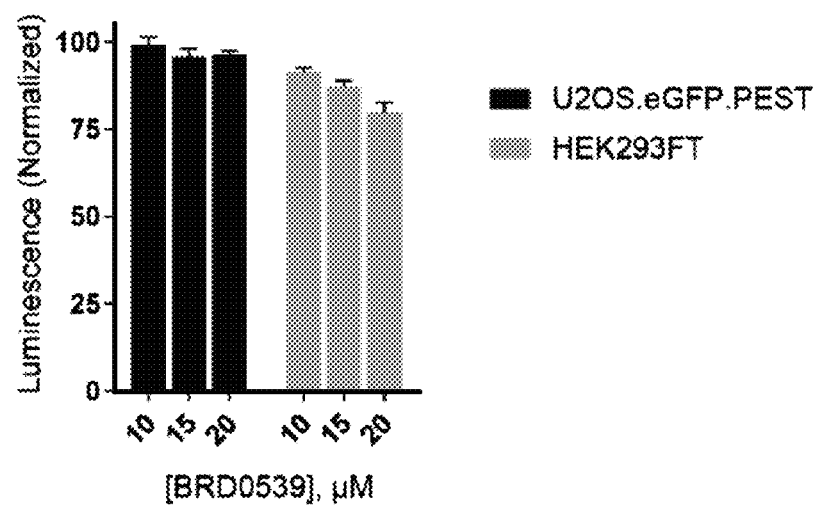
FIG. 32A-32B show cell viability of U2OS.eGFP.PEST and HEK293FT cells in the presence of small molecules. Cell viability was determined by measurement of ATP content of U2OS.eGFP.PEST and HEK293FT cells upon incubation with BRD0539 (10, 15, and 20 µM) for 24 h (FIG. 32A) and 72 h (FIG. 32B). Error bars represent ±s.d. across technical replicates (n=4).
Figure 32B:
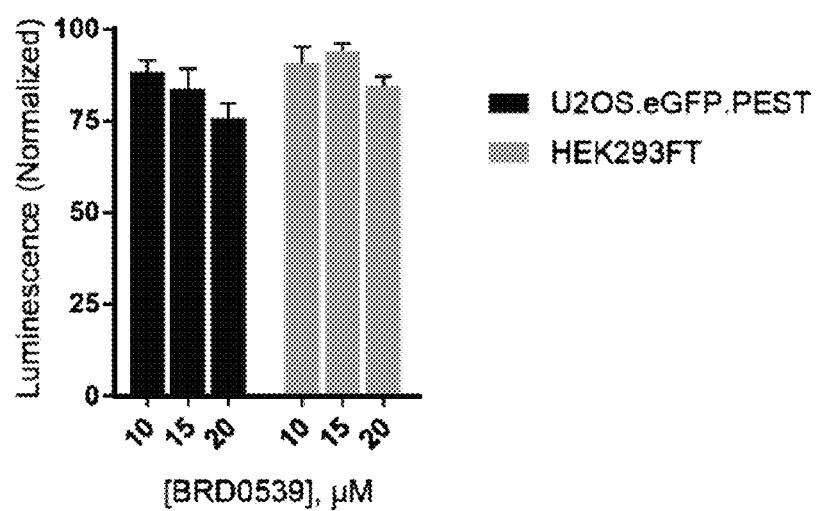

FIG. 32A-32B show cell viability of U2OS.eGFP.PEST and HEK293FT cells in the presence of small molecules. Cell viability was determined by measurement of ATP content of U2OS.eGFP.PEST and HEK293FT cells upon incubation with BRD0539 (10, 15, and 20 μM) for 24 h (FIG. 32A) and 72 h (FIG. 32B). Error bars represent ±s.d. across technical replicates (n=4).

Figure 33A:
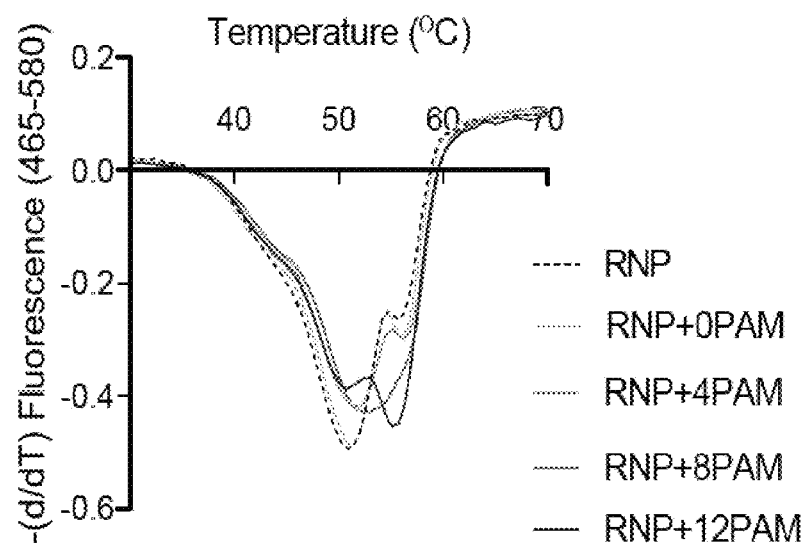
FIG. 33 show two replicate data for differential scanning fluorimetry studies of SpCas9:gRNA with DNA containing different PAM residues. SpCas9 (1 µM) was incubated with DNA (2 µM) bearing an increasing number of PAM sequence (0-12 PAM).
Figure 33B:
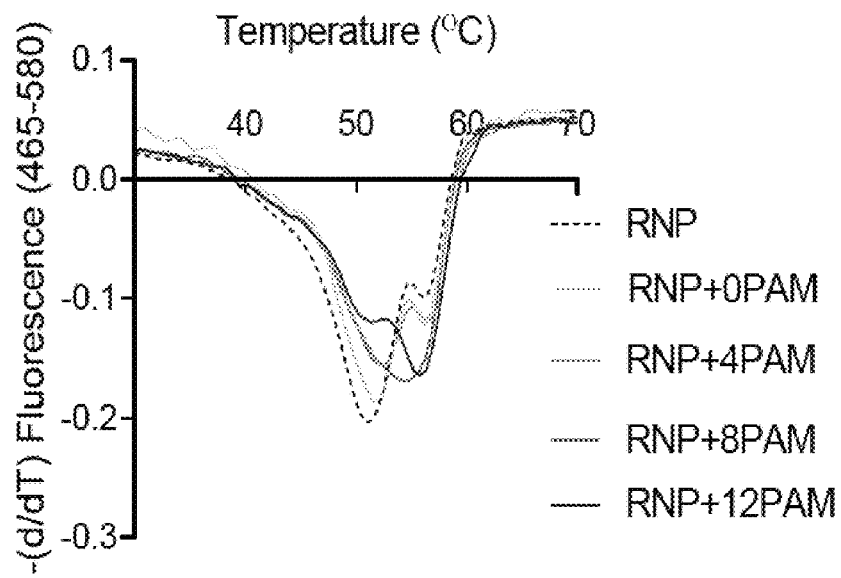

FIG. 33 show two replicate data for differential scanning fluorimetry studies of SpCas9:gRNA with DNA containing different PAM residues. SpCas9 (1 μM) was incubated with DNA (2 μM) bearing an increasing number of PAM sequence (0-12 PAM).

Figure 34:
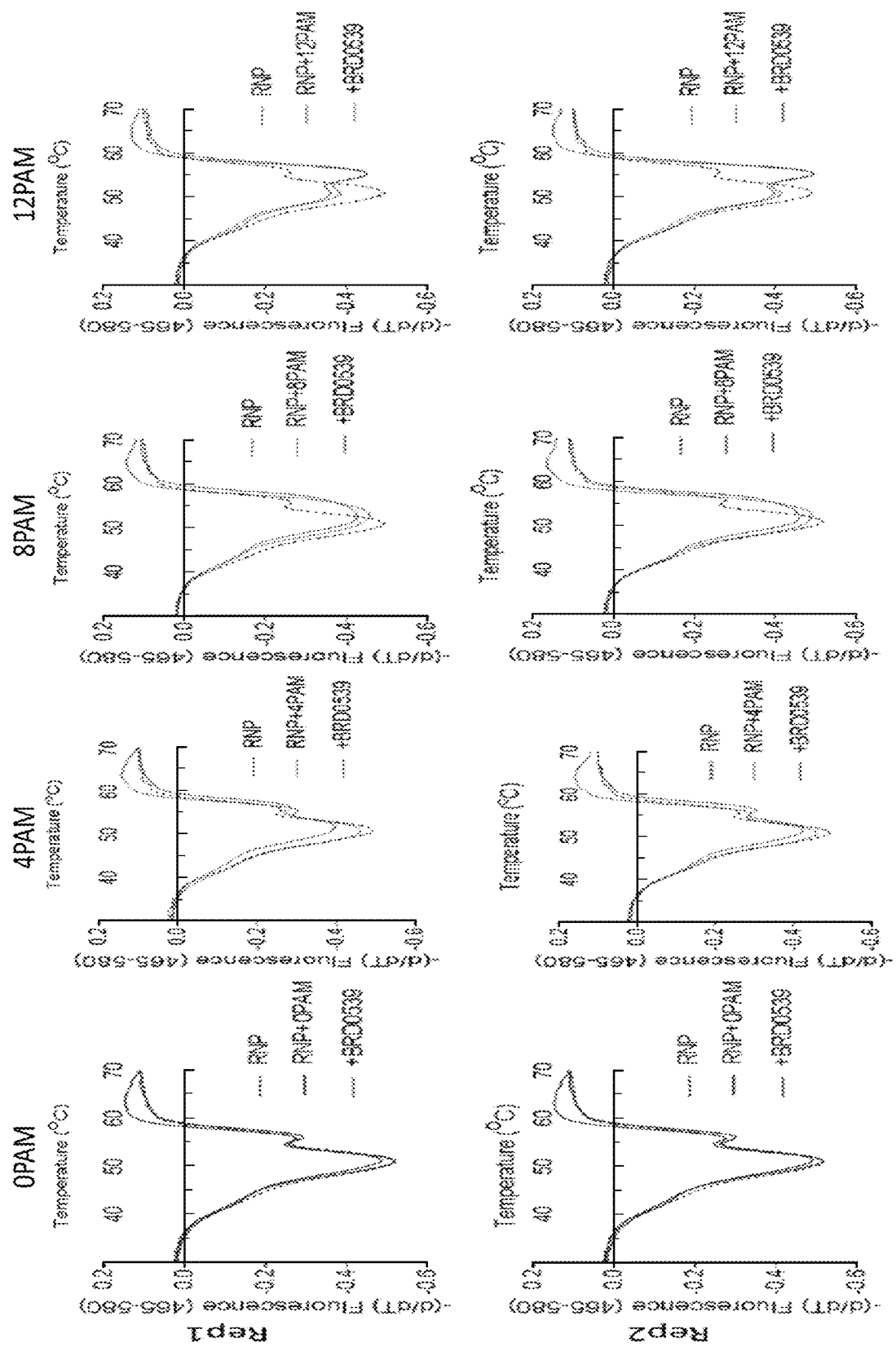
FIG. 34 shows differential scanning fluorimetry studies showing binding of SpCas9:gRNA to different PAM DNA and the effect of BRD0539. SpCas9:gRNA (1 µM) was incubated with PAM DNA (2 µM) in the presence of either DMSO or BRD0539 (20 µM).

FIG. 34 shows differential scanning fluorimetry studies showing binding of SpCas9:gRNA to different PAM DNA and the effect of BRD0539. SpCas9:gRNA (1 μM) was incubated with PAM DNA (2 μM) in the presence of either DMSO or BRD0539 (20 μM).

Figure 35:
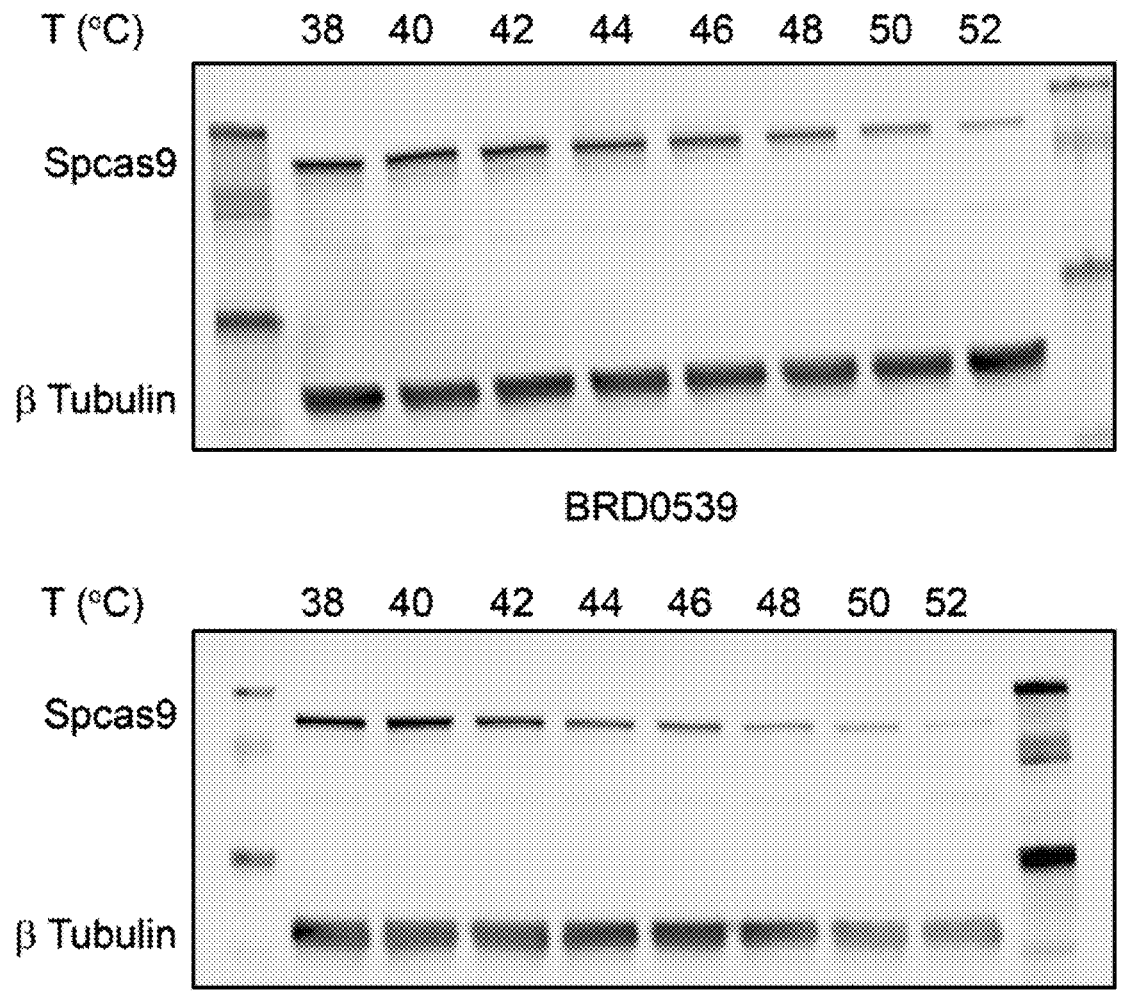
FIG. 35 shows original immunoblot images (FIG. 5G) of cellular thermal shift assay (CETSA) for SpCas9 in WM793 melanoma cells in the absence or presence of BRD0539. Stably SpCas9 expressing WM793 cells were incubated with 15 µM BRD0539 for 24 h before performing CETSA and analyzed by Western blot.

FIG. 35 shows original immunoblot images (FIG. 5G) of cellular thermal shift assay (CETSA) for SpCas9 in WM793 melanoma cells in the absence or presence of BRD0539. Stably SpCas9 expressing WM793 cells were incubated with 15 μM BRD0539 for 24 h before performing CETSA and analyzed by Western blot.

Figures 36A, 36B, 36C:
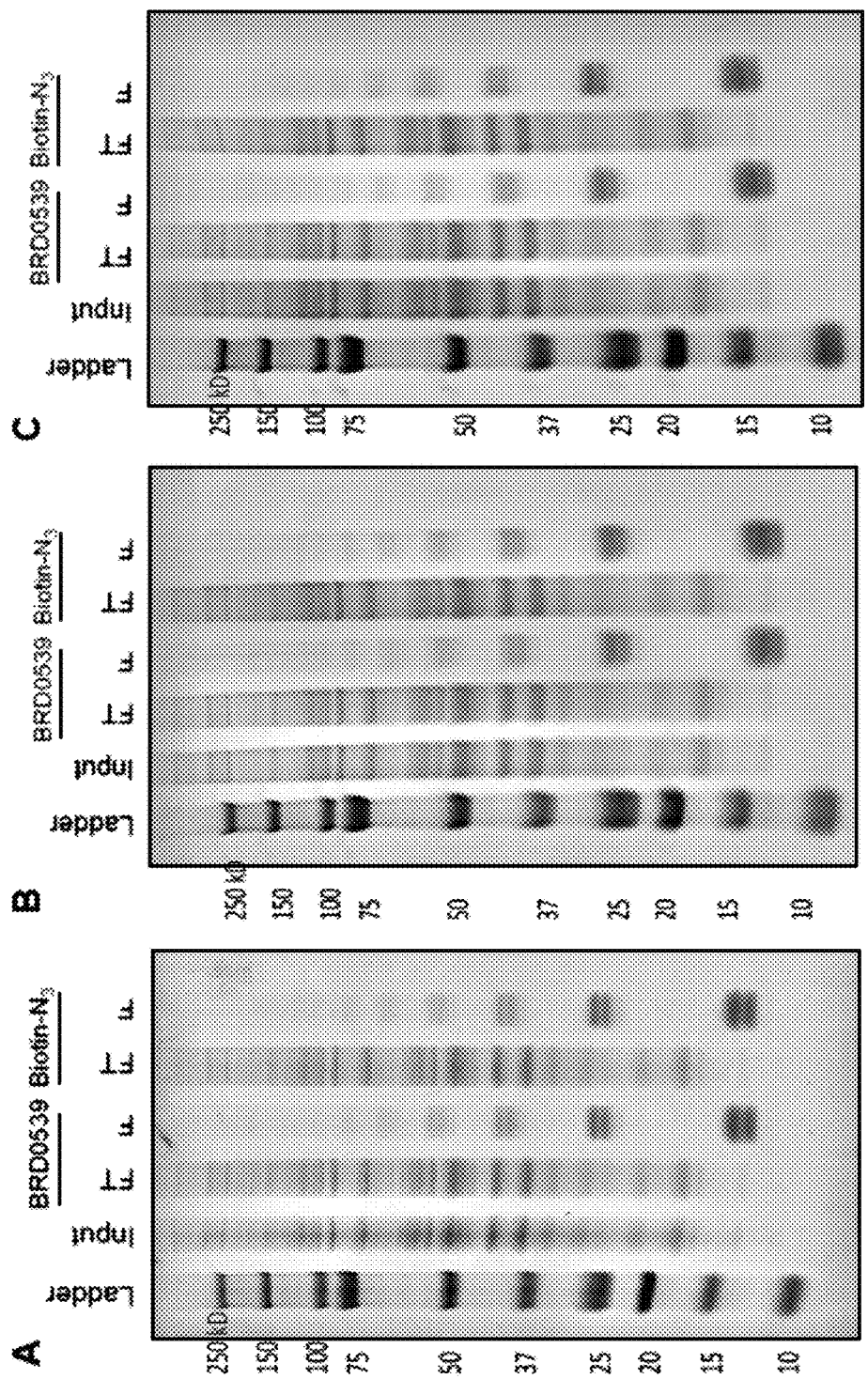
FIGS. 36A-36C show in vitro pulldown of proteins by the BRD0539-biotin conjugate from U2OS.eGFP.PEST cell lysate. Streptavidin magnetic beads pre-loaded with either BRD0539-biotin or biotin-azide with different amount of grafting (FIG. 36A: 100%, FIG. 36B: 50%, and FIG. 36C: 25%) were incubated with U2OS.eGFP.PEST cell lysate for 12 h before processing the samples for Western blotting. F and E represent the flow-through and eluent, respectively.

FIGS. 36A-36C show in vitro pulldown of proteins by the BRD0539-biotin conjugate from U2OS.eGFP.PEST cell lysate. Streptavidin magnetic beads pre-loaded with either BRD0539-biotin or biotin-azide with different amount of grafting (FIG. 36A: 100%, FIG. 36B: 50%, and FIG. 36C: 25%) were incubated with U2OS.eGFP.PEST cell lysate for 12 h before processing the samples for Western blotting. F and E represent the flow-through and eluent, respectively.

Resources used in the study are shown in Table 10.

TABLE 10

| REAGENT or RESOURCE | SOURCES | IDENTIFIER |
| --- | --- | --- |
| T4 PNK | NEB | #M0201S |
| T4 ligase | NEB | #M0202 |
| BsmBI | NEB | #R0580S |
| Tobacco Etch Virus (TEV) protease | SIGMA-ALDRICH Inc. | #T4455-10KU |
| Ni-NTA agarose resin | Thermo Fisher Scientific | #R90110 |
| QIAamp DNA Mini Kit | | #51306 |
| Phusion Hot Start II DNA polymerase | New England Biolabs | #F-549 |
| HCS NuclearMask | Thermo Fisher Scientific | #H10325 |
| DMEM (Medium for mammalian cell culture) | Life Technologies | #10564-011 |
| Fetal Bovine Serum (For mammalian cell culture) | Sigma Aldrich | #F4135 |
| Penicillin-Streptomycin (For mammalian cell culture) | Sigma Aldrich | #P4333 |
| poly-D-lysine | Sigma Aldrich | #P6407 |
| Lipofectamine 2000 | Thermo Fisher | #11668019 |
| SE Cell Line 4D-Nucleofector™ X Kit | Lonza | #V4XC-1024 |
| TaqMan probes | Life Technologies | #4331182 |
| Nano-Glo HiBiT Lytic Reagent | Promega | #N3030 |
| QuickExtract | Epicentre | #QE09050 |
| Surveyor Mutation Detection Kits | IDT | #706020 |
| the MiSeq Reagent Kit v2 300 | Illumina | #MS-102-2002 |
| streptavidin magnetic beads | Thermo Fisher Scientific | #88816 |
| BLI streptavidin sensors | ForteBio | #18-5119 |
| SYPRO ® Orange | Invitrogen | #S6650 |
| RevertAid RT Reverse Transcription Kit | Thermo Fischer Scientific | #K1691 |
| Q5 High-Fidelity DNA Polymerase | NEB | #M04915 |
| Experimental Models: Cell Lines | | |
| Human: HEK293T | ATCC | #CRL-3216 |
| Human: HEK293FT | Feng Zhang lab | NA |
| Human: U2OS.eGFP.PEST | Keith Joung lab | NA |
| Bone marrow stroma | Stuart Schreiber lab | NA |
| WM793-SpCas9 | Stuart Schreiber lab | NA |
| DH5 alpha cells | NEB | #C2987I |
| Recombinant DNA | | |
| pMJ806 | Addgene | #39312 |
| JDS246 | Addgene | #43861 |
| pFYF1320 EGFP Site#1 | Addgene | #47511 |
| BPK1520 | | #65777 |
| MS2-P65-HSF1 | Maji et al., 2017 | NA |
| dSpCas9 | Feng Zhang lab | NA |
| FITC labeled oligos | IDT | NA |
| Biotin oligos | IDT | NA |
| Primers | IDT and Eton Bio. | NA |
| Software and Algorithms | | |
| GraphPad Prism | GraphPad Prism Software Inc. | NA |
| Spotfire | Tibco | NA |
| MetaXpress | Molecular Device | NA |
| MATLAB | MathWorks | NA |

REFERENCES

Bondeson, D. P., Smith, B. E., Burslem, G. M., Buhimschi, A. D., Hines, J., Jaime-Figueroa, S., Wang, J., Hamman, B. D., Ishchenko, A., and Crews, C. M. (2018). Lessons in PROTAC design from selective degradation with a promiscuous warhead. Cell Chem Biol 25, 78-87.e75.

Champer, J., Buchman, A., and Akbari, O. S. (2016). Cheating evolution: engineering gene drives to manipulate the fate of wild populations. Nat Rev Genet 17, 146-159.

Charlesworth, C. T., Deshpande, P. S., Dever, D. P., Dejene, B., Gomez-Ospina, N., Mantri, S., Pavel-Dinu, M., Camarena, J., Weinberg, K. I., and Porteus, M. H. (2018). Identification of pre-existing adaptive immunity to Cas9 proteins in humans. bioRxiv.

Chen, J. S., and Doudna, J. A. (2017). The chemistry of Cas9 and its CRISPR colleagues. Nat Rev Chem 1, 0078.

Comer, E., Beaudoin, J. A., Kato, N., Fitzgerald, M. E., Heidebrecht, R. W., Lee, M. P., Masi, D., Mercier, M., Mulrooney, C., Muncipinto, G., et al. (2014a). Diversity-oriented synthesis-facilitated medicinal chemistry: towards the development of novel antimalarial agents. Journal of Medicinal Chemistry 57, 8496-8502.

Comer, E., Duvall, J. R., and duPont Lee, M.t. (2014b). Utilizing diversity-oriented synthesis in antimicrobial drug discovery. Future medicinal chemistry 6, 1927-1942.

Comer, E., Munoz, B., Beaudoin, J., A., Le Quement, S., T., Scherer, C., Duvall, J., Kato, N., Maetani, M., and Braibant, B. (2015). Compounds for the treatment of malaria In PCT Int Appl WO 2015002755, W. I. P. Organization, ed. (US).

Cox, D. B. T., Platt, R. J., and Zhang, F. (2015). Therapeutic genome editing: prospects and challenges. Nat Med 21, 121.

Dahlman, J. E., Abudayyeh, O. O., Joung, J., Gootenberg, J. S., Zhang, F., and Konermann, S. (2015). Orthogonal gene knockout and activation with a catalytically active Cas9 nuclease. Nature biotechnology.

Dandapani, S., Comer, E., Duvall, J. R., and Munoz, B. (2012). Hits, leads and drugs against malaria through diversity-oriented synthesis. Future medicinal chemistry 4, 2279-2294.

Dandapani, S., and Marcaurelle, L. A. (2010). Grand challenge commentary: Accessing new chemical space for 'undruggable' targets. Nature chemical biology 6, 861-863.

Davis, K. M., Pattanayak, V., Thompson, D. B., Zuris, J. A., and Liu, D. R. (2015). Small molecule-triggered Cas9 protein with improved genome-editing specificity. Nature chemical biology 11, 316-318.

Di, L., Kerns, E. H., Hong, Y., and Chen, H. (2005). Development and application of high throughput plasma stability assay for drug discovery. Int J Pharm 297, 110-119.

Esvelt, K. M., Smidler, A. L., Catteruccia, F., and Church, G. M. (2014). Concerning RNA-guided gene drives for the alteration of wild populations. eLife 3, e03401.

Fellmann, C., Gowen, B. G., Lin, P. C., Doudna, J. A., and Corn, J. E. (2017). Cornerstones of CRISPR-Cas in drug discovery and therapy. Nature reviews Drug discovery 16, 89-100.

Frock, R. L., Hu, J., Meyers, R. M., Ho, Y. J., Kii, E., and Alt, F. W. (2015). Genome-wide detection of DNA double-stranded breaks induced by engineered nucleases. Nature biotechnology 33, 179-186.

Fu, Y., Foden, J. A., Khayter, C., Maeder, M. L., Reyon, D., Joung, J. K., and Sander, J. D. (2013). High-frequency off-target mutagenesis induced by CRISPR-Cas nucleases in human cells. Nature biotechnology 31, 822-826.

Gantz, V. M., and Bier, E. (2016). The dawn of active genetics. BioEssays 38, 50-63.

Gerard, B., O'Shea, M. W., Donckele, E., Kesavan, S., Akella, L. B., Xu, H., Jacobsen, E. N., and Marcaurelle, L. A. (2012). Application of a catalytic asymmetric Povarov reaction using chiral ureas to the synthesis of a tetrahydroquinoline library. ACS Comb Sci 14, 621-630.

Hammond, A., and Galizi, R. (2016). A CRISPR-Cas9 gene drive system targeting female reproduction in the malaria mosquito vector Anopheles gambiae. Nature biotechnology 34, 78-83.

Hsu, P. D., Scott, D. A., Weinstein, J. A., Ran, F. A., Konermann, S., Agarwala, V., Li, Y., Fine, E. J., Wu, X., and Shalem, O. (2013). DNA targeting specificity of RNA-guided Cas9 nucleases. Nature biotechnology 31, 827-832.

Hynes, A. P., Rousseau, G. M., Lemay, M. L., Horvath, P., Romero, D. A., Fremaux, C., and Moineau, S. (2017). An anti-CRISPR from a virulent streptococcal phage inhibits Streptococcus pyogenes Cas9. Nature microbiology 2, 1374-1380.

Kato, N., Comer, E., Sakata-Kato, T., Sharma, A., Sharma, M., Maetani, M., Bastien, J., Brancucci, N. M., Bittker, J. A., Corey, V., et al. (2016). Diversity-oriented synthesis yields novel multistage antimalarial inhibitors. Nature 538, 344-349.

Kleinstiver, B. P., Prew, M. S., Tsai, S. Q., Nguyen, N. T., Topkar, V. V., Zheng, Z., and Joung, J. K. (2015a). Broadening the targeting range of Staphylococcus aureus CRISPR-Cas9 by modifying PAM recognition. Nature biotechnology 33, 1293-1298.

Kleinstiver, B. P., Prew, M. S., Tsai, S. Q., Topkar, V. V., Nguyen, N. T., Zheng, Z., Gonzales, A. P., Li, Z., Peterson, R. T., Yeh, J. R., et al. (2015b). Engineered CRISPR-Cas9 nucleases with altered PAM specificities. Nature 523, 481-485.

Koehler, A. N. (2010). A complex task? Direct modulation of transcription factors with small molecules. Curr Opin Chem Biol 14, 331-340.

Komor, A. C., Badran, A. H., and Liu, D. R. (2016a). CRISPR-based technologies for the manipulation of eukaryotic genomes. Cell 168, 20-36.

Komor, A. C., Kim, Y. B., Packer, M. S., Zuris, J. A., and Liu, D. R. (2016b). Programmable editing of a target base in genomic DNA without double-stranded DNA cleavage. Nature 533, 420-424.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2015a). Genome-scale transcriptional activation by an engineered CRISPR-Cas9 complex. Nature 517, 583-588.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2015b). Genome-scale transcriptional activation by an engineered CRISPR-Cas9 complex. Nature 517, 583-588.

Lai, A. C., and Crews, C. M. (2017). Induced protein degradation: an emerging drug discovery paradigm. Nature reviews Drug discovery 16, 101-114.

Lundblad, J. R., Laurance, M., and Goodman, R. H. (1996). Fluorescence polarization analysis of protein-DNA and protein-protein interactions. Molecular endocrinology (Baltimore, Md) 10, 607-612.

Maji, B., Moore, C. L., Zetsche, B., Volz, S. E., Zhang, F., Shoulders, M. D., and Choudhary, A. (2017). Multidimensional chemical control of CRISPR-Cas9. Nature chemical biology 13, 9-11.

Marcaurelle, L. A., and Johannes, C. W. (2008). Application of natural product-inspired diversity-oriented synthesis to drug discovery. Progress in drug research Fortschritte der Arzneimittelforschung Progres des recherches pharmaceutiques 66, 189-216.

Martinez Molina, D., Jafari, R., Ignatushchenko, M., Seki, T., Larsson, E. A., Dan, C., Sreekumar, L., Cao, Y., and Nordlund, P. (2013). Monitoring drug target engagement in cells and tissues using the cellular thermal shift assay. Science (New York, NY) 341, 84-87.

Martinez Molina, D., and Nordlund, P. (2016). The Cellular Thermal Shift Assay: A novel biophysical assay for in situ drug target engagement and mechanistic biomarker studies. Annu Rev Pharmacol Toxicol 56, 141-161.

Moore, R., Spinhirne, A., Lai, M. J., Preisser, S., Li, Y., Kang, T., and Bleris, L. (2015). CRISPR-based self-cleaving mechanism for controllable gene delivery in human cells. Nucleic Acids Res 43, 1297-1303.

Neve, R. L., Neve, K. A., Nestler, E. J., and Carlezon, W. A., Jr. (2005). Use of herpes virus amplicon vectors to study brain disorders. BioTechniques 39, 381-391.

Nguyen, D. P., Miyaoka, Y., Gilbert, L. A., Mayerl, S., Lee, B. H., Weissman, J. S., Conklin, B. R., and Wells, J.A. (2016a). Ligand-binding domains of nuclear receptors facilitate tight control of split CRISPR activity. Nat Commun 7, 12009.

Nguyen, D. P., Miyaoka, Y., Gilbert, L. A., Mayerl, S., Lee, B. H., Weissman, J. S., Conklin, B. R., and Wells, J.A. (2016b). Ligand-binding domains of nuclear receptors facilitate tight control of split CRISPR activity. Nat Commun 7, 12009.

Niesen, F. H., Berglund, H., and Vedadi, M. (2007). The use of differential scanning fluorimetry to detect ligand interactions that promote protein stability. Nature protocols 2, 2212-2221.

Nishimasu, H., Ran, F. A., Hsu, P. D., Konermann, S., Shehata, S. I., Dohmae, N., Ishitani, R., Zhang, F., and Nureki, O. (2014). Crystal structure of Cas9 in complex with guide RNA and target DNA. Cell 156, 935-949.

Nunez, J. K., Harrington, L. B., and Doudna, J. A. (2016). Chemical and biophysical modulation of Cas9 for tunable genome engineering. ACS chemical biology 11, 681-688.

Pattanayak, V., Guilinger, J. P., and Liu, D. R. (2014). Determining the specificities of TALENs, Cas9, and other genome-editing enzymes. Methods in enzymology 546, 47-78.

Pattanayak, V., Lin, S., Guilinger, J. P., Ma, E., Doudna, J. A., and Liu, D. R. (2013a). High-throughput profiling of off-target DNA cleavage reveals RNA-programmed Cas9 nuclease specificity. Nature biotechnology 31, 839-843.

Pattanayak, V., Lin, S., Guilinger, J. P., Ma, E., Doudna, J. A., and Liu, D. R. (2013b). High-throughput profiling of off-target DNA cleavage reveals RNA-programmed Cas9 nuclease specificity. Nature biotechnology 31, 839-843.

Pawluk, A., Amrani, N., Zhang, Y., Garcia, B., Hidalgo-Reyes, Y., Lee, J., Edraki, A., Shah, M., Sontheimer, E. J., Maxwell, K. L., et al. (2016a). Naturally occurring off-switches for CRISPR-Cas9. Cell 167, 1829-1838.e1829.

Pawluk, A., Staals, R. H., Taylor, C., Watson, B. N., Saha, S., Fineran, P. C., Maxwell, K. L., and Davidson, A. R. (2016b). Inactivation of CRISPR-Cas systems by anti-CRISPR proteins in diverse bacterial species. Nature microbiology 1, 16085.

Rauch, B. J., Silvis, M. R., Hultquist, J. F., Waters, C. S., McGregor, M. J., Krogan, N. J., and Bondy-Denomy, J. (2017). Inhibition of CRISPR-Cas9 with bacteriophage proteins. Cell 168, 150-158.e110.

Rees, H. A., Komor, A. C., Yeh, W. H., Caetano-Lopes, J., Warman, M., Edge, A. S. B., and Liu, D. R. (2017a). Improving the DNA specificity and applicability of base editing through protein engineering and protein delivery. Nat Commun 8, 15790.

Rees, H. A., Komor, A. C., Yeh, W. H., Caetano-Lopes, J., Warman, M., Edge, A. S. B., and Liu, D. R. (2017b). Improving the DNA specificity and applicability of base editing through protein engineering and protein delivery. Nat Commun 8, 15790.

Richardson, C. D., Ray, G. J., DeWitt, M. A., Curie, G. L., and Corn, J. E. (2016). Enhancing homology-directed genome editing by catalytically active and inactive CRISPR-Cas9 using asymmetric donor DNA. Nature biotechnology 34, 339-344.

Schreiber, S. L. (2000). Target-oriented and diversity-oriented organic synthesis in drug discovery. Science (New York, NY) 287, 1964-1969.

Schwinn, M. K., Machleidt, T., Zimmerman, K., Eggers, C. T., Dixon, A. S., Hurst, R., Hall, M. P., Encell, L. P., Binkowski, B. F., and Wood, K. V. (2018a). CRISPR-Mediated Tagging of Endogenous Proteins with a Luminescent Peptide. ACS Chem Biol 13, 467-474.

Schwinn, M. K., Machleidt, T., Zimmerman, K., Eggers, C. T., Dixon, A. S., Hurst, R., Hall, M. P., Encell, L. P., Binkowski, B. F., and Wood, K. V. (2018b). CRISPR-mediated tagging of endogenous proteins with a luminescent peptide. ACS chemical biology 13, 467-474.

Shing, J., Jiang, F., Liu, J.-J., Bray, N. L., Rauch, B. J., Baik, S. H., Nogales, E., Bondy-Denomy, J., Corn, J. E., and Doudna, J.A. (2017). Disabling Cas9 by an anti-CRISPR DNA mimic. Sci Adv 3, e1701620.

Sternberg, S. H., Redding, S., Jinek, M., Greene, E. C., and Doudna, J. A. (2014). DNA interrogation by the CRISPR RNA-guided endonuclease Cas9. Nature 507, 62-67.

Tsai, S. Q., Zheng, Z., Nguyen, N. T., Liebers, M., Topkar, V. V., Thapar, V., Wyvekens, N., Khayter, C., Iafrate, A. J., Le, L. P., et al. (2015). GUIDE-seq enables genome-wide profiling of off-target cleavage by CRISPR-Cas nucleases. Nature biotechnology 33, 187-197.

Tu, Z., Yang, W., Yan, S., Yin, A., Gao, J., Liu, X., Zheng, Y., Zheng, J., Li, Z., Yang, S., et al. (2017). Promoting Cas9 degradation reduces mosaic mutations in non-human primate embryos. Sci Rep 7, 42081.

Wang, H., Russa, M. L., and Qi, L. S. (2016). CRISPR/Cas9 in genome editing and beyond. Annu Rev Biochem 85, 227-264.

Wang, H., Yang, H., Shivalila, C. S., Dawlaty, M. M., Cheng, A. W., Zhang, F., and Jaenisch, R. (2013). One-step generation of mice carrying mutations in multiple genes by CRISPR/Cas-mediated genome engineering. Cell 153, 910-918.

Wawer, M. J., Li, K., Gustafsdottir, S. M., Ljosa, V., Bodycombe, N. E., Marton, M. A., Sokolnicki, K. L., Bray, M. A., Kemp, M. M., Winchester, E., et al. (2014). Toward performance-diverse small-molecule libraries for cell-based phenotypic screening using multiplexed high-dimensional profiling. Proceedings of the National Academy of Sciences of the United States of America 111, 10911-10916.

Wegrzyn, R. D., Lee, A. H., Jenkins, A. L., Stoddard, C. D., and Cheever, A. E. (2017). Genome editing: insights from chemical biology to support safe and transformative therapeutic applications. ACS chemical biology, DOI: 10.1021/acschembio.1027b00689.

Weiss, W. A., Taylor, S. S., and Shokat, K. M. (2007). Recognizing and exploiting differences between RNAi and small-molecule inhibitors. Nature chemical biology 3, 739-744.

Yen, S.-T., Zhang, M., Deng, J. M., Usman, S., Smith, C. N., Parker-Thornburg, J., Swinton, P. G., Martin, J. F., and Behringer, R. R. (2014). Somatic mosaicism and allele complexity induced by CRISPR/Cas9 RNA injections in mouse zygotes. Dev Biol 393, 3-9.

Zhang, J. H., Chung, T. D., and Oldenburg, K. R. (1999). A simple statistical parameter for use in evaluation and validation of high throughput screening assays. Journal of biomolecular screening 4, 67-73.

Various modifications and variations of the described methods, pharmaceutical compositions, and kits of the invention will be apparent to those skilled in the art without departing from the scope and spirit of the invention.

Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A compound having the structure of Formula (I):

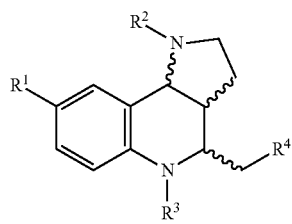

(I)

wherein $R^1$ is selected from alkynyl, bicyclic aryl, tricyclic aryl, and polycyclic aryl;

$R^2$ is selected from -$L_1$-X and -$L_1$-R;

$R^3$ is selected from hydrogen, —X, —R, -$L_2$-X, and -$L_2$-R;

$R^4$ is —OH;

Each $L_1$ is independently —CO— or —S(O)$_2$—;

Each $L_2$ is independently selected from —(CH$_2$)$_n$—, —(CH$_2$)$_n$—C(O)O—, —(CH$_2$)$_n$—C(O)—NH—, —C(O)—NH—(CH$_2$)$_n$—, —(CH$_2$)$_n$—NH—C(O)—, —(CH$_2$)$_n$—NH—SO$_2$—, —NH—SO$_2$—(CH$_2$)$_n$—, —(CH$_2$)$_n$—SO$_2$—NH—, —(CH$_2$)$_n$—SO$_2$—, —(CH$_2$)$_n$—SO$_2$—NH—C(O)—, —(CH$_2$)$_n$—R$^{L2}$—, —R$^{L2}$—C(O)—O—, —R$^{L2}$—NH—C(O)—(CH$_2$)$_n$—, —R$^{L2}$—NH—S(O)$_2$—(CH$_2$)$_n$—, —S—, —S(O)—, and —S(O)$_2$—, wherein each n is independently 0, 1, 2, 3, 4, 5, or 6;

Each X is selected from hydrogen, CN, OH, CF$_3$, COOH, OR, OR, NR$_2$, and halogen;

Each $R^{L2}$ is selected from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I, and combinations thereof; and Each R is selected from $C_{1-12}$ hydrocarbons, optionally substituted with one or more groups X and/or with 1-10 heteroatoms selected from O, S, N, P, F, Cl, Br, I, and combinations thereof.

2. The compound of claim 1, wherein the $L_1$ is —S(O)$_2$—.

3. The compound of claim 1, wherein $R^2$ is -$L_1$-R, wherein R is benzyl.

4. The compound of claim 1 having the structure:

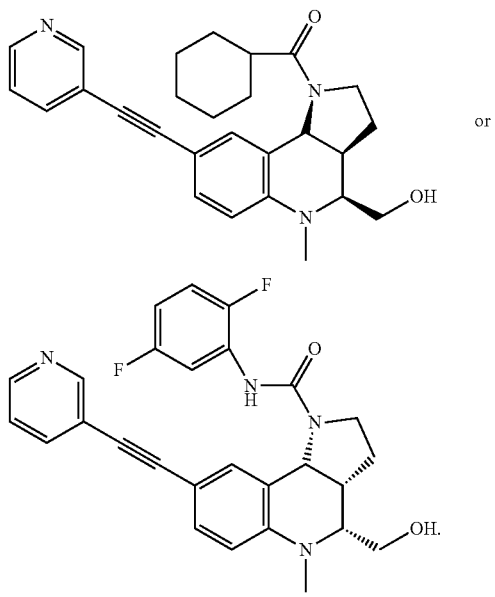

or

5. A compound of Formula 1A, 1B, 1C, or 1D:

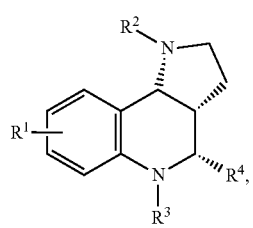

(IA)

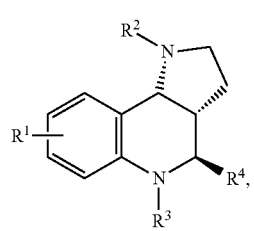

(IB)

-continued

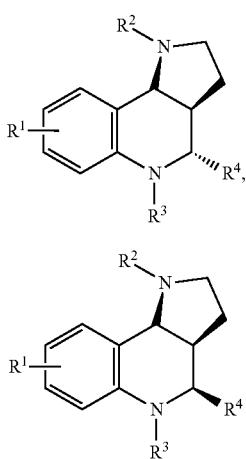

(IC)

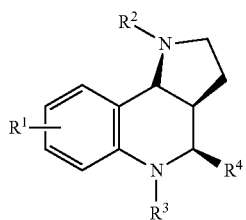

(ID)

wherein $R^1$ is selected from alkynyl, bicyclic aryl, tricyclic aryl, and polycyclic aryl;
$R^2$ is selected from $-L_1-X$ and $-L_1-R$;
$R^3$ is selected from hydrogen, —X, —R, $-L_2-X$, and $-L_2-R$;
$R^4$ is —(CH$_2$)—OH;
Each $L_1$ is selected from —CO— and —S(O)$_2$—;
Each $L_2$ is selected from —(CH$_2$)$_n$—, —(CH$_2$)$_n$—C(O)O—, (CH$_2$)$_n$—C(O)—NH—, —C(O)—NH—(CH$_2$)$_n$—, —(CH$_2$)$_n$—NH—C(O)—, —(CH$_2$)$_n$—NH—SO$_2$—, —NH—SO$_2$—(CH$_2$)$_n$—, —(CH$_2$)$_n$—SO$_2$—NH—, —(CH$_2$)$_n$—SO$_2$—, —(CH$_2$)$_n$—SO$_2$—NH—C(O)—, (CH$_2$)$_n$—$R^{L2}$—, —$R^{L2}$—C(O)—O—, —$R^{L2}$—NH—C(O)—(CH$_2$)$_n$—, —$R^{L2}$—NH—S(O)$_2$—(CH$_2$)$_n$—, —S—, —S(O)—, and —S(O)$_2$—, wherein each n is independently 0, 1, 2, 3, 4, 5, or 6;
Each X is selected from hydrogen, CN, OH, CF$_3$, COOH, OR, OR, NR$_2$, and halogen;
Each $R^{L2}$ is selected at each occurrence from $C_1$-$C_{12}$ linear and/or branched and/or cyclic and/or aromatic bivalent radicals; optionally substituted with one or more groups X and/or with 1-6 heteroatoms selected from O, S, N, P, F, Cl, Br, I, and combinations thereof; and Each R is selected from $C_{1-12}$ hydrocarbons, optionally substituted with one or more groups X and/or with 1-10 heteroatoms selected from O, S, N, P, F, Cl, Br, I, and combinations thereof.

6. The compound of claim 5, wherein the $L_1$ is —S(O)$_2$—.

7. The compound of claim 5, wherein $R^2$ is $-L_1-R$, wherein R is benzyl.

8. A method of inhibiting an activity of an RNA-guided endonuclease, the method comprising contacting the RNA-guided endonuclease with the compound of claim 1.

9. The method of claim 8, wherein the compound inhibits the activity of an RNA-guided endonuclease reversibly.

10. The method of claim 8, wherein the method is performed in vitro.

11. The method of claim 8, wherein the method is performed in vivo.

12. The method of claim 8, wherein the method is performed in a cell.

13. The method of claim 12, wherein the cell is a germline cell.

14. The method of claim 12, wherein the cell is a prokaryotic cell.

15. The method of claim 14, wherein the prokaryotic cell is a bacterium.

16. The method of claim 12, wherein the cell is a eukaryotic cell.

17. The method of claim 16, wherein the eukaryotic cell is a human cell, a mammalian cell, an insect cell, a plant cell, or a yeast cell.

18. The method of claim 12, wherein the cell is in an organism.

19. The method of claim 18, wherein the organism is a human, mammal, vertebrate, invertebrate, insect, or plant.

20. The method of claim 8, wherein the RNA-guided endonuclease is Cas9.

21. The method of claim 20, wherein the RNA-guided endonuclease is *Streptococcus pyogenes* Cas9 or a variant thereof.

22. A pharmaceutical formulation comprising the compound of claim 1 and a pharmaceutically acceptable carrier.

23. A kit comprising the compound of claim 1.

* * * * *